(12) United States Patent
Geneste et al.

(10) Patent No.: US 9,856,220 B2
(45) Date of Patent: Jan. 2, 2018

(54) INHIBITOR COMPOUNDS OF PHOSPHODIESTERASE TYPE 10A

(71) Applicants: AbbVie Deutschland GmbH & Co. KG, Wiesbaden (DE); AbbVie Inc., North Chicago, IL (US)

(72) Inventors: Hervé Geneste, Ludwigshafen (DE); Michael Ochse, Ludwigshafen (DE); Karla Drescher, Ludwigshafen (DE); Jürgen Dinges, North Chicago, IL (US); Clarissa Jakob, North Chicago, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 15/207,137

(22) Filed: Jul. 11, 2016

(65) Prior Publication Data

US 2016/0318871 A1 Nov. 3, 2016

Related U.S. Application Data

(63) Continuation of application No. 13/672,438, filed on Nov. 8, 2012, now abandoned.
(Continued)

(51) Int. Cl.
*C07D 217/26* (2006.01)
*A61K 31/47* (2006.01)
(Continued)

(52) U.S. Cl.
CPC ............ *C07D 217/26* (2013.01); *A61K 31/47* (2013.01); *C07D 217/24* (2013.01);
(Continued)

(58) Field of Classification Search
CPC ..... C07D 217/24; C07D 217/26; A61K 31/47
(Continued)

(56) References Cited

U.S. PATENT DOCUMENTS

2007/0155779 A1 7/2007 Verhoest et al.
2009/0163545 A1* 6/2009 Goldfarb ............... A61K 31/122
                                                              514/312
2009/0226422 A1 9/2009 Chaudhary et al.

FOREIGN PATENT DOCUMENTS

WO WO-03093499 A2 11/2003
WO WO-2005012485 A2 2/2005
(Continued)

OTHER PUBLICATIONS

Goldfarb, CAPLUS Abstract 2009:846111 (2009).*

PubChem CID 3244153 (2005).*
Jordan, Nature Reviews: Drug Discovery, vol. 2, Issue 3, pp. 205-213 (2003).*
Fujishige et al., Cloning and Characterization of a Novel Human Phosphodiesterase That Hydrolyzes both cAMP and cGMP (PDE10A), The Journal of Biological Chemistry, vol. 274, No. 26, pp. 18438-18445 (1999).*

(Continued)

*Primary Examiner* — Deepak Rao
(74) *Attorney, Agent, or Firm* — Neal, Gerber & Eisenberg LLP

(57) ABSTRACT

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

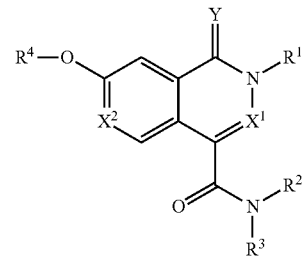

(I)

wherein
$X^1$ is CH or N, $X^2$ is C—$R^5$ or N, Y is O or S,
$R^1$ is inter alia $C_2$-$C_8$-alkyl, $C_2$-$C_8$-alkenyl, $C_1$-$C_4$-fluoroalkyl, $C_3$-$C_8$-cycloalkyl, $C_5$-$C_8$-cycloalkyl carrying a fused benzene ring, or a moiety $Z^1$—$Ar^1$;
$R^2$ is a radical of the formula $CR^{21}R^{22}R^{23}$ or phenyl or 5- or 6-membered hetaryl having 1, 2 or 3 heteroatoms as ring members which are selected from O, S and N, where phenyl and monocyclic hetaryl are unsubstituted or may carry 1, 2 or 3 identical or different substituents $R^a$,
$R^3$ is inter alia hydrogen, $C_1$-$C_8$-alkyl, $C_2$-$C_8$-alkenyl, $C_1$-$C_4$-fluoroalkyl, $C_3$-$C_8$-cycloalkyl, etc, or
$R^2$ and $R^3$ together with the nitrogen atom, to which they are bound form an optionally substituted saturated 5- to 7-membered heterocyclic ring which, in addition to the nitrogen atom, may have 1 or 2 further heteroatoms or heteroatom containing groups selected from the group of O, N, S, SO and $SO_2$;
$R^4$ is inter alia $C_1$-$C_4$-alkyl, $C_1$-$C_4$-fluoroalkyl, $C_3$-$C_6$-cycloalkyl, $C_3$-$C_6$-cycloalkyl-$C_1$-$C_4$-alkyl or $Z^4$—$Ar^4$;
$R^5$ is inter alia hydrogen, halogen, $C_1$-$C_4$-alkyl, $C_1$-$C_4$-fluoroalkyl, $C_1$-$C_4$-alkoxy, $C_1$-$C_4$-fluoroalkoxy, —$Z^5$—$Ar^5$, —O—$Z^5$—$Ar^5$, etc;
where $Z^1$ to $Z^5$, $Ar^1$ to $Ar^5$, $R^a$, $R^{21}$, $R^{22}$, and $R^{23}$ are as defined in the claims.

26 Claims, No Drawings

Related U.S. Application Data

(60) Provisional application No. 61/557,878, filed on Nov. 9, 2011.

(51) Int. Cl.

| | | |
|---|---|---|
| *C07D 401/06* | (2006.01) | |
| *C07D 413/06* | (2006.01) | |
| *C07D 401/14* | (2006.01) | |
| *C07D 237/32* | (2006.01) | |
| *C07D 417/06* | (2006.01) | |
| *C07D 409/08* | (2006.01) | |
| *C07D 471/04* | (2006.01) | |
| *C07D 217/24* | (2006.01) | |
| *C07D 401/12* | (2006.01) | |
| *C07D 417/12* | (2006.01) | |
| *C07D 409/12* | (2006.01) | |

(52) U.S. Cl.
CPC ......... *C07D 237/32* (2013.01); *C07D 401/06* (2013.01); *C07D 401/12* (2013.01); *C07D 401/14* (2013.01); *C07D 409/08* (2013.01); *C07D 409/12* (2013.01); *C07D 413/06* (2013.01); *C07D 417/06* (2013.01); *C07D 417/12* (2013.01); *C07D 471/04* (2013.01)

(58) Field of Classification Search
USPC .......................................... 546/141; 514/309
See application file for complete search history.

(56) References Cited

FOREIGN PATENT DOCUMENTS

| | | |
|---|---|---|
| WO | WO-2005120514 A1 | 12/2005 |
| WO | WO-2006028957 A1 | 3/2006 |
| WO | WO-2007022280 A1 | 2/2007 |
| WO | WO 2007082546 A1 | 7/2007 |
| WO | WO-2007085954 A2 | 8/2007 |
| WO | WO-2007096743 A1 | 8/2007 |
| WO | WO-2007098169 A1 | 8/2007 |
| WO | WO-2007098214 A1 | 8/2007 |
| WO | WO-2007100880 A1 | 9/2007 |
| WO | WO 2007103370 A2 | 9/2007 |
| WO | WO-2007103554 A1 | 9/2007 |
| WO | WO-2007137819 A1 | 12/2007 |
| WO | WO-2007137820 A1 | 12/2007 |
| WO | WO-2008001182 A1 | 1/2008 |
| WO | WO-2008004117 A1 | 1/2008 |
| WO | WO-2008006372 A1 | 1/2008 |
| WO | WO-2008020302 A2 | 2/2008 |
| WO | WO-2009025823 A1 | 2/2009 |
| WO | WO-2009025839 A2 | 2/2009 |
| WO | WO-2009029214 A1 | 3/2009 |
| WO | WO-2009036766 A1 | 3/2009 |
| WO | WO-2009068246 A2 | 6/2009 |
| WO | WO-2009068320 A1 | 6/2009 |
| WO | WO-2009070583 A1 | 6/2009 |
| WO | WO-2009070584 A1 | 6/2009 |
| WO | WO-2010028655 A1 | 3/2010 |

OTHER PUBLICATIONS

Buckley N.A., et al., "Cardiovascular Adverse Effects of Antipsychotic Drugs," Drug Safety, 2000, vol. 23 (3), pp. 215-218.
Bundgaard H, "Design of prodrugs: Bioreversible derivatives for various functional groups and chemical entities," in: Design of Prodrugs, Elsevier, Amsterdam, 1985, pp. 1-92.
Cantin L.D., et al., "PDE-10A Inhibitors as Insulin Secretagogues," Bioorganic and Medicinal Chemistry Letters, 2007, vol. 17 (10), pp. 2869-2873.
Chappie T., et al., "PDE10A Inhibitors: An Assessment of the Current CNS Drug Discovery Landscape," Current Opinion in Drug Discovery and Development, 2009, vol. 12 (4), pp. 458-467.
Compound summary for CID 5307222, PubChem Open Chemistry database, Retrieved from the Internet< URL: http://pubchemncbinlmnihgov, MLS000116159> 2005, p. 13.
Damasio A.R., "Alzheimer's Disease and Related Dementias" in: Cecil Textbook of Medicine, 20th Edition, vol. 2, Bennett J.C., et al., eds., W.B. Saunders Company, 1996, pp. 1992-1996.
De Hert M., et al., "Metabolic and Cardiovascular Adverse Effects Associated with Antipsychotic Drugs," Nature Reviews Endocrinology, 2011, vol. 8 (2), pp. 114-126.
De Hert M., et al., "Metabolic and Cardiovascular Adverse Effects Associated with Antipsychotic Drugs.," Nature Reviews. Endocrinology, 2012, vol. 8 (2), pp. 114-126.
Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.
Francis S.H., et al., "Mammalian Cyclic Nucleotide Phosphodiesterases: Molecular Mechanisms and Physiological Functions," Physiological Reviews, 2011, vol. 91 (2), pp. 651-690.
Goldfarb, "RN 892264-95-8, CAPLUS Abstract 151," 2009, pp. 928-938.
Goldfarb, "RN 892271-29-3, CAPLUS Abstract 151," 2009, pp. 70320.
Grauer S.M., et al., "Phosphodiesterase 10A Inhibitor Activity in Preclinical Models of the Positive, Cognitive, and Negative Symptoms of Schizophrenia," Journal of Pharmacology and Experimental Therapeutics, 2009, vol. 331 (2), pp. 574-590.
International Search Report and Written Opinion for Application No. PCT/EP2012/072175, dated Dec. 6, 2012, 7 pages.
Layzer R.B., "Degenerative Diseases of the Nervous System" in: Cecil Textbook of Medicine, 20th Edition, Bennett J.C., et al., eds., W.B. Saunder Company, vol. 2, 1996, pp. 2050-2057.
Nishi A., et al., "Distinct Roles of PDE4 and PDE10A in the Regulation of cAMP/PKA Signaling in the Striatum," The Journal of Neuroscience, 2008, vol. 28 (42), pp. 10460-10471.
Rodefer J.S., et al., "PDE10A Inhibition Reverses Subchronic PCP-Induced Deficits in Attentional Set-Shifting in Rats," European Journal of Neuroscience, 2005, vol. 21 (4), pp. 1070-1076.
Schmidt C.J., et al., "Preclinical Characterization of Selective Phosphodiesterase 10A Inhibitors: A New Therapeutic Approach to the Treatment of Schizophrenia," Journal of Pharmacology and Experimental Therapeutics, 2008, 325 (2), pp. 681-690.
Seeger T.F., et al., "Immunohistochernical localization of PDE10A in the Rat Brain," Brain Research, 2003, vol. 985 (2), pp. 113-126.
Silverman R.B., "Prodrugs and Drug Delivery Systems" in: The Organic Chemistry of Drug Design and Drug Action, Academic Press Inc., 1992, Chapter 8, pp. 352-400.
Singapore Search Report and Written Opinion for Application No. 11201402134V, dated Mar. 25, 2015, 10 pages.
Sotty F., et al., "Phosphodiesterase 10A Inhibition Modulates the Sensitivity of the Mesolimbic Dopaminergic System to D-amphetamine: Involvement of the D1-Regulated Feedback Control of Midbrain Dopamine Neurons," Journal of Neurochemistry, 2009, Vol, 109 (3), pp. 766-775.
Supporting Information [serialonline], [retrieved on Dec. 2, 2015]. Retrieved from the Internet URL: http://http://onlinelibrary.wiley.com/store/10.1002/cmdc.201000428/asset/supinfo/cmdc_201000428_sm_miscellaneous_information.pdf?v=1&s=cc19b2737f247f8146ba818aa54a367a6ae8dd52l.
Vidovic D., et al., "A Combined Ligand- and Structure-based Virtual Screening Protocol Identifies Submicromolar Pparγ Partial Agonists," ChemMedChem, 2011, vol. 6 (1), pp. 94-103.

\* cited by examiner

INHIBITOR COMPOUNDS OF PHOSPHODIESTERASE TYPE 10A

CROSS-REFERENCE TO RELATED APPLICATION

This is a continuation of U.S. patent application Ser. No. 13/672,438, filed Nov. 8, 2012, which claims priority to U.S. Provisional Patent Application No. 61/557,878, filed on Nov. 9, 2011, the contents of which are herein fully incorporated by reference.

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126). Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-31y]phenoxymethyl}-quinoline) and TP-10, i.e. 2-{4-[pyridine-4-yl-1-(2,2,2-trifluoroethyl)-1-H-pyrazol-3-31y]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitiors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Pyrido[3,2-e]pyridazines—see WO 2007/137819, WO 2007/137820, WO 2009/068246, WO 2009/068320, WO 2009/070583 and WO 2009/070584;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214;

MP10 and MP10 like compounds: US 2007/0155779, WO 2008/001182 and WO 2008/004117; and Benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodisesterases such as PDE3 or PDE4;
ii. metabolic stability, in particular microsomal stability, e.g. measured in vitro, in liver microsomes from various species (e.g. rat or human) in human cells, such as hepatocytes;
iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
iv. a suitable solubility in water (in mg/ml);
v. suitable pharmacokinetics (time course of the concentration of the compound of the invention in plasma or in tissue, for example brain). The pharmacokinetics can be described by the following parameters: half-life, volume of distribution (in l·kg$^{-1}$), plasma clearance (in l·h$^{-1}$·kg$^{-1}$), AUC (area under the curve, area under the concentration-time curve (in ng·h·l$^{-1}$), oral bioavailability, (the dose-normalized ratio of AUC after oral administration and AUC after intravenous administration), the so-called brain-plasma ratio (the ratio of AUC in brain tissue and AUC in plasma);
vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).
vii. high free fraction in brain, i.e. the fraction of the compound bound to proteins should be low.
viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal and/or cytosolic stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

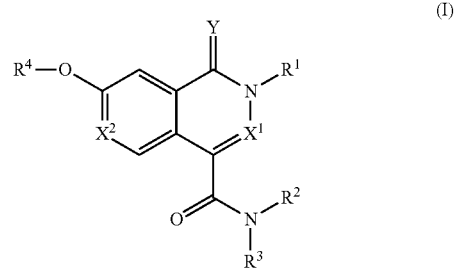

(I)

wherein
$X^1$ is CH or N,
$X^2$ is C—$R^5$ or N,
Y is O or S,
$R^1$ is selected from the group consisting of $C_2$-$C_8$-alkyl, $C_2$-$C_8$-alkenyl, $C_1$-$C_4$-fluoroalkyl, $C_3$-$C_8$-cycloalkyl, $C_5$-$C_8$-cycloalkyl carrying a fused benzene ring, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$) and a moiety $Z^1$—$Ar^1$;
$R^2$ is a radical of the formula $CR^{21}R^{22}R^{23}$ or phenyl or 5- or 6-membered hetaryl having 1, 2 or 3 heteroatoms as ring members which are selected from O, S and N, where phenyl and monocyclic hetaryl are unsubstituted or may carry 1, 2 or 3 identical or different substituents $R^a$, where
$R^{21}$ is selected from the group consisting of hydrogen, $C_1$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$), $(CH_2)_mC(O)O$—$R^d$, $(CH_2)_mC(O)N(R^e)(R^f)$ and $Z^2$—$Ar^2$,
$R^{22}$ is selected from the group consisting of hydrogen, fluorine, $C_1$-$C_8$-alkyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl and $C_1$-$C_4$-alkyl-N($R^b$)($R^c$), or
$R^{21}$ and $R^{22}$ together with the carbon atom, to which they are bound form a saturated 5- to 7-membered carbocyclic ring or a saturated 5- to 7-membered heterocyclic ring which has 1, 2 or 3 heteroatoms or heteroatom containing groups selected from the group of O, N, S, SO and $SO_2$ as ring members, where the carbocyclic ring and the heterocyclic ring may be unsubstituted or may be substituted by 1, 2 or 3 identical or different substituents $R^g$, and where the carbocyclic ring and the heterocyclic ring may carry a fused benzene ring or a fused 5- or 6-membered heteroaromatic ring, where the fused rings themselves are unsubstituted or carry 1, 2 or 3 substituents $R^h$, $R^{23}$ is selected from the group consisting of hydrogen, fluorine, $C_1$-$C_8$-alkyl and $C_1$-$C_4$-fluoroalkyl;

$R^3$ is selected from the group consisting of hydrogen, $C_1$-$C_8$-alkyl, $C_2$-$C_8$-alkenyl, $C_1$-$C_4$-fluoroalkyl, $C_3$-$C_8$-cycloalkyl, $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$), and trimethylsilyl, or $R^2$ and $R^3$ together with the nitrogen atom, to which they are bound form a saturated 5- to 7-membered heterocyclic ring which, in addition to the nitrogen atom, may have 1 or 2 further heteroatoms or heteroatom containing groups selected from the group of O, N, S, SO and $SO_2$ as ring members, where the heterocyclic ring may be unsubstituted or may be substituted by 1, 2 or 3 identical or different substituents $R^{31}$, and where the heterocyclic ring may carry a fused benzene ring or a fused 5- or 6-membered heteroaromatic ring, where the fused rings themselves are unsubstituted or carry 1 or 2 or 3 substituents $R^{32}$, where $R^{31}$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, N($R^b$)($R^c$), C(O)O—$R^d$, C(O)N($R^e$)($R^f$), where one radical $R^{31}$ may also be a moiety $Z^3$—$Ar^3$, $R^{32}$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, N($R^b$)($R^c$), C(O)O—$R^d$ and C(O)N($R^e$)($R^f$);

$R^4$ is selected from the group consisting of $C_1$-$C_4$-alkyl, $C_1$-$C_4$-fluoroalkyl, $C_3$-$C_6$-cycloalkyl, $C_3$-$C_6$-cycloalkyl-$C_1$-$C_4$-alkyl and $Z^4$—$Ar^4$, $R^5$ is selected from the group consisting of hydrogen, halogen, $C_1$-$C_4$-alkyl, $C_1$-$C_4$-fluoroalkyl, $C_1$-$C_4$-alkoxy, $C_1$-$C_4$-fluoroalkoxy, —$Z^5$—$Ar^5$, —O—$Z^5$—$Ar^5$, $C_3$-$C_6$-cycloalkyl, $C_3$-$C_6$-cycloalkyl-$C_1$-$C_4$-alkyl, $C_3$-$C_6$-cycloalkoxy and $C_3$-$C_6$-cycloalkyl-$C_1$-$C_4$-alkoxy, where the cyclic radical in the last four mentioned groups may be unsubstituted, partially or completely fluorinated or carries 1, 2, 3 or 4 methyl groups;

$Ar^1$ is selected from the group consisting of phenyl, monocyclic 5- or 6-membered hetaryl or bicyclic 9- or 10-membered hetaryl, where hetaryl has 1, 2 or 3 heteroatoms as ring members which are selected from O, S and N, where phenyl and hetaryl are unsubstituted or may carry 1, 2 or 3 identical or different substituents $R^h$;

$Ar^2$ is phenyl or monocyclic 5- or 6-membered hetaryl having 1, 2 or 3 heteroatoms as ring members which are selected from O, S and N, where phenyl and monocyclic hetaryl are unsubstituted or may carry 1, 2 or 3 identical or different substituents $R^h$;

$Ar^3$ is phenyl or monocyclic 5- or 6-membered hetaryl having 1, 2 or 3 heteroatoms as ring members which are selected from O, S and N, where phenyl and monocyclic hetaryl are unsubstituted or may carry 1, 2 or 3 identical or different substituents $R^h$;

$Ar^4$ and $Ar^5$ are independently of each other selected from the group consisting of phenyl and monocyclic 5- or 6-membered hetaryl having 1, 2 or 3 heteroatoms as ring members which are selected from O, S and N, where phenyl and monocyclic hetaryl are unsubstituted or may carry 1, 2 or 3 identical or different substituents $R^k$;

$Z^1$, $Z^4$, $Z^5$ are independently of each other $C_1$-$C_4$-alkylene;

$Z^2$ is a single bond or $C_1$-$C_4$-alkylene;

$Z^3$ is a single bond, $C_1$-$C_4$-alkylene, O, N, S, SO or $SO_2$;

$R^a$ is selected from the group consisting of halogen, CN, OH, $NO_2$, $C_1$-$C_4$-alkyl, fluorinated $C_1$-$C_4$-alkyl, $C_1$-$C_4$-alkoxy, fluorinated $C_1$-$C_4$-alkoxy, $(CH_2)_m$N($R^b$)($R^c$), C(O)O—$R^d$, C(O)N($R^e$)($R^f$), N($R^{ee}$)S(O)$_2$($R^{ff}$) and S(O)$_2$N($R^e$)($R^f$);

$R^b$, $R^c$, independently of each other are selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl or $R^b$ and $R^c$ form together with the N atom to which they are attached a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl;

$R^d$ is selected from the group consisting of $C_1$-$C_4$-alkyl, $C_1$-$C_4$-fluoroalkyl, $C_3$-$C_6$-cycloalkyl, $C_3$-$C_6$-cycloalkylmethyl and benzyl;

$R^e$, $R^f$, independently of each other are selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl or $R^e$ and $R^f$ form together with the N atom to which they are attached a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl;

$R^g$ is selected from the group consisting of halogen, CN, OH, $C_1$-$C_6$-alkyl, $C_2$-$C_6$-alkenyl, $C_1$-$C_4$-fluoroalkyl, $C_3$-$C_6$-cycloalkyl, fluorinated $C_3$-$C_6$-cycloalkyl, $C_3$-$C_6$-cycloalkyl-$C_1$-$C_4$-alkyl, fluorinated $C_3$-$C_6$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$), $C_1$-$C_4$-alkoxy, fluorinated $C_1$-$C_4$-alkoxy, one $R^g$ together with a carbon atom to which $R^g$ is attached may also form a carbonyl group, one $R^g$ may also be phenyl or benzyl, where the phenyl ring in the last 2 mentioned radicals is unsubstituted or carries 1, 2 or 3 radicals $R^h$;

$R^h$ is selected from the group consisting of halogen, CN, OH, $C_1$-$C_4$-alkyl, fluorinated $C_1$-$C_4$-alkyl, $C_1$-$C_6$-alkoxy, fluorinated $C_1$-$C_4$-alkoxy, $C_1$-$C_4$-alkylsulfanyl, $C_1$-$C_4$-alkoxy-$C_1$-$C_4$-alkoxy, $C_3$-$C_6$-cycloalkyl, fluorinated $C_3$-$C_6$-cycloalkyl, $C_3$-$C_6$-cycloalkoxy, $C_3$-$C_6$-cycloalkyl-$C_1$-$C_4$-alkoxy, phenoxy, N($R^b$)($R^c$), $C_1$-$C_4$-alkyl-N($R^b$)($R^c$), C(O)O—$R^d$, C(O)N($R^e$)($R^f$), N($R^{ee}$)S(O)$_2$($R^{ff}$), S(O)$_2$N($R^e$)($R^f$), 3- to 7-membered heterocyclyloxy, 3- to 7-membered heterocyclyl-$C_1$-$C_4$-alkoxy, where heterocyclyl in the two last mentioned radicals has 1, 2 or 3 heteroatoms as ring members which are selected from O, S and N, and 5- to 6-membered hetaryl-$C_1$-$C_4$-alkoxy, where hetaryl has 1, 2 or 3 heteroatoms as ring members which are selected from O, S and N;

$R^k$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, $N(R^b)(R^c)$, $C(O)O$—$R^d$, $C(O)N(R^e)(R^f)$, $N(R^{ee})S(O)_2(R^{ff})$ and $S(O)_2N(R^e)(R^f)$ or two radicals $R^k$ that are bound to adjacent carbon atoms together with said carbon atoms may form fused benzene ring or a fused 5- or 6-membered heteroaromatic ring having 1 or 2 ring members selected from O, N and S, where the fused benzene ring and the fused heteroaromatic ring are unsubstituted or may carry 1, 2 or 3 radicals $R^h$;

$R^{ee}$ is selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl;

$R^{ff}$ is selected from the group consisting of $C_1$-$C_4$-alkyl, $C_1$-$C_4$-fluoroalkyl and phenyl, which is unsubstituted or carries 1, 2 or 3 radicals $R^h$;

m is 0, 1, 2, 3 or 4.

The present invention therefore relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of a medical disorder, selected from neurological and psychiatric disorders which can be treated by modulation of phosphodiesterase type 10.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates effectively inhibit PDE10A even at low concentrations. They are additionally distinguished by a high selectivity in relation to the inhibition of the PDE10A vis-à-vis inhibition of other phosphodiesterease, such as PDE3 or PDE4. The compounds of the invention may additionally have one or more of the properties ii. to viii. mentioned above.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates are therefore particularly suitable for treating disorders and conditions in creatures, especially human creatures, which can be treated or controlled by inhibition of phosphodiesterase type 10A.

The invention therefore also relates to the use of the compounds of the formula I, their N-oxides, their tautomers, their hydrates and their pharmaceutically acceptable salts and the pharmaceutically acceptable salts of said N-oxides, prodrugs, tautomers or hydrates for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or an N-oxide, a tautomer, or a hydrate or a prodrug of said compound I, or a pharmaceutically acceptable salt of the compound of the formula I or a pharmaceutically acceptable salt of the N-oxide, the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—$CHR^p$—O—C(=O)—$R^q$ in which $R^p$ and $R^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug, tautomer, hydrate or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug, tautomer, hydrate or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

The present invention moreover relates to compounds as defined herein, wherein one or more of the atoms depicted in formula I have been replaced by its stable, preferably non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkoxy", "alkenyloxy", "fluoroalkyl", "fluoroalkoxy", "cycloalkyl", "fluorinated cycloalkyl", "alkylene", "alkandiyl", "hetaryl" and radicals derived therefrom, such as "hydroxylalkyl", "alkoxyalkyl", "alkoxyalkoxy", "cycloalkylalkyl" and "fluorinated cycloalkylalkyl" and "hetarylalkyl" represent groups of individual radicals. The groups of noncyclic radicals "alkyl", "alkenyl", "alkoxy", "alkenyloxy", "fluoroalkyl", "fluoroalkoxy", "alkylene", "alkandiyl", and the groups of radicals derived therefrom always include both unbranched and branched "alkyl", "alkenyl", "alkoxy", "alkenyloxy", "fluoroalkyl", "fluoroalkoxy", "alkylene" and "alkandiyl", respectively.

The prefix $C_n$—$C_m$— indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine.

Examples of other meanings are:

Alkyl, and the alkyl moieties for example in alkylcarbonyl, alkylsulfanyl, alkylsulfonyl, alkylsulfanylalkyl and alkylsulfanylalkoxy: saturated, straight-chain or branched hydrocarbon radicals having one or more C atoms, e.g. 1 to 10, 1 to 8, 1 to 6 or 1 to 4 carbon atoms. Examples of $C_1$-$C_4$-alkyl are methyl, ethyl, propyl, 1-methylethyl, n-butyl, 1-methylpropyl, 2-methylpropyl and 1,1-dimethylethyl. $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_8$-alkyl or $C_2$-$C_9$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl and 1-propylpentyl, 2-propylpentyl.

Fluoroalkyl and the fluoroalkyl moieties for example in fluoroalkylsulfonyl: an alkyl radical having ordinarily 1 to 4 C atoms, in particular 1 or 2 C-atoms ($C_1$-$C_2$-fluoroalkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy, cycloalkyl-$C_1$-$C_4$-alkyl or cycloalkyl-$C_1$-$C_4$-alkoxy: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl.

Fluorinated cycloalkyl, and the flourinted cycloalkyl moieties for example in fluorinated cycloalkoxy or fluorinated cycloalkyl-$C_1$-$C_4$-alkyl: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl, wherein at least one, e.g. 1, 2, 3, 4, 5 or 6 of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethy, cyclohexylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl or 2-cyclohexylethyl.

Fluorinated cycloalkylalkyl: a fluorinated cycloalkyl radical as defined above which is linked via an alkylene group, in particular via a methylene, 1,1-ethylene or 1,2-ethylene group, e.g. 1-fluorocyclopropylmethyl, 2-fluorocyclopropylmethyl, 2,2-difluorocyclopropylmethyl, 1,2-difluorocyclopropylmethyl, 2,3-difluorocyclopropylmethyl, 1-(1-fluorocyclopropyl)ethyl, 1-(2-fluorocyclopropyl)ethyl, 1-(2,2-difluorocyclopropyl)ethyl, 1-(1,2-difluorocyclopropyl)ethyl, 1-(2,3-difluorocyclopropyl)ethyl, 2-(1-fluorocyclopropyl)ethyl, 2-(2-fluorocyclopropyl)ethyl, 2-(2,2-difluorocyclopropyl)ethyl, 2-(1,2-difluorocyclopropyl)ethyl or 2-(2,3-difluorocyclopropyl)ethyl.

Alkenyl, and alkenyl moieties for example in alkenyloxy: monounsaturated, straight-chain or branched hydrocarbon radicals having two or more C atoms, e.g. 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkoxy or alkoxy moieties for example in alkoxyalkyl and alkoxyalkoxy:

an alkyl radical as defined above ordinarily having 1 to 6 C atoms, preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyetyl, 1-methyl-1-hydroxypropyl etc.

Alkylsulfanyl: alkyl as defined above preferably having 1 to 4 C atoms, which is connected via a sulfur atom to the remainder of the molecule, e.g. methylsulfanyl, ethylsulfanyl, n-propylsulfanyl and the like.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethyl-ethoxy)ethoxy, etc.

Cycloalkylalkoxy: an alkoxy radical ordinarily having 1 to 4 C atoms, preferably 1 to 2 C atoms, in which one hydrogen atom is replaced by a cycloalkyl radical ordinarily having 3 to 6 C atoms as defined above. Examples thereof are cyclopropylmethoxy, cyclobutylmethoxy, cyclopentylmethoxy, cyclohexylmethoxy, cyclopropylethoxy, cyclobutylethoxy, cyclopentylethoxy, cyclohexylethoxy and the like.

"Alkylen" or "alkanediyl": a saturated hydrocarbon chain having ordinarily from 1 to 4 carbon atoms, such as methylen (—$CH_2$—), 1,2-ethylen (—$CH_2CH_2$—), 1,1-ethanediyl (—$CH(CH_3)$—), 1,2-propanediyl, 1,3-propanediyl, 1,4-butanediyl, 1,2-butanediyl, 1,3-butanediyl, 1-methyl-1,2-propanediyl, 2-methyl-1,3-propanediyl, 1-methyl-1,1-ethanediyl, 1-methyl-1,2-propanediyl etc.

Saturated or partially unsaturated 5- to 7-membered monocarbocyclic radicals include cycloalkyl as defined above and cycloalkenyl having ordinarily from 4 to 7 carbon atoms as ring members, e.g. 1-cyclobuten-1-yl, 2-cyclobutenyl, 1-cyclopentenyl, 2-cyclopentenyl, 1-cyclohexenyl, 2-cyclohexenyl, 3-cyclohexenyl, 1-cycloheptenyl, 2-cycloheptenyl, 3-cycloheptenyl.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:
Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:
C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.
C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as: tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as: piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetra-hydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro- 1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetra-hydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as: 2,3-dihydro-1H-pyrrol-1-yl, 2, 5-dihydro-1H-pyrrol-1-yl, 4, 5-dihydro-1H-pyrazol-1-yl, 2,5-dihydro-1H-pyrazol-1-yl, 2, 3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydro-pyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Heterocyclyloxy: a heterocyclyl radical as defined above which is attached to the remainder of the molecule via an oxygen atom. The heterocyclyl radical ordinarily has 3, 4, 5, 6 or 7 ring atoms, in which besides carbon atoms as ring members ordinarily 1, 2 or 3, in particular 1 or 2, of the ring atoms are heteroatoms such as N, S or O, in particular 5- to 7-membered heterocycloyloxy, where heterocyclyl has 1 or 2 heteroatoms selected from O, S and N as ring members, for example tetrahydrofuran-2-yloxy, tetrahydrofuran-3-yloxy, tetrahydrothiophen-2-yloxy or tetrahydrothiophen-3-yloxy.

Heterocyclyl-$C_1$-$C_4$-alkoxy: a $C_1$-$C_4$-alkoxy group as defined above in which one hydrogen atom is replaced by a heterocyclyl radical as defined above. The heterocyclyl radical ordinarily has 3, 4, 5, 6 or 7 ring atoms, in which besides carbon atoms as ring members ordinarily 1, 2 or 3, in particular 1 or 2, of the ring atoms are heteroatoms such as N, S or O. In particular, 5- to 7-membered heterocyclyl-$C_1$-$C_2$-alkoxy, where heterocyclyl has 1 or 2 heteroatoms selected from O, S and N as ring members, for example tetrahydrofuran-2-yl-methoxy, tetrahydrofuran-2-yl-ethoxy, tetrahydrofuran-3-ylmethoxy, tetrahydrofuran-3-ylethoxy, tetrahydrothiophen-2-ylmethoxy, tetrahydrothiophen-2-ylethoxy, tetrahydrothiophen-3-ylmethoxy, tetrahydrothiophen-3-ylethoxy.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8-, 9- or 10-membered aromatic heterobicyclic radical (also termed 8-, 9- or 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

bicyclic 8-, 9-10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

5- to 6-membered hetaryl-$C_1$-$C_4$-alkoxy: a $C_1$-$C_4$-alkoxy group as defined above which carries a 5- to 6-membered hetaryl radical as defined above, where the hetaryl radical has ordinarily 1, 2 or 3, in particular 1 or 2, heteroatoms as ring members which are selected from O, S and N. Examples are furan-2-ylmethoxy, furan-3-ylmethoxy, furan-2-ylethoxy, furan-3-ylethoxy, thiophen-2-ylmethoxy, thiophen-3-ylmethoxy, thiophen-2-ylethoxy and thiophen-3-ylethoxy. The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In particular embodiments of the invention, $R^h$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, $C_3$-$C_6$-cycloalkyl, fluorinated $C_3$-$C_6$-cycloalkyl, $N(R^b)(R^c)$, $C_1$-$C_4$-alkyl-$N(R^b)(R^c)$, $C(O)O$—$R^d$, $C(O)N(R^e)(R^f)$, $N(R^{ee})S(O)_2(R^{ff})$ and $S(O)_2N(R^e)(R^f)$.

In relation to their use as inhibitors of PDE10A, the variables $X^1$, $X^2$, Y, $R^1$, $R^2$, $R^3$ and $R^4$ in formula I preferably have the following meanings, where these represent, both considered on their own and in combination with at least one other or all, special embodiments of the compounds of the formula I:

$R^1$ is preferably $C_2$-$C_8$-alkyl, $C_3$-$C_8$-cycloalkyl or $C_3$-$C_8$-cycloalkylmethyl, in particular $C_3$-$C_8$-cycloalkylmethyl or especially $C_2$-$C_8$-alkyl. Particularly, $R^1$ is alkyl of the formula $CHR^{1a}R^{1b}$, where $R^{1a}$ is selected from the group consisting of hydrogen and $C_1$-$C_3$-alkyl, in particular methyl, ethyl, n-propyl and where $R^{1b}$ is selected from the group consisting of $C_1$-$C_4$-alkyl, in particular methyl, ethyl, n-propyl or n-butyl. Particular examples of $R^1$ are selected from the group consisting of ethyl, isopropyl, 1-methylpropyl and 1-ethylpropyl.

Particular embodiments of the invention also relate to compounds, where $R^1$ is a moiety $Z^1$—$Ar^1$, where $Z^1$ and $Ar^1$ are as defined above and where $Z^1$ is preferably 1,2-ethanediyl or 1,3-propanediyl, wherein 1, 2, 3 or 4 hydrogen atoms may be replaced by a fluorine atom. According to a specific embodiment, $Z^1$ is 1,2-ethanediyl which is unsubstituted or 1,3-propanediyl which is unsubstituted. In these embodiments, $Ar^1$ is preferably monocyclic 6-membered hetaryl or bicyclic 9- or 10-membered hetaryl, where hetaryl has 1, 2 or 3 heteroatoms as ring members which are selected from O, S and N, where mono- and bicyclic hetaryl are unsubstituted or may carry 1, 2 or 3 identical or different substituents $R^h$.

$Ar^1$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^1$ is in particular selected from the group consisting of fused bicyclic hetaryl, which has 1 or 2 nitrogen atoms as ring members and optionally a further heteroatom selected from O, S and N as ring member and which may be unsubstituted or may carry 1, 2 or 3 substituents $R^h$, in particular 0, 1 or 2 substituents $R^h$ as defined above. Amongst these, particular preference is given to those compounds, where the $Ar^1$ radical has at least one imino-nitrogen as ring member, which is located in the position adjacent to carbon atom bound to the group $Z^1$. Amongst these, particular preference is given to those, where $Ar^1$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Particular examples of $Ar^1$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

In particular embodiments, $R^2$ is a radical of the formula $CR^{21}R^{22}R^{23}$, where $R^{21}$, $R^{22}$ and $R^{23}$ are as defined above and where $R^{21}$ is in particular different from hydrogen.

In other particular embodiments, $R^2$ is a phenyl or 5- or 6-membered hetaryl radical having 1, 2 or 3 heteroatoms as ring members which are selected from O, S and N, where phenyl and monocyclic hetaryl are unsubstituted or may carry 1, 2 or 3 identical or different substituents $R^a$ as defined above.

In the particular embodiments, where $R^2$ is a radical of the formula $CR^{21}R^{22}R^{23}$, where $R^{21}$, $R^{22}$ and $R^{23}$ are as defined above or where $R^2$ is a phenyl or 5- or 6-membered hetaryl radical having 1, 2 or 3 heteroatoms as ring members which are selected from O, S and N, where phenyl and monocyclic hetaryl are unsubstituted or may carry 1, 2 or 3 identical or different substituents $R^a$ as defined above, the radical $R^3$ is preferably selected from the group consisting of hydrogen and $C_1$-$C_4$-alkyl. In these embodiments, $R^3$ is in particular hydrogen.

In the particular embodiments, where $R^2$ is a radical of the formula $CR^{21}R^{22}R^{23}$, a particular group of embodiments relates to compounds, where the radicals $R^{21}$, $R^{22}$ and $R^{23}$ have the following meanings:
$R^{21}$ is selected from the group consisting of $C_1$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-$N(R^b)(R^c)$, $(CH_2)_mC(O)O$—$R^d$, $(CH_2)_mC(O)N(R^e)(R^f)$ and $Z^2$—$Ar^2$,
$R^{22}$ is selected from the group consisting of hydrogen, fluorine, $C_1$-$C_8$-alkyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl and $C_1$-$C_4$-alkyl-$N(R^b)(R^c)$, or
$R^{23}$ is selected from the group consisting of hydrogen, fluorine, $C_1$-$C_8$-alkyl and $C_1$-$C_4$-fluoroalkyl;

In the particular embodiments, where $R^2$ is a radical of the formula $CR^{21}R^{22}R^{23}$, a particular group of embodiments relates to compounds, where the radicals $R^{21}$, $R^{22}$ and $R^{23}$ preferably have the following meanings, both considered on their own and in combination with at least one other or all:
$R^{21}$ is selected from the group consisting of $C_2$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl and $Z^2$—$Ar^2$, where $Z^2$ and $Ar^2$, where $Z^2$ and $Ar^2$ are as defined above and where $Z^2$ is preferably a single bond or $CH_2$ and $Ar^2$ is preferably phenyl, pyridyl, pyrimidinyl, thienyl, thiazolyl or thiadiazolyl, which are unsubstituted or which carry 1, 2 or 3 identical or different substituents $R^h$;
$R^{22}$ is selected from the group consisting of hydrogen, fluorine, $C_1$-$C_8$-alkyl, in particular hydrogen; and
$R^{23}$ is hydrogen or $C_1$-$C_4$-alkyl, such as methyl, or especially hydrogen.

In the particular embodiments, where $R^2$ is a radical of the formula $CR^{21}R^{22}R^{23}$, a particular group of embodiments relates to compounds, where the radicals $R^{21}$, $R^{22}$ and $R^{23}$ preferably have the following meanings, both considered on their own and in combination with at least one other or all:
$R^{21}$ is selected from the group consisting of $C_2$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, and where $R^{21}$ is in particular $C_2$-$C_4$-alkyl;
$R^{22}$ is selected from the group consisting of hydrogen, fluorine, $C_1$-$C_8$-alkyl, in particular methyl or hydrogen; and
$R^{23}$ is hydrogen or $C_1$-$C_4$-alkyl, such as methyl, or especially hydrogen.

In the particular embodiments, where $R^2$ is a radical of the formula $CR^{21}R^{22}R^{23}$, another particular group of embodiments relates to compounds, where the radicals $R^{21}$, $R^{22}$ and $R^{23}$ preferably have the following meanings, both considered on their own and in combination with at least one other or all:
$R^{21}$ is a radical $Z^2$—$Ar^2$, where $Z^2$ and $Ar^2$ are as defined above and where $Z^2$ is preferably a single bond or $CH_2$ and $Ar^2$ is preferably phenyl, pyridyl, pyrimidinyl, thienyl, thiazolyl or thiadiazolyl, which are unsubstituted or which carry 1, 2 or 3 identical or different substituents $R^h$, particular examples of $R^{21}$ being 2-, 3- or 4-fluorophenyl, 2-, 3- or 4-methylphenyl, 2-, 3- or 4-methoxyphenyl, 2,3-difluorophenyl, 3,5-difluorophenyl, 3,4-difluorophenyl, thiazol-2-yl, thiazol-4-yl, 1,3,4-thiadiazol-2-yl, 2-(1-morpholinosulfonyl)phenyl, 3-(1-morpholinosulfonyl)phenyl, 2-(4-methylpiperazin-1-ylsulfonyl)phenyl or 3-(4-methylpiperazin-1-ylsulfonyl)phenyl.
$R^{22}$ is selected from the group consisting of hydrogen, fluorine, $C_1$-$C_8$-alkyl, in particular methyl or hydrogen; and
$R^{23}$ is hydrogen or $C_1$-$C_4$-alkyl, such as methyl, or especially hydrogen.

In the particular embodiments, where $R^2$ is a radical of the formula $CR^{21}R^{22}R^{23}$, a further group of embodiments relates to compounds, where the radicals $R^{21}$ and $R^{22}$ together with the carbon atom, to which they are bound form a saturated 5-, 6- or 7-membered carbocyclic ring, such as cyclopentyl, cyclohexyl or cycloheptyl, especially cyclopentyl, or a saturated 5-, 6- or 7-membered heterocyclic ring which has 1, 2 or 3 heteroatoms or heteroatom containing groups selected from the group of O, N, S, SO and $SO_2$ as ring members, especially 2- or 3-tetrahydrofuryl or 2- or 3-tetrahydrothienyl, where the carbocyclic ring and the heterocyclic ring may be unsubstituted or may be substituted by 1, 2 or 3 identical or different substituents $R^g$, and where the carbocyclic ring and the heterocyclic ring may carry a fused benzene ring or a fused 5- or 6-membered heteroaromatic ring, where the fused rings themselves are unsubstituted or carry 1, 2 or 3 substituents $R^h$, and where $R^g$, $R^h$ and $R^{23}$ are as defined above and where $R^{23}$ is in particular hydrogen or $C_1$-$C_4$-alkyl, such as methyl, or especially hydrogen.

In the particular embodiments, where $R^2$ is a radical of the formula $CR^{21}R^{22}R^{23}$, a further particular group of embodiments relates to compounds, where the radicals $R^{21}$, $R^{22}$ and $R^{23}$ preferably have the following meanings, both considered on their own and in combination with at least one other or all:

$R^{21}$ and $R^{22}$ together with the carbon atom, to which they are bound form a saturated 5-, 6- or 7-membered carbocyclic radical, namely a cyclopentyl, cyclohexyl or cycloheptyl radical or a 3-tetrahydrofuryl or 3-tetrahydrothienyl, where the 5- to 7-membered carbocyclic ring and the 3-tetrahydrofuryl or 3-tetrahydrothienyl ring carry a fused benzene ring or a fused 5- or 6-membered heteroaromatic ring, such as a fused thiophene or pyridine ring, where the fused rings themselves are unsubstituted or carry 1, 2 or 3 substituents $R^h$, and where $R^{21}$ and $R^{22}$ in particular form a bicyclic radical selected from the group consisting of 5-indanyl, 6-indanyl, 5,6,7,8-tetrahydronaphthalin-5-yl, 5,6,7,8-tetrahydronaphthalin-6-yl, 6,7,8,9-tetrahydro-5H-benzocycloheptene-5-yl, 6,7,8,9-tetrahydro-5H-benzocycloheptene-6-yl, 5,6-dihydro-4H-cyclopenta[b]thiophene-4-yl, 6,7-dihydro-5H-[1]-pyrindin-6-yl, 3,4-dihydrobenzofuran-3-yl, 2,3-dihydrobenzothiophen-3-yl or where these bicyclic radicals are in particular unsubstituted or where the aromatic moiety of these rings carry 1, 2 or 3 substituents $R^h$;

$R^{23}$ is hydrogen or $C_1$-$C_4$-alkyl, such as methyl, or especially hydrogen.

In further particular embodiments of the invention $R^2$ and $R^3$ together with the nitrogen atom, to which they are bound form a saturated 4-, 5-, 6- or 7-membered heterocyclic ring which, in addition to the nitrogen atom, may have 1 or 2 further heteroatoms or heteroatom containing groups selected from the group of O, N, S, SO and $SO_2$ as ring members, e.g. a pyrrolidine, piperidine, morpholine, thiomorpholine or piperazine ring, where the heterocyclic ring may be unsubstituted or may be substituted by 1, 2 or 3 identical or different substituents $R^{31}$, and where the heterocyclic ring may carry a fused benzene ring or a fused 5- or 6-membered heteroaromatic ring, such as a thiophene or pyridine ring, where the fused rings themselves are unsubstituted or carry 1, 2 or 3 substituents $R^{32}$, where $R^{31}$ and $R^{32}$ are as defined defined above.

$R^{31}$ is in particular selected from the group consisting of $C_1$-$C_4$-alkyl, $C_1$-$C_4$-alkoxy, halogen, phenyl and phenoxy, where the phenylring in the last two mentioned radicals itself is unsubstituted or carries 1 or 2 radicals selected from the group consisting of $C_1$-$C_4$-alkyl, $C_1$-$C_4$-alkoxy, halogen.

$R^{32}$ is in particular selected from the group consisting of $C_1$-$C_4$-alkyl, $C_1$-$C_4$-alkoxy and halogen.

$R^4$ is preferably $C_1$-$C_4$-alkyl and especially methyl.

Y is preferably O.

A particular group of embodiments of the invention relates to compounds of the formula I, to their salts, N-oxides, tautomers, hydrates and prodrugs and to the salts of said N-oxides, tautomers, hydrates and prodrugs, where $X^2$ is C—$R^5$. In this particular group of embodiments $R^5$ is preferably selected from the group consisting of hydrogen, fluorine, $C_1$-$C_4$-alkoxy or a radical O—$Z^5$—$Ar^5$, especially hydrogen, fluorine, methoxy or a radical O—$Z^5$—$Ar^5$. Amongst these compounds a first embodiment relates to compounds of the formula I, to their salts, tautomers, hydrates and prodrugs and to the salts of said tautomers, hydrates and prodrugs, where $R^5$ is hydrogen, fluorine, OH or $C_1$-$C_4$-alkoxy, especially hydrogen, fluorine, OH or methoxy, with methoxy being particularly preferred.

Amongst these compounds a second embodiment relates to compounds of the formula I, to their salts, tautomers, hydrates and prodrugs and to the salts of said tautomers, hydrates and prodrugs, where $R^5$ is a radical O—$Z^5$—$Ar^5$. In this second embodiment $R^4$ is in particular $C_1$-$C_4$-alkyl, especially methyl.

In the second embodiment, $Z^5$ is preferably 1,2-ethanediyl or 1,3-propanediyl, wherein 1, 2, 3 or 4 hydrogen atoms may be replaced by a fluorine atom. According to a specific embodiment, $Z^5$ is 1,2-ethanediyl which is unsubstituted or 1,3-propanediyl which is unsubstituted.

In the second embodiment, $Ar^5$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl may be unsubstituted or may carry 1, 2 or 3 identical or different substituents $R^k$, in particular 0, 1 or 2 substituents $R^k$ and bicyclic hetaryl may be unsubstituted or may carry 1 substituent $R^k$, and 0, 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^5$ is in particular selected from the group consisting of fused bicyclic hetaryl, which has 1 or 2 nitrogen atoms as ring members and optionally a further heteroatom selected from O, S and N as ring member and which may be unsubstituted or may carry 1 substituent $R^k$ and/or may carry 1, 2 or 3 substituents $R^h$, in particular 0, 1 or 2 substituents $R^h$ as defined above. Amongst these, particular preference is given to those compounds, where the $Ar^5$ radical has at least one imino-nitrogen as ring member, which is located in the position adjacent to carbon atom bound to the group $Z^5$. Amongst these, particular preference is given to those, where $Ar^5$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted or may carry 1 substituent $R^k$ and/or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Particular examples of $Ar^5$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

Amongst these compounds a third embodiment relates to compounds of the formula I, to their salts, tautomers, hydrates and prodrugs and to the salts of said tautomers, hydrates and prodrugs, where $R^4$ is a radical $Z^4$—$Ar^4$. In this third embodiment $R^5$ is in particular hydrogen, fluorine or $C_1$-$C_4$-alkoxy, especially methoxy.

In the third embodiment, $Z^4$ is preferably 1,2-ethanediyl or 1,3-propanediyl, wherein 1, 2, 3 or 4 hydrogen atoms may be replaced by a fluorine atom. According to a specific embodiment, $Z^4$ is 1,2-ethanediyl which is unsubstituted or 1,3-propanediyl which is unsubstituted.

In the third embodiment, $Ar^4$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl may be unsubstituted or may carry 1, 2 or 3 identical or different substituents $R^h$, in particular 0, 1 or 2 substituents $R^h$ and bicyclic hetaryl may be unsubstituted or may carry 1 substituent $R^k$, and 0, 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^4$ is in particular selected from the group consisting of fused bicyclic hetaryl, which has 1 or 2 nitrogen atoms as ring members and optionally a further heteroatom selected from O, S and N as ring member and which may be unsubstituted or may carry 1 substituent $R^k$ and/or may carry 1, 2 or 3 substituents $R^h$, in particular 0 or 1 or 2 substituents $R^h$ as defined above. Amongst these, particular preference is given to those compounds, where the $Ar^4$ radical has at least one imino-nitrogen as ring member, which is located in the position adjacent to carbon atom bound to the group $Z^4$. Amongst these, particular preference is given to those, where $Ar^4$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted or may carry 1 substituent $R^k$ and/or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Particular examples of $Ar^4$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

A first group of embodiments of the invention relates to compounds of the formula I, to their salts, N-oxides, tautomers, hydrates and prodrugs and to the salts of said N-oxides, tautomers, hydrates and prodrugs, where $X^1$ is C—H and $X^2$ is C—$R^5$. In this first group, Y, $R^1$, $R^2$, $R^3$, $R^4$ and $R^5$ are as defined above and preferably have the preferred or particular or special meanings given above. Amongst these compounds, a particular group of embodiments is represented by the following formula Ia

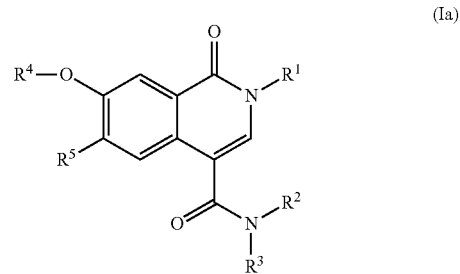

(Ia)

where $R^1$, $R^2$, $R^3$, $R^4$ and $R^5$ are as defined above.

A second group of embodiments of the invention relates to compounds of the formula I, to their salts, N-oxides, tautomers, hydrates and prodrugs and to the salts of said N-oxides, tautomers, hydrates and prodrugs, where $X^1$ is N and $X^2$ is C—$R^5$. In this second group, Y, $R^1$, $R^2$, $R^3$, $R^4$ and $R^5$ are as defined above and preferably have the preferred or particular or special meanings given above. Amongst these compounds, a particular group of embodiments is represented by the following formula Ib

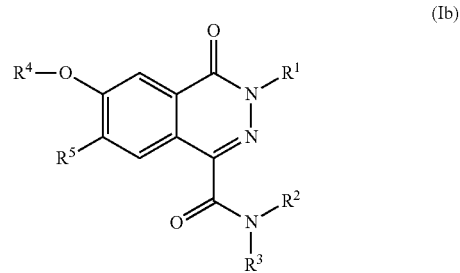

(Ib)

where $R^1$, $R^2$, $R^3$, $R^4$ and $R^5$ are as defined above.

A particular group of embodiments of the invention relates to compounds of the formulae Ia and Ib, to their salts, N-oxides, tautomers, hydrates and prodrugs and to the salts of said N-oxides, tautomers, hydrates and prodrugs, where $R^5$ is preferably selected from the group consisting of hydrogen, fluorine, $C_1$-$C_4$-alkoxy or a radical O—$Z^5$—$Ar^5$, especially hydrogen, fluorine, methoxy or a radical O—$Z^5$—$Ar^5$. Amongst these compounds a first embodiment relates to compounds of the formulae Ia and Ib, to their salts, tautomers, hydrates and prodrugs and to the salts of said tautomers, hydrates and prodrugs, where $R^5$ is hydrogen, fluorine, OH or $C_1$-$C_4$-alkoxy, especially hydrogen, fluorine, OH or methoxy, with methoxy being particularly preferred.

Amongst these compounds a second embodiment relates to compounds of the formula Ia and Ib, to their salts, tautomers, hydrates and prodrugs and to the salts of said tautomers, hydrates and prodrugs, where $R^5$ is a radical O—$Z^5$—$Ar^5$, where $Z^5$ and $Ar^5$ are as defined above and having in particular the preferred, particular or special meanings given above. In this second embodiment $R^4$ is in particular $C_1$-$C_4$-alkyl, especially methyl.

In the second embodiment of formulae Ia and Ib, $Z^5$ is preferably 1,2-ethanediyl or 1,3-propanediyl, wherein 1, 2, 3 or 4 hydrogen atoms may be replaced by a fluorine atom. According to a specific embodiment, $Z^5$ is 1,2-ethanediyl which is unsubstituted or 1,3-propanediyl which is unsubstituted.

In the second embodiment of formulae Ia and Ib, $Ar^5$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl may be unsubstituted or may carry 1, 2 or 3 identical or different substituents $R^k$, in particular 0, 1 or 2 substituents $R^k$ and bicyclic hetaryl may be unsubstituted or may carry 1 substituent $R^k$, and 0, 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In the second embodiment of formulae Ia and Ib, $Ar^5$ is in particular selected from the group consisting of fused bicyclic hetaryl, which has 1 or 2 nitrogen atoms as ring members and optionally a further heteroatom selected from O, S and N as ring member and which may be unsubstituted, or may carry 1 substituent $R^k$ and/or may carry 1, 2 or 3 substituents $R^h$, in particular 0, 1 or 2 substituents $R^h$ as defined above. Amongst these, particular preference is given to those compounds, where the $Ar^5$ radical has at least one imino-nitrogen as ring member, which is located in the position adjacent to carbon atom bound to the group $Z^5$. Amongst these, particular preference is given to those, where $Ar^5$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted, or may carry 1 substituent $R^k$ and/or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In the second embodiment of formulae Ia and Ib, $Ar^5$ is e.g. selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

Amongst these compounds a third embodiment relates to compounds of the formula Ia and Ib, to their salts, tautomers, hydrates and prodrugs and to the salts of said tautomers, hydrates and prodrugs, where $R^4$ is a radical $Z^4$—$Ar^4$, where $Z^4$ and $Ar^4$ are as defined above and having in particular the preferred, particular or special meanings given above. In this third embodiment $R^5$ is in particular hydrogen, fluorine or in particular $C_1$-$C_4$-alkoxy, especially methoxy.

In the third embodiment of formulae Ia and Ib, $Z^4$ is preferably 1,2-ethanediyl or 1,3-propanediyl, wherein 1, 2, 3 or 4 hydrogen atoms may be replaced by a fluorine atom. According to a specific embodiment, $Z^4$ is 1,2-ethanediyl which is unsubstituted or 1,3-propanediyl which is unsubstituted.

In the third embodiment of formulae Ia and Ib, $Ar^4$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl may be unsubstituted or may carry 1, 2 or 3 substituents $R^k$, in particular 0, 1 or 2 substituents $R^k$ and bicyclic hetaryl may be unsubstituted or may carry 1 substituent $R^k$, and 0, 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In the third embodiment of formulae Ia and Ib, $Ar^4$ is in particular selected from the group consisting of fused bicyclic hetaryl, which has 1 or 2 nitrogen atoms as ring members and optionally a further heteroatom selected from O, S and N as ring member and which may be unsubstituted, or may carry 1 substituent $R^k$ and/or may carry 1, 2 or 3 substituents $R^h$, in particular 0, 1 or 2 substituents $R^h$ as defined above. Amongst these, particular preference is given to those compounds, where the $Ar^4$ radical has at least one imino-nitrogen as ring member, which is located in the position adjacent to carbon atom bound to the group $Z^4$. Amongst these, particular preference is given to those, where $Ar^4$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted, or may carry 1 substituent $R^k$ and/or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In the third embodiment of formulae Ia and Ib, $Ar^4$ is e.g. selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

A third group of embodiments of the invention relates to compounds of the formula I, to their salts, N-oxides, tautomers, hydrates and prodrugs and to the salts of said N-oxides, tautomers, hydrates and prodrugs, where $X^1$ is C—H and $X^2$ is N. In this third group, Y, $R^1$, $R^2$, $R^3$ and $R^4$ are as defined above and preferably have the preferred or particular or special meanings given above. Amongst these compounds, a particular group of embodiments is represented by the following formula Ic

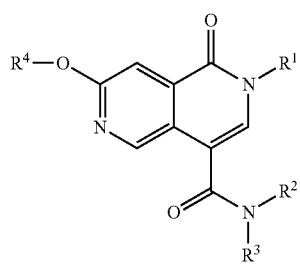

(Ic)

where $R^1$, $R^2$, $R^3$ and $R^4$ are as defined above.

A fourth group of embodiments of the invention relates to compounds of the formula I, to their salts, N-oxides, tautomers, hydrates and prodrugs and to the salts of said N-oxides, tautomers, hydrates and prodrugs, where $X^1$ is N and $X^2$ is N. In this second group, Y, $R^1$, $R^2$, $R^3$ and $R^4$ are as defined above and preferably have the preferred or particular or special meanings given above. Amongst these compounds, a particular group of embodiments is represented by the following formula Id

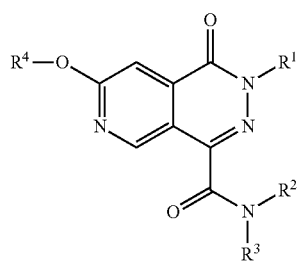

(Id)

where $R^1$, $R^2$, $R^3$, $R^4$ and $R^5$ are as defined above.

In relation to their use as inhibitors of PDE10A, the variables $R^1$, $R^2$, $R^3$ and $R^4$ in formulae Ia, Ib, Ic and Id preferably have the following meanings, where these represent, both considered on their own and in combination with at least one other or all, special embodiments of the compounds of the formula I:

In formulae Ia, Ib, Ic and Id, $R^1$ is preferably $C_2$-$C_8$-alkyl, $C_3$-$C_8$-cycloalkyl or $C_3$-$C_8$-cycloalkylmethyl, in particular $C_3$-$C_8$-cycloalkylmethyl or especially $C_2$-$C_8$-alkyl. Particularly, $R^1$ is alkyl of the formula $CHR^{1a}R^{1b}$, where $R^{1a}$ is selected from the group consisting of hydrogen and $C_1$-$C_3$-alkyl, in particular methyl, ethyl, n-propyl and where $R^{1b}$ is selected from the group consisting of $C_1$-$C_4$-alkyl, in particular methyl, ethyl, n-propyl or n-butyl. Particular examples of $R^1$ are selected from the group consisting of ethyl, isopropyl, 1-methylpropyl and 1-ethylpropyl.

In formulae Ia, Ib, Ic and Id, $R^1$ is likewise preferably a moiety $Z^1$—$Ar^1$, where $Z^1$ and $Ar^1$ are as defined above and where $Z^1$ is preferably 1,2-ethanediyl or 1,3-propanediyl, wherein 1, 2, 3 or 4 hydrogen atoms may be replaced by a fluorine atom. According to a specific embodiment, $Z^1$ is 1,2-ethanediyl which is unsubstituted or 1,3-propanediyl which is unsubstituted.

In formulae Ia, Ib, Ic and Id, where $R^1$ is a moiety $Z^1$—$Ar^1$, $Ar^1$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^h$, in particular 0, 1 or 2 substituents $R^h$. $Ar^1$ is in particular selected from the group consisting of fused bicyclic hetaryl, which has 1 or 2 nitrogen atoms as ring members and optionally a further heteroatom selected from O, S and N as ring member and which may be unsubstituted or may carry 1, 2 or 3 substituents $R^h$, in particular 0, 1 or 2 substituents $R^h$ as defined above. Amongst these, particular preference is given to those compounds, where the $Ar^1$ radical has at least one imino-nitrogen as ring member, which is located in the position adjacent to carbon atom bound to the group $Z^1$. Amongst these, particular preference is given to those, where $Ar^1$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In particular embodiments of formulae Ia, Ib, Ic and Id, $R^2$ is a radical of the formula $CR^{21}R^{22}R^{23}$, where $R^{21}$, $R^{22}$ and $R^{23}$ are as defined above and where $R^{21}$ is in particular different from hydrogen.

In other particular embodiments of formulae Ia, Ib, Ic and Id, $R^2$ is a phenyl or 5- or 6-membered hetaryl radical having 1, 2 or 3 heteroatoms as ring members which are selected from O, S and N, where phenyl and monocyclic hetaryl are unsubstituted or may carry 1, 2 or 3 identical or different substituents $R^a$ as defined above.

In the particular embodiments of formulae Ia, Ib, Ic and Id, where $R^2$ is a radical of the formula $CR^{21}R^{22}R^{23}$, where $R^{21}$, $R^{22}$ and $R^{23}$ are as defined above or where $R^2$ is a phenyl or 5- or 6-membered hetaryl radical having 1, 2 or 3 heteroatoms as ring members which are selected from O, S and N, where phenyl and monocyclic hetaryl are unsubstituted or may carry 1, 2 or 3 identical or different substituents $R^a$ as defined above, the radical $R^3$ is preferably selected from the group consisting of hydrogen and $C_1$-$C_4$-alkyl. In these embodiments, $R^3$ is in particular hydrogen.

In the particular embodiments of formulae Ia, Ib, Ic and Id, where $R^2$ is a radical of the formula $CR^{21}R^{22}R^{23}$, a particular group of embodiments relates to compounds, where the radicals $R^{21}$, $R^{22}$ and $R^{23}$ have the following meanings:

$R^{21}$ is selected from the group consisting of $C_1$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$), $(CH_2)_mC(O)O$—$R^d$, $(CH_2)_mC(O)N(R^e)(R^f)$ and $Z^2$—$Ar^2$, $R^{22}$ is selected from the group consisting of hydrogen, fluorine, $C_1$-$C_8$-alkyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl and $C_1$-$C_4$-alkyl-N($R^b$)($R^c$), or $R^{23}$ is selected from the group consisting of hydrogen, fluorine, $C_1$-$C_8$-alkyl and $C_1$-$C_4$-fluoroalkyl;

In the particular embodiments of formulae Ia, Ib, Ic and Id, where $R^2$ is a radical of the formula $CR^{21}R^{22}R^{23}$, a particular group of embodiments relates to compounds, where the radicals $R^{21}$, $R^{22}$ and $R^{23}$ preferably have the following meanings, both considered on their own and in combination with at least one other or all:

$R^{21}$ is selected from the group consisting of $C_2$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl and $Z^2$—$Ar^2$, where $Z^2$ and $Ar^2$, where $Z^2$ and $Ar^2$ are as defined above and where $Z^2$ is preferably a single bond or $CH_2$ and $Ar^2$ is preferably phenyl, pyridyl, pyrimidinyl, thienyl, thiazolyl or thiadiazolyl, which are unsubstituted or which carry 1, 2 or 3 identical or different substituents $R^h$;

$R^{22}$ is selected from the group consisting of hydrogen, fluorine, $C_1$-$C_8$-alkyl, in particular hydrogen; and $R^{23}$ is hydrogen or $C_1$-$C_4$-alkyl, such as methyl, or especially hydrogen.

In the particular embodiments of formulae Ia, Ib, Ic and Id, where $R^2$ is a radical of the formula $CR^{21}R^{22}R^{23}$, a particular group of embodiments relates to compounds, where the radicals $R^{21}$, $R^{22}$ and $R^{23}$ preferably have the following meanings, both considered on their own and in combination with at least one other or all:

$R^{21}$ is selected from the group consisting of $C_2$-$C_8$-alkyl, trimethylsilyl, $C_2$-$C_8$-alkenyl, $C_1$-$C_4$-fluoroalkyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, and where $R^{21}$ is in particular $C_2$-$C_4$-alkyl;

$R^{22}$ is selected from the group consisting of hydrogen, fluorine, $C_1$-$C_8$-alkyl, in particular methyl or hydrogen; and $R^{23}$ is hydrogen or $C_1$-$C_4$-alkyl, such as methyl, or especially hydrogen.

In the particular embodiments of formulae Ia, Ib, Ic and Id, where $R^2$ is a radical of the formula $CR^{21}R^{22}R^{23}$, another particular group of embodiments relates to compounds, where the radicals $R^{21}$, $R^{22}$ and $R^{23}$ preferably have the following meanings, both considered on their own and in combination with at least one other or all:

$R^{21}$ is a radical $Z^2$—$Ar^2$, where $Z^2$ and $Ar^2$, where $Z^2$ and $Ar^2$ are as defined above and where $Z^2$ is preferably a single bond or $CH_2$ and $Ar^2$ is preferably phenyl, pyridyl, pyrimidinyl, thienyl, thiazolyl or thiadiazolyl, which are unsubstituted or which carry 1, 2 or 3 identical or different substituents $R^h$, particular examples of $R^{21}$ being 2-, 3- or 4-fluorophenyl, 2-, 3- or 4-methylphenyl, 2-, 3- or 4-methoxyphenyl, 2,3-difluorophenyl, 3,5-difluorophenyl, 3,4-difluorophenyl, thiazol-2-yl, thiazol-4-yl, 1,3,4-thiadiazol-2-yl, 2-(1-morpholinosulfonyl)phenyl, 3-(1-morpholinosulfonyl)phenyl, 2-(4-methylpiperazin-1-ylsulfonyl)phenyl or 3-(4-methylpiperazin-1-ylsulfonyl)phenyl.

$R^{22}$ is selected from the group consisting of hydrogen, fluorine, $C_1$-$C_8$-alkyl, in particular methyl or hydrogen; and $R^{23}$ is hydrogen or $C_1$-$C_4$-alkyl, such as methyl, or especially hydrogen.

In the particular embodiments of formulae Ia, Ib, Ic and Id, where $R^2$ is a radical of the formula $CR^{21}R^{22}R^{23}$, a further group of embodiments relates to compounds, where the radicals $R^{21}$ and $R^{22}$ together with the carbon atom, to which they are bound form a saturated 5-, 6- or 7-membered carbocyclic ring, such as cyclopentyl, cyclohexyl or cycloheptyl, especially cyclopentyl, or a saturated 5-, 6- or 7-membered heterocyclic ring which has 1, 2 or 3 heteroatoms or heteroatom containing groups selected from the group of O, N, S, SO and $SO_2$ as ring members, especially 2- or 3-tetrahydrofuryl or 2- or 3-tetrahydrothienyl, where the carbocyclic ring and the heterocyclic ring may be unsubstituted or may be substituted by 1, 2 or 3 identical or different substituents $R^g$, and where the carbocyclic ring and the heterocyclic ring may carry a fused benzene ring or a fused 5- or 6-membered heteroaromatic ring, where the fused rings themselves are unsubstituted or carry 1, 2 or 3 substituents $R^h$, and where $R^g$, $R^h$ and $R^{23}$ are as defined above and where $R^{23}$ is in particular hydrogen or $C_1$-$C_4$-alkyl, such as methyl, or especially hydrogen.

In the particular embodiments of formulae Ia, Ib, Ic and Id, where $R^2$ is a radical of the formula $CR^{21}R^{22}R^{23}$, a further particular group of embodiments relates to compounds, where the radicals $R^{21}$, $R^{22}$ and $R^{23}$ preferably have the following meanings, both considered on their own and in combination with at least one other or all:

$R^{21}$ and $R^{22}$ together with the carbon atom, to which they are bound form a saturated 5-, 6- or 7-membered carbocyclic radical, namely a cyclopentyl, cyclohexyl or cycloheptyl radical or a 3-tetrahydrofuryl or 3-tetrahydrothienyl, where the 5 to 7 membered carbocyclic ring and the 3-tetrahydrofuryl or 3-tetrahydrothienyl ring carry a fused benzene ring or a fused 5- or 6-membered heteroaromatic ring, such as a fused thiophene or pyridine ring, where the fused rings themselves are unsubstituted or carry 1, 2 or 3 substituents $R^h$, and where $R^{21}$ and $R^{22}$ in particular form a bicyclic radical selected from the group consisting of 5-indanyl, 6-indanyl, 5,6,7,8-tetrahydronaphthalin-5-yl, 5,6,7,8-tetrahydronaphthalin-6-yl, 6,7,8,9-tetrahydro-5H-benzocycloheptene-5-yl, 6,7,8,9-tetrahydro-5H-benzocycloheptene-6-yl, 5,6-dihydro-4H-cyclopenta[b]thiophene-4-yl, 6,7-dihydro-5H-[1]-pyrindin-6-yl, 3,4-dihydrobenzofuran-3-yl, 2,3-dihydrobenzothiophen-3-yl or where these bicyclic radicals are in particular unsubstituted or where the aromatic moiety of these rings carry 1, 2 or 3 substituents $R^h$;

$R^{23}$ is hydrogen or $C_1$-$C_4$-alkyl, such as methyl, or especially hydrogen.

In further particular embodiments of the invention $R^2$ and $R^3$ together with the nitrogen atom, to which they are bound form a saturated 4-, 5-, 6- or 7-membered heterocyclic ring which, in addition to the nitrogen atom, may have 1 or 2 further heteroatoms or heteroatom containing groups selected from the group of O, N, S, SO and $SO_2$ as ring members, e.g. a pyrrolidine, piperidine, morpholine, thiomorpholine or piperazine ring, where the heterocyclic ring may be unsubstituted or may be substituted by 1, 2 or 3 identical or different substituents $R^{31}$, and where the heterocyclic ring may carry a fused benzene ring or a fused 5- or 6-membered heteroaromatic ring, such as a thiophene or pyridine ring, where the fused rings themselves are unsubstituted or carry 1, 2 or 3 substituents $R^{32}$, where $R^{31}$ and $R^{32}$ are as defined defined above.

$R^{31}$ is in particular selected from the group consisting of $C_1$-$C_4$-alkyl, $C_1$-$C_4$-alkoxy, halogen, phenyl and phenoxy, where the phenylring in the last two mentioned radicals itself is unsubstituted or carries 1 or 2 radicals selected from the group consisting of $C_1$-$C_4$-alkyl, $C_1$-$C_4$-alkoxy, halogen.

$R^{32}$ is in particular selected from the group consisting of $C_1$-$C_4$-alkyl, $C_1$-$C_4$-alkoxy and halogen.

In formulae Ia, Ib, Ic and Id, a particular embodiment relates to compounds where $R^4$ is $C_1$-$C_4$-alkyl and especially methyl.

In formulae Ia, Ib, Ic and Id, another particular embodiment relates to compounds where $R^4$ is a radical $Z^4$—$Ar^4$, where $Z^4$ and $Ar^4$ are as defined above and having in particular the preferred, particular or special meanings given above. In this embodiment in formulae Ia and Ib $R^5$ is in particular hydrogen, fluorine or in particular $C_1$-$C_4$-alkoxy, especially methoxy.

In this embodiment of formulae Ia, Ib, Ic and Id, $Z^4$ is preferably 1,2-ethanediyl or 1,3-propanediyl, wherein 1, 2, 3 or 4 hydrogen atoms may be replaced by a fluorine atom. According to a specific embodiment, $Z^4$ is 1,2-ethanediyl which is unsubstituted or 1,3-propanediyl which is unsubstituted.

In this embodiment of formulae Ia, Ib, Ic and Id, $Ar^4$ is preferably selected from the group consisting of C-bound 6-membered monocyclic hetaryl, which has 1 or 2 nitrogen atoms as ring members, and C-bound, fused bicyclic hetaryl, which has 1 or 2 nitrogen atoms as ring members and optionally a further heteroatom selected from O, S and N as ring member, where monocyclic hetaryl may be unsubstituted or may carry 1, 2 or 3 identical or different substituents $R^k$, in particular 0, 1 or 2 substituents $R^h$ and bicyclic hetaryl may be unsubstituted or may carry 1 substituent $R^k$, and 0, 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In this embodiment of formulae Ia, Ib, Ic and Id, $Ar^4$ is in particular selected from the group consisting of fused bicyclic hetaryl, which has 1 or 2 nitrogen atoms as ring members and optionally a further heteroatom selected from O, S and N as ring member and which may be unsubstituted, or may carry 1 substituent $R^k$ and/or may carry 1, 2 or 3 substituents $R^h$, in particular 0, 1 or 2 substituents $R^h$ as defined above. Amongst these, particular preference is given to those compounds, where the $Ar^4$ radical has at least one imino-nitrogen as ring member, which is located in the position adjacent to carbon atom bound to the group $Z^4$. Amongst these, particular preference is given to those, where $Ar^4$ is selected from the group consisting of C-bound, fused bicyclic hetaryl, which has 1 or 2 nitrogen atoms as ring members and optionally a further heteroatom selected from O, S and N as ring member, where bicyclic hetaryl may be unsubstituted or may carry 1 substituent $R^k$ and/or may carry 1, 2 or 3 substituents $R^h$, in particular 0, 1 or 2 substituents $R^h$. In this regard, $R^h$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. In this regard, $R^h$ is in particular selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

In this embodiment of formulae Ia, Ib, Ic and Id, $Ar^4$ is e.g. selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^h$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

Apart from that, the variables $Ar^3$, $Z^3$, $Z^4$, $R^a$, $R^b$, $R^c$, $R^d$, $R^e$, $R^f$, $R^g$, $R^h$ and $R^k$ preferably have, irrespectively of their occurrence and with regard to the formulae I, Ia, Ib, Ic and Id and with regard to each of the above mentioned embodiments groups of embodiments one of the following meanings:

$Ar^3$ is preferably phenyl, which is unsubstituted or substituted by 1, 2 or 3 radicals $R^h$.

$Z^3$ is preferably a single bond, $CH_2$ or $CH_2CH_2$.

$Z^4$ is preferably $CH_2$ or $CH_2CH_2$.

$R^a$ is preferably halogen, in particular fluorine, $C_1$-$C_4$-alkyl, $C_1$-$C_4$-alkoxy, $C_1$-$C_4$-fluoroalkyl, $C_1$-$C_4$-fluoroalkoxy, $N(R^b)(R^c)$, $CH_2N(R^b)(R^c)$, or $S(O)_2N(R^e)(R^f)$, $R^b$ is preferably hydrogen or $C_1$-$C_4$-alkyl;

$R^c$ is preferably hydrogen or $C_1$-$C_4$-alkyl; or $R^b$ and $R^c$ together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl and fluorine.

$R^d$ is preferably $C_1$-$C_4$-alkyl.

$R^e$ is preferably hydrogen or $C_1$-$C_4$-alkyl;

$R^f$ is preferably hydrogen or $C_1$-$C_4$-alkyl; or $R^e$ and $R^f$ together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl and fluorine.

$R^g$ is preferably halogen, in particular fluorine, $C_1$-$C_4$-alkyl, $C_1$-$C_4$-alkoxy, $C_1$-$C_4$-fluoroalkyl or $C_1$-$C_4$-fluoroalkoxy.

$R^h$ is preferably halogen, in particular fluorine, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, fluorinated $C_3$-$C_6$-cycloalkyl, $N(R^b)(R^c)$, $CH_2N(R^b)(R^c)$ or $S(O)_2N(R^e)(R^f)$. In addition, $R^h$ is preferably $C_1$-$C_2$-alkylsulfanyl, $C_1$-$C_2$-alkoxy-$C_1$-$C_4$-alkoxy, $C_3$-$C_6$-cycloalkoxy, $C_3$-$C_6$-cycloalkyl-$C_1$-$C_2$-alkoxy, phenoxy, 3- to 7-membered heterocyclyloxy, 3- to 7-membered heterocyclyl-$C_1$-$C_2$-alkoxy, where heterocyclyl in the two last mentioned radicals has 1 or 2 heteroatoms as ring members which are selected from O, S and N, and 5- to 6-membered hetaryl-$C_1$-$C_2$-alkoxy, where hetaryl has 1 or 2 heteroatoms as ring members which are selected from O, S and N. $R^h$ is in particular selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl. $R^h$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$R^k$ is preferably halogen, in particular fluorine, $C_1$-$C_4$-alkyl, $C_1$-$C_4$-alkoxy, $C_1$-$C_4$-fluoroalkyl or $C_1$-$C_4$-fluoroalkoxy.

Particular embodiments of the invention relates to the compounds of formula I, to the N-oxides, the prodrugs, the hydrates and the tautomers thereof and to the pharmaceutically suitable salts thereof, where the compounds of the formula I are selected from the group consisting of:

2-ethyl-6,7-dimethoxy-1-oxo-1,2-dihydro-isoquinoline-4-carboxylic acid butylamide,
2-ethyl-6,7-dimethoxy-1-oxo-1,2-dihydro-isoquinoline-4-carboxylic acid methylamide,
2-ethyl-6,7-dimethoxy-1-oxo-1,2-dihydro-isoquinoline-4-carboxylic acid cyclopropylmethyl-amide,
2-ethyl-6,7-dimethoxy-1-oxo-1,2-dihydro-isoquinoline-4-carboxylic acid methyl-phenethyl-amide,
2-ethyl-6,7-dimethoxy-1-oxo-1,2-dihydro-isoquinoline-4-carboxylic acid (2-methoxy-benzyl)-methyl-amide,
2-ethyl-6,7-dimethoxy-1-oxo-1,2-dihydro-isoquinoline-4-carboxylic acid (4-methoxy-benzyl)-methyl-amide,
2-ethyl-6,7-dimethoxy-1-oxo-1,2-dihydro-isoquinoline-4-carboxylic acid (3-methoxy-benzyl)-methyl-amide,
2-ethyl-6,7-dimethoxy-1-oxo-1,2-dihydro-isoquinoline-4-carboxylic acid methyl-(3-trifluoromethyl-benzyl)-amide,
2-ethyl-6,7-dimethoxy-1-oxo-1,2-dihydro-isoquinoline-4-carboxylic acid benzyl-(2-dimethylamino-ethyl)-amide,
2-ethyl-6,7-dimethoxy-1-oxo-1,2-dihydro-isoquinoline-4-carboxylic acid (1-benzyl-piperidin-4-yl)-methyl-amide,
2-ethyl-6,7-dimethoxy-1-oxo-1,2-dihydro-isoquinoline-4-carboxylic acid tert-butylamide,
2-ethyl-6,7-dimethoxy-1-oxo-1,2-dihydro-isoquinoline-4-carboxylic acid sec-butylamide,
2-ethyl-6,7-dimethoxy-1-oxo-1,2-dihydro-isoquinoline-4-carboxylic acid isobutyl-amide,
2-ethyl-6,7-dimethoxy-1-oxo-1,2-dihydro-isoquinoline-4-carboxylic acid cyclopentylamide,
2-ethyl-6,7-dimethoxy-1-oxo-1,2-dihydro-isoquinoline-4-carboxylic acid (1-methyl-butyl)-amide,
2-ethyl-6,7-dimethoxy-1-oxo-1,2-dihydro-isoquinoline-4-carboxylic acid (1,1-dimethyl-propyl)-amide,
2-ethyl-6,7-dimethoxy-1-oxo-1,2-dihydro-isoquinoline-4-carboxylic acid (1,2-dimethyl-propyl)-amide,
2-ethyl-6,7-dimethoxy-1-oxo-1,2-dihydro-isoquinoline-4-carboxylic acid (2,2-dimethyl-propyl)-amide,
2-ethyl-6,7-dimethoxy-1-oxo-1,2-dihydro-isoquinoline-4-carboxylic acid (1-ethyl-propyl)-amide,
2-ethyl-6,7-dimethoxy-1-oxo-1,2-dihydro-isoquinoline-4-carboxylic acid ethylamide,
2-ethyl-6,7-dimethoxy-1-oxo-1,2-dihydro-isoquinoline-4-carboxylic acid (2-methyl-butyl)-amide,
2-ethyl-6,7-dimethoxy-1-oxo-1,2-dihydro-isoquinoline-4-carboxylic acid pentylamide,
2-ethyl-6,7-dimethoxy-1-oxo-1,2-dihydro-isoquinoline-4-carboxylic acid cyclohexylamide,
2-ethyl-6,7-dimethoxy-1-oxo-1,2-dihydro-isoquinoline-4-carboxylic acid (1,3-dimethyl-butyl)-amide,
2-ethyl-6,7-dimethoxy-1-oxo-1,2-dihydro-isoquinoline-4-carboxylic acid (3,3-dimethyl-butyl)-amide,
2-ethyl-6,7-dimethoxy-1-oxo-1,2-dihydro-isoquinoline-4-carboxylic acid (2-ethyl-butyl)-amide,
2-ethyl-6,7-dimethoxy-1-oxo-1,2-dihydro-isoquinoline-4-carboxylic acid benzylamide,
2-ethyl-6,7-dimethoxy-1-oxo-1,2-dihydro-isoquinoline-4-carboxylic acid dicyclopropylmethyl-amide,
2-ethyl-6,7-dimethoxy-1-oxo-1,2-dihydro-isoquinoline-4-carboxylic acid (2-fluoro-ethyl)-amide,
2-ethyl-6,7-dimethoxy-1-oxo-1,2-dihydro-isoquinoline-4-carboxylic acid cyclohexylmethyl-amide,
2-ethyl-6,7-dimethoxy-1-oxo-1,2-dihydro-isoquinoline-4-carboxylic acid (1-phenyl-ethyl)-amide,
2-ethyl-6,7-dimethoxy-1-oxo-1,2-dihydro-isoquinoline-4-carboxylic acid 2-fluoro-benzylamide,
2-ethyl-6,7-dimethoxy-1-oxo-1,2-dihydro-isoquinoline-4-carboxylic acid 3-fluoro-benzylamide,
2-ethyl-6,7-dimethoxy-1-oxo-1,2-dihydro-isoquinoline-4-carboxylic acid 4-fluoro-benzylamide,
2-ethyl-6,7-dimethoxy-1-oxo-1,2-dihydro-isoquinoline-4-carboxylic acid 2,3-difluoro-benzylamide,
2-ethyl-6,7-dimethoxy-1-oxo-1,2-dihydro-isoquinoline-4-carboxylic acid 2,4-difluoro-benzylamide,
2-ethyl-6,7-dimethoxy-1-oxo-1,2-dihydro-isoquinoline-4-carboxylic acid 2,6-difluoro-benzylamide,
2-ethyl-6,7-dimethoxy-1-oxo-1,2-dihydro-isoquinoline-4-carboxylic acid 3,4-difluoro-benzylamide,
2-ethyl-6,7-dimethoxy-1-oxo-1,2-dihydro-isoquinoline-4-carboxylic acid (2,2,2-trifluoro-ethyl)-amide,
2-ethyl-6,7-dimethoxy-1-oxo-1,2-dihydro-isoquinoline-4-carboxylic acid 3,5-difluoro-benzylamide,
2-ethyl-6,7-dimethoxy-1-oxo-1,2-dihydro-isoquinoline-4-carboxylic acid phenethyl-amide,
2-ethyl-6,7-dimethoxy-1-oxo-1,2-dihydro-isoquinoline-4-carboxylic acid [1-(4-fluoro-phenyl)-ethyl]-amide,
2-ethyl-6,7-dimethoxy-1-oxo-1,2-dihydro-isoquinoline-4-carboxylic acid indan-1-ylamide,
2-ethyl-6,7-dimethoxy-1-oxo-1,2-dihydro-isoquinoline-4-carboxylic acid indan-2-ylamide,
2-ethyl-6,7-dimethoxy-1-oxo-1,2-dihydro-isoquinoline-4-carboxylic acid [1-(4-fluoro-phenyl)-1-methyl-ethyl]-amide,
4-(azetidine-1-carbonyl)-2-ethyl-6,7-dimethoxy-2H-isoquinolin-1-one,
2-ethyl-6,7-dimethoxy-1-oxo-1,2-dihydro-isoquinoline-4-carboxylic acid cyclopropylamide,
2-ethyl-6,7-dimethoxy-4-(2-methyl-pyrrolidine-1-carbonyl)-2H-isoquinolin-1-one,
2-ethyl-6,7-dimethoxy-4-(morpholine-4-carbonyl)-2H-isoquinolin-1-one,
2-ethyl-4-(3-fluoro-pyrrolidine-1-carbonyl)-6,7-dimethoxy-2H-isoquinolin-1-one,
2-ethyl-6,7-dimethoxy-4-(4-methyl-piperazine-1-carbonyl)-2H-isoquinolin-1-one,
4-(3,3-difluoro-pyrrolidine-1-carbonyl)-2-ethyl-6,7-dimethoxy-2H-isoquinolin-1-one,
4-(3-dimethylamino-pyrrolidine-1-carbonyl)-2-ethyl-6,7-dimethoxy-2H-isoquinolin-1-one,
2-ethyl-6,7-dimethoxy-4-((R)-2-methoxymethyl-pyrrolidine-1-carbonyl)-2H-isoquinolin-1-one,
4-(1,3-dihydro-isoindole-2-carbonyl)-2-ethyl-6,7-dimethoxy-2H-isoquinolin-1-one,
4-(4,4-difluoro-piperidine-1-carbonyl)-2-ethyl-6,7-dimethoxy-2H-isoquinolin-1-one,
2-ethyl-6,7-dimethoxy-1-oxo-1,2-dihydro-isoquinoline-4-carboxylic acid isopropylamide,
2-ethyl-4-(4-isopropyl-piperazine-1-carbonyl)-6,7-dimethoxy-2H-isoquinolin-1-one,
4-(4-dimethylamino-piperidine-1-carbonyl)-2-ethyl-6,7-dimethoxy-2H-isoquinolin-1-one,
2-ethyl-6,7-dimethoxy-4-(2-trifluoromethyl-pyrrolidine-1-carbonyl)-2H-isoquinolin-1-one, 4-(4-cyclopropylmethyl-piperazine-1-carbonyl)-2-ethyl-6,7-dimethoxy-2H-isoquinolin-1-one,
2-ethyl-6,7-dimethoxy-4-((S)-2-pyrrolidin-1-ylmethyl-pyrrolidine-1-carbonyl)-2H-isoquinolin-1-one,
2-ethyl-6,7-dimethoxy-4-(4-pyrrolidin-1-yl-piperidine-1-carbonyl)-2H-isoquinolin-1-one,
4-[4-(2-dimethylamino-ethyl)-piperazine-1-carbonyl]-2-ethyl-6,7-dimethoxy-2H-isoquinolin-1-one,
4-([1,4']bipiperidinyl-1'-carbonyl)-2-ethyl-6,7-dimethoxy-2H-isoquinolin-1-one,
4-[4-(3-dimethylamino-propyl)-piperazine-1-carbonyl]-2-ethyl-6,7-dimethoxy-2H-isoquinolin-1-one,
2-ethyl-6,7-dimethoxy-1-oxo-1,2-dihydro-isoquinoline-4-carboxylic acid propylamide,
2-ethyl-6,7-dimethoxy-4-[4-(2-pyrrolidin-1-yl-ethyl)-piperazine-1-carbonyl]-2H-isoquinolin-1-one,
2-ethyl-6,7-dimethoxy-1-oxo-1,2-dihydro-isoquinoline-4-carboxylic acid dimethylamide,
2-ethyl-6,7-dimethoxy-1-oxo-1,2-dihydro-isoquinoline-4-carboxylic acid ethyl-methyl-amide,
2-ethyl-6,7-dimethoxy-1-oxo-1,2-dihydro-isoquinoline-4-carboxylic acid isopropyl-methyl-amide,
2-ethyl-6,7-dimethoxy-1-oxo-1,2-dihydro-isoquinoline-4-carboxylic acid diethylamide,
2-ethyl-6,7-dimethoxy-1-oxo-1,2-dihydro-isoquinoline-4-carboxylic acid methyl-propyl-amide,
2-ethyl-6,7-dimethoxy-1-oxo-1,2-dihydro-isoquinoline-4-carboxylic acid ethyl-isopropyl-amide,
2-ethyl-6,7-dimethoxy-1-oxo-1,2-dihydro-isoquinoline-4-carboxylic acid tert-butyl-methyl-amide,
2-ethyl-6,7-dimethoxy-1-oxo-1,2-dihydro-isoquinoline-4-carboxylic acid isobutyl-methyl-amide,
2-ethyl-6,7-dimethoxy-1-oxo-1,2-dihydro-isoquinoline-4-carboxylic acid butyl-methyl-amide,
2-ethyl-6,7-dimethoxy-1-oxo-1,2-dihydro-isoquinoline-4-carboxylic acid ethyl-propyl-amide,
2-ethyl-6,7-dimethoxy-1-oxo-1,2-dihydro-isoquinoline-4-carboxylic acid (2-dimethylamino-ethyl)-methyl-amide,
2-ethyl-6,7-dimethoxy-1-oxo-1,2-dihydro-isoquinoline-4-carboxylic acid ethyl-(2-methoxy-ethyl)-amide,
2-ethyl-6,7-dimethoxy-1-oxo-1,2-dihydro-isoquinoline-4-carboxylic acid cyclopentyl-methyl-amide,
2-ethyl-6,7-dimethoxy-1-oxo-1,2-dihydro-isoquinoline-4-carboxylic acid butyl-ethyl-amide,
2-ethyl-6,7-dimethoxy-1-oxo-1,2-dihydro-isoquinoline-4-carboxylic acid methyl-pentyl-amide,
2-ethyl-6,7-dimethoxy-1-oxo-1,2-dihydro-isoquinoline-4-carboxylic acid diisopropylamide,
2-ethyl-6,7-dimethoxy-1-oxo-1,2-dihydro-isoquinoline-4-carboxylic acid isopropyl-propyl-amide,
2-ethyl-6,7-dimethoxy-1-oxo-1,2-dihydro-isoquinoline-4-carboxylic acid cyclobutylamide,
2-ethyl-6,7-dimethoxy-1-oxo-1,2-dihydro-isoquinoline-4-carboxylic acid dipropylamide,
2-ethyl-6,7-dimethoxy-1-oxo-1,2-dihydro-isoquinoline-4-carboxylic acid (3-dimethylamino-propyl)-methyl-amide,
2-ethyl-6,7-dimethoxy-1-oxo-1,2-dihydro-isoquinoline-4-carboxylic acid cyclohexyl-methyl-amide,
2-ethyl-6,7-dimethoxy-1-oxo-1,2-dihydro-isoquinoline-4-carboxylic acid cyclopropylmethyl-propyl-amide
2-ethyl-6,7-dimethoxy-1-oxo-1,2-dihydro-isoquinoline-4-carboxylic acid diisobutylamide,
2-ethyl-6,7-dimethoxy-1-oxo-1,2-dihydro-isoquinoline-4-carboxylic acid benzyl-methyl-amide,
2-ethyl-6,7-dimethoxy-1-oxo-1,2-dihydro-isoquinoline-4-carboxylic acid (2-fluoro-benzyl)-methyl-amide,
2-ethyl-6,7-dimethoxy-1-oxo-1,2-dihydro-isoquinoline-4-carboxylic acid (4-fluoro-benzyl)-methyl-amide,
2-ethyl-6,7-dimethoxy-1-oxo-1,2-dihydro-isoquinoline-4-carboxylic acid (3-fluoro-benzyl)-methyl-amide,
2-tert-butyl-6,7-dimethoxy-1-oxo-1,2-dihydro-isoquinoline-4-carboxylic acid butylamide,
2-sec-butyl-6,7-dimethoxy-1-oxo-1,2-dihydro-isoquinoline-4-carboxylic acid butylamide,
2-isobutyl-6,7-dimethoxy-1-oxo-1,2-dihydro-isoquinoline-4-carboxylic acid butylamide,
2-butyl-6,7-dimethoxy-1-oxo-1,2-dihydro-isoquinoline-4-carboxylic acid butylamide,
2-cyclopropylmethyl-6,7-dimethoxy-1-oxo-1,2-dihydro-isoquinoline-4-carboxylic acid butylamide,
2-(2-dimethylamino-ethyl)-6,7-dimethoxy-1-oxo-1,2-dihydro-isoquinoline-4-carboxylic acid butylamide,
2-cyclopentyl-6,7-dimethoxy-1-oxo-1,2-dihydro-isoquinoline-4-carboxylic acid butylamide,
2-(1-ethyl-propyl)-6,7-dimethoxy-1-oxo-1,2-dihydro-isoquinoline-4-carboxylic acid butylamide,
6,7-dimethoxy-1-oxo-2-(2,2,2-trifluoro-ethyl)-1,2-dihydro-isoquinoline-4-carboxylic acid butylamide
6,7-dimethoxy-1-oxo-2-(2-pyrrolidin-1-yl-ethyl)-1,2-dihydro-isoquinoline-4-carboxylic acid butylamide,
2-(2-fluoro-ethyl)-6,7-dimethoxy-1-oxo-1,2-dihydro-isoquinoline-4-carboxylic acid butylamide,
2-benzyl-6,7-dimethoxy-1-oxo-1,2-dihydro-isoquinoline-4-carboxylic acid butylamide,
2-(2,4-difluoro-benzyl)-6,7-dimethoxy-1-oxo-1,2-dihydro-isoquinoline-4-carboxylic acid butylamide,
2-cyclopropyl-6,7-dimethoxy-1-oxo-1,2-dihydro-isoquinoline-4-carboxylic acid butylamide,
6,7-dimethoxy-1-oxo-2-(2-piperidin-1-yl-ethyl)-1,2-dihydro-isoquinoline-4-carboxylic acid butylamide,
6,7-dimethoxy-1-oxo-2-phenethyl-1,2-dihydro-isoquinoline-4-carboxylic acid butylamide,
6,7-dimethoxy-2-(2-methoxy-benzyl)-1-oxo-1,2-dihydro-isoquinoline-4-carboxylic acid butylamide,
2-indan-1-yl-6,7-dimethoxy-1-oxo-1,2-dihydro-isoquinoline-4-carboxylic acid butylamide,
2-isopropyl-6,7-dimethoxy-1-oxo-1,2-dihydro-isoquinoline-4-carboxylic acid butylamide,
6,7-dimethoxy-1-oxo-2-propyl-1,2-dihydro-isoquinoline-4-carboxylic acid butylamide,
6,7-dimethoxy-1-oxo-2-(3,3,3-trifluoro-propyl)-1,2-dihydro-isoquinoline-4-carboxylic acid butylamide,
6,7-dimethoxy-2-(2-methoxy-ethyl)-1-oxo-1,2-dihydro-isoquinoline-4-carboxylic acid butylamide,
2-Cyclobutyl-6,7-dimethoxy-1-oxo-1,2-dihydro-isoquinoline-4-carboxylic acid butylamide,
3-Ethyl-6,7-dimethoxy-4-oxo-3,4-dihydro-phthalazine-1-carboxylic acid butylamide,
2-ethyl-7-methoxy-1-oxo-1,2-dihydro-isoquinoline-4-carboxylic acid butylamide,
2-(1-ethyl-propyl)-6,7-dimethoxy-1-oxo-1,2-dihydro-isoquinoline-4-carboxylic acid indan-1-ylamide,
2-ethyl-7-methoxy-1-oxo-6-(2-quinolin-2-yl-ethoxy)-1,2-dihydro-isoquinoline-4-carboxylic acid butylamide,
2-ethyl-7-methoxy-1-oxo-6-(3-quinolin-2-yl-propoxy)-1,2-dihydro-isoquinoline-4-carboxylic acid butylamide,
3-ethyl-6,7-dimethoxy-4-oxo-3,4-dihydro-phthalazine-1-carboxylic acid (6,7,8,9-tetrahydro-5H-benzocyclohepten-7-yl)-amide,
3-ethyl-6,7-dimethoxy-4-oxo-3,4-dihydro-phthalazine-1-carboxylic acid (R)-indan-1-ylamide,
2-ethyl-7-methoxy-1-oxo-1,2-dihydro-[2,6]naphthyridine-4-carboxylic acid indan-1-ylamide, 2-ethyl-7-methoxy-1-oxo-1,2-dihydro-[2,6]naphthyridine-4-carboxylic acid butylamide,
2-(1-ethyl-propyl)-7-methoxy-1-oxo-1,2-dihydro-isoquinoline-4-carboxylic acid indan-1-ylamide,
3-ethyl-6,7-dimethoxy-4-oxo-3,4-dihydro-phthalazine-1-carboxylic acid (6,7,8,9-tetrahydro-5H-benzocyclohepten-5-yl)-amide,
3-ethyl-6,7-dimethoxy-4-oxo-3,4-dihydro-phthalazine-1-carboxylic acid (1,2,3,4-tetrahydro-naphthalen-2-yl)-amide,
3-ethyl-6,7-dimethoxy-4-oxo-3,4-dihydro-phthalazine-1-carboxylic acid (1,2,3,4-tetrahydro-naphthalen-1-yl)-amide,
3-ethyl-6,7-dimethoxy-4-oxo-3,4-dihydro-phthalazine-1-carboxylic acid (4-bromo-indan-1-yl)-amide,
3-ethyl-6,7-dimethoxy-4-oxo-3,4-dihydro-phthalazine-1-carboxylic acid (5-bromo-indan-1-yl)-amide,
3-ethyl-6,7-dimethoxy-4-oxo-3,4-dihydro-phthalazine-1-carboxylic acid 2-dimethylaminomethyl-benzylamide,
3-ethyl-6,7-dimethoxy-4-oxo-3,4-dihydro-phthalazine-1-carboxylic acid (6,7-dihydro-5H-[1]pyrindin-5-yl)-amide,
3-ethyl-6,7-dimethoxy-4-oxo-3,4-dihydro-phthalazine-1-carboxylic acid (6,7-dihydro-5H-[1]pyrindin-7-yl)-amide,
3-ethyl-6,7-dimethoxy-4-oxo-3,4-dihydro-phthalazine-1-carboxylic acid 3-dimethylaminomethyl-benzylamide,
3-ethyl-6,7-dimethoxy-4-oxo-3,4-dihydro-phthalazine-1-carboxylic acid 4-dimethylaminomethyl-benzylamide,
7-methoxy-1-oxo-2-(2-quinolin-2-yl-ethyl)-1,2-dihydro-isoquinoline-4-carboxylic acid butylamide,
7-methoxy-1-oxo-2-(2-quinolin-2-yl-ethyl)-1,2-dihydro-isoquinoline-4-carboxylic acid indan-1-ylamide,
3-ethyl-6,7-dimethoxy-4-oxo-3,4-dihydro-phthalazine-1-carboxylic acid (S)-indan-1-ylamide,
2-(1-ethyl-propyl)-6,7-dimethoxy-1-oxo-1,2-dihydro-isoquinoline-4-carboxylic acid (6,7-dihydro-5H-[1]pyrindin-5-yl)-amide,
2-(1-ethyl-propyl)-6,7-dimethoxy-1-oxo-1,2-dihydro-isoquinoline-4-carboxylic acid 2-dimethylaminomethyl-benzylamide,
2-(1-ethyl-propyl)-6,7-dimethoxy-1-oxo-1,2-dihydro-isoquinoline-4-carboxylic acid 3,5-difluoro-benzylamide,
2-(1-ethyl-propyl)-6,7-dimethoxy-1-oxo-1,2-dihydro-isoquinoline-4-carboxylic acid 3,4-difluoro-benzylamide,
2-(1-ethyl-propyl)-6,7-dimethoxy-1-oxo-1,2-dihydro-isoquinoline-4-carboxylic acid cyclohexylmethyl-amide,
2-(1-ethyl-propyl)-6,7-dimethoxy-1-oxo-1,2-dihydro-isoquinoline-4-carboxylic acid (R)-indan-1-ylamide,
2-(1-ethyl-propyl)-6,7-dimethoxy-1-oxo-1,2-dihydro-isoquinoline-4-carboxylic acid (S)-indan-1-ylamide,
2-ethyl-6,7-dimethoxy-1-oxo-1,2-dihydro-isoquinoline-4-carboxylic acid (1,2,3,4-tetrahydro-naphthalen-1-yl)-amide,
2-ethyl-6,7-dimethoxy-1-oxo-1,2-dihydro-isoquinoline-4-carboxylic acid pyridin-3-ylamide,
2-ethyl-6,7-dimethoxy-1-oxo-1,2-dihydro-isoquinoline-4-carboxylic acid (pyrimidin-4-ylmethyl)-amide,
2-ethyl-6,7-dimethoxy-1-oxo-1,2-dihydro-isoquinoline-4-carboxylic acid 2-methoxy-benzylamide,
2-ethyl-6,7-dimethoxy-1-oxo-1,2-dihydro-isoquinoline-4-carboxylic acid (4-morpholin-4-yl-phenyl)-amide,
2-ethyl-6,7-dimethoxy-1-oxo-1,2-dihydro-isoquinoline-4-carboxylic acid 3-chloro-benzylamide,
2-ethyl-6,7-dimethoxy-1-oxo-1,2-dihydro-isoquinoline-4-carboxylic acid (pyridin-4-ylmethyl)-amide,
2-ethyl-6,7-dimethoxy-1-oxo-1,2-dihydro-isoquinoline-4-carboxylic acid o-tolylamide,
2-ethyl-6,7-dimethoxy-1-oxo-1,2-dihydro-isoquinoline-4-carboxylic acid m-tolylamide,
2-ethyl-6,7-dimethoxy-1-oxo-1,2-dihydro-isoquinoline-4-carboxylic acid (2-methoxy-phenyl)-amide,
2-ethyl-6,7-dimethoxy-1-oxo-1,2-dihydro-isoquinoline-4-carboxylic acid (3-methoxy-phenyl)-amide,
2-ethyl-6,7-dimethoxy-1-oxo-1,2-dihydro-isoquinoline-4-carboxylic acid (pyridin-3-ylmethyl)-amide,
2-ethyl-6,7-dimethoxy-1-oxo-1,2-dihydro-isoquinoline-4-carboxylic acid (pyridin-2-ylmethyl)-amide,
2-ethyl-6,7-dimethoxy-1-oxo-1,2-dihydro-isoquinoline-4-carboxylic acid (3-dimethylamino-propyl)-amide,
2-ethyl-6,7-dimethoxy-1-oxo-1,2-dihydro-isoquinoline-4-carboxylic acid phenylamide,
2-ethyl-6,7-dimethoxy-1-oxo-1,2-dihydro-isoquinoline-4-carboxylic acid 4-methoxy-benzylamide,
2-ethyl-6,7-dimethoxy-1-oxo-1,2-dihydro-isoquinoline-4-carboxylic acid 3-methyl-benzylamide,
2-ethyl-6,7-dimethoxy-1-oxo-1,2-dihydro-isoquinoline-4-carboxylic acid 2-methyl-benzylamide,
2-ethyl-6,7-dimethoxy-1-oxo-1,2-dihydro-isoquinoline-4-carboxylic acid (2-methoxy-ethyl)-amide,
2-ethyl-6,7-dimethoxy-1-oxo-1,2-dihydro-isoquinoline-4-carboxylic acid (4-fluoro-phenyl)-amide,
2-ethyl-6,7-dimethoxy-1-oxo-1,2-dihydro-isoquinoline-4-carboxylic acid (4-methoxy-phenyl)-amide,
2-ethyl-6,7-dimethoxy-1-oxo-1,2-dihydro-isoquinoline-4-carboxylic acid p-tolylamide,
2-ethyl-6,7-dimethoxy-1-oxo-1,2-dihydro-isoquinoline-4-carboxylic acid (3-fluoro-phenyl)-amide,
2-ethyl-6,7-dimethoxy-1-oxo-1,2-dihydro-isoquinoline-4-carboxylic acid (2-fluoro-phenyl)-amide,
2-ethyl-6,7-dimethoxy-1-oxo-1,2-dihydro-isoquinoline-4-carboxylic acid 4-methyl-benzylamide,
2-ethyl-6,7-dimethoxy-1-oxo-1,2-dihydro-isoquinoline-4-carboxylic acid 2-chloro-benzylamide,
2-ethyl-6,7-dimethoxy-1-oxo-1,2-dihydro-isoquinoline-4-carboxylic acid [(R)-1-(4-fluoro-phenyl)-ethyl]-amide,
2-ethyl-6,7-dimethoxy-1-oxo-1,2-dihydro-isoquinoline-4-carboxylic acid pyridin-4-ylamide,
2-ethyl-6,7-dimethoxy-1-oxo-1,2-dihydro-isoquinoline-4-carboxylic acid [(S)-1-(4-fluoro-phenyl)-ethyl]-amide,
2-ethyl-6,7-dimethoxy-1-oxo-1,2-dihydro-isoquinoline-4-carboxylic acid (6-methyl-indan-1-yl)-amide,
2-ethyl-6,7-dimethoxy-1-oxo-1,2-dihydro-isoquinoline-4-carboxylic acid 2-morpholin-4-ylmethyl-benzylamide,
2-ethyl-6,7-dimethoxy-1-oxo-1,2-dihydro-isoquinoline-4-carboxylic acid (5-chloro-indan-1-yl)-amide,
2-ethyl-6,7-dimethoxy-1-oxo-1,2-dihydro-isoquinoline-4-carboxylic acid (6-chloro-indan-1-yl)-amide,
2-ethyl-6,7-dimethoxy-1-oxo-1,2-dihydro-isoquinoline-4-carboxylic acid (6-fluoro-indan-1-yl)-amide,
2-ethyl-6,7-dimethoxy-1-oxo-1,2-dihydro-isoquinoline-4-carboxylic acid (5,6-dihydro-4H-cyclopenta[b]thiophen-4-yl)-amide,
2-ethyl-6,7-dimethoxy-1-oxo-1,2-dihydro-isoquinoline-4-carboxylic acid (4-fluoro-indan-1-yl)-amide,
2-ethyl-6,7-dimethoxy-1-oxo-1,2-dihydro-isoquinoline-4-carboxylic acid (4-methyl-indan-1-yl)-amide,
2-ethyl-6,7-dimethoxy-1-oxo-1,2-dihydro-isoquinoline-4-carboxylic acid (5-methyl-indan-1-yl)-amide,
2-ethyl-6,7-dimethoxy-1-oxo-1,2-dihydro-isoquinoline-4-carboxylic acid (6-methoxy-indan-1-yl)-amide,
2-ethyl-6,7-dimethoxy-1-oxo-1,2-dihydro-isoquinoline-4-carboxylic acid (5-fluoro-indan-1-yl)-amide, 2-ethyl-6,7-dimethoxy-1-oxo-1,2-dihydro-isoquinoline-4-carboxylic acid 2-diethylaminomethyl-benzylamide,
2-ethyl-6,7-dimethoxy-1-oxo-1,2-dihydro-isoquinoline-4-carboxylic acid 2-pyrrolidin-1-ylmethyl-benzylamide,
2-ethyl-6,7-dimethoxy-4-(4-methyl-piperidine-1-carbonyl)-2H-isoquinolin-1-one,
2-ethyl-6,7-dimethoxy-1-oxo-1,2-dihydro-isoquinoline-4-carboxylic acid (tetrahydro-furan-2-ylmethyl)-amide,
2-ethyl-6,7-dimethoxy-1-oxo-1,2-dihydro-isoquinoline-4-carboxylic acid (3-methoxy-propyl)-amide,
4-(3,5-dimethyl-piperidine-1-carbonyl)-2-ethyl-6,7-dimethoxy-2H-isoquinolin-1-one,
2-ethyl-4-(4-ethyl-piperazine-1-carbonyl)-6,7-dimethoxy-2H-isoquinolin-1-one,
2-isobutyl-6,7-dimethoxy-4-(4-methyl-piperazine-1-carbonyl)-2H-isoquinolin-1-one,
2-isobutyl-6,7-dimethoxy-1-oxo-1,2-dihydro-isoquinoline-4-carboxylic acid (2-dimethylamino-ethyl)-amide,
2-isobutyl-6,7-dimethoxy-1-oxo-1,2-dihydro-isoquinoline-4-carboxylic acid butyl-methyl-amide,
1(2-isobutyl-6,7-dimethoxy-1-oxo-1,2-dihydro-isoquinoline-4-carbonyl)-aminol-acetic acid methyl ester,
2-ethyl-6,7-dimethoxy-1-oxo-1,2-dihydro-isoquinoline-4-carboxylic acid (3-isopropoxy-propyl)-amide,
2-(1-ethyl-propyl)-6,7-dimethoxy-1-oxo-1,2-dihydro-isoquinoline-4-carboxylic acid (5,6-dihydro-4H-cyclopenta[b]thiophen-4-yl)-amide,
2-(1-ethyl-propyl)-6,7-dimethoxy-1-oxo-1,2-dihydro-isoquinoline-4-carboxylic acid (2,3-dihydro-benzofuran-3-yl)-amide,
2-(1-ethyl-propyl)-6,7-dimethoxy-1-oxo-1,2-dihydro-isoquinoline-4-carboxylic acid (6-oxo-5,6-dihydro-4H-cyclopenta[b]thiophen-4-yl)-amide,
2-cyclopropyl-6,7-dimethoxy-1-oxo-1,2-dihydro-isoquinoline-4-carboxylic acid indan-1-ylamide,
2-sec-butyl-6,7-dimethoxy-1-oxo-1,2-dihydro-isoquinoline-4-carboxylic acid indan-1-ylamide,
2-isopropyl-6,7-dimethoxy-1-oxo-1,2-dihydro-isoquinoline-4-carboxylic acid indan-1-ylamide,
2-(1-ethyl-propyl)-6,7-dimethoxy-4-(3-phenyl-piperidine-1-carbonyl)-2H-isoquinolin-1-one,
2-(1-ethyl-propyl)-6,7-dimethoxy-4-(3-phenoxy-piperidine-1-carbonyl)-2H-isoquinolin-1-one,
2-ethyl-6,7-dimethoxy-1-oxo-1,2-dihydro-isoquinoline-4-carboxylic acid (S)indan-1-ylamide,
2-ethyl-6,7-dimethoxy-1-oxo-1,2-dihydro-isoquinoline-4-carboxylic acid (R)indan-1-ylamide,
2-(1-ethyl-propyl)-6,7-dimethoxy-4-[3-(3-methoxy-phenyl)-piperazine-1-carbonyl]-2H-isoquinolin-1-one,
2-(1-ethyl-propyl)-6,7-dimethoxy-4-[8-(4-methyl-piperazine-1-sulfonyl)-3,4-dihydro-1H-isoquinoline-2-carbonyl]-2H-isoquinolin-1-one,
2-(1-ethyl-propyl)-6,7-dimethoxy-4-[8-(morpholine-4-sulfonyl)-3,4-dihydro-1H-isoquinoline-2-carbonyl]-2H-isoquinolin-1-one,
2-(1-ethyl-propyl)-6,7-dimethoxy-4-[3-(3-methoxy-phenyl)-4-methyl-piperazine-1-carbonyl]-2H-isoquinolin-1-one,
2-(1-ethyl-propyl)-6,7-dimethoxy-1-oxo-1,2-dihydro-isoquinoline-4-carboxylic acid ([1,3,4]thiadiazol-2-ylmethyl)-amide,
2-(1-ethyl-propyl)-6,7-dimethoxy-1-oxo-1,2-dihydro-isoquinoline-4-carboxylic acid 2-(morpholine-4-sulfonyl)-benzylamide,
2-(1-ethyl-propyl)-6,7-dimethoxy-1-oxo-1,2-dihydro-isoquinoline-4-carboxylic acid (thiazol-4-ylmethyl)-amide,
2-(1-ethyl-propyl)-6,7-dimethoxy-4-[(R)-3-(quinoxalin-2-yloxy)-pyrrolidine-1-carbonyl]-2H-isoquinolin-1-one,
2-ethyl-6,7-dimethoxy-1-oxo-1,2-dihydro-isoquinoline-4-carboxylic acid (S)(5,6-dihydro-4H-cyclopenta[b]thiophen-4-yl)-amide,
2-ethyl-6,7-dimethoxy-1-oxo-1,2-dihydro-isoquinoline-4-carboxylic acid (R)(5,6-dihydro-4H-cyclopenta[b]thiophen-4-yl)-amide,
2-(1-ethyl-propyl)-6,7-dimethoxy-1-oxo-1,2-dihydro-isoquinoline-4-carboxylic acid (thiophen-3-ylmethyl)-amide,
4-(7-Amino-3,4-dihydro-1H-isoquinoline-2-carbonyl)-2-(1-ethyl-propyl)-6,7-dimethoxy-2H-isoquinolin-1-one,
2-(1-ethyl-propyl)-6,7-dimethoxy-1-oxo-1,2-dihydro-isoquinoline-4-carboxylic acid 3-(4-chloro-benzenesulfonylamino)-benzylamide,
2-(1-ethyl-propyl)-6,7-dimethoxy-1-oxo-1,2-dihydro-isoquinoline-4-carboxylic acid (2,3-dihydro-benzo[b]thiophen-3-yl)-amide,
2-(1-ethyl-propyl)-7-methoxy-1-oxo-1,2-dihydro-[2,6]naphthyridine-4-carboxylic acid (5,6-dihydro-4H-cyclopenta[b]thiophen-4-yl)-amide,
2-(1-ethyl-propyl)-7-methoxy-1-oxo-1,2-dihydro-[2,6]naphthyridine-4-carboxylic acid (S)-indan-1-ylamide,
2-(1-ethyl-propyl)-6,7-dimethoxy-1-oxo-1,2-dihydro-isoquinoline-4-carboxylic acid 2-(4-methyl-piperazine-1-sulfonyl)-benzylamide,
2-(1-ethyl-propyl)-7-methoxy-1-oxo-1,2-dihydro-[2,6]naphthyridine-4-carboxylic acid 2-(morpholine-4-sulfonyl)-benzylamide,
2-(1-ethyl-propyl)-7-methoxy-1-oxo-1,2-dihydro-[2,6]naphthyridine-4-carboxylic acid (6,7-dihydro-5H-[1]pyrindin-5-yl)-amide,
2-(1-ethyl-propyl)-6,7-dimethoxy-1-oxo-1,2-dihydro-isoquinoline-4-carboxylic acid 3-(4-methoxy-benzenesulfonylamino)-benzylamide,
2-(1-ethyl-propyl)-7-methoxy-1-oxo-1,2-dihydro-[2,6]naphthyridine-4-carboxylic acid 3,5-difluoro-benzylamide,
2-(1-ethyl-propyl)-7-methoxy-1-oxo-1,2-dihydro-[2,6]naphthyridine-4-carboxylic acid 4-methyl-benzylamide,
2-(1-ethyl-propyl)-7-methoxy-1-oxo-1,2-dihydro-[2,6]naphthyridine-4-carboxylic acid cyclohexylmethyl-amide,
2-(1-ethyl-propyl)-7-methoxy-1-oxo-1,2-dihydro-[2,6]naphthyridine-4-carboxylic acid butylamide,
2-(1-ethyl-propyl)-7-methoxy-1-oxo-1,2-dihydro-[2,6]naphthyridine-4-carboxylic acid (2,3-dihydro-benzofuran-3-yl)-amide,
2-(1-ethyl-propyl)-6,7-dimethoxy-1-oxo-1,2-dihydro-isoquinoline-4-carboxylic acid (thiazol-2-ylmethyl)-amide,
2-(1-ethyl-propyl)-6,7-dimethoxy-1-oxo-1,2-dihydro-isoquinoline-4-carboxylic acid (thiophen-2-ylmethyl)-amide,
2-ethyl-7-methoxy-1-oxo-1,2-dihydro-[2,6]naphthyridine-4-carboxylic acid (5,6-dihydro-4H-cyclopenta[b]thiophen-4-yl)-amide,
3-(1-ethyl-propyl)-6,7-dimethoxy-4-oxo-3,4-dihydro-phthalazine-1-carboxylic acid (5,6-dihydro-4H-cyclopenta[b]thiophen-4-yl)-amide,
3-(1-ethyl-propyl)-6,7-dimethoxy-4-oxo-3,4-dihydro-phthalazine-1-carboxylic acid (2,3-dihydro-benzofuran-3-yl)-amide,
3-(1-ethyl-propyl)-6,7-dimethoxy-4-oxo-3,4-dihydro-phthalazine-1-carboxylic acid indan-1-ylamide, 3-(1-ethyl-propyl)-6,7-dimethoxy-4-oxo-3,4-dihydro-phthalazine-1-carboxylic acid (6,7-dihydro-5H-[1]pyridin-5-yl)-amide,
2-(1-ethyl-propyl)-6,7-dimethoxy-4-(3-phenyl-propionyl)-2H-isoquinolin-1-one, and
2-ethyl-6,7-dimethoxy-N-(4-nitrophenyl)-1-oxo-1,2-dihydroisoquinoline-4-carboxamide.

Particular embodiments of the invention also relates to the compounds of formula I, to the N-oxides, the prodrugs, the hydrates and the tautomers thereof and to the pharmaceutically suitable salts thereof, where the compounds of the formula I are selected from the group consisting of:
6,7-dimethoxy-1-oxo-2-(pentan-3-yl)-N-(pyridin-3-ylmethyl)-1,2-dihydroisoquinoline-4-carboxamide,
6,7-dimethoxy-N-((5-methylthiophen-2-yl)methyl)-1-oxo-2-(pentan-3-yl)-1,2-dihydroisoquinoline-4-carboxamide,
N-((3,5-dimethylisoxazol-4-yl)methyl)-6,7-dimethoxy-1-oxo-2-(pentan-3-yl)-1,2-dihydroisoquinoline-4-carboxamide,
6,7-dimethoxy-N-((5-methylthiazol-2-yl)methyl)-1-oxo-2-(pentan-3-yl)-1,2-dihydroisoquinoline-4-carboxamide,
6,7-dimethoxy-1-oxo-2-(pentan-3-yl)-N-(pyrimidin-4-ylmethyl)-1,2-dihydroisoquinoline-4-carboxamide,
6,7-dimethoxy-N-((3-methylisoxazol-5-yl)methyl)-1-oxo-2-(pentan-3-yl)-1,2-dihydroisoquinoline-4-carboxamide,
N-((2,5-dimethylthiophen-3-yl)methyl)-6,7-dimethoxy-1-oxo-2-(pentan-3-yl)-1,2-dihydroisoquinoline-4-carboxamide,
6,7-dimethoxy-N-((2-methylthiazol-5-yl)methyl)-1-oxo-2-(pentan-3-yl)-1,2-dihydroisoquinoline-4-carboxamide,
6,7-dimethoxy-N-((5-methylisoxazol-3-yl)methyl)-1-oxo-2-(pentan-3-yl)-1,2-dihydroisoquinoline-4-carboxamide,
(R)—N-(1-(4-fluorophenyl)ethyl)-6,7-dimethoxy-1-oxo-2-(pentan-3-yl)-1,2-dihydroisoquinoline-4-carboxamide,
(S)—N-(1-(4-fluorophenyl)ethyl)-6,7-dimethoxy-1-oxo-2-(pentan-3-yl)-1,2-dihydroisoquinoline-4-carboxamide,
6,7-dimethoxy-N-((4-methylthiazol-2-yl)methyl)-1-oxo-2-(pentan-3-yl)-1,2-dihydroisoquinoline-4-carboxamide,
6,7-dimethoxy-N-((2-methylthiazol-4-yl)methyl)-1-oxo-2-(pentan-3-yl)-1,2-dihydroisoquinoline-4-carboxamide,
6,7-dimethoxy-N-((4-methylthiazol-5-yl)methyl)-1-oxo-2-(pentan-3-yl)-1,2-dihydroisoquinoline-4-carboxamide,
6,7-dimethoxy-1-oxo-2-(pentan-3-yl)-N-((5-(trifluoromethyl)furan-2-yl)methyl)-1,2-dihydroisoquinoline-4-carboxamide,
6,7-dimethoxy-N-((5-methylfuran-2-yl)methyl)-1-oxo-2-(pentan-3-yl)-1,2-dihydroisoquinoline-4-carboxamide,
N-(5-fluoro-2,3-dihydro-1H-inden-1-yl)-6,7-dimethoxy-1-oxo-2-(pentan-3-yl)-1,2-dihydroiso-quinoline-4-carboxamide,
6,7-dimethoxy-N-(5-methyl-2,3-dihydro-1H-inden-1-yl)-1-oxo-2-(pentan-3-yl)-1,2-dihydroisoquinoline-4-carboxamide,
6,7-dimethoxy-N-(4-methyl-2,3-dihydro-1H-inden-1-yl)-1-oxo-2-(pentan-3-yl)-1,2-dihydroisoquinoline-4-carboxamide,
N-((2-ethylthiazol-4-yl)methyl)-6,7-dimethoxy-1-oxo-2-(pentan-3-yl)-1,2-dihydroisoquinoline-4-carboxamide,
6,7-dimethoxy-N-(6-methoxy-2,3-dihydro-1H-inden-1-yl)-1-oxo-2-(pentan-3-yl)-1,2-dihydroisoquinoline-4-carboxamide,
6,7-dimethoxy-N-((4-methylthiophen-2-yl)methyl)-1-oxo-2-(pentan-3-yl)-1,2-dihydroisoquinoline-4-carboxamide,
6,7-dimethoxy-N-((3-methylthiophen-2-yl)methyl)-1-oxo-2-(pentan-3-yl)-1,2-dihydroisoquinoline-4-carboxamide,
6,7-dimethoxy-N-((5-methyloxazol-2-yl)methyl)-1-oxo-2-(pentan-3-yl)-1,2-dihydroisoquinoline-4-carboxamide,
6,7-dimethoxy-N-(6-methyl-2,3-dihydro-1H-inden-1-yl)-1-oxo-2-(pentan-3-yl)-1,2-dihydroisoquinoline-4-carboxamide,
6,7-dimethoxy-1-oxo-2-(pentan-3-yl)-N-(pyridin-4-ylmethyl)-1,2-dihydroisoquinoline-4-carboxamide,
6,7-dimethoxy-N-(4-methylbenzyl)-1-oxo-2-(pentan-3-yl)-1,2-dihydroisoquinoline-4-carboxamide,
6,7-dimethoxy-1-oxo-2-(pentan-3-yl)-N-(pyridin-2-ylmethyl)-1,2-dihydroisoquinoline-4-carboxamide,
N-((5-cyanofuran-2-yl)methyl)-6,7-dimethoxy-1-oxo-2-(pentan-3-yl)-1,2-dihydroisoquinoline-4-carboxamide,
N-(4-chloro-2,3-dihydro-1H-inden-1-yl)-6,7-dimethoxy-1-oxo-2-(pentan-3-yl)-1,2-dihydroisoquinoline-4-carboxamide,
N-((5-ethylthiophen-2-yl)methyl)-6,7-dimethoxy-1-oxo-2-(pentan-3-yl)-1,2-dihydroisoquinoline-4-carboxamide,
6,7-dimethoxy-N-((3-methylfuran-2-yl)methyl)-1-oxo-2-(pentan-3-yl)-1,2-dihydroisoquinoline-4-carboxamide,
6,7-dimethoxy-N-((2-methylfuran-3-yl)methyl)-1-oxo-2-(pentan-3-yl)-1,2-dihydroisoquinoline-4-carboxamide,
6,7-dimethoxy-N-((1-methyl-1H-pyrazol-3-yl)methyl)-1-oxo-2-(pentan-3-yl)-1,2-dihydroisoquinoline-4-carboxamide,
N-[(3,4-dimethylphenyl)methyl]-2-ethyl-6,7-dimethoxy-1-oxo-isoquinoline-4-carboxamide,
N-[(2-chloro-4-methyl-phenyl)methyl]-2-ethyl-6,7-dimethoxy-1-oxo-isoquinoline-4-carboxamide,
N-[[2-(dimethylamino)-4-methyl-phenyl]methyl]-2-ethyl-6,7-dimethoxy-1-oxo-isoquinoline-4-carboxamide,
2-ethyl-N-[(2-fluoro-4-methyl-phenyl)methyl]-6,7-dimethoxy-1-oxo-isoquinoline-4-carboxamide,
2-ethyl-6,7-dimethoxy-N-[(3-methoxy-4-methyl-phenyl)methyl]-1-oxo-isoquinoline-4-carboxamide,
2-ethyl-6,7-dimethoxy-N-[(4-methyl-2-morpholino-phenyl)methyl]-1-oxo-isoquinoline-4-carboxamide,
N-[(2-tert-butoxy-4-methyl-phenyl)methyl]-2-ethyl-6,7-dimethoxy-1-oxo-isoquinoline-4-carboxamide,
N-[[2-(1,1-dimethylpropoxy)-4-methyl-phenyl]methyl]-2-ethyl-6,7-dimethoxy-1-oxo-isoquinoline-4-carboxamide,
N-[(2,3-difluoro-4-methyl-phenyl)methyl]-2-ethyl-6,7-dimethoxy-1-oxo-isoquinoline-4-carboxamide,
2-ethyl-N-[(3-fluoro-4-methyl-phenyl)methyl]-6,7-dimethoxy-1-oxo-isoquinoline-4-carboxamide,
N-[(3-chloro-4-methyl-phenyl)methyl]-2-ethyl-6,7-dimethoxy-1-oxo-isoquinoline-4-carboxamide,
2-ethyl-6,7-dimethoxy-1-oxo-N-[(2,4,6-trimethylphenyl)methyl]isoquinoline-4-carboxamide,
N-[(2,4-dimethylphenyl)methyl]-2-ethyl-6,7-dimethoxy-1-oxo-isoquinoline-4-carboxamide,
2-ethyl-6,7-dimethoxy-N-[[2-(3-methoxypropoxy)-4-methyl-phenyl]methyl]-1-oxo-isoquinoline-4-carboxamide,
N-[[2-(2-ethoxyethoxy)-4-methyl-phenyl]methyl]-2-ethyl-6,7-dimethoxy-1-oxo-isoquinoline-4-carboxamide,
N-[[2-(cyclopentoxy)-4-methyl-phenyl]methyl]-2-ethyl-6,7-dimethoxy-1-oxo-isoquinoline-4-carboxamide,
2-ethyl-6,7-dimethoxy-N-[(4-methyl-2-phenoxy-phenyl)methyl]-1-oxo-isoquinoline-4-carboxamide,
2-ethyl-6,7-dimethoxy-N-[[2-(2-methoxy-1-methyl-ethoxy)-4-methyl-phenyl]methyl]-1-oxo-isoquinoline-4-carboxamide,
2-ethyl-6,7-dimethoxy-N-[[4-methyl-2-(2,2,2-trifluoroethoxy)phenyl]methyl]-1-oxo-isoquinoline-4-carboxamide,
N-[[2-(cyclohexoxy)-4-methyl-phenyl]methyl]-2-ethyl-6,7-dimethoxy-1-oxo-isoquinoline-4-carboxamide,
N-[[2-(cyclopropylmethoxy)-4-methyl-phenyl]methyl]-2-ethyl-6,7-dimethoxy-1-oxo-isoquinoline-4-carboxamide, 2-ethyl-N-[(2-hexoxy-4-methyl-phenyl)methyl]-6,7-dimethoxy-1-oxo-isoquinoline-4-carboxamide,
2-ethyl-6,7-dimethoxy-N-[[4-methyl-2-(tetrahydrofuran-3-ylmethoxy)phenyl]methyl]-1-oxo-isoquinoline-4-carboxamide,
2-ethyl-6,7-dimethoxy-N-[[2-(2-methoxyethoxy)-4-methylphenyl]methyl]-1-oxo-isoquinoline-4-carboxamide,
2-ethyl-N-(2-isobutoxy-4-methylbenzyl)-6,7-dimethoxy-1-oxo-1,2-dihydroisoquinoline-4-carboxamide,
2-ethyl-N-(2-(furan-2-ylmethoxy)-4-methylbenzyl)-6,7-dimethoxy-1-oxo-1,2-dihydroisoquinoline-4-carboxamide,
2-ethyl-6,7-dimethoxy-N-(4-methyl-2-(pentyloxy)benzyl)-1-oxo-1,2-dihydroisoquinoline-4-carboxamide,
N-(2-ethoxy-4-methylbenzyl)-2-ethyl-6,7-dimethoxy-1-oxo-1,2-dihydroisoquinoline-4-carboxamide,
N-(2-sec-butoxy-4-methylbenzyl)-2-ethyl-6,7-dimethoxy-1-oxo-1,2-dihydroisoquinoline-4-carboxamide,
2-ethyl-N-(2-(isopentyloxy)-4-methylbenzyl)-6,7-dimethoxy-1-oxo-1,2-dihydroisoquinoline-4-carboxamide,
2-ethyl-6,7-dimethoxy-N-(4-methyl-2-propoxybenzyl)-1-oxo-1,2-dihydroisoquinoline-4-carboxamide,
2-ethyl-6,7-dimethoxy-N-(4-methyl-2-(methylthio)benzyl)-1-oxo-1,2-dihydroisoquinoline-4-carboxamide,
2-ethyl-N-(2-isopropoxy-4-methylbenzyl)-6,7-dimethoxy-1-oxo-1,2-dihydroisoquinoline-4-carboxamide,
2-ethyl-6,7-dimethoxy-N-(4-methyl-2-(tetrahydrofuran-3-yloxy)benzyl)-1-oxo-1,2-dihydroisoquinoline-4-carboxamide,
2-ethyl-6,7-dimethoxy-1-oxo-N-(2,4,5-trimethylbenzyl)-1,2-dihydroisoquinoline-4-carboxamide,
2-ethyl-6,7-dimethoxy-N-(4-methyl-2-((tetrahydrofuran-2-yl)methoxy)benzyl)-1-oxo-1,2-dihydroisoquinoline-4-carboxamide,
2-ethyl-6,7-dimethoxy-N-(4-methyl-2-(4-methylpentan-2-yloxy)benzyl)-1-oxo-1,2-dihydroisoquinoline-4-carboxamide,
2-ethyl-6,7-dimethoxy-N-(4-methyl-2-(4-methylpentyloxy)benzyl)-1-oxo-1,2-dihydroisoquinoline-4-carboxamide,
2-ethyl-6,7-dimethoxy-N-(2-methoxy-4-methylbenzyl)-1-oxo-1,2-dihydroisoquinoline-4-carboxamide,
2-ethyl-6,7-dimethoxy-1-oxo-N-(thiazol-4-ylmethyl)isoquinoline-4-carboxamide,
2-ethyl-6,7-dimethoxy-1-oxo-N-[[4-(trifluoromethyl)phenyl]methyl]isoquinoline-4-carboxamide,
2-ethyl-6,7-dimethoxy-1-oxo-N-[(1S)-1-(p-tolyl)ethyl]isoquinoline-4-carboxamide,
2-ethyl-N-[(4-isopropylphenyl)methyl]-6,7-dimethoxy-1-oxo-isoquinoline-4-carboxamide,
2-ethyl-N-[(4-ethylphenyl)methyl]-6,7-dimethoxy-1-oxo-isoquinoline-4-carboxamide,
2-ethyl-6,7-dimethoxy-1-oxo-N-[(1R)-1-(p-tolyl)ethyl]isoquinoline-4-carboxamide,
N-[[4-(difluoromethyl)phenyl]methyl]-2-ethyl-6,7-dimethoxy-1-oxo-isoquinoline-4-carboxamide,
2-ethyl-6,7-dimethoxy-N-[(2-methylthiazol-4-yl)methyl]-1-oxo-isoquinoline-4-carboxamide,
2-ethyl-6,7-dimethoxy-N-[(4-methyl-2-thienyl)methyl]-1-oxo-isoquinoline-4-carboxamide,
N-[(4-cyclopropylphenyl)methyl]-2-ethyl-6,7-dimethoxy-1-oxo-isoquinoline-4-carboxamide,
N-indan-1-yl-6,7-dimethoxy-2-[2-(5-methyl-2-pyridyl)ethyl]-1-oxo-isoquinoline-4-carboxamide,
N-butyl-6,7-dimethoxy-2-[2-(5-methyl-2-pyridyl)ethyl]-1-oxo-isoquinoline-4-carboxamide,
2-ethyl-6,7-dimethoxy-N-[2-(6-methoxy-2-pyridyl)ethyl]-1-oxo-isoquinoline-4-carboxamide,
N-butyl-6,7-dimethoxy-1-oxo-2-[2-(2-quinolyl)ethyl]isoquinoline-4-carboxamide, and
N-indan-1-yl-6,7-dimethoxy-1-oxo-2-[2-(2-quinolyl)ethyl]isoquinoline-4-carboxamide.

In particular embodiments, the compounds of the present invention are distinct from the group of the following compounds:
1-[(2-ethyl-1,2-dihydro-6,7-dimethoxy-1-oxo-4-isoquinolinyl)carbonyl]-(3-ethoxycarbonyl)piperidine,
1-[(2-(2-methylpropyl)-1,2-dihydro-6,7-dimethoxy-1-oxo-4-isoquinolinyl)-carbonyl]-(3-ethoxycarbonyl)piperidine,
2-{[(2-ethyl-1,2-dihydro-6,7-dimethoxy-1-oxo-4-isoquinolinyl)carbonyl]amino}-benzoic acid ethyl ester,
N-cycloheptyl-2-ethyl-1,2-dihydro-6,7-dimethoxy-1-oxo-4-isoquinoline carboxamide,
N-(3-ethoxypropyl)-2-ethyl-1,2-dihydro-6,7-dimethoxy-1-oxo-4-isoquinoline carboxamide,
N-(3-(1-methylethoxy)propyl)-2-ethyl-1,2-dihydro-6,7-dimethoxy-1-oxo-4-isoquinoline carboxamide,
N-(3-(1-methylethoxy)propyl)-2-(2-methylpropyl)-1,2-dihydro-6,7-dimethoxy-1-oxo-4-isoquinoline carboxamide,
N-(3-ethoxypropyl)-2-(2-methylpropyl)-1,2-dihydro-6,7-dimethoxy-1-oxo-4-isoquinoline carboxamide,
N-[3-(4-methyl-1-piperidinyl)propyl]-2-ethyl-1,2-dihydro-6,7-dimethoxy-1-oxo-4-isoquinoline carboxamide,
N-[3-(2-ethyl-1-piperidinyl)propyl]-2-(2-methylpropyl)-1,2-dihydro-6,7-dimethoxy-1-oxo-4-isoquinoline carboxamide,
N-[3-(3,5-dimethyl-1-piperidinyl)propyl]-2-ethyl-1,2-dihydro-6,7-dimethoxy-1-oxo-4-isoquinoline carboxamide,
N-[3-(3,5-dimethyl-1-piperidinyl)propyl]-2-(2-methylpropyl)-1,2-dihydro-6,7-dimethoxy-1-oxo-4-isoquinoline carboxamide,
N-(3-acetylaminophenyl)-2-ethyl-1,2-dihydro-6,7-dimethoxy-1-oxo-4-isoquinoline carboxamide,
N,N-diethyl-2-ethyl-1,2-dihydro-6,7-dimethoxy-1-oxo-4-isoquinoline carboxamide,
N-(5-methyl-2-furanylmethyl)-2-ethyl-1,2-dihydro-6,7-dimethoxy-1-oxo-4-isoquinoline carboxamide,
N-(5-methyl-2-furanylmethyl)-2-(2-methylpropyl)-1,2-dihydro-6,7-dimethoxy-1-oxo-4-isoquinoline carboxamide,
N-(2-furanylmethyl)-2-ethyl-1,2-dihydro-6,7-dimethoxy-1-oxo-4-isoquinoline carboxamide,
N-(tetrahydro-2-furanylmethyl)-2-ethyl-1,2-dihydro-6,7-dimethoxy-1-oxo-4-isoquinoline carboxamide,
N-(2-pyridylmethyl)-2-(2-methylpropyl)-1,2-dihydro-6,7-dimethoxy-1-oxo-4-isoquinoline carboxamide,
N-(3-pyridylmethyl)-2-ethyl-1,2-dihydro-6,7-dimethoxy-1-oxo-4-isoquinoline carboxamide,
N-(1,3-benzodioxol-5-ylmethyl)-2-ethyl-1,2-dihydro-6,7-dimethoxy-1-oxo-4-isoquinoline carboxamide,
N-(1,3-benzodioxol-5-ylmethyl)-2-(2-methylpropyl)-1,2-dihydro-6,7-dimethoxy-1-oxo-4-isoquinoline carboxamide,
N-(2,3-dihydro-1,4-benzodioxin-2-ylmethyl)-2-ethyl-1,2-dihydro-6,7-dimethoxy-1-oxo-4-isoquinoline carboxamide,
N-(2,3-dihydro-1,4-benzodioxin-6-yl)-2-ethyl-1,2-dihydro-6,7-dimethoxy-1-oxo-4-isoquinoline carboxamide,
N-ethyl-N-(2-methylphenyl)-2-ethyl-1,2-dihydro-6,7-dimethoxy-1-oxo-4-isoquinoline carboxamide,
N-ethyl-N-(2-ethylphenyl)-2-ethyl-1,2-dihydro-6,7-dimethoxy-1-oxo-4-isoquinoline carboxamide,
N-(3,4-dimethoxyphenyl)-2-ethyl-1,2-dihydro-6,7-dimethoxy-1-oxo-4-isoquinoline carboxamide,
N-(3-chlorophenyl)-2-(2-methylpropyl)-1,2-dihydro-6,7-dimethoxy-1-oxo-4-isoquinoline carboxamide, 4-[(4-propyl-1-piperazinyl)carbonyl]-2-(2-methylpropyl)-1,2-dihydro-6,7-dimethoxy-4-isoquinolin-1-one, 4-[(4-cyclohexyl-1-piperazinyl)carbonyl]-2-ethyl-1,2-dihydro-6,7-dimethoxy-4-isoquinolin-1-one, 4-[(4-cyclohexyl-1-piperazinyl)carbonyl]-2-(2-methylpropyl)-1,2-dihydro-6,7-dimethoxy-4-isoquinolin-1-one, 4-[(4-(2-pyridyl)-1-piperazinyl)carbonyl]-2-(2-methylpropyl)-1,2-dihydro-6,7-dimethoxy-4-isoquinolin-1-one, 4-[(4-(3-chlorophenyl)-1-piperazinyl)carbonyl]-2-ethyl-1,2-dihydro-6,7-dimethoxy-4-isoquinolin-1-one, 4-{[4-(2-furanylcarbonyl)-1-piperazinyl]carbonyl}-2-ethyl-1,2-dihydro-6,7-dimethoxy-4-isoquinolin-1-one, 4-[(3,4-dihydro-1(2H)quinolinyl)carbonyl]-2-ethyl-1,2-dihydro-6,7-dimethoxy-4-isoquinolin-1-one, N-[(2-ethyl-1,2-dihydro-6,7-dimethoxy-1-oxo-4-isoquinolinyl)carbonyl]glycine methyl ester, N-[(2-(2-methylpropyl)-1,2-dihydro-6,7-dimethoxy-1-oxo-4-isoquinolinyl)carbonyl]glycine methyl ester, N-[(2-ethyl-1,2-dihydro-6,7-dimethoxy-1-oxo-4-isoquinolinyl)carbonyl]glycine ethyl ester, the pharmaceutically acceptable salts thereof, the N-oxides thereof, the prodrugs thereof, the hydrates thereof, the tautomers the and the pharmaceutically acceptable salts of said N-oxides, prodrugs, tautomers or hydrates.

The compounds of the invention of the general formulae I, Ia, Ib, Ic and Id and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

Compounds of the formula I, wherein Y is oxygen, can be prepared e.g. by reacting a compound of the formula II with an amine of the formula III, as depicted in scheme 1.

Scheme I:

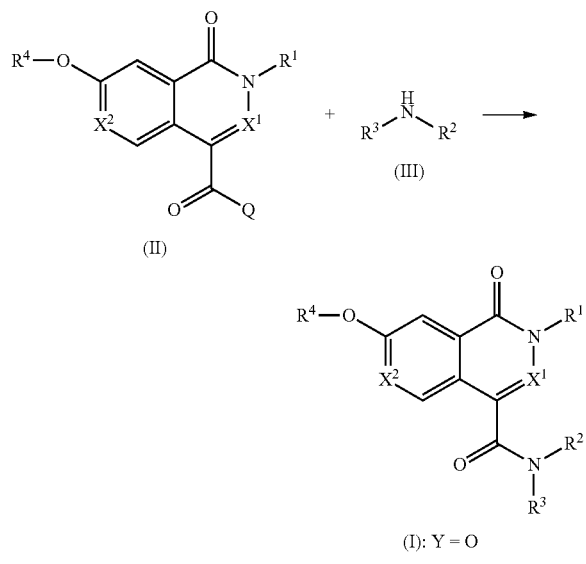

where $X^1$, $X^2$, $R^1$, $R^2$, $R^3$ and $R^4$ are as defined above. Q is a suitable leaving group such as chlorine, bromine or OH or a radical of an activated ester such as para-nitrophenoxy, pentafluorophenoxy, N-hydroxysuccinimide or hydroxybenzotriazol-1-yl. suitable reaction conditions have been described e.g. in Houben-Weyl: "Methoden der organ. Chemie" [Methods of Organic Chemistry], Georg-Thieme-Verlag, Stuttgart, New York 1985, Volume E5, pp. 941-1045).

The reaction of II with III may be performed in the presence of a base. Suitable base include but are not limited to If Q is OH, the reaction may be performed in the presence of a coupling agent.

Suitable coupling agents are, for example:

coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;

coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun 1972, 942];

coupling agents based on phosphonium salts, for example (benzotriazol-1-yloxy)tris(dimethylamino)phosphonium hexafluorophosphate [B. Castro, J. R. Domoy, G. Evin, C. Selve, Tetrahedron Lett. 1975, 14, 1219], (benzotriazol-1-yl-oxy)tripyrrolidinophosphonium hexafluorophosphate [J. Coste et al., Tetrahedron Lett. 1990, 31, 205];

coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];

coupling agents which form acid chlorides, for example bis-(2-oxo-oxazolidinyl)phosphinic chloride [J. Diago-Mesequer, Synthesis 1980, 547].

Apart from that, compounds of the formula I and likewise compounds of the formula II, where Q is S can be prepared by successively reacting compounds of the formulae I and II, where Q is O with a suitable sulfurizing agent, such as Lawenson's reagent or $P_2S_5$.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The compounds of the formulae II and III are well known in the art or can be prepared by anology to well established reactions of organic synthetic chemistry or by analogy to the methods as described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein.

The compounds of the formula II, where Q is OH can be easily transformed into compounds of the formula II, where Q is halogen, in particular chlorine by a suitable chlorination agent such as thionylchloride or oxalyl chloride.

Compounds of the formula II, where $X^2$ is C—$R^5$, where $R^5$ is a radical O—$Z^5$—$Ar^5$ can be prepared e.g. by reacting compounds of the formula II, where $X^2$ is C—OH with a compound of formula HO—$Z^5$—$Ar^5$ (formula IV) in terms of a Mitsunobu reaction, i.e. in the presence of dialkyl azodicarboxylate and triphenylphosphine (for suitable reaction conditions see e.g. A. J. Reynolds et al. Curr. Org. Chem. 13(16) (2009) pp. 1610-16-32; K. C. Swamy et al., Chem. Rev. 109(6) (2009), pp. 2551-2651; D. L. Hughes, Organic Preparations and Procedures International 28(2) (1996), pp. 127-164.

Compounds of the formula II, where $X^1$ is CH and Q is OH (compounds IIa), can be prepared e.g. according to the following reaction scheme 2:

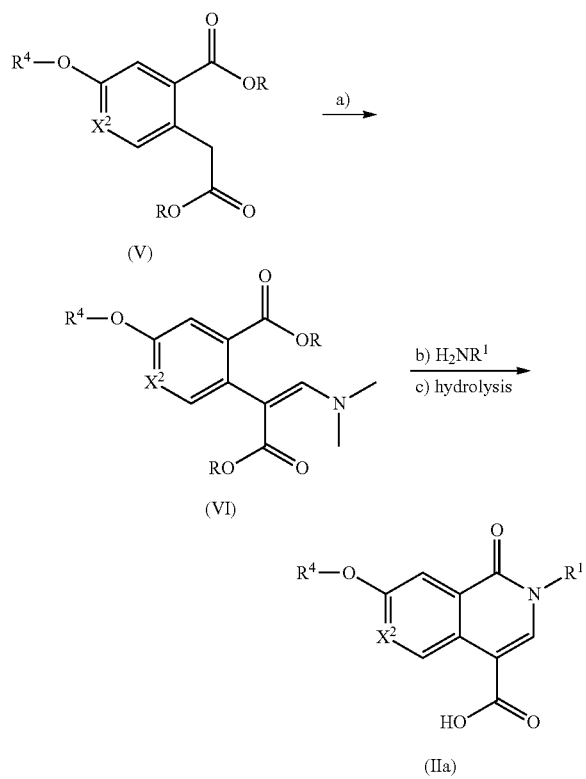

In scheme 2, $X^2$, $R^1$ and $R^4$ are as defined above. R is $C_1$-$C_4$-alkyl, in particular methyl.

Step a) is performed by reacting a compound of the formula V with dimethoxymethyl dimethylamine (also termed dimethylformamide dimethylacetal). Thereby the compound of formula VI is obtained, which can be cyclised in step b) to the compound of formula II, where Q is methoxy, by reaction with a primary amine of the formula $H_2N$—$R^1$ (compound VII). Subsequent hydrolysis of the primarily obtained ester in step c) yields the compound of the formula II, where $X^1$ is CH and Q is OH.

Compounds of the formula II, where $X^1$ is N and Q is OH (compounds III)), can be prepared e.g. according to the following reaction scheme 3:

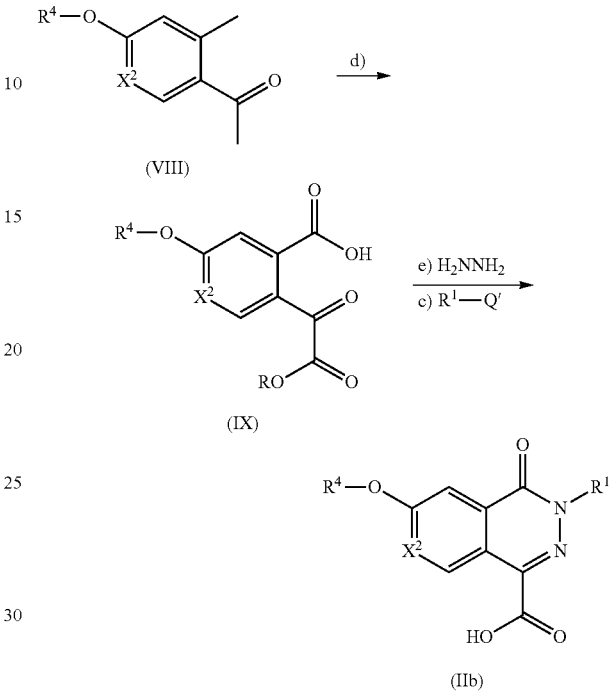

In scheme 3, $X^2$, $R^1$ and $R^4$ are as defined above.

Step d) is performed by reacting a compound of the formula VIII with an excess of a suitable oxidising agent in the presence of water, e.g. aqueous potassium permanganate. Thereby the compound of formula IX is obtained, which can be cyclised in step e) to a phthalazinone or phthalazinone analogue by reaction with hydrazine. Subsequent alkylation with an alkylating agent of formula $R^1$-Q' in step f) yields the compound of the formula II, where $X^1$ is CH and Q is OH.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from −10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian; a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance use disorders in a mammalian;
a method for treating or ameliorating the symptoms associated with diet-induced obesity in a mammalian;
a method for treating, controlling, ameliorating or reducing the risk of cognitive disturbances associated with Alzheimer's disease in a mammalian; a method for treating, controlling, ameliorating or reducing the risk of behavioral symptoms in Alzheimer's disease;
a method for treating, controlling, ameliorating or reducing the risk of anxiety in a mammalian;
a method for treating, controlling, ameliorating or reducing the risk of Huntington's disease in a mammalian;
which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe ftir Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

EXAMPLES

The compounds were either characterized via proton-NMR in $d_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Abbreviations

DMSO dimethylsulfoxide
DMF dimethylformamide
DMA dimethylacetamide
MeOH methanol
EtOH ethanol
AcOH acetic acid
EtOAc ethyl acetate
DCM dichloromethane
DIPEA or DIEA diisoproylethyl amine
TFA trifluoroacetic acid
HATU 2-(1H-7-azabenzotriazol-1-yl)-1,1,3,3-tetramethyl uronium hexafluorophosphate methanaminium
PS-TFP 4-hydroxy-2,3,5,6-tetrafluorobenzamidomethyl polystyrene
r.t. room temperature
RT retention time
Prep-TLC preperative thin layer chromatography

I. PREPARATION EXAMPLES

Example 1

2-Ethyl-6,7-dimethoxy-1-oxo-1,2-dihydro-isoquinoline-4-carboxylic acid butylamide 1.1 2-(2-Carboxy-4,5-dimethoxy-phenyl)-malonic acid dimethyl ester To rapidly stirred cold (0° C.) dimethyl malonate (20 mL) was added sodium (423 mg, 18.38 mmol) in portions. After the addition was complete, the mixture was stirred until the sodium disappeared and the mixture turned to a white colloidal suspension. Cuprous bromide (110 mg, 0.7660 mmol) and 2-bromo-4, 5-dimethoxybenzoic acid (2.00 g, 7.760 mmol) were added. The mixture was heated at 70° C. for 6 h. The reaction mixture was dissolved in water and extracted with toluene and EtOAc. The aqueous layer was acidified with HCl (2 N). The mixture was then extracted with EtOAc, dried over $Na_2SO_4$, filtered and concentrated in vacuo to give the product as an oil. After standing overnight the title compound was obtained as a solid (1.3 g, yield 54%).

$^1$H NMR (CDCl$_3$/TMS, 400 MHz) δ: 7.58 (s, 1H, ArH), 6.92 (s, 1H, ArH), 5.98 (s, 1H, CH), 3.87 (s, 3H, CH$_3$), 3.72 (s, 3H, CH$_3$).

LCMS (ESI+): m/z 313 (M+H)$^+$, RT: 1.29 min.

1.2 2-(2-Carboxy-4,5-dimethoxy-phenyl)-malonic acid

A solution of sodium hydroxide (1.92 g, 48.03 mmol) in water (20 mL) was added over 30 min to a solution of the compound obtained in step 1.1 (3.0 g, 9.6 mmol) in methanol (30 mL) at room temperature. After stirred for 3 h, methanol was removed under reduced pressure, and the contents were acidified with HCl (conc.) at r.t. to pH 3. The resulting white aqueous suspension was extracted twice with EtOAc (100 mL), and the organic layer was dried over $Na_2SO_4$. After filtration and concentration in vacuo the title product was obtained as a white solid (1.8 g, 67%).

$^1$H NMR (DMSO-d$_6$/TMS, 400 MHz) δ: 12.67 (s, 3H, COOH), 7.48 (s, 1H, ArH), 6.88 (s, 1H, ArH), 5.76 (s, 1H, CH), 3.81 (s, 3H, CH$_3$), 3.78 (s, 3H, CH$_3$).

LCMS (ESI+): m/z 307 (M+Na)$^+$, RT: 0.71 min.

1.3 2-Carboxymethyl-4,5-dimethoxy-benzoic acid

The product obtained in step 1.2 (1.8 g, 6.4 mmol) was suspended in toluene (40 mL), and the suspension was heated at 105° C. overnight. The precipitates were removed by filtration. The filtrate was concentrated to afford the title product as a white solid. This was used in the next step without further purification.

LCMS (ESI+): m/z 263 (M+Na)$^+$, RT: 1.32 min.

1.4 4,5-Dimethoxy-2-methoxycarbonylmethyl-benzoic acid methyl ester

Thionyl chloride (0.74 g, 6.245 mmol) was added dropwise to a solution of the compound obtained in step 1.3 (0.50 g, 2.082 mmol) in methanol (5 mL) at ambient temperature. After the addition was completed, the mixture was then heated at 65° C. overnight. The solvent was concentrated in vacuo. The concentrate was diluted with EtOAc (50 mL) and washed with saturated aqueous NaHCO$_3$ (10 mL), water (10 mL) and brine (10 mL). The organic layer was dried over Na$_2$SO$_4$, filtered and concentrated. The residue was purified on silica gel column (petrol ether:EtOAc=5:1) to afford the title product as a white solid (0.5 g, 60%).

$^1$H NMR (CDCl$_3$/TMS, 400 MHz) δ: 7.56 (s, 1H, ArH), 6.72 (s, 1H, ArH), 3.97 (s, 2H, CH$_2$), 3.93 (s, 3H, CH$_3$), 3.92 (s, 3H, CH$_3$), 3.86 (s, 3H, CH$_3$), 3.71 (s, 3H, CH$_3$).

LCMS (ESI+): m/z 269 (M+H)$^+$, RT: 1.69 min.

1.5 2-(2-Dimethylamino-1-methoxycarbonylvinyl)-4,5-dimethoxy-benzoic acid methyl ester A mixture of the compound obtained in step 1.4 (2.05 g, 7.641 mmol) in DMF-DMA (20 mL) was heated at 90° C. overnight. The reaction mixture was concentrated in vacuo. The residue was diluted with EtOAc and washed with brine. The organic layer was dried over Na$_2$SO$_4$, filtered and concentrated in vacuo. The residue was purified on silica gel column (petrol ether:EtOAc=3:1) to afford the title product as a white solid (0.78 g, 32%).

$^1$H NMR (CDCl$_3$/TMS, 400 MHz) δ: 7.43 (s, 1H, ArH), 7.38 (s, 1H, ArH), 6.59 (s, 1H, CH), 3.86 (s, 3H, CH$_3$), 3.84 (s, 3H, CH$_3$), 3.73 (s, 3H, CH$_3$), 3.53 (s, 3H, CH$_3$), 2.61 (s, 6H, N(CH$_3$)$_2$).

LCMS (ESI+): m/z 265 (M+H)$^+$, RT: 1.52 min.

1.6 2-Ethyl-6,7-dimethoxy-1-oxo-1,2-dihydroisoquinoline-4-carboxylic acid methyl ester A mixture of the compound obtained in step 1.5 (80 mg, 0.2474 mmol), ethylamine hydrochloride (61 mg, 0.7423 mmol) and DIPEA (1 mL) in methanol (5 mL) was heated at reflux overnight. The solvent was removed under reduced pressure. The residue was diluted with EtOAc (50 mL) and washed with HCl (2 N, 10 mL) and brine (10 ML). The organic layer was dried over Na$_2$SO$_4$, filtered and concentrated in vacuo to afford the title product as a white solid (68 mg, yield 95%). The product was pure enough to be used in the next step without further purification.

$^1$H NMR (CDCl$_3$/TMS, 400 MHz) δ: 8.40 (s, 1H, ArH), 8.13 (s, 1H, ArH), 7.83 (s, 1H, ArH), 4.12 (q, J=6.8 Hz, J=7.2 Hz, 2H, CH$_2$), 4.05 (s, 3H, CH$_3$), 4.01 (s, 3H, CH$_3$), 3.91 (s, 3H, CH$_3$), 1.43 (t, J=7.6 Hz, 3H, CH$_3$).

LCMS (ESI+): m/z 292 (M+H)$^+$, RT: 1.75 min.

1.7 2-Ethyl-6,7-dimethoxy-1-oxo-1,2-dihydroisoquinoline-4-carboxylic acid

A mixture of the compound obtained in step 1.6 (254 mg, 0.8720 mmol) and sodium hydroxide (42 mg, 1.046 mmol) in methanol (6 mL) and water (2 mL) was heated at 40° C. for 6 h. The reaction mixture was concentrated in vacuo. The concentrate was acidified with HCl (conc.) to pH=2~3. The resulting precipitates were collected by filtration. The solid was dried in vacuo and used in the next step without further purification (200 mg, yield 83%).

LCMS (ESI+): m/z 278 (M+H)$^+$, RT: 1.50 min.

1.8 2-Ethyl-6,7-dimethoxy-1-oxo-1,2-dihydro-iso-quinoline-4-carboxylic acid butylamide A suspension of the compound obtained in step 1.7 (50 mg, 0.1803 mmol) and thionyl chloride (64 mg, 0.5409 mmol) in DCM (3 mL) was refluxed for 3 h. The mixture was concentrated in vacuo and diluted in DCM (3 mL). The solution was added dropwise to a mixture of n-butylamine (26 mg, 0.3606 mmol) and triethylamine (55 mg, 0.5409 mmol) in DCM (4 mL) at ambient temperature. The reaction mixture was stirred at r.t. for another 3 h. Then the solvent was removed under reduced pressure, the residue was diluted with EtOAc and washed with HCl (2 N), NaOH (2 N) and brine successively. The organic layer was dried over Na$_2$SO$_4$, filtered and concentrated in vacuo. The residue was purified on silica gel column (eluted with DCM/EtOAc=4:1, v/v) to afford the title product as a white solid (53 mg, yield 88%).

LCMS: 1.70 min; M+H: 333.1

$^1$H NMR (CDCl$_3$/TMS, 400 MHz) δ: 7.80 (s, 1H, ArH), 7.57 (s, 1H, ArH), 7.35 (s, 1H, ArH), 5.96 (s, 1H, NH), 4.05 (q, J=7.6 Hz, 2H, CH$_2$), 4.01 (s, 3H, OCH$_3$), 3.99 (s, 3H, OCH$_3$), 3.48 (q, J=5.6 Hz, 2H, CH$_2$), 1.59-1.69 (m, 2H, CH$_2$), 1.41-1.51 (m, 2H, CH$_2$), 1.39 (t, J=6.8 Hz, 3H, CH$_3$), 0.99 (t, J=7.2 Hz, 3H, CH$_3$).

The following compounds were synthesized analogously, using in the last reaction step the respective amine.

Example 2

2-Ethyl-6,7-dimethoxy-1-oxo-1,2-dihydro-isoquinoline-4-carboxylic acid methylamide LCMS: 1.54 min; M+H: 291

$^1$H NMR (CDCl$_3$/TMS, 400 MHz) δ: 7.72 (s, 1H), 7.52 (s, 1H), 7.29 (s, 1H), 5.97 (s, 1H), 3.96 (m, 2H), 3.93 (s, 3H), 3.92 (s, 3H), 2.97 (d, J=4.8 Hz, 2H), 1.31 (t, J=7.2 Hz, 3H).

Example 3

2-Ethyl-6,7-dimethoxy-1-oxo-1,2-dihydro-isoquinoline-4-carboxylic acid ethylamide LCMS: 1.62 min; M+H: 305

$^1$H NMR (CDCl$_3$/TMS, 400 MHz) δ: 7.80 (s, 1H), 7.59 (s, 1H), 7.35 (s, 1H), 5.94 (s, 1H), 4.04 (m, 2H), 4.00 (s, 3H), 3.99 (s, 3H), 3.52 (m, 2H), 1.39 (t, J=7.2 Hz, 3H), 1.30 (t, J=7.4 Hz, 3H).

Example 4

2-Ethyl-6,7-dimethoxy-1-oxo-1,2-dihydro-isoquinoline-4-carboxylic acid (2-fluoro-ethyl)-amide LCMS: 1.56 min; M+H: 323

$^1$H NMR (CDCl$_3$/TMS, 400 MHz) δ: 7.75 (s, 1H), 7.53 (s, 1H), 7.37 (s, 1H), 6.26 (s, 1H), 4.66 (t, J=4.6 Hz, 1H), 4.54

(t, J=4.8 Hz, 1H), 3.99 (m, 2H), 3.94 (s, 3H), 3.92 (s, 3H), 3.77 (m, 1H), 3.70 (m, 1H), 1.33 (t, J=7.2 Hz).

Example 5

2-Ethyl-6,7-dimethoxy-1-oxo-1,2-dihydro-isoquinoline-4-carboxylic acid (2,2,2-trifluoro-ethyl)-amide LCMS: 1.77 min; M+H: 359
$^1$H NMR (CDCl$_3$/TMS, 400 MHz) δ: 7.81 (s, 1H), 7.52 (s, 1H), 7.46 (s, 1H), 6.21 (s, 1H), 4.13-4.18 (m, 2H), 4.06 (m, 2H), 4.01 (s, 3H), 3.99 (s, 3H), 1.41 (t, J=5.6 Hz, 3H).

Example 6

2-Ethyl-6,7-dimethoxy-1-oxo-1,2-dihydro-isoquinoline-4-carboxylic acid cyclopropylamide LCMS: 1.50 min; M+H: 317
$^1$H NMR (CDCl$_3$/TMS, 400 MHz) δ: 7.71 (s, 1H), 7.56 (s, 1H), 7.24 (s, 1H), 6.06 (s, 1H), 3.96 (m, 2H), 3.93 (s, 3H), 3.92 (s, 3H), 2.85-2.88 (m, 1H), 1.31 (t, J=7.4 Hz, 3H), 0.83-0.86 (m, 2H), 0.57-0.62 (m, 2H).

Example 7

2-Ethyl-6,7-dimethoxy-1-oxo-1,2-dihydro-isoquinoline-4-carboxylic acid isopropylamide LCMS: 1.58 min; M+H: 319
$^1$H NMR (CDCl$_3$/TMS, 400 MHz) δ: 7.75 (s, 1H), 7.51 (s, 1H), 7.27 (s, 1H), 5.65 (s, 1H), 4.20-4.29 (m, 1H), 3.97-4.03 (m, 2H), 3.94 (s, 3H), 3.92 (s, 3H), 1.33 (t, J=7.2 Hz, 3H), 1.24 (d, J=6.4 Hz, 6H).

Example 8

2-Ethyl-6,7-dimethoxy-1-oxo-1,2-dihydro-isoquinoline-4-carboxylic acid propylamide LCMS: 1.59 min; M+H: 319
$^1$H NMR (CDCl$_3$/TMS, 400 MHz) δ: 7.75 (s, 1H), 7.52 (s, 1H), 7.30 (s, 1H), 5.85 (s, 1H), 3.97-4.03 (m, 2H), 3.94 (s, 3H), 3.92 (s, 3H), 3.38 (br, 2H), 1.59-1.65 (m, 2H), 1.33 (t, J=6.8 Hz, 3H), 0.97 (t, J=7.4 Hz, 3H).

Example 9

2-Ethyl-6,7-dimethoxy-1-oxo-1,2-dihydro-isoquinoline-4-carboxylic acid cyclobutylamide LCMS: 1.74 min; M+H: 331
$^1$H NMR (CDCl$_3$/TMS, 400 MHz) δ: 7.84 (s, 1H), 7.60 (s, 1H), 7.40 (s, 1H), 6.02 (s, 1H), 4.63 (br, 1H), 4.10 (br, 2H), 4.01 (s, 3H), 4.00 (s, 3H), 2.48 (br, 2H), 1.99 (m, 2H), 1.80 (br, 2H), 1.41 (br, 3H).

Example 10

2-Ethyl-6,7-dimethoxy-1-oxo-1,2-dihydro-isoquinoline-4-carboxylic acid cyclopropylmethyl-amide LCMS: 1.72 min; M+H: 331
$^1$H NMR (CDCl$_3$/TMS, 400 MHz) δ: 7.76 (s, 1H), 7.54 (s, 1H), 7.34 (s, 1H), 5.94 (s, 1H), 3.99-4.04 (m, 2H), 3.94 (s, 3H), 3.93 (s, 3H), 3.26-3.29 (m, 2H), 1.34 (t, J=7.2 Hz, 3H), 0.98-1.07 (m, 1H), 0.51-0.55 (m, 2H), 0.23-0.27 (m, 2H).

Example 11

2-Ethyl-6,7-dimethoxy-1-oxo-1,2-dihydro-isoquinoline-4-carboxylic acid tert-butylamide LCMS: 1.72 min; M+H: 333
$^1$H NMR (CDCl$_3$/TMS, 400 MHz) δ: 7.75 (s, 1H), 7.45 (s, 1H), 7.26 (s, 1H), 5.66 (s, 1H), 3.97-4.01 (m, 2H), 3.94 (s, 3H), 3.92 (s, 3H), 1.44 (s, 9H), 1.33 (t, J=7.0 Hz, 3H).

Example 12

2-Ethyl-6,7-dimethoxy-1-oxo-1,2-dihydro-isoquinoline-4-carboxylic acid sec-butylamide LCMS: 1.67 min; M+H: 333
$^1$H NMR (CDCl$_3$/TMS, 400 MHz) δ: 7.75 (s, 1H), 7.49 (s, 1H), 7.28 (s, 1H), 5.63 (s, 1H), 4.08 (m, 1H), 3.98-4.01 (m, 2H), 3.94 (s, 3H), 3.92 (s, 3H), 1.49-1.55 (m, 2H), 1.33 (t, J=7.0 Hz, 3H), 1.21 (d, J=6.8 Hz, 3H), 0.95 (t, J=7.4 Hz, 3H).

Example 13

2-Ethyl-6,7-dimethoxy-1-oxo-1,2-dihydro-isoquinoline-4-carboxylic acid isobutyl-amide LCMS: 1.69 min; M+H: 333
$^1$H NMR (CDCl$_3$/TMS, 400 MHz) δ: 7.75 (s, 1H), 7.50 (s, 1H), 7.29 (s, 1H), 5.88 (s, 1H), 3.97-4.02 (m, 2H), 3.94 (s, 3H), 3.92 (s, 3H), 3.25 (t, J=6.4 Hz, 2H), 1.84-1.90 (m, 1H), 1.33 (t, J=7.2 Hz, 3H), 0.96 (d, J=6.4 Hz, 6H).

Example 14

2-Ethyl-6,7-dimethoxy-1-oxo-1,2-dihydro-isoquinoline-4-carboxylic acid cyclopentylamide LCMS: 1.71 min; M+H: 345
$^1$H NMR (CDCl$_3$/TMS, 400 MHz) δ: 7.75 (s, 1H), 7.50 (s, 1H), 7.27 (s, 1H), 5.77 (s, 1H), 4.34-4.39 (m, 1H), 3.97-4.02 (m, 2H), 3.94 (s, 3H), 3.92 (s, 3H), 2.05-2.10 (m, 2H), 1.61-1.69 (m, 4H), 1.43-1.46 (m, 2H), 1.33 (t, J=7.2 Hz, 3H).

Example 15

2-Ethyl-6,7-dimethoxy-1-oxo-1,2-dihydro-isoquinoline-4-carboxylic acid (1-methyl-butyl)-amide LCMS: 1.88 min; M+H: 347
$^1$H NMR (CDCl$_3$/TMS, 400 MHz) δ: 7.82 (s, 1H), 7.56 (s, 1H), 7.34 (s, 1H), 5.67 (s, 1H), 4.21-4.27 (m, 1H), 4.05-4.09 (m, 2H), 4.01 (s, 3H), 3.99 (s, 3H), 1.52-1.59 (m, 2H), 1.43-1.48 (m, 2H), 1.40 (t, J=5.4 Hz, 3H), 1.28 (d, J=5.2 Hz, 3H), 0.98 (t, J=5.6 Hz, 3H).

Example 16

2-Ethyl-6,7-dimethoxy-1-oxo-1,2-dihydro-isoquinoline-4-carboxylic acid (1,1-dimethyl-propyl)-amide LCMS: 1.91 min; M+H: 347
$^1$H NMR (CDCl$_3$/TMS, 400 MHz) δ: 7.86 (s, 1H), 7.53 (s, 1H), 7.41 (s, 1H), 5.63 (s, 1H), 4.13 (m, 2H), 4.03 (s, 3H), 4.00 (s, 3H), 1.88-1.93 (m, 2H), 1.46 (s, 6H), 1.41 (br, 3H), 0.97 (t, J=5.8 Hz, 3H).

Example 17

2-Ethyl-6,7-dimethoxy-1-oxo-1,2-dihydro-isoquinoline-4-carboxylic acid (1,2-dimethyl-propyl)-amide LCMS: 1.86 min; M+H: 347
$^1$H NMR (CDCl$_3$/TMS, 400 MHz) δ: 7.76 (s, 1H), 7.48 (s, 1H), 7.27 (s, 1H), 5.61 (s, 1H), 3.96-4.03 (m, 3H), 3.94 (s, 3H), 3.92 (s, 3H), 1.77 (m, 1H), 1.34 (t, J=7.2 Hz, 3H), 1.16 (d, J=6.8 Hz, 3H), 0.94 (d, J=4.0 Hz, 3H), 0.93 (d, J=4.0 Hz, 3H).

Example 18

2-Ethyl-6,7-dimethoxy-1-oxo-1,2-dihydro-isoquinoline-4-carboxylic acid (2,2-dimethyl-propyl)-amide LCMS: 1.89 min; M+H: 347
$^1$H NMR (CDCl$_3$/TMS, 400 MHz) δ: 7.83 (s, 1H), 7.55 (s, 1H), 7.37 (s, 1H), 5.99 (s, 1H), 4.07 (br, 2H), 4.01 (s, 3H), 3.98 (s, 3H), 3.31 (s, 2H), 1.40 (s, 3H), 1.03 (s, 9H).

Example 19

2-Ethyl-6,7-dimethoxy-1-oxo-1,2-dihydro-isoquinoline-4-carboxylic acid (1-ethyl-propyl)-amide LCMS: 1.86 min; M+H: 347
$^1$H NMR (CDCl$_3$/TMS, 400 MHz) δ: 7.83 (s, 1H), 7.55 (s, 1H), 7.35 (s, 1H), 5.55 (s, 1H), 4.03-4.09 (m, 3H), 4.01 (s, 3H), 3.98 (s, 3H), 1.64-1.70 (m, 2H), 1.51-1.55 (m, 2H), 1.41 (t, J=7.0 Hz, 3H), 1.02 (t, J=7.4 Hz, 6H).

Example 20

2-Ethyl-6,7-dimethoxy-1-oxo-1,2-dihydro-isoquinoline-4-carboxylic acid (2-methyl-butyl)-amide LCMS: 1.89 min; M+H: 347
$^1$H NMR (CDCl$_3$/TMS, 400 MHz) δ: 7.76 (s, 1H), 7.50 (s, 1H), 7.29 (s, 1H), 5.83 (s, 1H), 3.98-4.03 (m, 2H), 3.94 (s, 3H), 3.92 (s, 3H), 3.33-3.39 (m, 1H), 3.21-3.27 (m, 1H), 1.61-1.68 (m, 1H), 1.41-1.47 (m, 1H), 1.33 (t, J=5.6 Hz, 3H), 1.16-1.22 (m, 1H), 0.94 (d, J=5.6 Hz, 3H), 0.90 (t, J=6.0 Hz, 3H).

Example 21

2-Ethyl-6,7-dimethoxy-1-oxo-1,2-dihydro-isoquinoline-4-carboxylic acid pentylamide LCMS: 1.91 min; M+H: 347
$^1$H NMR (CDCl$_3$/TMS, 400 MHz) δ: 7.84 (s, 1H), 7.61 (s, 1H), 7.40 (s, 1H), 5.92 (s, 1H), 4.08-4.11 (m, 2H), 4.03 (s, 3H), 4.01 (s, 3H), 3.47-3.51 (s, 2H), 1.68 (m, 2H), 1.42 (m, 7H), 0.96 (t, J=7.2 Hz, 3H).

Example 22

2-Ethyl-6,7-dimethoxy-1-oxo-1,2-dihydro-isoquinoline-4-carboxylic acid cyclohexylamide LCMS: 1.90 min; M+H: 359
$^1$H NMR (CDCl$_3$/TMS, 400 MHz) δ: 7.75 (s, 1H), 7.51 (s, 1H), 7.29 (s, 1H), 5.69 (s, 1H), 3.98-4.02 (m, 3H), 3.94 (s, 3H), 3.92 (s, 3H), 2.01-2.03 (m, 2H), 1.71-1.73 (m, 2H), 1.38-1.42 (m, 2H), 1.33 (t, J=4.8 Hz, 3H), 1.16-1.22 (m, 4H).

Example 23

2-Ethyl-6,7-dimethoxy-1-oxo-1,2-dihydro-isoquinoline-4-carboxylic acid (1,3-dimethyl-butyl)-amide LCMS: 1.97 min; M+H: 361
$^1$H NMR (CDCl$_3$/TMS, 400 MHz) δ: 7.74 (s, 1H), 7.45 (s, 1H), 7.25 (s, 1H), 5.62 (s, 1H), 4.23-4.27 (m, 1H), 3.96-4.02 (m, 2H), 3.94 (s, 3H), 3.92 (s, 3H), 1.65 (m, 1H), 1.41 (m, 1H), 1.33 (m, 4H), 1.21 (d, J=6.4 Hz, 3H), 0.93 (d, J=6.4 Hz, 3H), 0.90 (d, J=6.8 Hz, 3H).

Example 24

2-Ethyl-6,7-dimethoxy-1-oxo-1,2-dihydro-isoquinoline-4-carboxylic acid (3,3-dimethyl-butyl)-amide LCMS: 1.98 min; M+H: 361
$^1$H NMR (CDCl$_3$/TMS, 400 MHz) δ: 7.75 (s, 1H), 7.54 (s, 1H), 7.28 (s, 1H), 5.71 (s, 1H), 3.98-4.02 (m, 2H), 3.94 (s, 3H), 3.93 (s, 3H), 3.42 (s, 2H), 1.48 (m, 2H), 1.33 (t, J=5.4 Hz, 3H), 0.93 (s, 9H).

Example 25

2-Ethyl-6,7-dimethoxy-1-oxo-1,2-dihydro-isoquinoline-4-carboxylic acid (2-ethyl-butyl)-amide LCMS: 1.98 min; M+H: 361
$^1$H NMR (CDCl$_3$/TMS, 400 MHz) δ: 7.84 (s, 1H), 7.56 (s, 1H), 7.38 (s, 1H), 5.87 (s, 1H), 4.06-4.10 (m, 2H), 4.02 (s, 3H), 3.99 (s, 3H), 3.44-3.46 (m, 2H), 1.52-1.55 (m, 1H), 1.40-1.45 (m, 7H), 0.96 (t, J=6.4 Hz, 3H).

Example 26

2-Ethyl-6,7-dimethoxy-1-oxo-1,2-dihydro-isoquinoline-4-carboxylic acid benzylamide LCMS: 1.84 min; M+H: 367
$^1$H NMR (CDCl$_3$/TMS, 400 MHz) δ: 7.82 (s, 1H), 7.56 (s, 1H), 7.33-7.42 (m, 6H), 6.16 (s, 1H), 4.67 (s, 2H), 4.03-4.07 (m, 2H), 4.00 (s, 3H), 3.90 (s, 3H), 1.39 (m, 3H).

Example 27

2-Ethyl-6,7-dimethoxy-1-oxo-1,2-dihydro-isoquinoline-4-carboxylic acid dicyclopropylmethyl-amide LCMS: 1.91 min; M+H: 371
$^1$H NMR (CDCl$_3$/TMS, 400 MHz) δ: 7.77 (s, 1H), 7.48 (s, 1H), 7.32 (s, 1H), 5.85 (s, 1H), 4.00-4.04 (m, 2H), 3.94 (s, 3H), 3.92 (s, 3H), 3.26 (m, 1H), 1.34 (t, J=7.0 Hz, 3H), 0.93 (m, 2H), 0.54 (m, 2H), 0.37-0.45 (m, 6H).

Example 28

2-Ethyl-6,7-dimethoxy-1-oxo-1,2-dihydro-isoquinoline-4-carboxylic acid cyclohexylmethyl-amide LCMS: 2.00 min; M+H: 373
$^1$H NMR (CDCl$_3$/TMS, 400 MHz) δ: 7.82 (s, 1H), 7.57 (s, 1H), 7.36 (s, 1H), 5.95 (s, 1H), 4.04-4.08 (m, 2H), 4.01 (s, 3H), 3.99 (s, 3H), 3.33 (s, 2H), 1.76-1.84 (m, 4H), 1.68-1.72 (m, 2H), 1.40 (s, 3H), 1.21-1.29 (m, 3H), 1.02-1.06 (m, 2H).

Example 29

2-Ethyl-6,7-dimethoxy-1-oxo-1,2-dihydro-isoquinoline-4-carboxylic acid (1-phenyl-ethyl)-amide LCMS: 1.89 min; M+H: 381
$^1$H NMR (CDCl$_3$/TMS, 400 MHz) δ: 7.69 (s, 1H), 7.38-7.40 (m, 2H), 7.31-7.35 (m, 4H), 7.22-7.25 (m, 1H), 6.25 (s, 1H), 5.33 (s, 1H), 3.92-3.96 (m, 2H), 3.89 (s, 3H), 3.76 (s, 3H), 1.59 (d, J=5.2 Hz, 3H), 1.31 (s, 3H).

Example 30

2-Ethyl-6,7-dimethoxy-1-oxo-1,2-dihydro-isoquinoline-4-carboxylic acid 2-fluoro-benzylamide LCMS: 1.86 min; M+H: 385
$^1$H NMR (CDCl$_3$/TMS, 400 MHz) δ: 7.81 (s, 1H), 7.53 (s, 1H), 7.46-7.49 (m, 1H), 7.41 (s, 1H), 7.30.7.33 (m, 1H), 7.15-7.18 (m, 1H), 7.08-7.12 (m, 1H), 6.28 (s, 1H), 4.72 (d, J=4.4 Hz, 2H), 4.03-4.08 (m, 2H), 4.00 (s, 3H), 3.92 (s, 3H), 1.38 (d, J=5.8 Hz, 3H).

Example 31

2-Ethyl-6,7-dimethoxy-1-oxo-1,2-dihydro-isoquinoline-4-carboxylic acid 3-fluoro-benzylamide LCMS: 1.87 min; M+H: 385
$^1$H NMR (CDCl$_3$/TMS, 400 MHz) δ: 7.82 (s, 1H), 7.58 (s, 1H), 7.42 (s, 1H), 7.33-7.37 (m, 1H), 7.18 (d, J=6.0 Hz, 1H), 7.13 (d, J=8.0 Hz, 1H), 7.00-7.04 (m, 1H), 6.22 (s, 1H), 4.67 (d, J=4.8 Hz, 2H), 4.04-4.08 (m, 2H), 4.00 (s, 3H), 3.94 (s, 3H), 1.39 (d, J=5.2 Hz, 3H).

Example 32

2-Ethyl-6,7-dimethoxy-1-oxo-1,2-dihydro-isoquinoline-4-carboxylic acid 4-fluoro-benzylamide LCMS: 1.86 min; M+H: 385
$^1$H NMR (CDCl$_3$/TMS, 400 MHz) δ: 7.78 (s, 1H), 7.55 (s, 1H), 7.38-7.41 (m, 3H), 7.05-7.09 (m, 2H), 6.32 (s, 1H), 4.63 (d, J=4.4 Hz, 2H), 4.00-4.04 (m, 2H), 3.98 (s, 3H), 3.92 (s, 3H), 1.37 (d, J=5.6 Hz, 3H).

Example 33

2-Ethyl-6,7-dimethoxy-1-oxo-1,2-dihydro-isoquinoline-4-carboxylic acid 2,3-difluoro-benzylamide LCMS: 1.90 min; M+H: 403
$^1$H NMR (CDCl$_3$/TMS, 400 MHz) δ: 7.81 (s, 1H), 7.54 (s, 1H), 7.41 (s, 1H), 7.24 (m, 1H), 7.08-7.16 (m, 2H), 6.29 (s, 1H), 4.73 (d, J=5.6 Hz, 2H), 4.04-4.07 (m, 2H), 4.00 (s, 3H), 3.94 (s, 3H), 1.39 (t, J=7.2 Hz, 3H).

Example 34

2-Ethyl-6,7-dimethoxy-1-oxo-1,2-dihydro-isoquinoline-4-carboxylic acid 2,4-difluoro-benzylamide LCMS: 1.90 min; M+H: 403
$^1$H NMR (CDCl$_3$/TMS, 400 MHz) δ: 7.74 (s, 1H), 7.47 (s, 1H), 7.36-7.43 (m, 1H), 7.32 (s, 1H), 6.76-6.85 (m, 2H), 6.17 (s, 1H), 4.59 (d, J=5.6 Hz, 2H), 3.96-4.01 (m, 2H), 3.93 (s, 3H), 3.87 (s, 3H), 1.32 (t, J=7.2 Hz, 3H).

Example 35

2-Ethyl-6,7-dimethoxy-1-oxo-1,2-dihydro-isoquinoline-4-carboxylic acid 2,6-difluoro-benzylamide LCMS: 1.86 min; M+H: 403
$^1$H NMR (CDCl$_3$/TMS, 400 MHz) δ: 7.75 (s, 1H), 7.47 (s, 1H), 7.25 (s, 1H), 7.19 (m, 1H), 6.88 (m, 2H), 6.16 (s, 1H), 4.71 (d, J=5.2 Hz, 2H), 3.96-4.01 (m, 2H), 3.93 (s, 3H), 3.87 (s, 3H), 1.32 (t, J=7.2 Hz, 3H).

Example 36

2-Ethyl-6,7-dimethoxy-1-oxo-1,2-dihydro-isoquinoline-4-carboxylic acid 3,4-difluoro-benzylamide LCMS: 1.91 min; M+H: 403
$^1$H NMR (CDCl$_3$/TMS, 400 MHz) δ: 7.74 (s, 1H), 7.51 (s, 1H), 7.33 (s, 1H), 7.06-7.17 (m, 3H), 6.17 (s, 1H), 4.55 (d, J=5.6 Hz, 2H), 3.96-4.02 (m, 2H), 3.93 (s, 3H), 3.88 (s, 3H), 1.32 (t, J=7.2 Hz, 3H).

Example 37

2-Ethyl-6,7-dimethoxy-1-oxo-1,2-dihydro-isoquinoline-4-carboxylic acid 3,5-difluoro-benzylamide LCMS: 1.92 min; M+H: 403
$^1$H NMR (CDCl$_3$/TMS, 400 MHz) δ: 7.74 (s, 1H), 7.51 (s, 1H), 7.35 (s, 1H), 6.85-6.89 (m, 2H), 6.67-6.72 (m, 1H), 6.24 (s, 1H), 4.58 (d, J=6.0 Hz, 2H), 3.97-4.02 (m, 2H), 3.93 (s, 3H), 3.89 (s, 3H), 1.33 (t, J=7.0 Hz, 3H).

Example 38

2-Ethyl-6,7-dimethoxy-1-oxo-1,2-dihydro-isoquinoline-4-carboxylic acid phenethyl-amide LCMS: 1.88 min; M+H: 381
$^1$H NMR (CDCl$_3$/TMS, 400 MHz) δ: 7.79 (s, 1H), 7.55 (s, 1H), 7.33-7.36 (s, 2H), 7.25-7.28 (m, 3H), 7.16 (s, 1H), 5.88 (s, 1H), 3.93-4.01 (m, 8H), 3.76 (s, 2H), 3.00 (t, J=5.2 Hz, 3H), 1.36 (t, J=4.8 Hz, 3H).

Example 39

2-Ethyl-6,7-dimethoxy-1-oxo-1,2-dihydro-isoquinoline-4-carboxylic acid [1-(4-fluoro-phenyl)-ethyl]-amide LCMS: 1.92 min; M+H: 399
$^1$H NMR (CDCl$_3$/TMS, 400 MHz) δ: 7.77 (s, 1H), 7.41-7.44 (m, 3H), 7.35 (s, 1H), 7.07 (m, 2H), 6.23 (s, 1H), 5.37 (s, 1H), 4.01-4.04 (m, 2H), 3.97 (s, 3H), 3.88 (s, 3H), 1.64 (d, J=5.6 Hz, 2H), 1.38 (t, J=5.2 Hz, 3H).

Example 40

2-Ethyl-6,7-dimethoxy-1-oxo-1,2-dihydro-isoquinoline-4-carboxylic acid indan-1-ylamide LCMS: 1.94 min; M+H: 393
¹H NMR (CDCl₃/TMS, 400 MHz) δ: 7.75 (s, 1H), 7.58 (s, 1H), 7.34-7.38 (m, 2H), 7.17-7.23 (m, 3H), 6.05 (m, 1H), 5.66 (s, 1H), 3.96-4.00 (m, 2H), 3.93 (s, 3H), 3.90 (s, 3H), 2.97-3.03 (m, 1H), 2.86-2.71 (m, 1H), 2.64-2.71 (m, 1H), 1.89-1.95 (m, 1H), 1.32 (t, J=5.2 Hz, 3H).

Example 41

2-Ethyl-6,7-dimethoxy-1-oxo-1,2-dihydro-isoquinoline-4-carboxylic acid indan-2-ylamide LCMS: 1.93 min; M+H: 393
¹H NMR (CDCl₃/TMS, 400 MHz) δ: 7.80 (s, 1H), 7.47 (s, 1H), 7.39 (s, 1H), 7.28-7.30 (m, 2H), 7.20-7.22 (m, 2H), 6.15 (s, 1H), 4.96 (s, 1H), 3.98-4.05 (m, 5H), 3.83 (s, 3H), 3.43-3.48 (m, 2H), 2.96-3.01 (m, 2H), 1.37 (s, 3H).

Example 42

2-Ethyl-6,7-dimethoxy-1-oxo-1,2-dihydro-isoquinoline-4-carboxylic acid [1-(4-fluoro-phenyl)-1-methyl-ethyl]-amide LCMS: 1.98 min; M+H: 413
¹H NMR (CDCl₃/TMS, 400 MHz) δ: 7.82 (s, 1H), 7.44-7.47 (m, 3H), 7.39 (s, 1H), 7.03-7.07 (m, 2H), 6.18 (s, 1H), 4.06-4.10 (m, 2H), 4.00 (s, 3H), 3.92 (s, 3H), 1.84 (s, 6H), 1.42 (s, 3H).

Example 43

4-(Azetidine-1-carbonyl)-2-ethyl-6,7-dimethoxy-2H-isoquinolin-1-one

LCMS: 1.58 min; M+H: 317
¹H NMR (CDCl₃/TMS, 400 MHz) δ: 7.76 (s, 1H), 7.42 (s, 1H), 7.20 (s, 1H), 4.13 (t, J=7.6 Hz, 4H), 3.98-4.03 (m, 2H), 3.94 (s, 6H), 2.24-2.32 (m, 2H), 1.32 (t, J=7.2 Hz, 3H).

Example 44

2-Ethyl-6,7-dimethoxy-4-(2-methyl-pyrrolidine-1-carbonyl)-2H-isoquinolin-1-one

LCMS: 1.74 min; M+H: 345
¹H NMR (CDCl₃/TMS, 400 MHz) δ: 7.84 (s, 1H), 7.18 (s, 1H), 7.03 (br, 1H), 4.41 (br, 1H), 4.03-4.07 (m, 2H), 4.01 (s, 3H), 3.95 (s, 3H), 3.38 (br, 2H), 1.63-2.13 (m, 4H), 1.39 (t, J=5.6 Hz, 3H), 1.15-1.41 (br, 3H).

Example 45

2-Ethyl-6,7-dimethoxy-4-(morpholine-4-carbonyl)-2H-isoquinolin-1-one

LCMS: 1.54 min; M+H: 347
¹H NMR (CDCl₃/TMS, 400 MHz) δ: 7.78 (s, 1H), 7.10 (s, 1H), 6.87 (s, 1H), 3.97-4.03 (m, 2H), 3.94 (s, 3H), 3.91 (s, 3H), 3.48-3.64 (br, 8H), 1.33 (t, J=7.4 Hz, 3H).

Example 46

2-Ethyl-4-(3-fluoro-pyrrolidine-1-carbonyl)-6,7-dimethoxy-2H-isoquinolin-1-one

LCMS: 1.61 min; M+H: 349
¹H NMR (CDCl₃/TMS, 400 MHz) δ: 7.77 (s, 1H), 7.17 (s, 1H), 6.94 (s, 1H), 5.22-5.34 (br, 1H), 3.98-4.03 (m, 2H), 3.94 (s, 3H), 3.88 (s, 3H), 3.44-3.76 (br, 4H), 2.25 (br, 1H), 1.95-2.06 (br, 1H), 1.33 (t, J=7.0 Hz, 3H).

Example 47

2-Ethyl-6,7-dimethoxy-4-(4-methyl-piperazine-1-carbonyl)-2H-isoquinolin-1-one

LCMS: 1.52 min; M+H: 360
¹H NMR (CDCl₃/TMS, 400 MHz) δ: 7.77 (s, 1H), 7.09 (s, 1H), 6.86 (s, 1H), 3.97-4.01 (m, 2H), 3.94 (s, 3H), 3.91 (s, 3H), 3.61 (br, 4H), 2.41 (br, 4H), 2.30 (s, 3H), 1.33 (t, J=7.2 Hz, 3H).

Example 48

4-(3,3-Difluoro-pyrrolidine-1-carbonyl)-2-ethyl-6,7-dimethoxy-2H-isoquinolin-1-one LCMS: 1.74 min; M+H: 367
¹H NMR (CDCl₃/TMS, 400 MHz) δ: 7.85 (s, 1H), 7.23 (s, 1H), 7.00 (s, 1H), 4.06-4.10 (m, 2H), 4.02 (s, 3H), 3.97 (s, 3H), 3.86 (br, 4H), 2.43 (s, 2H), 1.40 (t, J=6.0 Hz, 3H).

Example 49

4-(3-Dimethylamino-pyrrolidine-1-carbonyl)-2-ethyl-6,7-dimethoxy-2H-isoquinolin-1-one LCMS: 1.55 min; M+H: 374
¹H NMR (CDCl₃/TMS, 400 MHz) δ: 7.84 (s, 1H), 7.22 (s, 1H), 7.03 (s, 1H), 4.04-4.09 (m, 2H), 4.01 (s, 3H), 3.97 (s, 3H), 2.81-3.57 (br, 4H), 1.61-2.33 (m, 9H), 1.39 (t, J=5.6 Hz, 3H).

Example 50

2-Ethyl-6,7-dimethoxy-4-((R)-2-methoxymethyl-pyrrolidine-1-carbonyl)-2H-isoquinolin-1-one LCMS: 1.72 min; M+H: 375
¹H NMR (CDCl₃/TMS, 400 MHz) δ: 7.84 (s, 1H), 7.25 (s, 1H), 7.13 (s, 1H), 4.45 (br, 1H), 4.06-4.10 (m, 2H), 4.01 (s, 3H), 3.97 (s, 3H), 3.37-3.49 (m, 5H), 1.76-2.08 (m, 4H), 1.41 (s, 3H).

Example 51

4-(1,3-Dihydro-isoindole-2-carbonyl)-2-ethyl-6,7-dimethoxy-2H-isoquinolin-1-one

LCMS: 1.86 min; M+H: 379
$^1$H NMR (CDCl$_3$/TMS, 400 MHz) δ: 7.87 (s, 1H), 7.27-7.37 (m, 4H), 7.16 (s, 1H), 7.01 (s, 1H), 5.07 (s, 2H), 4.75 (s, 2H), 4.07-4.11 (m, 2H), 4.02 (s, 3H), 3.90 (s, 3H), 1.42 (t, J=5.2 Hz, 3H).

Example 52

4-(4,4-Difluoro-piperidine-1-carbonyl)-2-ethyl-6,7-dimethoxy-2H-isoquinolin-1-one LCMS: 1.80 min; M+H: 381
$^1$H NMR (CDCl$_3$/TMS, 400 MHz) δ: 7.85 (s, 1H), 7.19 (s, 1H), 6.90 (s, 1H), 5.07 (s, 2H), 4.75 (s, 2H), 4.04-4.07 (m, 2H), 4.02 (s, 3H), 3.96 (s, 3H), 3.73 (br, 4H), 2.02 (br, 4H), 1.40 (t, J=5.4 Hz, 3H).

Example 53

2-Ethyl-4-(4-isopropyl-piperazine-1-carbonyl)-6,7-dimethoxy-2H-isoquinolin-1-one LCMS: 1.70 min; M+H: 388
$^1$H NMR (CDCl$_3$/TMS, 400 MHz) δ: 7.84 (s, 1H), 7.16 (s, 1H), 6.93 (s, 1H), 4.03-4.08 (m, 2H), 4.01 (s, 3H), 3.97 (s, 3H), 3.29-3.79 (br, 4H), 2.73 (s, 1H), 2.51 (br, 4H), 1.40 (t, J=5.6 Hz, 3H), 1.05 (d, J=4.8 Hz, 6H).

Example 54

4-(4-Dimethylamino-piperidine-1-carbonyl)-2-ethyl-6,7-dimethoxy-2H-isoquinolin-1-one LCMS: 1.50 min; M+H: 388
$^1$H NMR (CDCl$_3$/TMS, 400 MHz) δ: 7.84 (s, 1H), 7.14 (s, 1H), 6.92 (s, 1H), 4.08 (m, 2H), 4.01 (s, 3H), 3.96 (s, 3H), 2.96 (s, 2H), 2.35-2.43 (br, 7H), 1.97 (br, 2H), 1.53 (br, 4H), 1.39 (t, J=7.0 Hz, 3H).

Example 55

2-Ethyl-6,7-dimethoxy-4-(2-trifluoromethyl-pyrrolidine-1-carbonyl)-2H-isoquinolin-1-one LCMS: 1.89 min; M+H: 399
$^1$H NMR (CDCl$_3$/TMS, 400 MHz) δ: 7.83 (s, 1H), 7.32 (s, 1H), 7.09 (s, 1H), 5.16 (s, 1H), 4.02-4.12 (m, 2H), 4.01 (s, 3H), 3.94 (s, 3H), 3.47 (t, J=5.6 Hz, 2H), 2.15-2.25 (m, 2H), 2.04-2.09 (m, 1H), 1.88-1.93 (m, 1H), 1.41 (t, J=5.8 Hz, 3H).

Example 56

4-(4-Cyclopropylmethyl-piperazine-1-carbonyl)-2-ethyl-6,7-dimethoxy-2H-isoquinolin-1-one LCMS: 1.74 min; M+H: 400
$^1$H NMR (CDCl$_3$/TMS, 400 MHz) δ: 7.84 (s, 1H), 7.16 (s, 1H), 6.93 (s, 1H), 4.02-4.08 (m, 2H), 4.01 (s, 3H), 3.97 (s, 3H), 3.63 (br, 4H), 2.55 (br, 4H), 2.31 (s, 2H), 1.40 (t, J=6.4 Hz, 3H), 0.87 (s, 1H), 0.54 (s, 2H), 0.12 (s, 2H).

Example 57

2-Ethyl-6,7-dimethoxy-4-((S)-2-pyrrolidin-1-ylmethyl-pyrrolidine-1-carbonyl)-2H-isoquinolin-1-one LCMS: 1.65 min; M+H: 414
$^1$H NMR (CDCl$_3$/TMS, 400 MHz) δ: 7.84 (s, 1H), 7.26 (s, 1H), 7.05 (s, 1H), 4.59 (br, 1H), 4.04-4.42 (m, 2H), 4.01 (s, 3H), 3.96 (s, 3H), 3.45 (br, 2H), 2.76 (br, 6H), 1.38-2.05 (m, 8H), 1.40 (t, J=5.8 Hz, 3H).

Example 58

2-Ethyl-6,7-dimethoxy-4-(4-pyrrolidin-1-yl-piperidine-1-carbonyl)-2H-isoquinolin-1-one LCMS: 1.58 min; M+H: 414
$^1$H NMR (CDCl$_3$/TMS, 400 MHz) δ: 7.84 (s, 1H), 7.13 (s, 1H), 6.92 (s, 1H), 4.66 (br, 1H), 4.05 (s, 2H), 4.01 (s, 3H), 3.97 (s, 3H), 3.02 (br, 4H), 2.64 (br, 4H), 2.36 (br, 2H), 2.00 (br, 2H), 1.85 (br, 4H), 1.38 (t, J=6.0 Hz, 3H).

Example 59

4-[4-(2-Dimethylamino-ethyl)-piperazine-1-carbonyl]-2-ethyl-6,7-dimethoxy-2H-isoquinolin-1-one LCMS: 1.46 min; M+H: 417
$^1$H NMR (CDCl$_3$/TMS, 400 MHz) δ: 7.84 (s, 1H), 7.15 (s, 1H), 6.92 (s, 1H), 4.07 (s, 2H), 4.01 (s, 3H), 3.97 (s, 3H), 3.67 (br, 4H), 2.53-2.68 (m, 14H), 1.39 (t, J=5.6 Hz, 3H).

Example 60

4-([1,4']Bipiperidinyl-1'-carbonyl)-2-ethyl-6,7-dimethoxy-2H-isoquinolin-1-one

LCMS: 1.66 min; M+H: 428
$^1$H NMR (CDCl$_3$/TMS, 400 MHz) δ: 7.84 (s, 1H), 7.14 (br, 1H), 6.89 (br, 1H), 3.79-4.83 (b, 10H), 2.93 (br, 4H), 2.55 (br, 4H), 1.97 (br, 4H), 1.63 (br, 5H), 1.39 (t, J=5.6 Hz, 3H).

Example 61

4-[4-(3-Dimethylamino-propyl)-piperazine-1-carbonyl]-2-ethyl-6,7-dimethoxy-2H-isoquinolin-1-one LCMS: 1.45 min; M+H: 431
$^1$H NMR (CDCl$_3$/TMS, 400 MHz) δ: 7.84 (s, 1H), 7.14 (s, 1H), 6.92 (s, 1H), 4.06 (br, 2H), 4.01 (s, 3H), 3.97 (s, 3H), 3.63 (br, 4H), 2.80 (br, 2H), 2.59 (br, 6H), 2.46 (br, 6H), 1.92 (br, 2H), 1.39 (t, J=6.0 Hz, 3H).

Example 62

2-Ethyl-6,7-dimethoxy-4-[4-(2-pyrrolidin-1-yl-ethyl)-piperazine-1-carbonyl]-2H-isoquinolin-1-one LCMS: 1.48 min; M+H: 443

¹H NMR (CDCl₃/TMS, 400 MHz) δ: 7.77 (s, 1H), 7.08 (s, 1H), 6.85 (s, 1H), 3.99 (m, 2H), 3.94 (s, 3H), 3.90 (s, 3H), 3.56 (br, 4H), 2.45-2.67 (br, 11H), 1.81 (br, 5H), 1.32 (t, J=7.2 Hz, 3H).

Example 63

2-Ethyl-6,7-dimethoxy-1-oxo-1,2-dihydro-isoquinoline-4-carboxylic acid dimethylamide LCMS: 1.55 min; M+H: 305

¹H NMR (CDCl₃/TMS, 400 MHz) δ: 7.85 (s, 1H), 7.15 (s, 1H), 6.90 (s, 1H), 4.07 (br, 2H), 4.01 (s, 3H), 3.96 (s, 3H), 3.10 (br, 6H), 1.39 (t, J=4.8 Hz, 3H).

Example 64

2-Ethyl-6,7-dimethoxy-1-oxo-1,2-dihydro-isoquinoline-4-carboxylic acid ethyl-methyl-amide LCMS: 1.63 min; M+H: 319

¹H NMR (CDCl₃/TMS, 400 MHz) δ: 7.85 (s, 1H), 7.12 (s, 1H), 6.87 (s, 1H), 4.04-4.09 (m, 2H), 4.01 (s, 3H), 3.95 (s, 3H), 3.50 (br, 2H), 3.04 (br, 3H), 1.39 (t, J=7.2 Hz, 3H), 1.21 (br, 3H).

Example 65

2-Ethyl-6,7-dimethoxy-1-oxo-1,2-dihydro-isoquinoline-4-carboxylic acid isopropyl-methyl-amide LCMS: 1.73 min; M+H: 333

¹H NMR (CDCl₃/TMS, 400 MHz) δ: 7.78 (s, 1H), 7.02 (s, 1H), 6.76 (s, 1H), 3.99 (m, 3H), 3.94 (s, 3H), 3.87 (s, 3H), 2.85 (br, 3H), 1.32 (t, J=7.2 Hz, 3H), 1.14 (s, 6H).

Example 66

2-Ethyl-6,7-dimethoxy-1-oxo-1,2-dihydro-isoquinoline-4-carboxylic acid diethylamide LCMS: 1.72 min; M+H: 333

¹H NMR (CDCl₃/TMS, 400 MHz) δ: 7.85 (s, 1H), 7.10 (s, 1H), 6.85 (s, 1H), 4.08 (br, 2H), 4.01 (s, 3H), 3.94 (s, 3H), 3.56 (br, 4H), 3.04 (br, 3H), 1.40 (br, 3H), 1.21 (br, 6H).

Example 67

2-Ethyl-6,7-dimethoxy-1-oxo-1,2-dihydro-isoquinoline-4-carboxylic acid methyl-propyl-amide LCMS: 1.73 min; M+H: 333

¹H NMR (CDCl₃/TMS, 400 MHz) δ: 7.85 (s, 1H), 7.11 (s, 1H), 6.88 (s, 1H), 4.07 (br, 2H), 4.02 (s, 3H), 3.95 (s, 3H), 3.42 (br, 2H), 3.02 (br, 3H), 1.63 (br, 2H), 1.39 (br, 3H), 0.89 (br, 3H).

Example 68

2-Ethyl-6,7-dimethoxy-1-oxo-1,2-dihydro-isoquinoline-4-carboxylic acid ethyl-isopropyl-amide LCMS: 1.81 min; M+H: 347

¹H NMR (CDCl₃/TMS, 400 MHz) δ: 7.85 (s, 1H), 7.06 (s, 1H), 6.85 (s, 1H), 4.07 (br, 3H), 4.01 (s, 3H), 3.93 (s, 3H), 3.34-3.60 (br, 2H), 1.39 (t, J=5.6 Hz, 3H), 1.19 (br, 9H).

Example 69

2-Ethyl-6,7-dimethoxy-1-oxo-1,2-dihydro-isoquinoline-4-carboxylic acid tert-butyl-methyl-amide LCMS: 1.87 min; M+H: 347

¹H NMR (CDCl₃/TMS, 400 MHz) δ: 7.77 (s, 1H), 7.13 (s, 1H), 6.98 (s, 1H), 4.00 (m, 2H), 3.94 (s, 3H), 3.89 (s, 3H), 2.80 (s, 3H), 1.51 (s, 9H), 1.33 (t, J=6.8 Hz, 3H).

Example 70

2-Ethyl-6,7-dimethoxy-1-oxo-1,2-dihydro-isoquinoline-4-carboxylic acid isobutyl-methyl-amide LCMS: 1.83 min; M+H: 347

¹H NMR (CDCl₃/TMS, 400 MHz) δ: 7.78 (s, 1H), 7.03 (s, 1H), 6.82 (s, 1H), 4.00 (m, 2H), 3.94 (s, 3H), 3.87 (s, 3H), 3.36 (br, 2H), 2.95 (br, 3H), 1.95 (br, 1H), 1.32 (t, J=6.8 Hz, 3H), 0.78-0.91 (br, 6H).

Example 71

2-Ethyl-6,7-dimethoxy-1-oxo-1,2-dihydro-isoquinoline-4-carboxylic acid butyl-methyl-amide LCMS: 1.84 min; M+H: 347

¹H NMR (CDCl₃/TMS, 400 MHz) δ: 7.85 (s, 1H), 7.11 (s, 1H), 6.87 (s, 1H), 4.04-4.09 (m, 2H), 4.01 (s, 3H), 3.95 (s, 3H), 3.44 (br, 2H), 3.03 (br, 3H), 1.65 (br, 2H), 1.39 (t, J=5.8 Hz, 3H), 1.19 (br, 2H), 0.82 (br, 3H).

Example 72

2-Ethyl-6,7-dimethoxy-1-oxo-1,2-dihydro-isoquinoline-4-carboxylic acid ethyl-propyl-amide LCMS: 1.82 min; M+H: 347

¹H NMR (CDCl₃/TMS, 400 MHz) δ: 7.77 (s, 1H), 7.01 (s, 1H), 6.78 (s, 1H), 4.01 (m, 2H), 3.94 (s, 3H), 3.86 (s, 3H), 3.26-3.43 (br, 4H), 1.61 (br, 2H), 1.32 (t, J=7.2 Hz, 3H), 1.10 (br, 3H), 0.81 (br, 3H).

Example 73

2-Ethyl-6,7-dimethoxy-1-oxo-1,2-dihydro-isoquinoline-4-carboxylic acid (2-dimethylamino-ethyl)-methyl-amide LCMS: 1.56 min; M+H: 362

$^1$H NMR (CDCl$_3$/TMS, 400 MHz) δ: 7.84 (s, 1H), 7.20 (s, 1H), 7.00 (s, 1H), 4.04-4.10 (m, 2H), 4.01 (s, 3H), 3.96 (s, 3H), 3.47-3.71 (br, 2H), 3.01 (s, 3H), 2.58 (br, 2H), 2.28 (br, 6H), 1.40 (t, J=7.2 Hz, 3H).

Example 74

2-Ethyl-6,7-dimethoxy-1-oxo-1,2-dihydro-isoquinoline-4-carboxylic acid ethyl-(2-methoxy-ethyl)-amide LCMS: 1.70 min; M+H: 363

$^1$H NMR (CDCl$_3$/TMS, 400 MHz) δ: 7.77 (s, 1H), 7.10 (s, 1H), 6.87 (s, 1H), 3.96-4.02 (m, 2H), 3.94 (s, 3H), 3.88 (s, 3H), 3.29-3.52 (br, 9H), 1.32 (t, J=7.2 Hz, 3H), 1.07 (br, 3H).

Example 75

2-Ethyl-6,7-dimethoxy-1-oxo-1,2-dihydro-isoquinoline-4-carboxylic acid cyclopentyl-methyl-amide LCMS: 1.86 min; M+H: 359

$^1$H NMR (CDCl$_3$/TMS, 400 MHz) δ: 7.85 (s, 1H), 7.11 (s, 1H), 6.84 (s, 1H), 4.07 (br, 3H), 4.02 (s, 3H), 3.94 (s, 3H), 2.95 (br, 3H), 1.59-1.72 (m, 6H), 1.56 (br, 2H), 1.40 (br, 3H).

Example 76

2-Ethyl-6,7-dimethoxy-1-oxo-1,2-dihydro-isoquinoline-4-carboxylic acid ethyl-butyl-amide LCMS: 1.93 min; M+H: 361

$^1$H NMR (CDCl$_3$/TMS, 400 MHz) δ: 7.78 (s, 1H), 7.01 (s, 1H), 6.78 (s, 1H), 3.97-4.02 (m, 2H), 3.94 (s, 3H), 3.87 (s, 3H), 3.20-3.48 (br, 4H), 1.44 (br, 4H), 1.32 (t, J=5.4 Hz, 3H), 0.78-1.11 (br, 6H).

Example 77

2-Ethyl-6,7-dimethoxy-1-oxo-1,2-dihydro-isoquinoline-4-carboxylic acid methyl-pentyl-amide LCMS: 1.94 min; M+H: 361

$^1$H NMR (CDCl$_3$/TMS, 400 MHz) δ: 7.85 (s, 1H), 7.12 (s, 1H), 6.87 (s, 1H), 4.07 (br, 2H), 4.01 (s, 3H), 3.95 (s, 3H), 2.97-3.59 (br, 5H), 1.60 (br, 4H), 1.39 (br, 3H), 1.23 (br, 2H), 0.87 (br, 3H).

Example 78

2-Ethyl-6,7-dimethoxy-1-oxo-1,2-dihydro-isoquinoline-4-carboxylic acid diisopropylamide LCMS: 1.92 min; M+H: 361

$^1$H NMR (CDCl$_3$/TMS, 400 MHz) δ: 7.84 (s, 1H), 6.99 (s, 1H), 6.86 (s, 1H), 4.02-4.08 (m, 2H), 4.01 (s, 3H), 3.94 (s, 3H), 3.74 (br, 2H), 1.38 (t, J=7.2 Hz, 3H), 1.36 (br, 12H).

Example 79

2-Ethyl-6,7-dimethoxy-1-oxo-1,2-dihydro-isoquinoline-4-carboxylic acid isopropyl-propyl-amide LCMS: 1.91 min; M+H: 361

$^1$H NMR (CDCl$_3$/TMS, 400 MHz) δ: 7.85 (s, 1H), 7.05 (s, 1H), 6.85 (s, 1H), 4.06 (br, 3H), 4.01 (s, 3H), 3.93 (s, 3H), 3.18-3.44 (br, 2H), 1.69 (br, 2H), 1.38 (t, J=5.8 Hz, 3H), 0.98-1.17 (br, 9H).

Example 80

2-Ethyl-6,7-dimethoxy-1-oxo-1,2-dihydro-isoquinoline-4-carboxylic acid dipropylamide LCMS: 1.92 min; M+H: 361

$^1$H NMR (CDCl$_3$/TMS, 400 MHz) δ: 7.65 (s, 1H), 7.51 (s, 1H), 6.75 (s, 1H), 3.97-4.03 (m, 2H), 3.88 (s, 3H), 3.81 (s, 3H), 3.42 (s, 2H), 3.13 (s, 2H), 1.47-1.67 (br, 4H), 1.23 (t, J=7.0 Hz, 3H), 0.66-0.95 (br, 6H).

Example 81

2-Ethyl-6,7-dimethoxy-1-oxo-1,2-dihydro-isoquinoline-4-carboxylic acid (3-dimethylamino-propyl)-methyl-amide LCMS: 1.48 min; M+H: 376

$^1$H NMR (CDCl$_3$/TMS, 400 MHz) δ: 7.77 (s, 1H), 7.09 (s, 1H), 6.81 (s, 1H), 3.97-4.03 (m, 2H), 3.94 (s, 3H), 3.88 (s, 3H), 3.44 (br, 3H), 3.00 (s, 3H), 1.84-2.17 (br, 9H), 1.32 (t, J=7.2 Hz, 3H).

Example 82

2-Ethyl-6,7-dimethoxy-1-oxo-1,2-dihydro-isoquinoline-4-carboxylic acid cyclohexyl-methyl-amide LCMS: 1.93 min; M+H: 373

$^1$H NMR (CDCl$_3$/TMS, 400 MHz) δ: 7.78 (s, 1H), 7.02 (s, 1H), 6.78 (s, 1H), 3.97-4.03 (m, 3H), 3.94 (s, 3H), 3.87 (s, 3H), 2.73-2.95 (br, 3H), 1.51-1.74 (br, 8H), 1.32 (t, J=5.8 Hz, 3H), 1.01 (br, 2H).

Example 83

2-Ethyl-6,7-dimethoxy-1-oxo-1,2-dihydro-isoquinoline-4-carboxylic acid cyclopropylmethyl-propyl-amide LCMS: 1.94 min; M+H: 373

$^1$H NMR (CDCl$_3$/TMS, 400 MHz) δ: 7.77 (s, 1H), 7.03 (s, 1H), 6.83 (s, 1H), 3.97-4.03 (m, 2H), 3.94 (s, 3H), 3.87 (s, 3H), 3.28 (br, 4H), 1.52 (br, 1H), 1.32 (t, J=7.2 Hz, 3H), 0.81 (br, 4H), 0.48 (s, 2H).

Example 84

2-Ethyl-6,7-dimethoxy-1-oxo-1,2-dihydro-isoquinoline-4-carboxylic acid diisobutylamide LCMS: 2.08 min; M+H: 389
$^1$H NMR (CDCl$_3$/TMS, 400 MHz) δ: 7.85 (s, 1H), 7.06 (s, 1H), 6.93 (s, 1H), 4.04-4.09 (m, 2H), 4.02 (s, 3H), 3.93 (s, 3H), 3.07-3.42 (br, 4H), 1.88-2.15 (br, 2H), 1.39 (t, J=5.6 Hz, 3H), 1.05 (br, 6H), 0.77 (br, 6H).

Example 85

2-Ethyl-6,7-dimethoxy-1-oxo-1,2-dihydro-isoquinoline-4-carboxylic acid benzyl-methyl-amide LCMS: 1.88 min; M+H: 381
$^1$H NMR (CDCl$_3$/TMS, 400 MHz) δ: 7.75 (s, 1H), 7.24-7.32 (m, 4H), 7.08 (s, 2H), 6.70 (br, 1H), 4.65 (br, 2H), 3.65-3.93 (br, 8H), 2.86 (br, 3H), 1.26 (s, 3H).

Example 86

2-Ethyl-6,7-dimethoxy-1-oxo-1,2-dihydro-isoquinoline-4-carboxylic acid (2-fluoro-benzyl)-methyl-amide LCMS: 1.89 min; M+H: 399
$^1$H NMR (CDCl$_3$/TMS, 400 MHz) δ: 7.82 (s, 1H), 7.40 (br, 1H), 7.29-7.34 (m, 1H), 7.15-7.18 (m, 2H), 7.06-7.10 (m, 1H), 6.79 (br, 1H), 4.79 (br, 2H), 4.02-4.06 (m, 2H), 4.00 (s, 3H), 3.79 (br, 3H), 2.97 (br, 3H), 1.36 (br, 3H).

Example 87

2-Ethyl-6,7-dimethoxy-1-oxo-1,2-dihydro-isoquinoline-4-carboxylic acid (4-fluoro-benzyl)-methyl-amide LCMS: 1.90 min; M+H: 399
$^1$H NMR (CDCl$_3$/TMS, 400 MHz) δ: 7.83 (s, 1H), 7.40 (br, 1H), 7.15 (br, 2H), 7.06 (m, 2H), 6.73 (br, 1H), 4.70 (br, 2H), 4.04 (br, 2H), 4.00 (s, 3H), 3.79 (br, 3H), 2.93 (br, 3H), 1.35 (br, 3H).

Example 88

2-Ethyl-6,7-dimethoxy-1-oxo-1,2-dihydro-isoquinoline-4-carboxylic acid (3-fluoro-benzyl)-methyl-amide LCMS: 1.90 min; M+H: 399
$^1$H NMR (CDCl$_3$/TMS, 400 MHz) δ: 7.83 (s, 1H), 7.32-7.36 (m, 1H), 6.82-7.16 (m, 5H), 4.74 (br, 2H), 4.04 (br, 2H), 4.00 (s, 3H), 3.80 (br, 3H), 2.93 (br, 3H), 1.36 (br, 3H).

Example 89

2-Ethyl-6,7-dimethoxy-1-oxo-1,2-dihydro-isoquinoline-4-carboxylic acid methyl-phenethyl-amide LCMS: 1.89 min; M+H: 395
$^1$H NMR (CDCl$_3$/TMS, 400 MHz) δ: 7.75 (s, 1H), 7.19 (br, 5H), 7.02 (br, 1H), 6.72 (br, 1H), 3.93 (s, 3H), 3.87 (br, 2H), 3.82 (s, 3H), 3.44 (br, 2H), 2.86-3.08 (br, 5H), 1.26 (t, J=7.0 Hz, 3H).

Example 90

2-Ethyl-6,7-dimethoxy-1-oxo-1,2-dihydro-isoquinoline-4-carboxylic acid (2-methoxy-benzyl)-methyl-amide LCMS: 1.89 min; M+H: 411
$^1$H NMR (CDCl$_3$/TMS, 400 MHz) δ: 7.75 (s, 1H), 7.24 (s, 1H), 6.80-7.06 (m, 5H), 4.45-4.75 (br, 2H), 3.65-3.93 (m, 11H), 2.83-3.06 (m, 3H), 1.18 (br, 3H).

Example 91

2-Ethyl-6,7-dimethoxy-1-oxo-1,2-dihydro-isoquinoline-4-carboxylic acid (4-methoxy-benzyl)-methyl-amide LCMS: 1.86 min; M+H: 411
$^1$H NMR (CDCl$_3$/TMS, 400 MHz) δ: 7.83 (s, 1H), 7.38 (br, 1H), 6.72-7.15 (m, 5H), 3.72-4.69 (m, 13H), 2.88 (br, 3H), 1.35 (br, 3H).

Example 92

2-Ethyl-6,7-dimethoxy-1-oxo-1,2-dihydro-isoquinoline-4-carboxylic acid (3-methoxy-benzyl)-methyl-amide LCMS: 1.88 min; M+H: 411
$^1$H NMR (CDCl$_3$/TMS, 400 MHz) δ: 7.76 (s, 1H), 7.22 (m, 2H), 6.76-7.09 (m, 4H), 4.60 (br, 2H), 3.73-3.93 (m, 11H), 2.85 (br, 3H), 1.27 (br, 3H).

Example 93

2-Ethyl-6,7-dimethoxy-1-oxo-1,2-dihydro-isoquinoline-4-carboxylic acid methyl-(3-trifluoromethyl-benzyl)-amide LCMS: 202 min; M+H: 449
$^1$H NMR (CDCl$_3$/TMS, 400 MHz) δ: 7.76 (s, 1H), 7.52 (m, 3H), 7.45 (m, 1H), 7.09 (s, 1H), 6.75 (s, 1H), 4.71 (s, 2H), 3.96 (s, 2H), 3.93 (s, 3H), 3.74 (s, 3H), 2.91 (s, 3H), 1.27 (s, 3H).

Example 94

2-Ethyl-6,7-dimethoxy-1-oxo-1,2-dihydro-isoquinoline-4-carboxylic acid benzyl-(2-dimethylamino-ethyl)-amide LCMS: 1.88 min; M+H: 438
$^1$H NMR (CDCl$_3$/TMS, 400 MHz) δ: 7.75 (s, 1H), 7.23-7.27 (m, 4H), 7.08 (br, 3H), 4.47 (br, 2H), 3.17-3.93 (m, 10H), 1.98-2.53 (m, 8H), 1.22 (s, 3H).

Example 95

2-Ethyl-6,7-dimethoxy-1-oxo-1,2-dihydro-isoquinoline-4-carboxylic acid (1-benzyl-piperidin-4-yl)-methyl-amide LCMS: 1.94 min; M+H: 464
$^1$H NMR (CDCl$_3$/TMS, 400 MHz) δ: 7.84 (s, 1H), 7.29 (br, 4H), 7.25 (br, 1H), 7.10 (s, 1H), 6.81 (s, 1H), 4.02-4.08 (m, 3H), 4.01 (s, 3H), 3.91 (s, 3H), 3.50 (br, 2H), 2.96 (br, 5H), 1.72-2.17 (m, 6H), 1.38 (t, J=5.8 Hz, 3H).

The compounds of the following examples 96 to 118 were prepared in analogy to example 1, where however, in step 1.6, ethylamine was replaced by the respective amine and in step 1.8 butylamine was used instead of methylamine.

Example 96

6,7-Dimethoxy-1-oxo-2-(2,2,2-trifluoro-ethyl)-1,2-dihydro-isoquinoline-4-carboxylic acid butylamide LCMS: 1.94 min; M+H: 387
$^1$H NMR (CDCl$_3$/TMS, 400 MHz) δ: 7.82 (s, 1H), 7.58 (s, 1H), 7.31 (s, 1H), 5.85 (s, 1H), 4.68 (q, J=7.6 Hz, 2H), 4.01 (s, 3H), 4.00 (s, 3H), 3.48 (q, J=5.6 Hz, 2H), 1.64 (m, 2H), 1.45 (m, 2H), 0.99 (t, J=7.2 Hz, 3H).

Example 97

2-(2-Fluoro-ethyl)-6,7-dimethoxy-1-oxo-1,2-dihydro-isoquinoline-4-carboxylic acid butylamide LCMS: 1.77 min; M+H: 351
$^1$H NMR (CDCl$_3$/TMS, 400 MHz) δ: 7.80 (s, 1H), 7.66 (s, 1H), 7.39 (s, 1H), 5.84 (s, 1H), 4.84 (s, 1H), 4.71 (s, 1H), 4.37 (s, 1H), 4.28 (s, 1H), 4.01 (s, 6H), 3.46 (d, J=5.2 Hz, 2H), 1.61-1.65 (m, 2H), 1.41-1.48 (m, 2H), 0.99 (t, J=7.6 Hz, 3H).

Example 98

2-Cyclopropyl-6,7-dimethoxy-1-oxo-1,2-dihydro-isoquinoline-4-carboxylic acid butylamide LCMS: 1.81 min; M+H: 345
$^1$H NMR (CDCl$_3$/TMS, 400 MHz) δ: 7.79 (s, 1H), 7.53 (s, 1H), 7.38 (s, 1H), 6.10 (br, 1H), 4.01 (s, 3H), 4.00 (s, 3H), 3.47-3.53 (m, 2H), 3.32-3.36 (m, 1H), 1.64-1.71 (m, 2H), 1.45-1.53 (m, 2H), 1.14-1.20 (m, 2H), 0.99 (t, J=7.2 Hz, 3H), 0.89-0.94 (m, 2H).

Example 99

2-Isopropyl-6,7-dimethoxy-1-oxo-1,2-dihydro-isoquinoline-4-carboxylic acid butylamide LCMS: 1.85 min; M+H: 347
$^1$H NMR (CDCl$_3$/TMS, 400 MHz) δ: 7.84 (s, 1H), 7.56 (s, 1H), 7.40 (s, 1H), 5.83 (br, 1H), 5.31-5.40 (m, 1H), 4.01 (s, 3H), 3.99 (s, 3H), 3.46-3.53 (m, 2H), 1.60-1.69 (m, 2H), 1.41-1.49 (m, 2H), 1.41 (d, J=6.8 Hz, 6H), 0.99 (t, J=7.2 Hz, 3H).

Example 100

6,7-Dimethoxy-1-oxo-2-propyl-1,2-dihydro-isoquinoline-4-carboxylic acid butylamide LCMS: 1.86 min; M+H: 347
$^1$H NMR (CDCl$_3$/TMS, 400 MHz) δ: 7.83 (s, 1H), 7.61 (s, 1H), 7.36 (s, 1H), 5.83 (br, 1H), 3.98-4.03 (m, 8H), 3.45-3.52 (m, 2H), 1.82 (br, 2H), 1.60-1.68 (m, 2H), 1.41-1.50 (m, 2H), 0.99 (t, J=7.2 Hz, 3H).

Example 101

6,7-Dimethoxy-1-oxo-2-(3,3,3-trifluoro-propyl)-1,2-dihydro-isoquinoline-4-carboxylic acid butylamide LCMS: 1.94 min; M+H: 401
$^1$H NMR (CDCl$_3$/TMS, 400 MHz) δ: 7.79 (s, 1H), 7.61 (s, 1H), 7.32 (s, 1H), 5.81 (br, 1H), 4.22 (t, J=6.6 Hz, 2H), 4.01 (s, 6H), 3.45-3.51 (m, 2H), 2.60-73 (m, 2H), 1.60-1.68 (m, 2H), 1.41-1.49 (m, 2H), 0.99 (t, J=7.4 Hz, 3H).

Example 102

6,7-Dimethoxy-2-(2-methoxy-ethyl)-1-oxo-1,2-dihydro-isoquinoline-4-carboxylic acid butylamide LCMS: 1.76 min; M+H: 363
$^1$H NMR (CDCl$_3$/TMS, 400 MHz) δ: 7.81 (s, 1H), 7.69 (s, 1H), 7.45 (s, 1H), 5.88 (br, 1H), 4.20 (t, J=4.8 Hz, 2H), 4.00 (s, 6H), 3.72 (t, J=4.8 Hz, 2H), 3.43-3.51 (m, 2H), 3.33 (s, 3H), 1.58-1.67 (m, 2H), 1.41-1.49 (m, 2H), 0.99 (t, J=7.4 Hz, 3H).

Example 103

2-Cyclobutyl-6,7-dimethoxy-1-oxo-1,2-dihydro-isoquinoline-4-carboxylic acid butylamide LCMS: 1.90 min; M+H: 359
$^1$H NMR (CDCl$_3$/TMS, 400 MHz) δ: 7.81 (s, 1H), 7.56 (s, 1H), 7.50 (s, 1H), 5.85 (br, 1H), 5.16-5.23 (m, 1H), 4.00 (s, 6H), 3.46-3.53 (m, 2H), 2.53 (br, 2H), 2.25-2.29 (m, 2H), 1.88-1.92 (m, 2H), 1.60-1.69 (m, 2H), 1.43-1.51 (m, 2H), 1.00 (t, J=7.2 Hz, 3H).

Example 104

2-tert-Butyl-6,7-dimethoxy-1-oxo-1,2-dihydro-isoquinoline-4-carboxylic acid butylamide LCMS: 1.97 min; M+H: 361
$^1$H NMR (CDCl$_3$/TMS, 400 MHz) δ: 7.76 (s, 1H), 7.60 (s, 1H), 7.43 (s, 1H), 5.75 (br, 1H), 3.93 (s, 3H), 3.92 (s, 3H), 3.38-3.42 (m, 2H), 1.53-1.59 (m, 2H), 1.35-1.41 (m, 2H), 1.18 (s, 9H), 0.92 (t, J=7.4 Hz, 3H).

Example 105

2-sec-Butyl-6,7-dimethoxy-1-oxo-1,2-dihydro-isoquinoline-4-carboxylic acid butylamide LCMS: 1.93 min; M+H: 361
$^1$H NMR (CDCl$_3$/TMS, 400 MHz) δ: 7.84 (s, 1H), 7.57 (s, 1H), 7.33 (s, 1H), 5.85 (br, 1H), 5.14-5.20 (m, 1H), 4.01 (s, 3H), 3.99 (s, 3H), 3.46-3.51 (m, 2H), 1.73-1.78 (m, 2H), 1.61-1.67 (m, 2H), 1.43-1.49 (m, 2H), 1.39 (d, J=7.2 Hz, 3H), 0.99 (t, J=7.4 Hz, 3H), 0.89 (t, J=7.4 Hz, 3H).

Example 106

2-Isobutyl-6,7-dimethoxy-1-oxo-1,2-dihydro-isoquinoline-4-carboxylic acid butylamide LCMS: 1.94 min; M+H: 361
$^1$H NMR (CDCl$_3$/TMS, 400 MHz) δ: 7.82 (s, 1H), 7.61 (s, 1H), 7.30 (s, 1H), 5.85 (br, 1H), 4.01 (s, 3H), 4.00 (s, 3H), 3.82 (d, J=7.6 Hz, 2H), 3.45-3.50 (m, 2H), 2.17-2.23 (m, 1H), 1.61-1.67 (m, 2H), 1.42-1.49 (m, 2H), 0.96-1.01 (m, 9H).

Example 107

2-Butyl-6,7-dimethoxy-1-oxo-1,2-dihydro-isoquinoline-4-carboxylic acid butylamide LCMS: 1.98 min; M+H: 361
$^1$H NMR (CDCl$_3$/TMS, 400 MHz) δ: 7.82 (s, 1H), 7.60 (s, 1H), 7.34 (s, 1H), 5.83 (br, 1H), 3.99-4.03 (m, 8H), 3.45-3.50 (m, 2H), 1.73-1.78 (m, 2H), 1.61-1.67 (m, 2H), 1.39-1.49 (m, 4H), 0.95-1.01 (m, 6H).

Example 108

2-Cyclopropylmethyl-6,7-dimethoxy-1-oxo-1,2-dihydro-isoquinoline-4-carboxylic acid butylamide LCMS: 1.88 min; M+H: 359
$^1$H NMR (CDCl$_3$/TMS, 400 MHz) δ: 7.83 (s, 1H), 7.61 (s, 1H), 7.46 (s, 1H), 5.83 (br, 1H), 4.01 (s, 3H), 4.00 (s, 3H), 3.90 (d, J=6.8 Hz, 2H), 3.45-3.51 (m, 2H), 1.60-1.66 (m, 2H), 1.42-1.50 (m, 2H), 1.23-1.29 (m, 1H), 0.99 (t, J=7.4 Hz, 3H), 0.60-0.64 (m, 2H), 0.41-0.46 (m, 2H).

Example 109

2-Cyclopentyl-6,7-dimethoxy-1-oxo-1,2-dihydro-isoquinoline-4-carboxylic acid butylamide LCMS: 1.97 min; M+H: 373
$^1$H NMR (CDCl$_3$/TMS, 400 MHz) δ: 7.83 (s, 1H), 7.55 (s, 1H), 7.40 (s, 1H), 5.79 (br, 1H), 5.34-5.38 (m, 1H), 4.01 (s, 3H), 3.99 (s, 3H), 3.46-3.52 (m, 2H), 2.18-2.22 (m, 2H), 1.89 (br, 2H), 1.73-1.78 (m, 4H), 1.61-1.67 (m, 2H), 1.42-1.50 (m, 2H), 0.99 (t, J=7.4 Hz, 3H).

Example 110

2-(1-Ethyl-propyl)-6,7-dimethoxy-1-oxo-1,2-dihydro-isoquinoline-4-carboxylic acid butylamide LCMS: 1.99 min; M+H: 375
$^1$H NMR (CDCl$_3$/TMS, 400 MHz) δ: 7.86 (s, 1H), 7.59 (s, 1H), 7.26 (s, 1H), 5.78 (br, 1H), 5.03 (br, 1H), 4.01 (s, 3H), 3.99 (s, 3H), 3.45-3.51 (m, 2H), 1.81-1.87 (m, 2H), 1.61-1.67 (m, 4H), 1.43-1.49 (m, 2H), 0.99 (t, J=7.2 Hz, 3H), 0.86 (t, J=7.2 Hz, 6H).

Example 111

6,7-Dimethoxy-2-(2-methoxy-benzyl)-1-oxo-1,2-dihydro-isoquinoline-4-carboxylic acid butylamide LCMS: 2.00 min; M+H: 425
$^1$H NMR (CDCl$_3$/TMS, 400 MHz) δ: 7.84 (s, 1H), 7.64 (s, 1H), 7.57 (s, 1H), 7.33-7.36 (m, 1H), 7.25 (br, 1H), 6.89-6.95 (m, 2H), 5.77 (br, 1H), 5.22 (s, 2H), 3.99 (s, 6H), 3.88 (s, 3H), 3.43-3.47 (m, 2H), 1.58-1.62 (m, 2H), 1.41-1.47 (m, 2H), 0.98 (t, J=7.4 Hz, 3H).

Example 112

2-Indan-1-yl-6,7-dimethoxy-1-oxo-1,2-dihydro-isoquinoline-4-carboxylic acid butylamide LCMS: 2.05 min; M+H: 421
$^1$H NMR (CDCl$_3$/TMS, 400 MHz) δ: 7.89 (s, 1H), 7.61 (s, 1H), 7.30-7.38 (m, 2H), 7.11 (s, 1H), 7.00 (s, 1H), 6.68 (br, 1H), 5.53 (br, 1H), 4.03 (s, 4H), 3.99 (s, 3H), 3.36 (br, 2H), 3.05-3.14 (m, 2H), 2.82 (br, 1H), 2.05 (br, 1H), 1.41-1.51 (m, 2H), 1.25-1.33 (m, 2H), 0.91 (t, J=6.8 Hz, 3H).

Example 113

2-(2-Dimethylamino-ethyl)-6,7-dimethoxy-1-oxo-1,2-dihydro-isoquinoline-4-carboxylic acid butylamide

Example 114

6,7-Dimethoxy-1-oxo-2-(2-pyrrolidin-1-yl-ethyl)-1,2-dihydro-isoquinoline-4-carboxylic acid butylamide

Example 115

2-Benzyl-6,7-dimethoxy-1-oxo-1,2-dihydro-isoquinoline-4-carboxylic acid butylamide

Example 116

2-(2,4-Difluoro-benzyl)-6,7-dimethoxy-1-oxo-1,2-dihydro-isoquinoline-4-carboxylic acid butylamide

Example 117

6,7-Dimethoxy-1-oxo-2-(2-piperidin-1-yl-ethyl)-1,2-dihydro-isoquinoline-4-carboxylic acid butylamide

Example 118

6,7-Dimethoxy-1-oxo-2-phenethyl-1,2-dihydro-isoquinoline-4-carboxylic acid butylamide

Example 119

3-Ethyl-6,7-dimethoxy-4-oxo-3,4-dihydro-phthalazine-1-carboxylic acid butylamide

119.1 1-(4,5-Dimethoxy-2-methyl-phenyl)-ethanone

A solution of 1,2-dimethoxy-4-methylbenzene in CS$_2$ (20 mL) was added dropwise to a mixture of acetyl chloride (2.063 g, 26.3 mmol) and aluminium trichloride (3.50 g, 26.3 mmol) in CS$_2$ (80 mL). The reaction mixture was stirred for 12 h at 25° C., then poured into ice-water and extracted with DCM. The organic layer was separated and concentrated. The obtained residue was purified by column chromatography on silica gel (PE:EtOAc=20:1) to give the title compound (3.2 g, 62%) as a yellow oil.

LCMS (ESI+): m/z 195 (M+H)$^+$, RT: 0.776 min.

119.2 4,5-Dimethoxy-2-oxalyl-benzoic acid

A solution of potassium permanganate (11.39 g, 72.1 mmol) in water (45 mL) was added dropwise to a mixture of 1-(4,5-dimethoxy-2-methyl-phenyl)-ethanone obtained in step 119.1 (2 g, 10.30 mmol) and potassium carbonate (2.135 g, 15.45 mmol) in H$_2$O (5 mL), and the reaction mixture was stirred for 3 h at 50° C. Then ethanol was added and the resulting mixture was stirred for 30 min. The solid was filtered off, the filtrate was adjusted to pH=2 with conc.

HCl, EtOAc was added, and the organic layer was separated and concentrated to give the title compound (1.7 g, 64.9%) as a white solid.
LCMS (ESI+): m/z 255 (M+H)$^+$, RT: 0.524 min.

119.3 6,7-Dimethoxy-4-oxo-3,4-dihydro-phthalazine-1-carboxylic acid

A solution of 4,5-dimethoxy-2-oxalyl-benzoic acid obtained in step 119.2 (1.15 g, 4.52 mmol) and hydrazine hydrate (254 mg, 4.98 mmol) in ethanol (20 mL) was stirred for 2 h at 75° C. The solid was filtered to give the title compound (910 mg, 80%) as a white solid.
LCMS (ESI+): m/z 251 (M+H)$^+$, RT: 0.587 min.

119.4 3-Ethyl-6,7-dimethoxy-4-oxo-3,4-dihydro-phthalazine-1-carboxylic acid ethyl ester A mixture of 6,7-dimethoxy-4-oxo-3,4-dihydro-phthalazine-1-carboxylic acid obtained in step 119.3 (500 mg, 1.998 mmol), cesium carbonate (1954 mg, 6.00 mmol) and iodoethane (768 mg, 4.92 mmol) in DMF (8 mL) was stirred at 65° C. for 12 h. Water was added, and the solid was filtered to give the title compound (300 mg, 49.0%) as a white solid.
LCMS (ESI+): m/z 307 (M+H)$^+$, RT: 0.839 min.

119.5 3-Ethyl-6,7-dimethoxy-4-oxo-3,4-dihydro-phthalazine-1-carboxylic acid

A solution of 3-ethyl-6,7-dimethoxy-4-oxo-3,4-dihydro-phthalazine-1-carboxylic acid ethyl ester obtained in step 119.4 (400 mg, 1.306 mmol) and lithium hydroxide (46.9 mg, 1.959 mmol) in ethanol and water (2 mL) was stirred at 35° C. for 3 h. The reaction solution was adjusted to pH=4 with dilute HCl, and the solid was filtered and washed with water to give the title compound (280 mg, 77%) as a white solid.
LCMS (ESI+): m/z 279 (M+H)$^+$, RT: 0.862 min.

119.6 3-Ethyl-6,7-dimethoxy-4-oxo-3,4-dihydro-phthalazine-1-carboxylic acid butylamide A solution of 3-ethyl-6,7-dimethoxy-4-oxo-3,4-dihydro-phthalazine-1-carboxylic acid obtained in step 119.5 (200 mg, 0.719 mmol) in SOCl$_2$ (2 mL) was stirred at 76° C. for 2 h. Then SOCl$_2$ was removed and the residue was dissolved in DCM (5 mL).
Butan-1-amine (79 mg, 1.078 mmol) and triethylamine (109 mg, 1.078 mmol) were added dropwise and the resulting reaction was stirred at r.t. for 3 h. The solvent was removed and the obtained residue was washed with EtOAc to give the title compound (140 mg, 58.4%) as a white solid.
LCMS (ESI+): m/z 334 (M+H)$^+$, RT: 1.910 min.
$^1$H-NMR (400 MHz, CDCl$_3$): δ 8.75 (s, 1H), 7.78 (s, 1H), 7.37 (br, 1H), 4.33 (t, J=7.2 Hz, 2H), 4.06 (s, 6H), 3.47 (t, J=7.2 Hz, 2H), 1.65 (t, J=7.2 Hz, 2H), 1.47-1.42 (m, 5H), 0.98 (t, J=7.2 Hz, 3H).
The compounds of the following examples 120 to 132 were prepared in analogy to example 119.

Example 120

3-Ethyl-6,7-dimethoxy-4-oxo-3,4-dihydro-phthalazine-1-carboxylic acid (6,7,8,9-tetrahydro-5H-benzocyclohepten-7-yl)-amide ESI-MS: [M+Na$^+$]=444.20, [M+H$^+$]=422.20;

Example 121

3-Ethyl-6,7-dimethoxy-4-oxo-3,4-dihydro-phthalazine-1-carboxylic acid (R)-indan-1-ylamide ESI-MS: [M+Na$^+$]=416.10, [M+H$^+$]=394.10;

Example 122

3-Ethyl-6,7-dimethoxy-4-oxo-3,4-dihydro-phthalazine-1-carboxylic acid (1,2,3,4-tetrahydro-naphthalen-1-yl)-amide ESI-MS: [M+Na$^+$]=430.10, [M+H$^+$]=408.10;

Example 123

3-Ethyl-6,7-dimethoxy-4-oxo-3,4-dihydro-phthalazine-1-carboxylic acid (R)-(1,2,3,4-tetrahydro-naphthalen-1-yl)-amide ESI-MS: [M+Na$^+$]=430.10, [M+H$^+$]=408.10;

Example 124

3-Ethyl-6,7-dimethoxy-4-oxo-3,4-dihydro-phthalazine-1-carboxylic acid (6,7,8,9-tetrahydro-5H-benzocyclohepten-5-yl)-amide ESI-MS: [M+Na$^+$]=444.10, [M+H$^+$]=422.10;

Example 125

3-Ethyl-6,7-dimethoxy-4-oxo-3,4-dihydro-phthalazine-1-carboxylic acid (1,2,3,4-tetrahydro-naphthalen-2-yl)-amide ESI-MS: [M+Na$^+$]=430.10, [M+H$^+$]=408.10;

Example 126

3-Ethyl-6,7-dimethoxy-4-oxo-3,4-dihydro-phthalazine-1-carboxylic acid (4-bromo-indan-1-yl)-amide ESI-MS: 495.10, [M+Na$^+$]=494.10, 474.10, [M$^+$]=472.10;

Example 127

3-Ethyl-6,7-dimethoxy-4-oxo-3,4-dihydro-phthalazine-1-carboxylic acid (5-bromo-indan-1-yl)-amide ESI-MS: 496.00, [M+Na$^+$]=494.00, 474.00, [M$^+$]=472.00;

Example 128

3-Ethyl-6,7-dimethoxy-4-oxo-3,4-dihydro-phthalazine-1-carboxylic acid 2-dimethylaminomethyl-benzylamide

ESI-MS: [M+H$^+$]=425.20;

Example 129

3-Ethyl-6,7-dimethoxy-4-oxo-3,4-dihydro-phthalazine-1-carboxylic acid (6,7-dihydro-5H-[1]pyrindin-5-yl)-amide ESI-MS: [M+Na$^+$]=417.10, [M+H$^+$]=395.10;

Example 130

3-Ethyl-6,7-dimethoxy-4-oxo-3,4-dihydro-phthalazine-1-carboxylic acid (6,7-dihydro-5H-[1]pyrindin-7-yl)-amide

ESI-MS: [M+H$^+$]=395.10;

Example 131

3-Ethyl-6,7-dimethoxy-4-oxo-3,4-dihydro-phthalazine-1-carboxylic acid 3-dimethylaminomethyl-benzylamide ESI-MS: [M+Na$^+$]=447.20, [M+H$^+$]=425.20;

Example 132

3-Ethyl-6,7-dimethoxy-4-oxo-3,4-dihydro-phthalazine-1-carboxylic acid 4-dimethylaminomethyl-benzylamide ESI-MS: [M+Na$^+$]=447.20, [M+H$^+$]=425.20;

Example 133

2-Ethyl-7-methoxy-1-oxo-1,2-dihydro-isoquinoline-4-carboxylic acid butylamide

133.1 2-(2-Carboxy-4-methoxy-phenyl)-malonic acid dimethyl ester

To a solution of dimethyl malonate (45 mL) was added sodium (0.915 g, 39.8 mmol), and the resulting mixture was stirred until sodium had disappeared. Then copper(I) bromide (0.248 g, 1.731 mmol) and 2-bromo-5-methoxy-benzoic acid (4 g, 17.31 mmol) were added and the resulting reaction was stirred at 70° C. for 12 h. Water and EtOAc were added and the organic layer was separated off. The aqueous layer was acidified with conc. HCl, then EtOAc was added and the organic layer was separated and concentrated to give the title compound (3.2 g, 65.5%) as a yellow solid.

LCMS (ESI+): m/z 283 (M+H)$^+$, RT: 0.724 min.

133.2 2-(2-Carboxy-4-methoxy-phenyl)-malonic acid

A solution of 2-(2-carboxy-4-methoxy-phenyl)-malonic acid dimethyl ester obtained in step 133.1 (2.5 g, 8.86 mmol) and lithium hydroxide (1.061 g, 44.3 mmol) in CH$_3$OH (30 mL) and water (8 mL) was stirred for 12 h at 40° C. The solvent was removed, the residue was adjusted pH=4 with dilute HCl, EtOAc was added, and the organic layer was separated and concentrated to give the title compound (1.67 g, 74.2%) as a white solid.

LCMS (ESI+): m/z 255 (M+H)$^+$, RT: 0.453 min.

133.3 2-Carboxymethyl-5-methoxy-benzoic acid

A suspension of 2-(2-carboxy-4-methoxy-phenyl)-malonic acid obtained in step 133.2 (200 mg, 0.787 mmol) in toluene (8 mL) was stirred for 12 h at 105° C. The solid was filtered to give the title compound (100 mg, 60.5%) as a white solid.

LCMS (ESI+): m/z 211 (M+H)$^+$, RT: 0.630 min.

133.4 5-Methoxy-2-methoxycarbonylmethyl-benzoic acid methyl ester

A mixture of 2-carboxymethyl-5-methoxy-benzoic acid obtained in step 133.3 (100 mg, 0.476 mmol) and sulfurous dichloride (170 mg, 1.427 mmol) in CH$_3$OH (10 mL) was stirred at 65° C. for 12 h. The solvent was removed to give the crude title compound (100 mg, 88%) as a yellow oil.

LCMS (ESI+): m/z 239 (M+H)$^+$, RT: 0.820 min.

133.5 2-(2-Dimethylamino-1-methoxycarbonyl-vinyl)-5-methoxy-benzoic acid methyl ester A solution of 5-methoxy-2-methoxycarbonylmethyl-benzoic acid methyl ester obtained in step 133.4 (700 mg, 2.94 mmol) and HOAc (0.5 mL) in DMF-DMA (15 mL) was stirred 12 h at 90° C., then poured to water and extracted with EtOAc. The organic layer was separated and concentrated to give a residue which was purified by Prep-TLC (PE:EtOAc=1:1) to give the title compound (600 mg, 69.6%) as a yellow oil.

LCMS (ESI+): m/z 267 (M−27)$^+$, RT: 0.735 min.

133.6 2-Ethyl-7-methoxy-1-oxo-1,2-dihydro-isoquinoline-4-carboxylic acid methyl ester A solution of 2-(2-dimethylamino-1-methoxycarbonyl-vinyl)-5-methoxy-benzoic acid methyl ester obtained in step 133.5 (500 mg, 1.705 mmol), ethanamine (231 mg, 5.11 mmol) and DIPEA (1.5 ml) in MeOH (15 mL) was stirred at 65° C. for 12 h. The solvent was removed, water and EtOAc were added to the residue, the organic layer was separated and concentrated to give the crude title compound (420 mg, 94%) as a white solid.

LCMS (ESI+): m/z 262 (M+H)$^+$, RT: 0.867 min.

133.7 2-Ethyl-7-methoxy-1-oxo-1,2-dihydro-isoquinoline-4-carboxylic acid

2-Ethyl-7-methoxy-1-oxo-1,2-dihydro-isoquinoline-4-carboxylic acid methyl ester obtained in step 133.6 and lithium hydroxide (77 mg, 3.22 mmol) in CH$_3$OH (15 mL) and water (2 mL) were stirred at 35° C. for 5 h. The reaction solution was concentrated and the obtained residue was dissolved in water and adjusted pH=4 with dilute HCl. The solid was filtered to give the title compound (362 mg, 91%) as white solid.

LCMS (ESI+): m/z 248 (M+H)$^+$, RT: 0.737 min.

133.8 2-Ethyl-7-methoxy-1-oxo-1,2-dihydro-isoquinoline-4-carboxylic acid butylamide A solution of 2-ethyl-7-methoxy-1-oxo-1,2-dihydro-isoquinoline-4-carboxylic acid obtained in step 133.7 (300 mg, 1.209 mmol) in SOCl$_2$ (4 mL) was stirred at 76° C. for 2 h; then SOCl$_2$ was removed. The obtained residue was dissolved in DCM (6 mL) and butan-1-amine (133 mg, 1.813 mmol) and triethylamine (183 mg, 1.813 mmol) were added dropwise. The resulting reaction was stirred at RT for 3 h.

The solvent was removed and the obtained residue was washed with EtOAc to give the title compound (200 mg, 0.659 mmol, 54.6% yield).

$^1$H-NMR (400 MHz, MeOD): 7.93 (d, J=8.8 Hz, 1H), 7.68 (d, J=2.8 Hz, 1H), 7.44 (s, 1H), 7.25 (dd, 9.2 Hz, 2.8 Hz, 1H), 4.01 (t, J=7.2 Hz, 2H), 3.81 (s, 3H), 3.28 (t, J=7.6 Hz, 2H), 1.56-1.51 (m, 2H), 1.39-1.32 (m, 2H), 1.28 (t, J=7.6 Hz, 3H), 0.89 (t, J=7.6 Hz, 3H).

The compounds of the following examples 134 to 136 were prepared in analogy to example 133.

Example 134

2-(1-Ethyl-propyl)-7-methoxy-1-oxo-1,2-dihydro-isoquinoline-4-carboxylic acid indan-1-ylamide ESI-MS: [M+Na$^+$]=427.10, [M$^+$]=405.10;

Example 135

2-(1-Ethyl-propyl)-6,7-dimethoxy-1-oxo-1,2-dihydro-isoquinoline-4-carboxylic acid indan-1-ylamide

135.1 2-(1-Ethyl-propyl)-6,7-dimethoxy-1-oxo-1,2-dihydro-isoquinoline-4-carboxylic acid methyl ester A solution of 2-(2-dimethylamino-1-methoxycarbonylvinyl)-4,5-dimethoxy-benzoic acid methyl ester obtained in step 1.5 (800 mg, 2.474 mmol), pentan-3-amine (323 mg, 3.71 mmol) and HOAc (1.5 mL) in MeOH (15 mL) was stirred at 65° C. for 12 h. The solvent was removed and water and EtOAc were added to the obtained residue. The organic layer was separated and concentrated to give the title compound (750 mg, 91%) as a white solid.

LCMS (ESI+): m/z 334 (M+H)$^+$, RT: 0.941 min.

135.2 2-(1-Ethyl-propyl)-6,7-dimethoxy-1-oxo-1,2-dihydro-isoquinoline-4-carboxylic acid A mixture of 2-(1-ethyl-propyl)-6,7-dimethoxy-1-oxo-1,2-dihydro-isoquinoline-4-carboxylic acid methyl ester obtained in step 135.1 (750 mg, 2.250 mmol) and lithium hydroxide (108 mg, 4.50 mmol) in CH$_3$OH (8 mL) and water (2 mL) was stirred at 35° C. for 5 h. The reaction solution was concentrated and the obtained residue was dissolved in water and adjusted pH=4 with dilute HCl. The solid was filtered to give the title compound (700 mg, 97%) as a white solid.

LCMS (ESI+): m/z 320 (M+H)$^+$, RT: 0.804 min.

135.3 2-(1-Ethyl-propyl)-6,7-dimethoxy-1-oxo-1,2-dihydro-isoquinoline-4-carboxylic acid indan-1-ylamide A solution of 2-(1-ethyl-propyl)-6,7-dimethoxy-1-oxo-1,2-dihydro-isoquinoline-4-carboxylic acid obtained in step 135.2 (300 mg, 0.939 mmol) in SOCl$_2$ (5 mL) was stirred at 76° C. for 2 h. SOCl$_2$ was removed. The obtained residue was dissolved in DCM (5 mL), 2,3-dihydro-1H-inden-1-amine (188 mg, 1.409 mmol) was added dropwise and the resulting reaction was stirred at RT for 3 h. The solvent was removed and the obtained residue was washed with EtOAc to give the title compound (200 mg, 49%) as a yellow solid.

LCMS (ESI+): m/z 435 (M+H)$^+$, RT: 2.084 min.

$^1$H-NMR (400 MHz, MeOD): δ 7.61 (s, 1H), 7.49 (s, 1H), 7.43 (m, 1H), 7.28-7.22 (m, 3H), 5.67 (t, J=7.6 Hz, 1H), 3.95 (s, 3H), 3.94 (s, 3H), 3.09-3.05 (m, 1H), 2.97-2.91 (m, 1H), 2.65-2.60 (m, 1H), 2.08-2.01 (m, 1H), 1.88-1.77 (m, 4H), 1.29 (m, 1H), 0.84 (t, J=1.6 Hz, 6H).

Example 136

2-Ethyl-7-methoxy-1-oxo-6-(2-quinolin-2-yl-ethoxy)-1,2-dihydro-isoquinoline-4-carboxylic acid butylamide

136.1 1-Bromo-4-methoxy-2-methyl-benzene

To a solution of 1-methoxy-3-methylbenzene (51.6 ml, 405 mmol) in DCM (300 mL), 1-bromopyrrolidine-2,5-dione (72.1 g, 405 mmol) was added. The resulting reaction was stirred at about 20° C. overnight. The reaction mixture was diluted with 30-60° C. petroleum ether (200 mL). The mixture was stirred for 30 min. The reaction mixture was filtered. The filtrate was concentrated under reduced pressure to provide the desired product (80 g, 98%) as a yellow oil, which was used in next step without further purification.

136.2 1-Bromo-4-methoxy-2-methyl-5-nitro-benzene

1-Bromo-4-methoxy-2-methylbenzene obtained in step 136.1 (60 g, 298 mmol) was dissolved in acetic acid (150 ml) and TFA (150 ml). The mixture was cooled to −5° C. in an ice bath. Fuming nitric acid (14.56 ml, 328 mmol) was added slowly to the reaction. The resulting mixture was stirred at −5° C. for about 2 h. The reaction mixture was diluted with water (100 ml). The aqueous layer was extracted with ethyl acetate (3×100 mL) and washed with sat. NaCl (100 mL), sat. NaHCO$_3$ (100 mL) and sat. NaCl (100 mL). The organic layer was dried with Na$_2$SO$_4$, filtered and concentrated. The resulting solid was purified with silica gel column chromatography (hexane/EtOAc=50:1). The proper fractions were collected and concentrated to give the title compound (20 g, 27%).

136.3 1-Bromo-4-methoxy-5-nitro-benzoic acid

In a 1 L round-bottomed flask, 1-bromo-4-methoxy-2-methyl-5-nitro-benzene obtained in step 136.2 (70 g, 0.28 mol) and KMnO$_4$ (270 g, 1.707 mol) were dissolved in water (500 ml) and pyridine (250 ml) and the mixture was stirred and heated to about 110° C. over night. The reaction was cooled to ambient temperature and filtered through a sintered glass funnel. The aqueous layer was adjusted to pH=2 and extracted with ethyl acetate (2×750 mL). The organic layer was washed with sat. NaCl (300 mL), dried with Na$_2$SO$_4$, filtered and concentrated to afford the crude title compound (60 g). This was recrystallized in ethanol to afford the pure title compound (38 g, 48.4%).

LCMS (ESI+): m/z 263 (M+Na)$^+$, RT: 1.32 min.

$^1$H NMR (MeOD/TMS, 400 MHz) δ: 8.09 (s, 1H), 7.64 (s, 1H), 4.00 (s, 3H).

136.4 2-(2-Carboxy-4-methoxy-5-nitro-phenyl)-malonic acid diethyl ester

To rapidly stirred diethyl malonate (58.0 g, 362 mmol) was added sodium (0.999 g, 43.5 mmol) in portions at r.t. After the addition was complete, the mixture was stirred at 50° C. until the sodium had disappeared. Copper(I) bromide (0.260 g, 1.811 mmol) and then 2-bromo-5-methoxy-4- nitro-benzoic acid obtained in step 136.3 (5.0 g, 18.11 mmol) were added. The mixture was heated at 70° C. overnight. The reaction mixture was dissolved in water and extracted with toluene and EtOAc. The aqueous layer was acidified with HCl (2 N). The mixture was then extracted with EtOAc and dried over $Na_2SO_4$, filtered and concentrated in vacuo. The residue was purified on a silica gel column (DCM/MeOH=10:1, v/v) to afford the title compound as a yellow solid (5.02 g, 78%).

LCMS (ESI+): m/z 356 (M+H)+, RT: 1.56 min.

$^1$H NMR (CDCl$_3$/TMS, 400 MHz) δ: 7.95 (s, 1H), 7.80 (s, 1H), 5.62 (s, 1H), 4.25-4.28 (m, 4H), 4.03 (s, 3H), 1.27-1.33 (m, 6H).

136.5 2-Carboxymethyl-5-methoxy-4-nitro-benzoic acid

NaOH (3.05 g, 76 mmol) in water (15 mL) was added over 30 min to a solution of 2-(2-carboxy-4-methoxy-5-nitro-phenyl)-malonic acid diethyl ester obtained in step 136.4 (5.42 g, 15.25 mmol) in EtOH (40 mL) at room temperature. The mixture was then stirred at 50° C. overnight, the solvent was removed under reduced pressure, the contents were acidified with HCl (conc.) at r.t. to pH=3 and the resulting white aqueous suspension was extracted twice with EtOAc (100 mL). The organic layer was dried over $Na_2SO_4$, filtered and concentrated in vacuo. The residue was dissolved in toluene (50 mL), and the mixture was heated at 105° C. The mixture was concentrated under reduced pressure and the concentrate was used in the next step without further purification.

136.6 5-Methoxy-2-methoxycarbonylmethyl-4-nitro-benzoic acid methyl ester $SOCl_2$ (17.16 mL, 235 mmol) was added dropwise to a solution of 2-carboxymethyl-5-methoxy-4-nitrobenzoic acid obtained in step 136.5 (20.0 g, 78 mmol) in MeOH (150 mL) at ambient temperature. After the addition was completed, the mixture was heated at 65° C. overnight. The mixture was concentrated in vacuo. The residue was diluted with EtOAc (200 mL) and washed with saturated aqueous $NaHCO_3$ (60 mL), water (60 mL) and brine (60 mL). The organic layer was dried over $Na_2SO_4$, filtered and concentrated. The residue was purified on a silica gel column (PE/EtOAc=5:1, v/v) to afford the title compound (20.7 g, 93%) as a yellow solid.

LCMS (ESI+): m/z 284 (M+H)+, RT: 1.95 min.

$^1$H NMR(CDCl$_3$/TMS, 400 MHz) δ: 7.72 (s, 2H), 4.01 (s, 3H), 3.97 (s, 2H), 3.92 (s, 3H), 3.71 (s, 3H).

136.7 2-((Z)-2-Dimethylamino-1-methoxycarbonyl-vinyl)-5-methoxy-4-nitro-benzoic acid methyl ester A mixture of methyl 5-methoxy-2-methoxycarbonylmethyl-4-nitro-benzoic acid methyl ester obtained in step 136.6 (250 mg, 0.883 mmol) in DMF-DMA (5.909 ml, 44.1 mmol) was heated at 90° C. overnight. The reaction mixture was concentrated under reduced pressure. The residue was diluted with EtOAc (20 mL) and washed with brine (6 mL*3). The organic layer was dried over $Na_2SO_4$, filtered and concentrated in vacuo. The crude oil was pure enough for next step.

LCMS (ESI+): m/z 339 (M+H)+, RT: 1.93 min.

136.8 2-Ethyl-7-methoxy-6-nitro-1-oxo-1,2-dihydro-isoquinoline-4-carboxylic acid methyl ester A mixture of 2-((Z)-2-dimethylamino-1-methoxycarbonyl-vinyl)-5-methoxy-4-nitro-benzoic acid methyl ester obtained in step 136.7 (237 mg, 0.701 mmol), ethanamine (95 mg, 2.102 mmol) and DIPEA (0.734 mL, 4.20 mmol) in MeOH (5 mL) was heated at reflux overnight. The solvent was removed under reduced pressure. The residue was diluted with EtOAc (50 mL) and washed with HCl (2 N, 10 mL) and brine (10 mL). The organic layer was dried over $Na_2SO_4$, filtered and concentrated in vacuo. The residue was purified on a silica column (PE/EtOAc=5:1, v/v) to afford the title compound (200 mg, 93%) as a yellow solid.

LCMS (ESI+): m/z 207 (M+H)+, RT: 2.05 min.

$^1$H NMR(CDCl$_3$/TMS, 400 MHz) δ: 9.24 (s, 1H), 8.16 (s, 1H), 8.04 (s, 1H), 4.14 (q, 2H), 4.06 (s, 3H), 3.93 (s, 3H), 1.45 (t, J=7.2 Hz, 3H).

136.9 6-Amino-2-ethyl-7-methoxy-1-oxo-1,2-dihydro-isoquinoline-4-carboxylic acid methyl ester To a suspension of 2-ethyl-7-methoxy-6-nitro-1-oxo-1,2-dihydro-isoquinoline-4-carboxylic acid methyl ester obtained in step 136.8 (200 mg, 0.653 mmol) in ethanol (10 mL) and saturated $NH_4Cl$ solution (2 mL) was added zinc (427 mg, 6.53 mmol) in one portion. The mixture was stirred at r.t. for 30 min, then filtered. The filtrate was concentrated in vacuo. The residue was diluted with EtOAc (20 mL) and washed with brine (6*2 mL). The organic layer was dried over $Na_2SO_4$, filtered and concentrated to afford the title compound (163 mg, 90%) as a white solid.

LCMS (ESI+): m/z 277 (M+H)+, RT: 1.83 min.

$^1$H NMR (DMSO-d6/TMS, 400 MHz) δ: 8.22 (s, 1H), 7.87 (s, 1H), 7.50 (s, 1H), 5.86 (br, 2H), 4.00-4.04 (q, 2H), 3.88 (s, 3H), 3.81 (s, 3H), 1.24 (t, J=7.2 Hz, 3H).

136.10 6-Bromo-2-ethyl-7-methoxy-1-oxo-1,2-dihydro-isoquinoline-4-carboxylic acid methyl ester To a suspension of 6-amino-2-ethyl-7-methoxy-1-oxo-1,2-dihydro-isoquinoline-4-carboxylic acid methyl ester obtained in step 136.9 (1.20 g, 4.34 mmol) in 2 N $H_2SO_4$ solution (25 mL) was added a solution of sodium nitrite (0.899 g, 13.03 mmol) in water (5 mL) dropwise at 0° C. The mixture was stirred at 0° C. for 2 h, then it was added dropwise to a solution of copper(I) bromide (2.492 g, 17.37 mmol) in HBr (48%, 5 mL). The mixture was stirred for another 1 h at 0° C., diluted with EtOAc (100 mL) and washed with brine (30 mL*3). The organic layer was dried over $Na_2SO_4$, filtered and concentrated in vacuo. The residue was purified on a silica column (PE/EtOAc=5:1, v/v) to afford the title compound (1.31 g, 89%).

LCMS (ESI+): m/z 340 (M+H)+, RT: 2.04 min.

$^1$H NMR(CDCl$_3$/TMS, 400 MHz) δ: 9.02 (s, 1H), 8.01 (s, 1H), 7.76 (s, 1H), 4.01-4.07 (q, 2H), 3.95 (s, 3H), 3.85 (s, 3H), 1.36 (t, J=7.2 Hz, 3H).

136.11 2-Ethyl-7-methoxy-4-(methoxycarbonyl)-1-oxo-1,2-dihydroisoquinolin-6-yl-boronic acid A mixture of 6-bromo-2-ethyl-7-methoxy-1-oxo-1,2-dihydro-isoquinoline-4-carboxylic acid methyl ester obtained in step 136.10 (1.31 g, 3.85 mmol), 4,4,4',4',5,5,5',5'-octamethyl-2,2'-bi(1,3,2-dioxaborolane) (1.174 g, 4.62 mmol), potassium acetate (1.134 g, 11.55 mmol) and $PdCl_2(dppf)$-$CH_2Cl_2$ adduct (0.314 g, 0.385 mmol) in DMF (100 mL)

was stirred at 90° C. overnight. The mixture was diluted with EtOAc (200 mL) and washed with brine (60 mL×4). The organic layer was dried over $Na_2SO_4$, filtered and concentrated in vacuo. The residue was used in the next step directly without further purification.

LCMS (ESI+): m/z 306 (M+H)$^+$, RT: 1.82 min.

136.12 2-Ethyl-6-hydroxy-7-methoxy-1-oxo-1,2-dihydro-isoquinoline-4-carboxylic acid methyl ester A mixture of 2-ethyl-7-methoxy-4-(methoxycarbonyl)-1-oxo-1,2-dihydroisoquinolin-6-yl-boronic acid obtained in step 136.11 (838 mg, 2.75 mmol), water (32 mL), acetone (4 mL), NaOH (110 mg, 2.75 mmol) and sodium bicarbonate (231 mg, 2.75 mmol) was warmed to 50° C. for 1 h. After cooling to r.t., 30% $H_2O_2$ (0.337 mL, 10.99 mmol) was added dropwise. The reaction was stirred at r.t. overnight, then it was acidified to pH=4 by dropwise addition of 2 N HCl, and extracted with DCM (50 mL*3). The DCM layer was washed with brine (50 mL), dried over $Na_2SO_4$, filtered and concentrated in vacuo. The residue was purified on a silica column (PE/EtOAc=2:1, v/v) to afford the title compound (220 mg, 28.9%) as a white solid.

LCMS (ESI+): m/z 278 (M+H)$^+$, RT: 1.87 min.
$^1$H NMR (DMSO-d6/TMS, 400 MHz) δ: 10.27 (s, 1H), 8.30 (s, 1H), 8.15 (s, 1H), 7.64 (s, 1H), 4.04-4.08 (m, 2H), 3.88 (s, 3H), 3.82 (s, 3H), 1.26 (t, J=7.2 Hz, 3H).

136.13 2-Ethyl-7-methoxy-1-oxo-6-(2-quinolin-2-yl-ethoxy)-1,2-dihydro-isoquinoline-4-carboxylic acid methyl ester To a solution of 2-ethyl-6-hydroxy-7-methoxy-1-oxo-1,2-dihydro-isoquinoline-4-carboxylic acid methyl ester of step 136.12 (50 mg, 0.180 mmol), 2-(quinolin-2-yl)ethanol (31.2 mg, 0.180 mmol) and $Ph_3P$ (142 mg, 0.541 mmol) in anhydrous THF (3 mL) was added DEAD (0.086 mL, 0.541 mmol) dropwise at 0° C. The mixture was stirred at 0° C. for 30 min. Then it was allowed to warm to ambient temperature and stirred overnight. The mixture was diluted with EtOAc (20 mL) and washed with 2 N HCl (10 mL*3). The aqueous layer was basified with 2 N NaOH to pH=10, then extracted with EtOAc (15 mL*3). The organic layer was dried over $Na_2SO_4$, filtered and concentrated in vacuo. The residue was purified by prep-TLC (PE/EtOAc=1:1, v/v) to afford the title compound (55 mg, 47.3%).

LCMS (ESI+): m/z 433 (M+H)$^+$, RT: 1.91 min.
$^1$H NMR(CDCl$_3$/TMS, 400 MHz) δ: 8.43 (s, 1H), 8.09-8.13 (m, 3H), 7.80 (s, 1H), 7.65-7.70 (m, 2H), 7.47-7.51 (m, 2H), 4.69 (t, J=6.8 Hz, 2H), 4.08-4.12 (m, 2H), 3.97 (s, 3H), 3.88 (s, 3H), 3.62 (t, J=6.8 Hz, 2H), 1.41 (t, J=7.2 Hz, 3H).

136.14 2-Ethyl-7-methoxy-1-oxo-6-(2-quinolin-2-yl-ethoxy)-1,2-dihydro-isoquinoline-4-carboxylic acid A mixture of methyl 2-ethyl-7-methoxy-1-oxo-6-(2-quinolin-2-yl-ethoxy)-1,2-dihydro-isoquinoline-4-carboxylic acid ethyl ester obtained in step 136.13 (55 mg, 0.085 mmol) and NaOH (10.22 mg, 0.256 mmol) in MeOH (3 mL) and water (1 mL) was heated at 50° C. for 3 h. The reaction mixture was concentrated in vacuo. The residue was dissolved in water (5 mL) and acidified with HCl (2 N) to pH=5~6. The aqueous solution was extracted with EtOAc (15 mL*3). The organic layer was dried over $Na_2SO_4$, filtered and concentrated in vacuo. The residue was used in the next step without further purification.

LCMS (ESI+): m/z 419 (M+H)$^+$, RT: 2.08 min.

136.15 2-Ethyl-7-methoxy-1-oxo-6-(2-quinolin-2-yl-ethoxy)-1,2-dihydro-isoquinoline-4-carboxylic acid butylamide A suspension of 2-ethyl-7-methoxy-1-oxo-6-(2-quinolin-2-yl-ethoxy)-1,2-dihydro-isoquinoline-4-carboxylic acid obtained in step 136.14 (80 mg, 0.080 mmol), DMF (6.22 µL, 0.080 mmol) and SOCl$_2$ (0.018 mL, 0.241 mmol) in DCM (2 mL) was refluxed for 3 h. The mixture was concentrated in vacuo. The residue was dissolved in DCM (2 mL). The solution was added dropwise to a mixture of butan-1-amine (11.75 mg, 0.161 mmol) and Et$_3$N (0.034 mL, 0.241 mmol) in DCM (2 mL) at ambient temperature. The reaction mixture was stirred at r.t. for another 3 h. Then the solvent was removed under reduced pressure, the residue was diluted with EtOAc (15 mL) and washed with brine (5 mL*3). The organic layer was dried over $Na_2SO_4$, filtered and concentrated in vacuo. The residue was purified on a silica column (PE/EtOAc=1:1, v/v) to afford the title compound as a white solid (50 mg), (purity 94.6% by LCMS). Further purification pre-HPLC afford the title compound (12 mg, 31.6%) as a white solid.

$^1$H NMR (CDCl$_3$/TMS, 400 MHz) δ: 7.35-8.17 (m, 9H), 5.88 (s, 1H), 4.65 (m, 2H), 4.03-4.08 (m, 2H), 3.95 (s, 3H), 3.41-3.66 (m, 4H), 1.60-1.63 (m, 2H), 1.37-1.44 (m, 5H), 0.93 (t, J=7.2 Hz, 3H).

LCMS (ESI+): m/z 474 (M+H)$^+$, RT: 2.05 min.

Example 137

2-Ethyl-7-methoxy-1-oxo-6-(3-quinolin-2-yl-propoxy)-1,2-dihydro-isoquinoline-4-carboxylic acid butyl amide

137.1 (E)-3-Quinolin-2-yl-acrylic acid ethyl ester (2-Ethoxy-2-oxoethyl)triphenylphosphonium bromide (16.8 g, 39.1 mmol) and quinoline-2-carbaldehyde (5.8 g, 36.9 mmol) were dissolved in EtOH (100 ml). The mixture was heated at about 80° C. over night. The solvent was removed under reduced pressure, and the residue was purified with silica column (eluted with 5:1 hexane/EtOAc). The proper fractions were collected and concentrated to give the title compound (6.8 g, 76%) as yellow oil.

LCMS (ESI+): m/z 228 (M+H)$^+$, RT: 1.871 min

137.2 3-Quinolin-2-yl-propan-1-ol

To a suspension of LiAlH$_4$ (0.534 g, 14.05 mmol) in THF (10 ml), at −78° C. was added (E)-3-quinolin-2-yl-acrylic acid ethyl ester obtained in step 137.1 (1.6 g, 7.04 mmol) slowly. The mixture was allowed to warm to room temperature and stirred for 3 h. Water (0.1 ml) was added slowly. The reaction mixture was filtered through a pad of celite. The solvent was removed under reduced pressure to provide the desired crude product as an off-white solid. The crude product was purified with plate TLC (eluted with 1:1 hexane/EtOAc) to give the title compound (55 mg, 4.2%).

LCMS (ESI+): m/z 188 (M+H)$^+$, RT: 1.074 min.

137.3 2-Ethyl-7-methoxy-1-oxo-6-(3-quinolin-2-yl-propoxy)-1,2-dihydro-isoquinoline-4-carboxylic acid methyl ester To a solution of 2-ethyl-6-hydroxy-7-methoxy-1-oxo-1,2-dihydro-isoquinoline-4-carboxylic acid methyl ester obtained in step 136.12 (148 mg, 0.534 mmol) and Ph$_3$P (420 mg, 1.602 mmol) in anhydrous THF (3 mL) was added DEAD (0.254 mL, 1.602 mmol) dropwise at −30° C. The mixture was stirred at −30° C. for 30 min. Then a solution of 3-quinolin-2-yl-propan-1-ol obtained in step 137.2 (100 mg, 0.534 mmol) in anhydrous THF (2 mL) was added. The reaction mixture was allowed to warm to ambient temperature and stirred overnight. The mixture was diluted with EtOAc (10 mL) and washed with 2 N HCl (5 mL*3). The aqueous layer was basified with 2 N NaOH to pH=10, then extracted with EtOAc (10 mL*3). The organic layer was dried over Na$_2$SO$_4$, filtered and concentrated in vacuo. The residue was purified by pre-TLC (PE/EtOAc=1:1, v/v) to afford the title compound (43 mg, 11.36%).

LCMS (ESI+): m/z 447 (M+H)$^+$, RT: 2.08 min.

137.4 2-Ethyl-7-methoxy-1-oxo-6-(3-quinolin-2-yl-propoxy)-1,2-dihydro-isoquinoline-4-carboxylic acid A mixture of 2-ethyl-7-methoxy-1-oxo-6-(3-quinolin-2-yl-propoxy)-1,2-dihydro-isoquinoline-4-carboxylic acid methyl ester obtained in step 137.3 (43 mg, 0.061 mmol) and sodium hydroxide (7.28 mg, 0.182 mmol) in MeOH (3 mL) and water (1 mL) was heated at 50° C. for 3 h. The reaction mixture was acidified with HCl (2 N) to pH=4~5. The aqueous solution was concentrated in vacuo. and re-evaporated with MeOH (5 mL*3). The residue was used in the next step without further purification.

LCMS (ESI+): m/z 433 (M+H)$^+$, RT: 1.39 min.

137.5 2-Ethyl-7-methoxy-1-oxo-6-(3-quinolin-2-yl-propoxy)-1,2-dihydro-isoquinoline-4-carboxylic acid butylamide A suspension of 2-ethyl-7-methoxy-1-oxo-6-(3-quinolin-2-yl-propoxy)-1,2-dihydro-isoquinoline-4-carboxylic acid obtained in step 137.4 (23 mg, 0.023 mmol), DMF (3.54 μL, 0.046 mmol) and sulfurous dichloride (8.16 mg, 0.069 mmol) in DCM (2 mL) was refluxed for 3 h. The mixture was concentrated in vacuo. The residue was dissolved in DCM (2 mL). The solution was added dropwise to a mixture of butan-1-amine (1.673 mg, 0.023 mmol) and Et$_3$N (9.56 μL, 0.069 mmol) in DCM (2 mL) at ambient temperature. The reaction mixture was stirred at r.t. for another 3 h. Then the solvent was removed under reduced pressure, the residue was diluted with EtOAc (15 mL) and washed with brine (5 mL*3). The organic layer was dried over Na$_2$SO$_4$, filtered and concentrated in vacuo. The residue was purified by pre-HPLC to afford the title compound (3 mg, 26.9%) as a white solid.

$^1$H NMR (MeOD/TMS, 400 MHz) δ: 8.15 (d, J=8.0 Hz, 1H), 7.87 (d, J=8.0 Hz, 1H), 7.79 (d, J=8.4 Hz, 1H), 7.61-7.64 (m, 2H), 7.52 (s, 1H), 7.49 (s, 1H), 7.41-7.45 (m, 1H), 7.40 (d, J=8.4 Hz, 1H), 4.12 (t, J=5.8 Hz, 2H), 3.99-4.02 (m, 2H), 3.76 (s, 3H), 3.25-3.29 (m, 2H), 3.12 (t, J=7.6 Hz, 2H), 2.30 (m, 2H), 1.49-1.53 (m, 2H), 1.26-1.34 (m, 5H), 0.86 (t, J=7.4 Hz, 3H).

LCMS (ESI+): m/z 488 (M+H)$^+$, RT: 2.08 min.

The compounds of the following examples 138 to 166 were prepared according to following general procedure:

A 4 ml scintillation vial was charged with a stir bar, a solution of 2-ethyl-6,7-dimethoxy-1-oxo-1,2-dihydroisoquinoline-4-carboxylic acid as prepared in step 1.7 (16.57 mg, 0.059 mmol) in 1.0 mL of N,N-dimethylacetamide (DMA), a solution of the respective amine (1.2 eq, 0.0717 mmol) in DMA, a solution of HATU (27.26 mg, 0.0717 mmol, 1.2 eq) in DMA, and DIEA (3 eq, 0.179 mmol, 18.27 mg) neat. The mixture was capped and placed in the Anton Paar Synthos 3000 optimizer at 150° C. for 30 minutes. The vial was decapped and placed to concentrate to dryness. An additional 1.4 mL of DMSO/MeOH (1:1 v/v) was added for dissolution and submission for reverse phase HPLC purification.

Example 138

2-Ethyl-6,7-dimethoxy-1-oxo-N-(pyridin-3-yl)-1,2-dihydroisoquinoline-4-carboxamide ESI-MS [M+H$^+$]=353.9 m/z.
$^1$H NMR (500 MHz, DMSO/D$_2$O) δ ppm 1.33 (t, 3H) 3.85-3.87 (m, 3H) 3.89-3.91 (m, 3H) 4.07 (q, 1H) 7.50 (dd, J=8.39, 4.73 Hz, 1H) 7.69 (s, 1H) 7.74 (s, 1H) 8.06 (s, 1H) 8.21 (d, 1H) 8.35 (s, 1H) 8.90 (s, 1H).

Example 139

2-Ethyl-6,7-dimethoxy-1-oxo-N-(pyrimidin-4-ylmethyl)-1,2-dihydroisoquinoline-4-carboxamide ESI-MS [M+H$^+$]=368.15 m/z.
$^1$H NMR (500 MHz, DMSO/D$_2$O) δ ppm 1.32 (t, J=7.17 Hz, 3H) 3.84 (s, 3H) 3.88 (s, 3H) 4.05 (q, J=7.02 Hz, 3H) 4.57 (s, 2H) 7.56 (dd, J=5.19, 1.22 Hz, 1H) 7.67 (s, 1H) 7.77 (s, 1H) 7.92 (s, 1H) 8.77 (d, J=5.19 Hz, 1H) 9.13 (d, J=1.22 Hz, 1H).

Example 140

2-Ethyl-6,7-dimethoxy-4-(2-methoxybenzylamino)carbonyl)isoquinolin-1(2H)-one ESI-MS [M+H$^+$]=397.0 m/z.
$^1$H NMR (500 MHz, DMSO/D$_2$O) δ ppm 1.30 (t, J=7.02 Hz, 3H) 3.83 (d, J=10.07 Hz, 6H) 3.88 (s, 3H) 4.03 (d, J=7.02 Hz, 2H) 4.46 (s, 2H) 6.96 (t, 1H) 7.03 (d, 1H) 7.30 (q, 2H) 7.66 (s, 1H) 7.71 (s, 1H) 7.80 (s, 1H)

Example 141

2-Ethyl-6,7-dimethoxy-N-(4-morpholinophenyl)-1-oxo-1,2-dihydroisoquinoline-4-carboxamide ESI-MS [M+H$^+$]=438.0 m/z.
$^1$H NMR (500 MHz, DMSO/D$_2$O) δ ppm 1.33 (t, J=7.17 Hz, 3H) 3.11-3.14 (m, 4H) 3.76-3.79 (m, 4H) 3.85 (s, 3H) 3.89 (s, 3H) 4.06 (q, J=7.12 Hz, 2H) 7.03 (d, J=8.85 Hz, 2H) 7.61 (d, J=8.85 Hz, 2H) 7.68 (s, 1H) 7.71 (s, 1H) 7.92 (s, 1H)

Example 142

N-(3-Chlorobenzyl)-2-ethyl-6,7-dimethoxy-1-oxo-1,2-dihydroisoquinoline-4-carboxamide ESI-MS [M+H$^+$]=400.9 m/z.
$^1$H NMR (500 MHz, DMSO/D$_2$O) δ ppm 1.30 (t, J=7.02 Hz, 3H) 3.83 (s, 3H) 3.88 (s, 3H) 4.03 (q, J=7.12 Hz, 2H) 4.49 (s, 2H) 7.32-7.44 (m, 4H) 7.66 (s, 1H) 7.70 (s, 1H) 7.82 (s, 1H).

Example 143

2-Ethyl-6,7-dimethoxy-1-oxo-N-(pyridin-4-ylmethyl)-1,2-dihydroisoquinoline-4-carboxamide ESI-MS [M+H$^+$]=368.0 m/z.
$^1$H NMR (500 MHz, DMSO/D$_2$O) δ ppm 1.33 (t, J=7.17 Hz, 3H) 3.83 (s, 3H) 3.88 (s, 3H) 4.03-4.10 (m, 2H) 4.69 (s, 2H) 7.67 (s, 1H) 7.75 (s, 1H) 7.88 (d, J=5.80 Hz, 2H) 7.97 (s, 1H) 8.76 (s, 2H).

Example 144

2-Ethyl-6,7-dimethoxy-1-oxo-N-o-tolyl-1,2-dihydroisoquinoline-4-carboxamide

ESI-MS [M+H$^+$]=367.0 m/z.
$^1$H NMR (500 MHz, DMSO/D$_2$O) δ ppm 1.33 (t, J=7.17 Hz, 3H) 2.29 (s, 3H) 3.85 (s, 3H) 3.89 (s, 3H) 4.07 (q, J=7.12 Hz, 2H) 7.17-7.22 (m, 1H) 7.23-7.28 (m, 1H) 7.30 (d, J=7.63 Hz, 1H) 7.37-7.41 (m, 1H) 7.69 (s, 1H) 7.76 (s, 1H) 8.00 (s, 1H)

Example 145

2-Ethyl-6,7-dimethoxy-1-oxo-N-m-tolyl-1,2-dihydroisoquinoline-4-carboxamide

ESI-MS [M+H$^+$]=367.0 m/z.
$^1$H NMR (500 MHz, DMSO/D$_2$O) δ ppm 1.33 (t, J=7.17 Hz, 3H) 2.33 (s, 3H) 3.87 (d, 6H) 4.06 (q, J=7.02 Hz, 2H) 6.96 (d, J=7.63 Hz, 1H) 7.26 (t, J=7.93 Hz, 1H) 7.50 (d, J=8.24 Hz, 1H) 7.55 (s, 1H) 7.70 (d, J=14.34 Hz, 2H) 7.95 (s, 1H)

Example 146

2-Ethyl-6,7-dimethoxy-N-(2-methoxyphenyl)-1-oxo-1,2-dihydroisoquinoline-4-carboxamide ESI-MS [M+H$^+$]=383.0 m/z.
$^1$H NMR (500 MHz, DMSO/D$_2$O) δ ppm 1.32 (t, J=7.17 Hz, 3H) 3.84 (d, J=10.68 Hz, 6H) 3.89 (s, 3H) 4.06 (q, J=7.02 Hz, 2H) 6.97-7.02 (m, 1H) 7.11 (d, J=7.32 Hz, 1H) 7.18-7.24 (m, 1H) 7.68 (s, 1H) 7.73-7.79 (m, 2H) 7.96 (s, 1H)

Example 147

2-Ethyl-6,7-dimethoxy-N-(3-methoxyphenyl)-1-oxo-1,2-dihydroisoquinoline-4-carboxamide ESI-MS [M+H$^+$]=383.0 m/z.
$^1$H NMR (500 MHz, DMSO/D$_2$O) δ ppm 1.33 (t, J=7.17 Hz, 3H) 3.77 (s, 3H) 3.86 (s, 3H) 3.89 (s, 3H) 4.06 (q, J=7.22 Hz, 2H) 6.70-6.75 (m, 1H) 7.28-7.30 (m, 2H) 7.38 (d, J=1.83 Hz, 1H) 7.69 (d, J=6.41 Hz, 2H) 7.95 (s, 1H)

Example 148

2-Ethyl-6,7-dimethoxy-1-oxo-N-(pyridin-3-ylmethyl)-1,2-dihydroisoquinoline-4-carboxamide ESI-MS [M+H$^+$]=368.0 m/z.
$^1$H NMR (500 MHz, DMSO/D$_2$O) δ ppm 1.31 (t, J=7.02 Hz, 3H) 3.83 (s, 3H) 3.88 (s, 3H) 4.04 (q, J=7.02 Hz, 2H) 4.63 (s, 2H) 7.66 (s, 1H) 7.73 (s, 1H) 7.88-7.94 (m, 2H) 8.40 (d, J=7.93 Hz, 1H) 8.73 (d, J=5.19 Hz, 1H) 8.83 (s, 1H)

Example 149

2-Ethyl-6,7-dimethoxy-1-oxo-N-(pyridin-2-ylmethyl)-1,2-dihydroisoquinoline-4-carboxamide ESI-MS [M+H$^+$]=368.0 m/z.
$^1$H NMR (500 MHz, DMSO/D$_2$O) δ ppm 1.31 (t, J=7.02 Hz, 3H) 3.83 (s, 3H) 3.88 (s, 3H) 4.04 (q, J=7.02 Hz, 2H) 4.63 (s, 2H) 7.66 (s, 1H) 7.73 (s, 1H) 7.88-7.94 (m, 2H) 8.40 (d, J=7.93 Hz, 1H) 8.73 (d, J=5.19 Hz, 1H) 8.83 (s, 1H)

Example 150

N-(3-(Dimethylamino)propyl)-2-ethyl-6,7-dimethoxy-1-oxo-1,2-dihydroisoquinoline-4-carboxamide ESI-MS [M+H$^+$]=362.0
$^1$H NMR (500 MHz, DMSO/D$_2$O) δ ppm 1.30 (t, J=7.17 Hz, 3H) 1.87-1.96 (m, 2H) 2.81 (s, 6H) 3.11-3.18 (m, 2H) 3.34 (t, J=6.56 Hz, 2H) 3.87 (d, J=7.93 Hz, 6H) 4.02 (q, J=7.22 Hz, 2H) 7.66 (s, 1H) 7.74 (s, 1H) 7.77 (s, 1H)

Example 151

2-Ethyl-6,7-dimethoxy-1-oxo-N-phenyl-1,2-dihydroisoquinoline-4-carboxamide

ESI-MS [M+H$^+$]=353.0 m/z.
$^1$H NMR (500 MHz, DMSO/D$_2$O) δ ppm 1.33 (t, J=7.17 Hz, 3H) 3.86 (s, 3H) 3.89 (s, 3H) 4.06 (q, J=7.02 Hz, 2H) 7.14 (t, J=7.48 Hz, 1H) 7.37-7.41 (m, 2H) 7.68-7.73 (m, 4H) 7.97 (s, 1H)

Example 152

2-Ethyl-6,7-dimethoxy-N-(4-methoxybenzyl)-1-oxo-1,2-dihydroisoquinoline-4-carboxamide ESI-MS [M+H$^+$]=397.0 m/z.
$^1$H NMR (500 MHz, DMSO/D$_2$O) δ ppm 1.29 (t, J=7.17 Hz, 3H) 3.74 (s, 3H) 3.82 (s, 3H) 3.88 (s, 3H) 4.01 (q, J=7.02 Hz, 2H) 4.42 (d, J=5.80 Hz, 2H) 6.91-6.95 (m, 2H) 7.31-7.34 (m, 2H) 7.65 (s, 1H) 7.70 (s, 1H) 7.75 (s, 1H) 8.86 (t, J=5.80 Hz, 1H)

Example 153

2-Ethyl-6,7-dimethoxy-N-(4-methylbenzyl)-1-oxo-1,2-dihydroisoquinoline-4-carboxamide ESI-MS [M+H$^+$]=381.0 m/z.
$^1$H NMR (500 MHz, DMSO/D$_2$O) δ ppm 1.29 (t, J=7.17 Hz, 3H) 2.31 (s, 3H) 3.82 (s, 3H) 3.88 (s, 3H) 4.02 (q, J=7.22 Hz, 2H) 4.45 (d, J=5.80 Hz, 2H) 7.09 (d, J=7.63 Hz, 1H) 7.16-7.21 (m, 2H) 7.23-7.28 (m, 1H) 7.66 (s, 1H) 7.71 (s, 1H) 7.78 (s, 1H) 8.90 (t, J=5.95 Hz, 1H)

Example 154

2-Ethyl-6,7-dimethoxy-N-(2-methylbenzyl)-1-oxo-1,2-dihydroisoquinoline-4-carboxamide ESI-MS [M+H$^+$]=381.0 m/z.
$^1$H NMR (500 MHz, DMSO/D$_2$O) δ ppm 1.29 (t, J=7.17 Hz, 3H) 2.35 (s, 3H) 3.81 (s, 3H) 3.88 (s, 3H) 4.02 (q, J=7.22

Hz, 2H) 4.47 (s, 2H) 7.18-7.22 (m, 3H) 7.33 (t, J=3.51 Hz, 1H) 7.66 (s, 1H) 7.70 (s, 1H) 7.78 (s, 1H)

Example 155

2-Ethyl-6,7-dimethoxy-N-(2-methoxyethyl)-1-oxo-1,2-dihydroisoquinoline-4-carboxamide ESI-MS [M+H$^+$]=335.0 m/z.
$^1$H NMR (500 MHz, DMSO/D$_2$O) δ ppm 1.29 (t, J=7.02 Hz, 3H) 3.30 (s, 3H) 3.44 (t, J=5.49 Hz, 2H) 3.51 (t, J=5.80 Hz, 2H) 3.87 (d, J=7.63 Hz, 6H) 4.01 (q, J=7.02 Hz, 2H) 7.65 (s, 1H) 7.72 (d, J=2.75 Hz, 2H)

Example 156

2-Ethyl-N-(4-fluorophenyl)-6,7-dimethoxy-1-oxo-1,2-dihydroisoquinoline-4-carboxamide ESI-MS [M+H$^+$]=371.0 m/z.
$^1$H NMR (500 MHz, DMSO/D$_2$O) δ ppm 1.33 (t, J=7.02 Hz, 3H) 3.86 (s, 3H) 3.89 (s, 3H) 4.06 (q, J=7.22 Hz, 2H) 7.19-7.27 (m, 2H) 7.68 (s, 1H) 7.71-7.75 (m, 3H) 7.97 (s, 1H)

Example 157

2-Ethyl-6,7-dimethoxy-N-(4-nitrophenyl)-1-oxo-1,2-dihydroisoquinoline-4-carboxamide ESI-MS [M+H$^+$]=383.0 m/z.
$^1$H NMR (500 MHz, DMSO/D$_2$O) δ ppm 1.33 (t, J=7.17 Hz, 3H) 3.76 (s, 3H) 3.85 (s, 3H) 3.89 (s, 3H) 4.06 (q, J=7.22 Hz, 2H) 6.96 (tt, 2H) 7.62 (dt, 2H) 7.68 (s, 1H) 7.71 (s, 1H) 7.93 (s, 1H)

Example 158

2-Ethyl-6,7-dimethoxy-1-oxo-N-p-tolyl-1,2-dihydroisoquinoline-4-carboxamide

ESI-MS [M+H$^+$]=367.0 m/z.
$^1$H NMR (500 MHz, DMSO/D$_2$O) δ ppm 1.33 (t, J=7.17 Hz, 3H) 2.30 (s, 3H) 3.85 (s, 3H) 3.89 (s, 3H) 4.06 (q, J=7.22 Hz, 2H) 7.19 (d, J=8.24 Hz, 2H) 7.59 (dd, J=8.39, 2.59 Hz, 2H) 7.68 (s, 1H) 7.71 (s, 1H) 7.94 (s, 1H)

Example 159

2-Ethyl-N-(3-fluorophenyl)-6,7-dimethoxy-1-oxo-1,2-dihydroisoquinoline-4-carboxamide ESI-MS [M+H$^+$]=371.0 m/z.
$^1$H NMR (500 MHz, DMSO/D$_2$O) δ ppm 1.33 (t, J=7.02 Hz, 3H) 3.86 (s, 3H) 3.89 (s, 3H) 4.06 (q, J=7.02 Hz, 2H) 6.93-6.99 (m, 1H) 7.39-7.45 (m, 1H) 7.46-7.50 (m, 1H) 7.66-7.72 (m, 3H) 8.00 (s, 1H)

Example 160

2-Ethyl-N-(2-fluorophenyl)-6,7-dimethoxy-1-oxo-1,2-dihydroisoquinoline-4-carboxamide ESI-MS [M+H$^+$]=371.0 m/z.
$^1$H NMR (500 MHz, DMSO/D$_2$O) δ ppm 1.33 (t, J=7.17 Hz, 3H) 3.85 (s, 3H) 3.89 (s, 3H) 4.07 (d, J=7.32 Hz, 2H) 7.22-7.35 (m, 3H) 7.66-7.72 (m, 2H) 7.78 (s, 1H) 8.01 (s, 1H)

Example 161

2-Ethyl-6,7-dimethoxy-N-(4-methylbenzyl)-1-oxo-1,2-dihydroisoquinoline-4-carboxamide ESI-MS [M+H$^+$]=381.0 m/z.
$^1$H NMR (500 MHz, DMSO/D$_2$O) δ ppm 1.29 (t, J=7.02 Hz, 3H) 2.29 (s, 3H) 3.81 (s, 3H) 3.88 (s, 3H) 4.02 (q, J=7.22 Hz, 2H) 4.44 (d, J=5.19 Hz, 2H) 7.17 (d, J=7.63 Hz, 2H) 7.28 (d, J=7.93 Hz, 2H) 7.65 (s, 1H) 7.70 (s, 1H) 7.77 (s, 1H)

Example 162

N-(2-Chlorobenzyl)-2-ethyl-6,7-dimethoxy-1-oxo-1,2-dihydroisoquinoline-4-carboxamide ESI-MS [M+H$^+$]=401.0 m/z.
$^1$H NMR (500 MHz, DMSO/D$_2$O) δ ppm 1.31 (t, J=7.17 Hz, 3H) 3.82 (s, 3H) 3.88 (s, 3H) 4.04 (q, J=7.22 Hz, 2H) 4.56 (d, J=5.49 Hz, 2H) 7.31-7.41 (m, 2H) 7.49 (dd, J=7.78, 1.37 Hz, 2H) 7.66 (s, 1H) 7.71 (s, 1H) 7.85 (s, 1H) 8.93 (t, J=5.80 Hz, 1H)

Example 163

(R)-2-Ethyl-N-(1-(4-fluorophenyl)ethyl)-6,7-dimethoxy-1-oxo-1,2-dihydroisoquinoline-4-carboxamide ESI-MS [M+H$^+$]=399.0 m/z.
$^1$H NMR (500 MHz, DMSO/D$_2$O) δ ppm (t, J=7.17 Hz, 3H) 1.48 (d, J=7.32 Hz, 3H) 3.79 (s, 3H) 3.87 (s, 3H) 4.04 (q, J=7.02 Hz, 2H) 5.14 (q, J=6.92 Hz, 1H) 7.14-7.21 (m, 2H) 7.44-7.50 (m, 2H) 7.60 (s, 1H) 7.65 (s, 1H) 7.78 (s, 1H)

Example 164

2-Ethyl-6,7-dimethoxy-1-oxo-N-(pyridin-4-yl)-1,2-dihydroisoquinoline-4-carboxamide ESI-MS [M+H$^+$]=353.9 m/z.
$^1$H NMR (500 MHz, DMSO/D$_2$O) δ ppm 1.35 (t, J=7.17 Hz, 3H) 3.88 (s, 3H) 3.90 (s, 3H) 4.09 (q, J=7.02 Hz, 2H) 7.70 (s, 1H) 7.79 (s, 1H) 8.17 (d, J=7.32 Hz, 2H) 8.24 (s, 1H) 8.70 (d, J=7.32 Hz, 2H).

Example 165

(S)-2-Ethyl-N-(1-(4-fluorophenyl)ethyl)-6,7-dimethoxy-1-oxo-1,2-dihydroisoquinoline-4-carboxamide ESI-MS [M+H$^+$]=399.0 m/z.
$^1$H NMR (500 MHz, DMSO/D$_2$O) δ ppm 1.31 (t, J=7.17 Hz, 3H) 1.48 (d, J=7.32 Hz, 3H) 3.79 (s, 3H) 3.87 (s, 3H) 4.00-4.07 (m, 2H) 5.14 (q, J=7.12 Hz, 1H) 7.15-7.21 (m, 2H) 7.45-7.49 (m, 2H) 7.60 (s, 1H) 7.65 (s, 1H) 7.78 (s, 1H).

Example 166

2-Ethyl-6,7-dimethoxy-1-oxo-N-(1,2,3,4-tetrahydronaphthalen-1-yl)-1,2,3,8a-tetrahydroisoquinoline-4-carboxamide ESI-MS [M+H$^+$]=407.2 m/z.
$^1$H NMR (500 MHz, DMSO/D$_2$O) δ ppm 1.28 (t, J=7.17 Hz, 3H) 1.75-1.88 (m, 2H) 1.93-2.00 (m, 1H) 2.01-2.08 (m, 1H) 2.72-2.85 (m, 2H) 3.87 (s, 3H) 3.89 (s, 3H) 4.00 (q, J=7.12 Hz, 2H) 5.24 (q, 1H) 7.13-7.16 (m, 1H) 7.17-7.21 (m, 2H) 7.31-7.35 (m, 1H) 7.67 (s, 1H) 7.71 (s, 1H) 7.74 (s, 1H).

The compounds of the following examples 167 to 179 were prepared according to following general procedure:

In a 4 ml microwave vial was added 2-ethyl-6,7-dimethoxy-1-oxo-1,2-dihydroiso-quinoline-4-carboxylic acid as prepared in step 1.7 (25 mg, 0.09 mmol), followed by 2-(1H-7-azabenzotriazol-1-yl)-1,1,3,3-tetramethyl uronium hexafluorophosphate methanaminium (HATU; 42 mg, 0.10 mmol), triethylamine (37 μl, 0.27 mmol) and the respective amine (0.11 mmol). This mixture was placed in Anton Par with stir bar and heated at 150° C. for 30 minutes. The crude mixture was checked via LCMS for completion and concentrated to dryness. The residue was then dissolved in 1.4 mL of DMSO:MeOH (1:1) and purified through reverse phase HPLC (TFA method using MeOH) to afford pure products.

Example 167

2-Ethyl-6,7-dimethoxy-N-(6-methyl-2,3-dihydro-1H-inden-1-yl)-1-oxo-1,2-dihydroisoquinoline-4-carboxamide $^1$H NMR (500 MHz) δ ppm 1.28 (t, J=7.02 Hz, 3H) 1.95 (dd, J=12.66, 8.09 Hz, 1H) 2.29 (s, 3H) 2.74-2.85 (m, 1H) 2.90-3.02 (m, 1H) 3.88 (d, J=3.97 Hz, 6H) 4.01 (q, J=7.22 Hz, 2H) 5.50 (t, J=7.78 Hz, 1H) 7.06 (d, J=7.63 Hz, 1H) 7.17 (d, 2H) 7.66 (s, 1H) 7.78 (d, J=11.90 Hz, 2H).
MS (ESI+) M/Z 407 [M+H]$^+$.

Example 168

2-Ethyl-6,7-dimethoxy-N-(2-(morpholinomethyl)benzyl)-1-oxo-1,2-dihydroiso-quinoline-4-carboxamide $^1$H NMR (500 MHz δ ppm 1.24-1.33 (m, 4H) 3.40 (d, 4H) 3.81 (s, 3H) 3.87-3.89 (m, 3H) 4.04 (q, J=7.02 Hz, 4H) 4.58 (d, J=11.60 Hz, 4H) 7.43 (t, J=7.48, 1.37 Hz, 1H) 7.50-7.57 (m, 2H) 7.60-7.67 (m, 3H) 7.84 (s, 1H).
MS (ESI+) M/Z 466 [M+H]$^+$.

Example 169

N-(5-Chloro-2,3-dihydro-1H-inden-1-yl)-2-ethyl-6,7-dimethoxy-1-oxo-1,2-dihydroisoquinoline-4-carboxamide $^1$H NMR (500 MHz) δ ppm 1.28 (t, J=7.02 Hz, 3H) 2.00 (dd, J=12.82, 7.93 Hz, 1H) 2.88 (d, J=8.24 Hz, 1H) 2.97-3.06 (m, 1H) 3.87 (d, J=6.10 Hz, 6H) 4.00 (q, J=7.02 Hz, 2H) 5.50 (t, J=7.78 Hz, 1H) 7.28 (dd, J=8.09, 1.98 Hz, 1H) 7.37 (t, 2H) 7.66 (s, 1H) 7.77 (d, J=3.36 Hz, 2H).
MS (ESI+) M/Z 427 [M+H]$^+$.

Example 170

N-(6-Chloro-2,3-dihydro-1H-inden-1-yl)-2-ethyl-6,7-dimethoxy-1-oxo-1,2-dihydroisoquinoline-4-carboxamide $^1$H NMR (500 MHz) δ ppm 1.28 (t, J=7.17 Hz, 3H) 2.01 (dd, J=12.66, 8.09 Hz, 1H) 2.77-2.87 (m, 1H) 2.92-3.06 (m, 1H) 3.88 (d, J=1.22 Hz, 6H) 4.01 (q, J=7.02 Hz, 2H) 5.52 (t, J=7.78 Hz, 1H) 7.27-7.34 (m, 2H) 7.39 (s, 1H) 7.66 (s, 1H) 7.77 (d, J=18.92 Hz, 2H).
MS (ESI+) M/Z 427 [M+H]$^+$.

Example 171

2-Ethyl-N-(6-fluoro-2,3-dihydro-1H-inden-1-yl)-6,7-dimethoxy-1-oxo-1,2-dihydroisoquinoline-4-carboxamide $^1$H NMR (500 MHz) δ ppm 1.28 (t, J=7.02 Hz, 3H) 1.96-2.06 (m, 1H) 2.77-2.88 (m, 1H) 2.93-3.01 (m, 1H) 3.88 (d, J=4.88 Hz, 6H) 4.01 (q, J=7.02 Hz, 2H) 5.52 (t, J=7.78 Hz, 1H) 7.06 (t, 1H) 7.16 (dd, J=8.85, 2.14 Hz, 1H) 7.30 (dd, J=8.24, 5.19 Hz, 1H) 7.66 (s, 1H) 7.78 (d, J=13.43 Hz, 2H).
MS (ESI+) M/Z 411 [M+H]$^+$.

Example 172

N-(5,6-Dihydro-4H-cyclopenta[b]thiophen-4-yl)-2-ethyl-6,7-dimethoxy-1-oxo-1,2-dihydroisoquinoline-4-carboxamide $^1$H NMR (500 MHz, Solvent) δ ppm 1.27 (t, J=7.02 Hz, 3H) 2.33-2.41 (m, 1H) 2.82-2.95 (m, 2H) 3.03 (d, 1H) 3.87 (d, J=6.71 Hz, 6H) 3.99 (q, J=7.02 Hz, 2H) 5.37 (t, 1H) 6.99 (d, J=5.19 Hz, 1H) 7.39 (d, J=5.19 Hz, 1H) 7.65 (s, 1H) 7.73 (d, J=13.12 Hz, 2H).
MS (ESI+) M/Z 399 [M+H]$^+$.

Example 173

2-Ethyl-N-(4-fluoro-2,3-dihydro-1H-inden-1-yl)-6,7-dimethoxy-1-oxo-1,2-dihydroisoquinoline-4-carboxamide $^1$H NMR (500 MHz) δ ppm 1.28 (t, J=7.17 Hz, 3H) 2.03 (dd, J=12.66, 8.39 Hz, 1H) 2.79-2.96 (m, 1H) 3.04 (d, J=5.19 Hz, 1H) 3.87 (d, J=7.02 Hz, 6H) 4.01 (q, J=7.02 Hz, 2H) 5.58 (d, J=7.93 Hz, 1H) 6.93-7.14 (m, 1H) 7.16-7.36 (m, 2H) 7.66 (s, 1H) 7.77 (d, J=1.22 Hz, 2H) 8.78 (d, J=8.24 Hz, 1H).
MS (ESI+) M/Z 411 [M+H]$^+$.

Example 174

2-Ethyl-6,7-dimethoxy-N-(4-methyl-2,3-dihydro-1H-inden-1-yl)-1-oxo-1,2-dihydroisoquinoline-4-carboxamide $^1$H NMR (500 MHz) δ ppm 1.28 (t, J=7.17 Hz, 3H) 1.96 (dd, J=12.51, 8.54 Hz, 1H) 2.25 (s, 3H) 2.71-2.81 (m, 1H) 2.94 (dd, J=8.85, 3.36 Hz, 1H) 3.87 (d, J=7.93 Hz, 6H) 4.00 (q, J=7.12 Hz, 2H) 5.54 (t, J=7.78 Hz, 1H) 7.07 (d, J=7.32 Hz, 1H) 7.10-7.24 (m, 2H) 7.66 (s, 1H) 7.76 (d, J=14.34 Hz, 2H).
MS (ESI+) M/Z 407 [M+H]$^+$.

Example 175

2-Ethyl-6,7-dimethoxy-N-(5-methyl-2,3-dihydro-1H-inden-1-yl)-1-oxo-1,2-dihydroisoquinoline-4-carboxamide $^1$H NMR (500 MHz) δ ppm 1.27 (t, J=7.17 Hz, 3H) 1.89-2.02 (m, 1H) 2.30 (s, 3H) 2.76-2.87 (m, 1H) 2.91-3.01

(m, 1H) 3.87 (d, J=7.63 Hz, 6H) 4.00 (q, J=7.12 Hz, 2H) 5.48 (t, J=7.63 Hz, 1H) 6.98-7.14 (m, 2H) 7.25 (d, J=7.63 Hz, 1H) 7.66 (s, 1H) 7.76 (d, J=15.56 Hz, 2H).
MS (ESI+) M/Z 407 [M+H]$^+$.

Example 176

2-Ethyl-6,7-dimethoxy-N-(6-methoxy-2,3-dihydro-1H-inden-1-yl)-1-oxo-1,2-dihydroisoquinoline-4-carboxamide $^1$H NMR (500 MHz) δ ppm 1.28 (t, J=7.17 Hz, 3H) 1.97 (dd, J=12.51, 7.93 Hz, 1H) 2.70-2.85 (m, 1H) 2.91 (dd, J=8.85, 3.36 Hz, 1H) 3.72 (s, 3H) 3.87 (d, J=9.76 Hz, 6H) 4.01 (q, J=7.02 Hz, 2H) 5.49 (t, J=7.93 Hz, 1H) 6.82 (dd, J=7.93, 2.14 Hz, 1H) 6.92 (d, J=2.14 Hz, 1H) 7.19 (d, J=8.24 Hz, 1H) 7.66 (s, 1H) 7.78 (d, J=5.80 Hz, 2H).
MS (ESI+) M/Z 423 [M+H]$^+$.

Example 177

2-Ethyl-N-(5-fluoro-2,3-dihydro-1H-inden-1-yl)-6,7-dimethoxy-1-oxo-1,2-dihydroisoquinoline-4-carboxamide $^1$H NMR (500 MHz) δ ppm 1.28 (t, J=7.17 Hz, 3H) 2.01 (dd, J=12.51, 7.93 Hz, 1H) 2.76-2.93 (m, 1H) 2.96-3.13 (m, 1H) 3.87 (d, J=6.10 Hz, 6H) 4.00 (q, J=7.02 Hz, 2H) 5.50 (d, J=7.63 Hz, 1H) 6.95-7.19 (m, 2H) 7.38 (dd, J=8.09, 5.34 Hz, 1H) 7.66 (s, 1H) 7.77 (d, J=6.10 Hz, 2H) 8.73 (d, J=8.24 Hz, 1H).
MS (ESI+) M/Z 411 [M+H]$^+$.

Example 178

N-(2-((Diethylamino)methyl)benzyl)-2-ethyl-6,7-dimethoxy-1-oxo-1,2-dihydroisoquinoline-4-carboxamide $^1$H NMR (500 MHz) δ ppm 1.18-1.45 (m, 9H) 3.25 (q, 4H) 3.79 (s, 3H) 3.87 (s, 3H) 4.04 (q, J=7.02 Hz, 2H) 4.53 (d, J=14.04 Hz, 4H) 7.43 (t, J=7.48, 1.37 Hz, 1H) 7.50-7.57 (m, 2H) 7.59 (t, 2H) 7.65 (s, 1H) 7.85 (s, 1H).
MS (ESI+) M/Z 452 [M+H]$^+$.

Example 179

2-Ethyl-6,7-dimethoxy-1-oxo-N-(2-(pyrrolidin-1-ylmethyl)benzyl)-1,2-dihydroisoquinoline-4-carboxamide $^1$H NMR (500 MHz) δ ppm 1.22-1.34 (m, 4H) 1.89-1.97 (m, 2H) 2.08-2.16 (m, 2H) 3.19-3.26 (m, 2H) 3.47-3.55 (m, 2H) 3.80 (s, 3H) 3.86-3.89 (m, 4H) 3.97-4.07 (m, 2H) 4.58 (d, J=3.36 Hz, 4H) 7.41 (t, 1H) 7.49-7.58 (m, 3H) 7.65 (d, 2H) 7.83 (s, 1H).
MS (ESI+) M/Z 450 [M+H]$^+$.

The compounds of the following examples 180 and 181 were prepared by analogy to example 133 starting from 2-ethyl-7-methoxy-1-oxo-1,2-dihydro-[2,6]naphthyridine-2-carboxylic acid, which in turn was prepared by analogy to steps 133.1-133.7 of example 133 starting from commercially available 5-bromo-2-methoxy-isonicotinic acid.

Example 180

2-Ethyl-7-methoxy-1-oxo-1,2-dihydro-[2,6]naphthyridine-4-carboxylic acid indan-1-ylamide ESI-MS: [M+Na$^+$]=386.20, [M+H$^+$]=364.10.

Example 181

2-Ethyl-7-methoxy-1-oxo-1,2-dihydro-[2,6]naphthyridine-4-carboxylic acid butylamide ESI-MS: [M+Na$^+$]=629.20, [M+H$^+$]=304.10.

The compound of the following example 182 was prepared according to example 133 starting from (Z)-methyl 2-(1-(dimethylamino)-3-methoxy-3-oxoprop-1-en-2-yl)-5-methoxybenzoate, which in turn was prepared according to step 133.6 of example 133 starting from starting from 2-(quinolin-2-yl)ethanamine.

Example 182

7-Methoxy-1-oxo-2-(2-quinolin-2-yl-ethyl)-1,2-dihydro-isoquinoline-4-carboxylic acid butylamide

ESI-MS: [M+H$^+$]=430.20.

The following compounds were prepared in analogy to the above examples.

Example 183

7-Methoxy-1-oxo-2-(2-quinolin-2-yl-ethyl)-1,2-dihydro-isoquinoline-4-carboxylic acid indan-1-ylamide
ESI-MS: [M+H$^+$]=490.20.

Example 184

(S)-3-ethyl-6,7-dimethoxy-4-oxo-N-(1,2,3,4-tetrahydronaphthalen-1-yl)-3,4-dihydrophthalazine-1-carboxamide ESI-MS: [M+Na$^+$]=430.20, [M+H$^+$]=408.20.

Example 185

3-Ethyl-6,7-dimethoxy-4-oxo-3,4-dihydro-phthalazine-1-carboxylic acid (S)-indan-1-ylamide ESI-MS: [M+Na$^+$]=416.20, [M+H$^+$]=394.20.

Example 186

2-(1-Ethyl-propyl)-6,7-dimethoxy-1-oxo-1,2-dihydro-isoquinoline-4-carboxylic acid (6,7-dihydro-5H-[1]pyrindin-5-yl)-amide

ESI-MS: [M+H$^+$]=436.20.

Example 187

2-(1-Ethyl-propyl)-6,7-dimethoxy-1-oxo-1,2-di-hydro-isoquinoline-4-carboxylic acid 2-dimethyl-aminomethyl-benzylamide hydrochloride

ESI-MS: [M+H$^+$]=466.30.

Example 188

2-(1-Ethyl-propyl)-6,7-dimethoxy-1-oxo-1,2-di-hydro-isoquinoline-4-carboxylic acid 3,5-difluoro-benzylamide

ESI-MS: [M+H$^+$]=445.20;

Example 189

2-(1-Ethyl-propyl)-6,7-dimethoxy-1-oxo-1,2-di-hydro-isoquinoline-4-carboxylic acid 3,4-difluoro-benzylamide

ESI-MS: [M+H$^+$]=445.20.

Example 190

2-(1-Ethyl-propyl)-6,7-dimethoxy-1-oxo-1,2-di-hydro-isoquinoline-4-carboxylic acid cyclohexylmethyl-amide

ESI-MS: [M+H$^+$]=415.30;

Example 191

2-(1-Ethyl-propyl)-6,7-dimethoxy-1-oxo-1,2-di-hydro-isoquinoline-4-carboxylic acid (R)-indan-1-ylamide

ESI-MS: [M+H$^+$]=435.30.

Example 192

2-(1-Ethyl-propyl)-6,7-dimethoxy-1-oxo-1,2-di-hydro-isoquinoline-4-carboxylic acid (S)-indan-1-ylamide

ESI-MS: [M+H$^+$]=435.30.

Example 193

2-(1-Ethyl-propyl)-6,7-dimethoxy-1-oxo-1,2-di-hydro-isoquinoline-4-carboxylic acid (5,6-dihydro-4H-cyclopenta[b]thiophen-4-yl)-amide

ESI-MS: 442.10, [M+H$^+$]=441.10.

Example 194

2-(1-Ethyl-propyl)-6,7-dimethoxy-1-oxo-1,2-di-hydro-isoquinoline-4-carboxylic acid (2,3-dihydro-benzofuran-3-yl)-amide ESI-MS: [M+Na$^+$]=459.15, 438.20, [M+H$^+$]=437.15.

Example 195

2-(1-Ethyl-propyl)-6,7-dimethoxy-1-oxo-1,2-di-hydro-isoquinoline-4-carboxylic acid (6-oxo-5,6-dihydro-4H-cyclopenta[b]thiophen-4-yl)-amide ESI-MS: [M+Na$^+$]=477.05, 456.10, [M+H$^+$]=455.10.

Example 196

2-Cyclopropyl-6,7-dimethoxy-1-oxo-1,2-dihydro-isoquinoline-4-carboxylic acid indan-1-ylamide

ESI-MS: 406.10, [M+H$^+$]=405.10.

Example 197

2-sec-Butyl-6,7-dimethoxy-1-oxo-1,2-dihydro-iso-quinoline-4-carboxylic acid indan-1-ylamide

ESI-MS: 422.15, [M+H$^+$]=421.10.

Example 198

2-Isopropyl-6,7-dimethoxy-1-oxo-1,2-dihydro-iso-quinoline-4-carboxylic acid indan-1-ylamide

ESI-MS: 408.20, [M+H$^+$]=407.15;

Example 199

(+)-2-(1-Ethyl-propyl)-6,7-dimethoxy-1-oxo-1,2-dihydro-isoquinoline-4-carboxylic acid (6,7-di-hydro-5H-[1]pyrindin-5-yl)-amide

ESI-MS: 437.20, [M+H$^+$]=436.20.

Example 200

(−)-2-(1-Ethyl-propyl)-6,7-dimethoxy-1-oxo-1,2-dihydro-isoquinoline-4-carboxylic acid (6,7-di-hydro-5H-[1]pyrindin-5-yl)-amide

ESI-MS: 437.20, [M+H$^+$]=436.20.

Example 201

2-(1-Ethyl-propyl)-6,7-dimethoxy-1-oxo-1,2-di-hydro-isoquinoline-4-carboxylic acid ([1,3,4]thiadi-azol-2-ylmethyl)-amide

ESI-MS: 418.20, [M+H$^+$]=417.10.

Example 202

2-(1-Ethyl-propyl)-6,7-dimethoxy-1-oxo-1,2-di-hydro-isoquinoline-4-carboxylic acid 2-(morpho-line-4-sulfonyl)-benzylamide

ESI-MS: 560.20, 559.20, [M+H$^+$]=558.20;

Example 203

2-(1-Ethyl-propyl)-6,7-dimethoxy-1-oxo-1,2-di-hydro-isoquinoline-4-carboxylic acid (thiazol-4-ylmethyl)-amide

ESI-MS: 417.10, [M+H$^+$]=416.10.

Example 204

(+)-2-Ethyl-6,7-dimethoxy-1-oxo-1,2-dihydro-iso-quinoline-4-carboxylic acid (5,6-dihydro-4H-cyclopenta[b]thiophen-4-yl)-amide

ESI-MS: [M+H$^+$]=399.10.

Example 205

(−)-2-Ethyl-6,7-dimethoxy-1-oxo-1,2-dihydro-iso-quinoline-4-carboxylic acid (5,6-dihydro-4H-cyclopenta[b]thiophen-4-yl)-amide

ESI-MS: [M+H$^+$]=399.10.

Example 206

2-(1-Ethyl-propyl)-6,7-dimethoxy-1-oxo-1,2-di-hydro-isoquinoline-4-carboxylic acid (thiophen-3-ylmethyl)-amide

ESI-MS: 416.10, [M+H$^+$]=415.10.

Example 207

2-(1-Ethyl-propyl)-6,7-dimethoxy-4-(3-phenyl-piperidine-1-carbonyl)-2H-isoquinolin-1-one

ESI-MS: [M+H$^+$]=463.10.

Example 208

2-(1-Ethyl-propyl)-6,7-dimethoxy-4-(3-phenoxy-piperidine-1-carbonyl)-2H-isoquinolin-1-one

ESI-MS: [M+H$^+$]=479.20.

Example 209

2-(1-Ethyl-propyl)-6,7-dimethoxy-4-[3-(3-methoxy-phenyl)-piperazine-1-carbonyl]-2H-isoquinolin-1-one

ESI-MS: [M+H$^+$]=494.20.

Example 210

2-(1-Ethyl-propyl)-6,7-dimethoxy-4-[8-(4-methyl-piperazine-1-sulfonyl)-3,4-dihydro-1H-isoquinoline-2-carbonyl]-2H-isoquinolin-1-one

ESI-MS: [M+H$^+$]=597.20.

Example 211

2-(1-Ethyl-propyl)-6,7-dimethoxy-4-[8-(morpholine-4-sulfonyl)-3,4-dihydro-1H-isoquinoline-2-carbonyl]-2H-isoquinolin-1-one

ESI-MS: [M+H$^+$]=584.20.

Example 212

2-(1-Ethyl-propyl)-6,7-dimethoxy-4-[3-(3-methoxy-phenyl)-4-methyl-piperazine-1-carbonyl]-2H-isoquinolin-1-one

ESI-MS: [M+H$^+$]=508.30.

Example 213

2-(1-Ethyl-propyl)-6,7-dimethoxy-4-[(R)-3-(quinoxalin-2-yloxy)-pyrrolidine-1-carbonyl]-2H-isoquinolin-1-one

ESI-MS: [M+H]$^+$=517.20.

Example 214

4-(7-Amino-3,4-dihydro-1H-isoquinoline-2-carbonyl)-2-(1-ethyl-propyl)-6,7-dimethoxy-2H-isoquinolin-1-one trifluoroacetate

ESI-MS: [M+H]$^+$=450.20.

Example 215

2-(1-Ethyl-propyl)-6,7-dimethoxy-1-oxo-1,2-di-hydro-isoquinoline-4-carboxylic acid 3-(4-chloro-benzenesulfonylamino)-benzylamide

ESI-MS: [M]$^+$=598.20.

Example 216

2-(1-Ethyl-propyl)-6,7-dimethoxy-1-oxo-1,2-di-hydro-isoquinoline-4-carboxylic acid (2,3-dihydro-benzo[b]thiophen-3-yl)-amide ESI-MS: [M+Na]$^+$=475.20, [M+H$^+$]=453.20.

Example 217

2-(1-Ethyl-propyl)-7-methoxy-1-oxo-1,2-dihydro-[2,6]naphthyridine-4-carboxylic acid (5,6-dihydro-4H-cyclopenta[b]thiophen-4-yl)-amide ESI-MS: [M+Na]$^+$=434.10, [M+H$^+$]=412.10.

Example 218

2-(1-Ethyl-propyl)-7-methoxy-1-oxo-1,2-dihydro-[2,6]naphthyridine-4-carboxylic acid (S)-indan-1-yl-amide ESI-MS: [M+Na]$^+$=428.10, [M+H$^+$]=406.20.

Example 219

2-(1-Ethyl-propyl)-6,7-dimethoxy-1-oxo-1,2-di-hydro-isoquinoline-4-carboxylic acid 2-(4-methyl-piperazine-1-sulfonyl)-benzylamide

ESI-MS: [M+H]$^+$=571.30.

Example 220

2-(1-Ethyl-propyl)-7-methoxy-1-oxo-1,2-dihydro-[2,6]naphthyridine-4-carboxylic acid 2-(morpholine-4-sulfonyl)-benzylamide ESI-MS: [M+Na]$^+$=551.20, [M+H]$^+$=529.20.

Example 221

2-(1-Ethyl-propyl)-7-methoxy-1-oxo-1,2-dihydro-[2,6]naphthyridine-4-carboxylic acid (6,7-dihydro-5H-[1]pyrindin-5-yl)-amide ESI-MS: [M+Na]$^+$=429.15, [M+H]$^+$=407.20.

Example 222

2-(1-Ethyl-propyl)-6,7-dimethoxy-1-oxo-1,2-di-hydro-isoquinoline-4-carboxylic acid 3-(4-methoxy-benzenesulfonylamino)-benzylamide ESI-MS: [M+Na]$^+$=616.20, [M+H]$^+$=594.30.

Example 223

2-(1-Ethyl-propyl)-7-methoxy-1-oxo-1,2-dihydro-[2,6]naphthyridine-4-carboxylic acid 3,5-difluoro-benzylamide ESI-MS: [M+Na]$^+$=438.15, [M+H]$^+$=416.10

Example 224

2-(1-Ethyl-propyl)-7-methoxy-1-oxo-1,2-dihydro-[2,6]naphthyridine-4-carboxylic acid 4-methyl-benzyl-amide ESI-MS: [M+Na]$^+$=416.20, [M+H]$^+$=394.20.

Example 225

2-(1-Ethyl-propyl)-7-methoxy-1-oxo-1,2-dihydro-[2,6]naphthyridine-4-carboxylic acid cyclohexylm-ethyl-amide ESI-MS: [M+Na]$^+$=408.20, [M+H]$^+$=386.20.

Example 226

2-(1-Ethyl-propyl)-7-methoxy-1-oxo-1,2-dihydro-[2,6]naphthyridine-4-carboxylic acid butylamide

ESI-MS: [M+H]$^+$=346.20.

Example 227

2-(1-Ethyl-propyl)-7-methoxy-1-oxo-1,2-dihydro-[2,6]naphthyridine-4-carboxylic acid (2,3-dihydro-benzofuran-3-yl)-amide ESI-MS: [M+Na]$^+$=430.20, [M+H]$^+$=408.20.

Example 228

2-(1-Ethyl-propyl)-6,7-dimethoxy-1-oxo-1,2-di-hydro-isoquinoline-4-carboxylic acid (thiazol-2-ylmethyl)-amide ESI-MS: [M+Na]$^+$=438.10, [M+H]$^+$=416.10.

Example 229

2-(1-Ethyl-propyl)-6,7-dimethoxy-1-oxo-1,2-di-hydro-isoquinoline-4-carboxylic acid (thiophen-2-ylmethyl)-amide ESI-MS: [M+Na]$^+$=437.10, [M+H]$^+$=415.10.

Example 230

2-Ethyl-7-methoxy-1-oxo-1,2-dihydro-[2,6]naphthyridine-4-carboxylic acid (5,6-dihydro-4H-cyclopenta[b]thiophen-4-yl)-amide ESI-MS: [M+Na]$^+$=392.10, [M+H]$^+$=370.10.

Example 231

3-(1-Ethyl-propyl)-6,7-dimethoxy-4-oxo-3,4-di-hydro-phthalazine-1-carboxylic acid (5,6-dihydro-4H-cyclopenta[b]thiophen-4-yl)-amide trifluoroacetate ESI-MS: [M+Na]$^+$=464.10, [M+H]$^+$=442.15.

Example 232

3-(1-Ethyl-propyl)-6,7-dimethoxy-4-oxo-3,4-di-hydro-phthalazine-1-carboxylic acid (2,3-dihydro-benzofuran-3-yl)-amide trifluoroacetate ESI-MS: [M+Na]$^+$=460.20, [M+H]$^+$=438.20.

Example 233

3-(1-Ethyl-propyl)-6,7-dimethoxy-4-oxo-3,4-di-hydro-phthalazine-1-carboxylic acid (6,7-dihydro-5H-[1]pyrindin-5-yl)-amide ESI-MS: [M+Na$^+$]=459.20, [M+H]$^+$=437.20.

Example 234

2-(1-Ethyl-propyl)-6,7-dimethoxy-4-(3-phenyl-pro-pionyl)-2H-isoquinolin-1-one

ESI-MS: [M+Na]$^+$=430.20, [M+H]$^+$=408.20

Example 235

3-(1-Ethyl-propyl)-6,7-dimethoxy-4-oxo-3,4-dihydro-phthalazine-1-carboxylic acid indan-1-ylamide ESI-MS: [M+Na]$^+$=458.20, [M+H]$^+$=436.20.

Example 236

6,7-Dimethoxy-1-oxo-2-(pentan-3-yl)-N-(pyridin-3-ylmethyl)-1,2-dihydroisoquinoline-4-carboxamide A microwave vial was charged with a stir bar and 284 mg of PS-TFP (10 eq.). To the vessel were added 6,7-dimethoxy-1-oxo-2-(pentan-3-yl)-1,2-dihydroisoquinoline-4-carboxylic acid (29 mg, 0.09 mmol) dissolved in dry THF (1.0 mL) and CCl$_3$CN (36 µL, 0.36 mmol) dissolved in dry THF (0.5 mL). The reaction vessel was sealed and heated to 120° C. for 1800 seconds. Then pyridin-3-ylmethanamine (15 mg, 0.135 mmol) dissolved in THF (0.5 mL) was added followed by DIEA (47 µL, 0.27 mmol). The mixture was heated again to 150° C. for 1800 seconds. After cooling the reaction mixture was filtered and products were collected and concentrated to dryness. The residues were dissolved in 1:1 DMSO/MeOH. Purification by reverse phase HPLC provided the title compound (14.7 mg, 31%).

ESI-MS=410 [M+H]$^+$;
$^1$H NMR (500 MHz, DMSO-D$_2$O, T: 25° C.) δ ppm 8.86 (s, 1H) 8.76 (d, J=5.49 Hz, 1H) 8.47 (d, J=7.93 Hz, 1H) 7.97 (dd, J=7.93, 5.49 Hz, 1H) 7.74 (s, 1H) 7.67 (d, J=10.99 Hz, 2H) 4.86 (s, 1H) 4.65 (s, 2H) 3.86 (d, J=28.08 Hz, 6H) 1.69-1.90 (m, 4H) 0.74 (t, J=7.32 Hz, 6H).

The following compounds of examples 237 to 244 were prepared in an analogous manner to the process described in example 236.

Example 237

6,7-Dimethoxy-N-((5-methylthiophen-2-yl)methyl)-1-oxo-2-(pentan-3-yl)-1,2-dihydroisoquinoline-4-carboxamide ESI-MS=429 [M+H]$^+$;
$^1$H NMR (500 MHz, DMSO-D$_2$O, T: 25° C.) δ ppm 7.72 (s, 1H) 7.67 (s, 1H) 7.50 (s, 1H) 6.83 (d, J=3.36 Hz, 1H) 6.65 (d, J=2.14 Hz, 1H) 4.85 (s, 1H) 4.55 (s, 2H) 3.86 (d, J=21.36 Hz, 6H) 2.39 (s, 3H) 1.65-1.85 (m, 4H) 0.72 (t, J=7.32 Hz, 6H).

Example 238

N-((3,5-Dimethylisoxazol-4-yl)methyl)-6,7-dimethoxy-1-oxo-2-(pentan-3-yl)-1,2-dihydroisoquinoline-4-carboxamide ESI-MS=428[M+H]$^+$;
$^1$H NMR (500 MHz, DMSO-D$_2$O, T: 25° C.) δ ppm 7.67 (s, 1H) 7.63 (s, 1H) 7.45 (s, 1H) 4.83 (s, 1H) 4.26 (s, 2H) 3.85 (d, J=28.99 Hz, 6H) 2.43 (s, 3H) 2.26 (s, 3H) 1.65-1.85 (m, 4H) 0.72 (t, J=7.17 Hz, 6H).

Example 239

6,7-Dimethoxy-N-((5-methylthiazol-2-yl)methyl)-1-oxo-2-(pentan-3-yl)-1,2-dihydroisoquinoline-4-carboxamide ESI-MS=430 [M+H]$^+$;
$^1$H NMR (500 MHz, DMSO-D$_2$O, T: 25° C.) δ ppm 7.80 (s, 1H) 7.69 (s, 1H) 7.60 (s, 1H) 7.42 (s, 1H) 4.87 (s, 1H) 4.68 (s, 2H) 3.88 (d, J=14.04 Hz, 6H) 2.42 (s, 3H) 1.68-1.88 (m, 4H) 0.74 (t, J=7.32 Hz, 6H).

Example 240

6,7-Dimethoxy-1-oxo-2-(pentan-3-yl)-N-(pyrimidin-4-ylmethyl)-1,2-dihydroisoquinoline-4-carboxamide ESI-MS=411 [M+H]$^+$;
$^1$H NMR (500 MHz, DMSO-D$_2$O, T: 25° C.) δ ppm 9.13 (s, 1H) 8.76-8.79 (m, 1H) 7.77-7.81 (m, 1H) 7.67-7.70 (m, 2H) 7.55 (d, J=4.88 Hz, 1H) 4.87 (s, 1H) 4.56-4.61 (m, 2H) 3.89 (s, 3H) 3.84 (s, 3H) 1.77-1.86 (m, 4H) 0.75 (t, J=7.32 Hz, 6H).

Example 241

6,7-Dimethoxy-N-((3-methylisoxazol-5-yl)methyl)-1-oxo-2-(pentan-3-yl)-1,2-dihydroisoquinoline-4-carboxamide ESI-MS=414 [M+H]$^+$;
$^1$H NMR (500 MHz, DMSO-D$_2$O, T: 25° C.) δ ppm 7.75 (s, 1H) 7.68 (s, 1H) 7.58 (s, 1H) 6.30 (s, 1H) 4.85 (s, 1H) 4.57 (s, 2H) 3.87 (d, J=16.48 Hz, 6H) 2.22 (s, 3H) 1.71-1.87 (m, 4H) 0.73 (t, J=7.32 Hz, 6H).

Example 242

N-((2,5-dimethylthiophen-3-yl)methyl)-6,7-dimethoxy-1-oxo-2-(pentan-3-yl)-1,2-dihydroisoquinoline-4-carboxamide ESI-MS=443 [M+H]$^+$;
$^1$H NMR (500 MHz, DMSO-D$_2$O, T: 25° C.) δ ppm 7.67 (s, 1H) 7.63 (s, 1H) 7.47 (s, 1H) 6.69 (s, 1H) 4.84 (s, 1H) 4.30 (s, 2H) 3.85 (d, J=30.21 Hz, 6H) 2.31-2.39 (m, 6H) 1.67-1.84 (m, 4H) 0.72 (t, J=7.32 Hz, 6H).

Example 243

6,7-Dimethoxy-N-((2-methylthiazol-5-yl)methyl)-1-oxo-2-(pentan-3-yl)-1,2-dihydroisoquinoline-4-carboxamide ESI-MS=430 [M+H]$^+$;
$^1$H NMR (500 MHz, DMSO-D$_2$O, T: 25° C.) δ ppm 7.73 (s, 1H) 7.67 (s, 1H) 7.58 (s, 1H) 7.51 (s, 1H) 4.84 (s, 2H) 4.60 (s, 2H) 3.87 (d, 6H) 2.62 (s, 3H) 1.66-1.85 (m, 4H) 0.72 (t, J=7.32 Hz, 6H).

Example 244

6,7-Dimethoxy-N-((5-methylisoxazol-3-yl)methyl)-1-oxo-2-(pentan-3-yl)-1,2-dihydroisoquinoline-4-carboxamide ESI-MS=414 [M+H]$^+$;
$^1$H NMR (500 MHz, DMSO-D$_2$O, T: 25° C.) δ ppm 7.78 (s, 1H) 7.68 (s, 1H) 7.55-7.59 (m, 1H) 6.25 (s, 1H) 4.85 (s, 1H) 4.48 (s, 2H) 3.87 (d, J=10.38 Hz, 6H) 2.39 (s, 3H) 1.70-1.85 (m, 4H) 0.73 (t, J=7.32 Hz, 6H).

Example 245

(R)—N-(1-(4-fluorophenyl)ethyl)-6,7-dimethoxy-1-oxo-2-(pentan-3-yl)-1,2-dihydroisoquinoline-4-carboxamide The title compound was prepared in analogy to the process described in example 236 but using (R)-1-(4-fluorophenyl)ethanamine instead of pyridine-3-ylmethanamine.
ESI-MS=441 [M+H]$^+$;
$^1$H NMR (500 MHz, DMSO-D$_2$O, T: 25° C.) δ ppm 7.67 (s, 1H) 7.43-7.53 (m, 4H) 7.19 (t, J=8.85 Hz, 2H) 5.17 (q, J=6.92 Hz, 1H) 4.84 (s, 1H) 3.83 (d, J=50.35 Hz, 6H) 1.67-1.88 (m, 4H) 1.50 (d, J=7.32 Hz, 3H) 0.69-0.78 (m, 6H).

Example 246

(S)—N-(1-(4-fluorophenyl)ethyl)-6,7-dimethoxy-1-oxo-2-(pentan-3-yl)-1,2-dihydroisoquinoline-4-carboxamide The title compound was prepared in analogy to the process described in example 236 but using (S)-1-(4-fluorophenyl)ethanamine instead of pyridine-3-ylmethanamine.
ESI-MS=441 [M+H]$^+$;
$^1$H NMR (500 MHz, DMSO-D$_2$O, T: 25° C.) δ ppm 7.67 (s, 1H) 7.42-7.55 (m, 4H) 7.19 (t, J=8.85 Hz, 2H) 5.17 (q, J=7.02 Hz, 1H) 4.84 (s, 1H) 3.83 (d, J=50.35 Hz, 6H) 1.67-1.90 (m, 4H) 1.50 (d, J=7.32 Hz, 3H) 0.68-0.78 (m, 6H).

The compounds of examples 247 to 269 were prepared in an analogous manner to the process described in example 236.

Example 247

6,7-Dimethoxy-N-((4-methylthiazol-2-yl)methyl)-1-oxo-2-(pentan-3-yl)-1,2-dihydroisoquinoline-4-carboxamide ESI-MS=430 [M+H]$^+$;
$^1$H NMR (500 MHz, DMSO-D$_2$O, T: 25° C.) δ ppm 7.78 (s, 1H) 7.69 (s, 1H) 7.62 (s, 1H) 7.20 (s, 1H) 4.81-4.94 (m, J=10.38 Hz, 1H) 4.72 (s, 2H) 3.87 (d, J=19.53 Hz, 6H) 2.36 (s, 3H) 1.68-1.87 (m, 4H) 0.74 (t, J=7.32 Hz, 6H).

Example 248

6,7-Dimethoxy-N-((2-methylthiazol-4-yl)methyl)-1-oxo-2-(pentan-3-yl)-1,2-dihydroisoquinoline-4-carboxamide
ESI-MS=430 [M+H]$^+$;
$^1$H NMR (500 MHz, DMSO-D$_2$O, T: 25° C.) δ ppm 7.75 (s, 1H) 7.68 (s, 1H) 7.60 (s, 1H) 7.32 (s, 1H) 4.85 (s, 1H) 4.53 (s, 2H) 3.86 (d, J=20.45 Hz, 6H) 2.66 (s, 3H) 1.67-1.87 (m, 4H) 0.73 (t, J=7.32 Hz, 6H).

Example 249

6,7-Dimethoxy-N-((4-methylthiazol-5-yl)methyl)-1-oxo-2-(pentan-3-yl)-1,2-dihydroisoquinoline-4-carboxamide ESI-MS=430[M+H]$^+$;
$^1$H NMR (500 MHz, DMSO-D$_2$O, T: 25° C.) δ ppm 8.96 (s, 1H) 7.68 (d, J=8.54 Hz, 2H) 7.50 (s, 1H) 4.85 (s, 1H) 4.61 (s, 2H) 3.86 (d, J=22.28 Hz, 6H) 2.45 (s, 3H) 1.67-1.89 (m, 4H) 0.73 (t, J=7.32 Hz, 6H).

Example 250

6,7-Dimethoxy-1-oxo-2-(pentan-3-yl)-N-((5-(trifluoromethyl)furan-2-yl)methyl)-1,2-dihydroisoquinoline-4-carboxamide ESI-MS=467 [M+H]$^+$;
$^1$H NMR (500 MHz, DMSO-D$_2$O, T: 25° C.) δ ppm 7.72 (s, 1H) 7.68 (s, 1H) 7.56 (s, 1H) 7.17 (d, J=2.14 Hz, 1H) 6.58 (d, J=3.05 Hz, 1H) 4.85 (s, 1H) 4.56 (s, 2H) 3.86 (d, 6H) 1.67-1.87 (m, 4H) 0.73 (t, J=7.32 Hz, 6H).

Example 251

6,7-Dimethoxy-N-((5-methylfuran-2-yl)methyl)-1-oxo-2-(pentan-3-yl)-1,2-dihydroisoquinoline-4-carboxamide ESI-MS=413 [M+H]$^+$;
$^1$H NMR (500 MHz, DMSO-D$_2$O, T: 25° C.) δ ppm 7.73 (s, 1H) 7.67 (s, 1H) 7.53 (s, 1H) 6.21 (d, J=2.75 Hz, 1H) 6.03 (d, J=2.14 Hz, 1H) 4.85 (s, 1H) 4.42 (s, 2H) 3.86 (d, J=20.14 Hz, 6H) 2.24 (s, 3H) 1.66-1.87 (m, 4H) 0.73 (t, J=7.32 Hz, 6H).

Example 252

N-(5-Fluoro-2,3-dihydro-1H-inden-1-yl)-6,7-dimethoxy-1-oxo-2-(pentan-3-yl)-1,2-dihydroisoquinoline-4-carboxamide ESI-MS [M+H]$^+$=453 [M+H]$^+$;
$^1$H NMR (500 MHz, DMSO-D$_2$O, T: 25° C.) δ ppm 7.73 (s, 1H) 7.68 (s, 1H) 7.52 (s, 1H) 7.38 (dd, J=8.24, 5.49 Hz, 1H) 7.10-7.13 (m, 1H) 7.02-7.07 (m, 1H) 5.53 (t, J=7.78 Hz, 1H) 4.83 (s, 1H) 3.87 (d, J=11.90 Hz, 6H) 2.96-3.05 (m, 1H) 2.81-2.92 (m, 1H) 2.54-2.59 (m, 1H) 1.96-2.10 (m, 1H) 1.65-1.86 (m, 4H) 0.73 (q, J=7.02 Hz, 6H).

Example 253

6,7-Dimethoxy-N-(5-methyl-2,3-dihydro-1H-inden-1-yl)-1-oxo-2-(pentan-3-yl)-1,2-dihydroisoquinoline-4-carboxamide ESI-MS=449 [M+H]$^+$;
$^1$H NMR (500 MHz, DMSO-D$_2$O, T: 25° C.) δ ppm 7.73 (s, 1H) 7.68 (s, 1H) 7.50 (s, 1H) 7.24 (d, J=7.63 Hz, 1H) 7.10 (s, 1H) 7.05 (d, J=7.63 Hz, 1H) 5.52 (t, J=7.78 Hz, 1H) 4.83 (s, 1H) 3.87 (d, J=14.34 Hz, 6H) 2.92-3.02 (m, 1H) 2.77-2.89 (m, 1H) 2.46-2.51 (m, 1H) 2.30 (s, 3H) 1.91-2.03 (m, 1H) 1.65-1.85 (m, 4H) 0.73 (q, J=7.02 Hz, 6H).

Example 254

6,7-Dimethoxy-N-(4-methyl-2,3-dihydro-1H-inden-1-yl)-1-oxo-2-(pentan-3-yl)-1,2-dihydroisoquinoline-4-carboxamide ESI-MS=449 [M+H]$^+$;
$^1$H NMR (500 MHz, DMSO-D$_2$O, T: 25° C.) δ ppm 7.74 (s, 1H) 7.68 (s, 1H) 7.51 (s, 1H) 7.12-7.21 (m, 2H) 7.07 (d, J=7.32 Hz, 1H) 5.57 (t, J=7.93 Hz, 1H) 4.84 (s, 1H) 3.87 (d, J=14.34 Hz, 6H) 2.90-3.02 (m, 1H) 2.72-2.83 (m, 1H) 2.55-2.59 (m, 1H) 2.25 (s, 3H) 1.92-2.04 (m, 1H) 1.66-1.83 (m, 4H) 0.68-0.77 (m, 6H).

Example 255

N-((2-Ethylthiazol-4-yl)methyl)-6,7-dimethoxy-1-oxo-2-(pentan-3-yl)-1,2-dihydroisoquinoline-4-carboxamide ESI-MS=444 [M+H]$^+$;
$^1$H NMR (500 MHz, DMSO-D$_2$O, T: 25° C.) δ ppm 7.75 (s, 1H) 7.68 (s, 1H) 7.60 (s, 1H) 7.33 (s, 1H) 4.86 (s, 1H) 4.54 (s, 2H) 3.86 (d, J=21.06 Hz, 6H) 2.98 (q, J=7.53 Hz, 2H) 1.70-1.86 (m, 4H) 1.30 (t, J=7.48 Hz, 3H) 0.73 (t, J=7.32 Hz, 6H).

Example 256

6,7-Dimethoxy-N-(6-methoxy-2,3-dihydro-1H-inden-1-yl)-1-oxo-2-(pentan-3-yl)-1,2-dihydroisoquinoline-4-carboxamide ESI-MS=465 [M+H]$^+$;
$^1$H NMR (500 MHz, DMSO-D$_2$O, T: 25° C.) δ ppm 7.75 (s, 1H) 7.68 (s, 1H) 7.54 (s, 1H) 7.20 (d, J=8.24 Hz, 1H) 6.90 (d, J=1.83 Hz, 1H) 6.83 (dd, J=8.24, 2.44 Hz, 1H) 5.52 (t, J=7.93 Hz, 1H) 4.84 (s, 1H) 3.87 (d, J=16.17 Hz, 6H) 3.72 (s, 3H) 2.89-2.99 (m, 1H) 2.74-2.83 (m, 1H) 2.47-2.52 (m, 1H) 1.95-2.04 (m, 1H) 1.67-1.85 (m, 4H) 0.73 (q, J=7.02 Hz, 6H).

Example 257

6,7-Dimethoxy-N-((4-methylthiophen-2-yl)methyl)-1-oxo-2-(pentan-3-yl)-1,2-dihydroisoquinoline-4-carboxamide ESI-MS=429 [M+H]$^+$;
$^1$H NMR (500 MHz, DMSO-D$_2$O, T: 25° C.) δ ppm 7.72 (s, 1H) 7.67 (s, 1H) 7.51 (s, 1H) 6.97 (s, 1H) 6.88 (s, 1H) 4.85 (s, 1H) 4.58 (s, 2H) 3.80-3.90 (m, 6H) 2.16-2.19 (m, 3H) 1.66-1.87 (m, 4H) 0.73 (t, J=7.32 Hz, 6H).

Example 258

6,7-Dimethoxy-N-((3-methylthiophen-2-yl)methyl)-1-oxo-2-(pentan-3-yl)-1,2-dihydroisoquinoline-4-carboxamide ESI-MS=429 [M+H]$^+$;
$^1$H NMR (500 MHz, DMSO-D$_2$O, T: 25° C.) δ ppm 7.68 (d, J=6.10 Hz, 2H) 7.46-7.51 (m, 1H) 7.30 (d, J=4.88 Hz, 1H) 6.86 (d, J=4.88 Hz, 1H) 4.85 (s, 1H) 4.57 (s, 2H) 3.79-3.91 (m, 6H) 2.24 (s, 3H) 1.63-1.86 (m, 4H) 0.73 (t, J=7.32 Hz, 6H).

Example 259

6,7-Dimethoxy-N-((5-methyloxazol-2-yl)methyl)-1-oxo-2-(pentan-3-yl)-1,2-dihydroisoquinoline-4-carboxamide ESI-MS=414 [M+H]$^+$;
$^1$H NMR (500 MHz, DMSO-D$_2$O, T: 25° C.) δ ppm 7.81 (s, 1H) 7.68 (s, 1H) 7.60 (s, 1H) 6.79 (d, J=1.22 Hz, 1H) 4.86 (s, 1H) 4.54 (s, 2H) 3.88 (d, J=10.38 Hz, 6H) 2.28 (s, 3H) 1.66-1.88 (m, 4H) 0.73 (t, J=7.32 Hz, 6H).

Example 260

6,7-Dimethoxy-N-(6-methyl-2,3-dihydro-1H-inden-1-yl)-1-oxo-2-(pentan-3-yl)-1,2-dihydroisoquinoline-4-carboxamide ESI-MS=449 [M+H]$^+$;
$^1$H NMR (500 MHz, DMSO-D$_2$O, T: 25° C.) δ ppm 7.74 (s, 1H) 7.69 (s, 1H) 7.52 (s, 1H) 7.14-7.20 (m, 2H) 7.06 (d, J=7.93 Hz, 1H) 5.54 (t, J=7.93 Hz, 1H) 4.84 (s, 1H) 3.88 (d, J=11.29 Hz, 6H) 2.88-3.01 (m, 1H) 2.74-2.87 (m, 1H) 2.46-2.51 (m, 1H) 2.28 (s, 3H) 1.92-2.01 (m, 1H) 1.66-1.85 (m, 4H) 0.73 (q, J=7.63 Hz, 6H).

Example 261

6,7-Dimethoxy-1-oxo-2-(pentan-3-yl)-N-(pyridin-4-ylmethyl)-1,2-dihydroisoquinoline-4-carboxamide ESI-MS=410 [M+H]$^+$;
$^1$H NMR (500 MHz, DMSO-D$_2$O, T: 25° C.) δ ppm 8.81 (d, J=6.71 Hz, 2H) 7.96 (d, J=6.41 Hz, 2H) 7.77 (s, 1H) 7.73 (s, 1H) 7.69 (s, 1H) 4.80-4.95 (m, J=6.10 Hz, 1H) 4.73 (s, 2H) 3.84 (d, 6H) 1.70-1.89 (m, 4H) 0.75 (t, J=7.32 Hz, 6H).

Example 262

6,7-Dimethoxy-N-(4-methylbenzyl)-1-oxo-2-(pentan-3-yl)-1,2-dihydroisoquinoline-4-carboxamide ESI-MS=423 [M+H]$^+$;
$^1$H NMR (500 MHz, DMSO-D$_2$O, T: 25° C.) δ ppm 7.69 (d, J=10.99 Hz, 2H) 7.54 (s, 1H) 7.27 (d, J=7.93 Hz, 2H) 7.18 (d, J=7.93 Hz, 2H) 4.85 (s, 1H) 4.45 (s, 2H) 3.85 (d, 6H) 2.29 (s, 3H) 1.67-1.87 (m, 4H) 0.73 (t, J=7.32 Hz, 6H).

Example 263

6,7-Dimethoxy-1-oxo-2-(pentan-3-yl)-N-(pyridin-2-ylmethyl)-1,2-dihydroisoquinoline-4-carboxamide ESI-MS=410 [M+H]$^+$;
$^1$H NMR (500 MHz, DMSO-D$_2$O, T: 25° C.) δ ppm 8.73 (d, J=4.88 Hz, 1H) 8.28-8.34 (m, 1H) 7.85 (d, J=7.93 Hz, 1H) 7.78 (s, 1H) 7.72-7.76 (m, 2H) 7.69 (s, 1H) 4.88 (s, 1H) 4.74 (s, 2H) 3.85 (d, J=31.43 Hz, 6H) 1.68-1.92 (m, 4H) 0.75 (t, J=7.32 Hz, 6H).

Example 264

N-((5-Cyanofuran-2-yl)methyl)-6,7-dimethoxy-1-oxo-2-(pentan-3-yl)-1,2-dihydroisoquinoline-4-carboxamide ESI-MS=424 [M+H]$^+$;
$^1$H NMR (500 MHz, DMSO-D$_2$O, T: 27° C.) δ ppm 7.71 (s, 1H) 7.68 (s, 1H) 7.57 (s, 1H) 7.54 (d, J=3.66 Hz, 1H) 6.64

(d, J=3.66 Hz, 1H) 4.84 (s, 1H) 4.56 (s, 2H) 3.87 (d, J=14.04 Hz, 6H) 1.67-1.89 (m, J=12.82 Hz, 4H) 0.73 (t, J=7.32 Hz, 6H).

Example 265

N-(4-Chloro-2,3-dihydro-1H-inden-1-yl)-6,7-dimethoxy-1-oxo-2-(pentan-3-yl)-1,2-dihydroisoquinoline-4-carboxamide ESI-MS=469 [M+H]$^+$;
$^1$H NMR (500 MHz, DMSO-D$_2$O, T: 27° C.) δ ppm 7.67-7.74 (m, J=17.70 Hz, 2H) 7.52 (s, 1H) 7.25-7.37 (m, 3H) 5.64 (q, J=7.93 Hz, 1H) 4.83 (s, 1H) 3.87 (d, J=10.68 Hz, 6H) 3.00-3.10 (m, 1H) 2.83-2.95 (m, 1H) 2.55-2.62 (m, 1H) 1.97-2.12 (m, 1H) 1.64-1.86 (m, 4H) 0.67-0.79 (m, 6H).

Example 266

N-((5-Ethylthiophen-2-yl)methyl)-6,7-dimethoxy-1-oxo-2-(pentan-3-yl)-1,2-dihydroisoquinoline-4-carboxamide ESI-MS=443 [M+H]$^+$;
$^1$H NMR (500 MHz, DMSO-D$_2$O, T: 27° C.) δ ppm 7.72 (s, 1H) 7.67 (s, 1H) 7.51 (s, 1H) 6.85 (d, J=3.36 Hz, 1H) 6.68 (d, J=3.36 Hz, 1H) 4.84 (s, 1H) 4.57 (s, 2H) 3.86 (d, J=16.78 Hz, 6H) 2.76 (q, J=7.43 Hz, 2H) 1.64-1.90 (m, 4H) 1.21 (t, J=7.63 Hz, 3H) 0.73 (t, J=7.32 Hz, 6H).

Example 267

6,7-Dimethoxy-N-((3-methylfuran-2-yl)methyl)-1-oxo-2-(pentan-3-yl)-1,2-dihydroisoquinoline-4-carboxamide ESI-MS=413 [M+H]$^+$;
$^1$H NMR (500 MHz, DMSO-D$_2$O, T: 27° C.) δ ppm 7.68 (d, J=8.24 Hz, 2H) 7.44-7.52 (m, 2H) 6.32 (d, J=1.83 Hz, 1H) 4.83 (s, 1H) 4.45 (s, 2H) 3.85 (d, J=18.62 Hz, 6H) 2.06 (s, 3H) 1.65-1.85 (m, 4H) 0.72 (t, J=7.32 Hz, 6H).

Example 268

6,7-Dimethoxy-N-((2-methylfuran-3-yl)methyl)-1-oxo-2-(pentan-3-yl)-1,2-dihydroisoquinoline-4-carboxamide ESI-MS=413 [M+H]$^+$;
$^1$H NMR (500 MHz, DMSO-D$_2$ 0, T: 27° C.) δ ppm 7.67 (s, 2H) 7.42-7.48 (m, 2H) 6.44 (d, J=1.53 Hz, 1H) 4.83 (s, 1H) 4.25 (s, 2H) 3.85 (d, J=19.84 Hz, 6H) 2.30 (s, 3H) 1.59-1.89 (m, 4H) 0.72 (t, J=7.32 Hz, 6H).

Example 269

6,7-Dimethoxy-N-((1-methyl-1H-pyrazol-3-yl)methyl)-1-oxo-2-(pentan-3-yl)-1,2-dihydroisoquinoline-4-carboxamide ESI-MS=413 [M+H]$^+$;
$^1$H NMR (500 MHz, DMSO-D$_2$O, T: 27° C.) δ ppm 7.75 (s, 1H) 7.68 (s, 1H) 7.62 (d, J=2.14 Hz, 1H) 7.55 (s, 1H) 6.22 (d, J=2.14 Hz, 1H) 4.84 (s, 1H) 4.43 (s, 2H) 3.87 (d, J=14.04 Hz, 6H) 3.80 (s, 3H) 1.65-1.86 (m, 4H) 0.73 (t, J=7.17 Hz, 6H).

Example 270

N-[(3,4-Dimethylphenyl)methyl]-2-ethyl-6,7-dimethoxy-1-oxo-isoquinoline-4-carboxamide To a solution of 2-ethyl-6,7-dimethoxy-1-oxo-1,2-dihydroisoquinoline-4-carboxylic acid (25 mg, 0.09 mmol) in DMA (1.0 mL) was added a solution of HATU (41 mg, 0.1 mmol) in DMA (0.5 mL). The reaction mixture was placed to shake for 45 minutes at room temperature. Then a solution of (3,4-dimethylphenyl)methanamine (18 mg, 0.13 mmol) dissolved in DMA (0.4 mL) was added followed by triethylamine neat (40 µL, 0.27 mmol). The reaction was shaken at 65° C. overnight. The reaction was checked by LC/MS and concentrated to dryness. The residues were dissolved in 1:1 DMSO/MeOH. Purification by reverse phase HPLC provided the titled compound (17.9 mg, 50%)

ESI-MS: m/z 395 [M+H]$^+$;
$^1$H NMR (500 MHz, DMSO-D$_2$O, T: 27° C.) δ ppm 7.75 (s, 1H) 7.70 (s, 1H) 7.65 (s, 1H) 7.15 (s, 1H) 7.11 (s, 2H) 4.41 (s, 2H) 4.02 (q, J=7.12 Hz, 2H) 3.88 (s, 3H) 3.81 (s, 3H) 2.21 (d, J=6.10 Hz, 6H) 1.29 (t, J=7.17 Hz, 3H).

The compounds of examples 271 to 292 were prepared in analogy to the process described in example 270.

Example 271

N-[(2-Chloro-4-methyl-phenyl)methyl]-2-ethyl-6,7-dimethoxy-1-oxo-isoquinoline-4-carboxamide ESI-MS: m/z 415 [M+H]$^+$
$^1$H NMR (500 MHz, DMSO-D$_2$O, T: 27° C.) δ ppm 7.81 (s, 1H) 7.71 (s, 1H) 7.66 (s, 1H) 7.36 (d, J=7.63 Hz, 1H) 7.31 (s, 1H) 7.18 (d, J=8.24 Hz, 1H) 4.51 (s, 2H) 4.03 (q, J=7.12 Hz, 2H) 3.88 (s, 3H) 3.82 (s, 3H) 2.30 (s, 3H) 1.30 (t, J=7.17 Hz, 3H).

Example 272

N-[[2-(Dimethylamino)-4-methyl-phenyl]methyl]-2-ethyl-6,7-dimethoxy-1-oxo-isoquinoline-4-carboxamide ESI-MS: m/z 424 [M+H]$^+$.
$^1$H NMR (500 MHz, DMSO-D$_2$O, T: 27° C.) δ ppm 8.75 (t, J=5.80 Hz, 1H) 7.78 (s, 1H) 7.75 (s, 1H) 7.66 (s, 1H) 7.22 (d, J=7.63 Hz, 1H) 6.96 (s, 1H) 6.87 (d, J=7.93 Hz, 1H) 4.53 (d, J=5.49 Hz, 2H) 4.02 (q, J=7.22 Hz, 2H) 3.88 (s, 3H) 3.81-3.85 (m, 3H) 2.66 (s, 6H) 2.28 (s, 3H) 1.29 (t, J=7.17 Hz, 3H);

Example 273

2-Ethyl-N-[(2-fluoro-4-methyl-phenyl)methyl]-6,7-dimethoxy-1-oxo-isoquinoline-4-carboxamide ESI-MS: m/z 399 [M+H]$^+$
$^1$H NMR (500 MHz, DMSO-D$_2$O, T: 27° C.) δ ppm 8.86 (t, J=5.65 Hz, 1H) 7.77 (s, 1H) 7.69 (s, 1H) 7.65 (s, 1H) 7.34 (t, J=8.09 Hz, 1H) 7.01-7.06 (m, 2H) 4.43-4.50 (m, 2H) 4.02 (q, J=7.02 Hz, 2H) 3.88 (s, 3H) 3.82 (s, 3H) 2.31 (s, 3H) 1.29 (t, J=7.17 Hz, 3H).

Example 274

2-Ethyl-6,7-dimethoxy-N-[(3-methoxy-4-methyl-phenyl)methyl]-1-oxo-isoquinoline-4-carboxamide ESI-MS: m/z 411 [M+H]$^+$;
$^1$H NMR (500 MHz, DMSO-D$_2$O, T: 27° C.) δ ppm 7.77 (s, 1H) 7.71 (s, 1H) 7.66 (s, 1H) 7.11 (d, J=7.93 Hz, 1H) 6.95 (s, 1H) 6.84-6.90 (m, 1H) 4.45 (s, 2H) 4.02 (q, J=7.12 Hz, 2H) 3.88 (s, 3H) 3.81 (s, 3H) 3.78 (s, 3H) 2.13 (s, 3H) 1.29 (t, J=7.17 Hz, 3H).

Example 275

2-Ethyl-6,7-dimethoxy-N-[(4-methyl-2-morpholino-phenyl)methyl]-1-oxo-isoquinoline-4-carboxamide ESI-MS: m/z 466 [M+H]$^+$.
$^1$H NMR (500 MHz, DMSO-D$_2$O, T: 27° C.) δ ppm 7.76 (d, J=7.02 Hz, 2H) 7.65-7.68 (m, 1H) 7.26 (d, J=7.63 Hz, 1H) 6.97 (s, 1H) 6.94 (d, J=7.93 Hz, 1H) 4.55 (s, 2H) 4.02 (q, J=7.02 Hz, 2H) 3.88 (s, 3H) 3.84 (s, 3H) 3.75-3.79 (m, J=4.27 Hz, 4H) 2.83-2.90 (m, 4H) 2.29 (s, 3H) 1.29 (t, 3H).

Example 276

N-[(2-tert-Butoxy-4-methyl-phenyl)methyl]-2-ethyl-6,7-dimethoxy-1-oxo-isoquinoline-4-carboxamide ESI-MS: m/z 453 [M+H]$^+$
$^1$H NMR (500 MHz, DMSO-D$_2$O, T: 27° C.) δ ppm 7.76 (s, 1H) 7.72 (s, 1H) 7.66 (s, 1H) 7.22 (d, J=7.93 Hz, 1H) 6.91 (s, 1H) 6.86 (d, J=7.63 Hz, 1H) 4.45 (s, 2H) 4.02 (q, J=7.02 Hz, 2H) 3.88 (s, 3H) 3.83 (s, 3H) 2.28 (s, 3H) 1.38 (s, 9H) 1.29 (t, J=7.17 Hz, 3H).

Example 277

N-[[2-(1,1-Dimethylpropoxy)-4-methyl-phenyl]methyl]-2-ethyl-6,7-dimethoxy-1-oxo-isoquinoline-4-carboxamide ESI-MS: m/z 467 [M+H]$^+$;
$^1$H NMR (500 MHz, DMSO-D$_2$O, T: 27° C.) δ ppm 7.77 (s, 1H) 7.73 (s, 1H) 7.66 (s, 1H) 7.20 (d, J=7.93 Hz, 1H) 6.88 (s, 1H) 6.84 (d, J=7.63 Hz, 1H) 4.44 (s, 2H) 4.02 (q, J=7.22 Hz, 2H) 3.88 (s, 3H) 3.83 (s, 3H) 2.28 (s, 3H) 1.75 (q, J=7.63 Hz, 2H) 1.32 (s, 6H) 1.29 (t, J=7.17 Hz, 3H) 0.97 (t, J=7.32 Hz, 3H).

Example 278

N-[(2,3-Difluoro-4-methyl-phenyl)methyl]-2-ethyl-6,7-dimethoxy-1-oxo-isoquinoline-4-carboxamide ESI-MS: m/z 417 [M+H]$^+$
$^1$H NMR (500 MHz, DMSO-D$_2$O, T: 27° C.) δ ppm 7.78 (s, 1H) 7.69 (s, 1H) 7.65 (s, 1H) 7.17 (t, J=7.93 Hz, 1H) 7.11 (t, J=7.32 Hz, 1H) 4.51 (s, 2H) 3.98-4.07 (m, 2H) 3.88 (s, 3H) 3.82 (s, 3H) 2.27 (d, J=1.83 Hz, 3H) 1.30 (t, 3H).

Example 279

2-Ethyl-N-[(3-fluoro-4-methyl-phenyl)methyl]-6,7-dimethoxy-1-oxo-isoquinoline-4-carboxamide $^1$H NMR (500 MHz, DMSO-D$_2$O, T: 27° C.) δ ppm 7.80 (s, 1H) 7.70 (s, 1H) 7.66 (s, 1H) 7.27 (t, J=8.09 Hz, 1H) ESI-MS: m/z 399 [M+H]$^+$ 7.10-7.15 (m, 2H) 4.45 (s, 2H) 4.03 (q, J=7.12 Hz, 2H) 3.88 (s, 3H) 3.82 (s, 3H) 2.22 (d, J=1.22 Hz, 3H) 1.29 (t, J=7.02 Hz, 3H).

Example 280

N-[(3-chloro-4-methyl-phenyl)methyl]-2-ethyl-6,7-dimethoxy-1-oxo-isoquinoline-4-carboxamide ESI-MS: m/z 413 [M+H]$^-$
$^1$H NMR (500 MHz, DMSO-D$_2$O, T: 27° C.) δ ppm 7.79 (s, 1H) 7.69 (s, 1H) 7.66 (s, 1H) 7.41 (d, J=1.53 Hz, 1H) 7.32-7.36 (m, 1H) 7.24-7.28 (m, 1H) 4.44 (s, 2H) 4.02 (q, J=7.22 Hz, 2H) 3.88 (s, 3H) 3.82 (s, 3H) 2.31 (s, 3H) 1.30 (t, 3H).

Example 281

2-Ethyl-6,7-dimethoxy-1-oxo-N-[(2,4,6-trimethyl-phenyl)methyl]isoquinoline-4-carboxamide ESI-MS: m/z 409 [M+H]$^+$;
$^1$H NMR (500 MHz, DMSO-D$_2$O, T: 27° C.) δ ppm 7.64 (s, 2H) 7.61 (s, 1H) 6.87 (s, 2H) 4.47 (s, 2H) 3.97 (q, J=7.12 Hz, 2H) 3.87 (s, 3H) 3.80 (s, 3H) 2.33-2.36 (m, 6H) 2.22 (s, 3H) 1.25 (t, J=7.02 Hz, 3H).

Example 282

N-[(2,4-Dimethylphenyl)methyl]-2-ethyl-6,7-dimethoxy-1-oxo-isoquinoline-4-carboxamide ESI-MS: m/z 395 [M+H]$^+$;
$^1$H NMR (500 MHz, DMSO-D$_2$O, T: 27° C.) δ ppm 7.74 (s, 1H) 7.69 (s, 1H) 7.65 (s, 1H) 7.21 (d, J=7.63 Hz, 1H) 6.98-7.03 (m, 2H) 4.43 (s, 2H) 3.95-4.06 (m, 2H) 3.88 (s, 3H) 3.80-3.82 (m, 3H) 2.31 (s, 3H) 2.26 (s, 3H) 1.29 (t, J=7.17 Hz, 3H).

Example 283

2-Ethyl-6,7-dimethoxy-N-[[2-(3-methoxypropoxy)-4-methyl-phenyl]methyl]-1-oxo-isoquinoline-4-carboxamide ESI-MS: m/z 469 [M+H]$^+$;
$^1$H NMR (500 MHz, DMSO-D$_2$O, T: 27° C.) δ ppm 7.76 (s, 1H) 7.72 (s, 1H) 7.66 (s, 1H) 7.17 (d, J=7.63 Hz, 1H) 6.83 (s, 1H) 6.75 (d, J=7.63 Hz, 1H) 4.42 (s, 2H) 3.97-4.07 (m, 4H) 3.88 (s, 3H) 3.81 (s, 3H) 3.50 (t, J=6.26 Hz, 2H) 3.20 (s, 3H) 2.29 (s, 3H) 1.93-2.03 (m, 2H) 1.29 (t, J=7.17 Hz, 3H).

Example 284

N-[[2-(2-Ethoxyethoxy)-4-methyl-phenyl]methyl]-2-ethyl-6,7-dimethoxy-1-oxo-isoquinoline-4-carboxamide ESI-MS: m/z 469 [M+H]$^+$
$^1$H NMR (500 MHz, DMSO-D$_2$O, T: 27° C.) δ ppm 7.76 (s, 1H) 7.69 (s, 1H) 7.66 (s, 1H) 7.18 (d, J=7.63 Hz, 1H) 6.86 (s, 1H) 6.77 (d, J=7.63 Hz, 1H) 4.43 (s, 2H) 4.10-4.15 (m, 2H) 4.02 (q, J=7.22 Hz, 2H) 3.88 (s, 3H) 3.81 (s, 3H) 3.74

(s, 2H) 3.48 (q, J=7.02 Hz, 2H) 2.29 (s, 3H) 1.29 (t, J=7.02 Hz, 3H) 1.05 (t, J=7.02 Hz, 3H).

Example 285

N-[[2-(Cyclopentoxy)-4-methyl-phenyl]methyl]-2-ethyl-6,7-dimethoxy-1-oxo-isoquinoline-4-carboxamide ESI-MS: m/z 465 [M+H]$^+$;
$^1$H NMR (500 MHz, DMSO-D$_2$O, T: 27° C.) δ ppm 7.74 (d, J=4.58 Hz, 2H) 7.66 (s, 1H) 7.15 (d, J=7.63 Hz, 1H) 6.81 (s, 1H) 6.73 (d, J=7.63 Hz, 1H) 4.82-4.90 (m, 1H) 4.38 (s, 2H) 4.01 (q, J=7.22 Hz, 2H) 3.88 (s, 3H) 3.82 (s, 3H) 2.29 (s, 3H) 1.82-1.97 (m, 2H) 1.64-1.81 (m, 4H) 1.50-1.64 (m, 2H) 1.29 (t, J=7.17 Hz, 3H).

Example 286

2-Ethyl-6,7-dimethoxy-N-[(4-methyl-2-phenoxy-phenyl)methyl]-1-oxo-isoquinoline-4-carboxamide ESI-MS: m/z 473 [M+H]$^+$;
$^1$H NMR (500 MHz, DMSO-D$_2$O, T: 27° C.) δ ppm 7.70 (s, 1H) 7.64 (d, J=3.36 Hz, 2H) 7.35-7.42 (m, 3H) 7.11 (t, J=7.32 Hz, 1H) 6.95-7.05 (m, 3H) 6.73 (s, 1H) 4.45 (s, 2H) 3.97 (q, J=7.12 Hz, 2H) 3.87 (s, 3H) 3.80 (s, 3H) 2.26 (s, 3H) 1.27 (t, J=7.02 Hz, 3H).

Example 287

2-Ethyl-6,7-dimethoxy-N-[[2-(2-methoxy-1-methyl-ethoxy)-4-methyl-phenyl]methyl]-1-oxo-isoquinoline-4-carboxamide
ESI-MS: m/z 469 [M+H]$^+$
$^1$H NMR (500 MHz, DMSO-D$_2$O, T: 27° C.) δ ppm 7.75 (s, 1H) 7.70 (s, 1H) 7.66 (s, 1H) 7.17 (d, J=7.63 Hz, 1H) 6.88 (s, 1H) 6.75 (d, J=7.32 Hz, 1H) 4.57-4.67 (m, 1H) 4.33-4.49 (m, 2H) 4.02 (q, J=7.02 Hz, 2H) 3.88 (s, 3H) 3.81 (s, 3H) 3.42-3.55 (m, 2H) 3.23 (s, 3H) 2.29 (s, 3H) 1.22-1.34 (m, 6H).

Example 288

2-Ethyl-6,7-dimethoxy-N-[[4-methyl-2-(2,2,2-trifluoroethoxy)phenyl]methyl]-1-oxo-isoquinoline-4-carboxamide ESI-MS: m/z 479 [M+H]$^+$;
$^1$H NMR (500 MHz, DMSO-D$_2$O, T: 27° C.) δ ppm 7.78 (s, 1H) 7.73 (s, 1H) 7.66 (s, 1H) 7.23 (d, J=7.63 Hz, 1H) 6.96 (s, 1H) 6.88 (d, J=7.32 Hz, 1H) 4.75 (q, J=8.65 Hz, 2H) 4.44 (s, 2H) 4.02 (q, J=7.22 Hz, 2H) 3.88 (s, 3H) 3.83 (s, 3H) 2.31 (s, 3H) 1.29 (t, J=7.17 Hz, 3H).

Example 289

N-[[2-(Cyclohexyloxy)-4-methyl-phenyl]methyl]-2-ethyl-6,7-dimethoxy-1-oxo-isoquinoline-4-carboxamide ESI-MS: m/z 479 [M+H]$^+$;
$^1$H NMR (500 MHz, DMSO-D$_2$O, T: 27° C.) δ ppm 7.76 (d, J=6.10 Hz, 2H) 7.66 (s, 1H) 7.16 (d, J=7.93 Hz, 1H) 6.84 (s, 1H) 6.73 (d, J=7.63 Hz, 1H) 4.37-4.46 (m, 2H) 4.01 (q, J=7.22 Hz, 2H) 3.88 (s, 3H) 3.82 (s, 3H) 2.25-2.31 (m, 3H) 1.83-1.93 (m, J=7.93, 3.97 Hz, 2H) 1.64-1.76 (m, 2H) 1.44-1.58 (m, 3H) 1.32-1.45 (m, 2H) 1.29 (t, J=7.17 Hz, 4H).

Example 290

N-[[2-(Cyclopropylmethoxy)-4-methyl-phenyl]methyl]-2-ethyl-6,7-dimethoxy-1-oxo-isoquinoline-4-carboxamide ESI-MS: m/z 451 [M+H]$^+$;
$^1$H NMR (500 MHz, DMSO-D$_2$O, T: 27° C.) δ ppm 7.79 (s, 1H) 7.73 (s, 1H) 7.66 (s, 1H) 7.17 (d, J=7.63 Hz, 1H) 6.81 (s, 1H) 6.75 (d, J=7.02 Hz, 1H) 4.44 (s, 2H) 4.02 (q, J=7.02 Hz, 2H) 3.85-3.90 (m, 5H) 3.82 (s, 3H) 2.28 (s, 3H) 1.19-1.35 (m, 4H) 0.51-0.61 (m, 2H) 0.31-0.37 (m, 2H).

Example 291

2-Ethyl-N-[(2-hexoxy-4-methyl-phenyl)methyl]-6,7-dimethoxy-1-oxo-isoquinoline-4-carboxamide ESI-MS: m/z 481 [M+H]$^+$;
$^1$H NMR (500 MHz, DMSO-D$_2$O, T: 27° C.) δ ppm 7.77 (s, 1H) 7.74 (s, 1H) 7.66 (s, 1H) 7.16 (d, J=7.63 Hz, 1H) 6.82 (s, 1H) 6.74 (d, J=7.63 Hz, 1H) 4.41 (s, 2H) 3.92-4.09 (m, 4H) 3.88 (s, 3H) 3.81 (s, 3H) 2.29 (s, 3H) 1.66-1.76 (m, 2H) 1.36-1.49 (m, 2H) 1.15-1.34 (m, 7H) 0.81 (t, 3H).

Example 292

2-Ethyl-6,7-dimethoxy-N-[[4-methyl-2-(tetrahydrofuran-3-ylmethoxy)phenyl]methyl]-1-oxo-isoquinoline-4-carboxamide ESI-MS: m/z 481 [M+H]$^+$
$^1$H NMR (500 MHz, DMSO-D$_2$O, T: 27° C.) δ ppm 7.77 (s, 1H) 7.73 (s, 1H) 7.66 (s, 1H) 7.17 (d, J=7.63 Hz, 1H) 6.85 (s, 1H) 6.76 (d, J=7.93 Hz, 1H) 4.42 (s, 2H) 3.96-4.08 (m, 3H) 3.89-3.95 (m, 1H) 3.88 (s, 3H) 3.81 (s, 3H) 3.76-3.80 (m, 2H) 3.62-3.69 (m, 1H) 3.55-3.62 (m, J=8.54, 5.49 Hz, 1H) 2.62-2.75 (m, 1H) 2.29 (s, 3H) 1.98-2.10 (m, 1H) 1.66-1.76 (m, 1H) 1.29 (t, J=7.17 Hz, 3H).

Example 293

2-Ethyl-6,7-dimethoxy-N-[[2-(2-methoxyethoxy)-4-methyl-phenyl]methyl]-1-oxo-isoquinoline-4-carboxamide 2-Ethyl-6,7-dimethoxy-1-oxo-1,2-dihydroisoquinoline-4-carboxylic acid (22 mg, 0.08 mmol) dissolved in N,N-dimethylacetamide (1.0 mL) was added to a 4 mL vial charged with a stir bar followed by a solution of HATU (36 mg, 0.09 mmol) dissolved in N,N-dimethylacetamide (1.0 mL). This was placed to shake for one hour at room temperature. Then a solution of (2-(2-methoxyethoxy)-4-methylphenyl)methanamine (19.5 mg, 0.1 mmol) dissolved in N,N-dimethylacetamide (0.4 mL) was added followed by triethylamine neat (33 μL, 0.24 mmol) and the mixture was stirred and heated at 65° C. overnight. The reaction was controlled by LC/MS and concentrated to dryness. The residue was dissolved in 1:1 MeOH:DMSO. Purification by reverse phase HPLC gave 16.5 mg of the title compound (46%).

ESI-MS: m/z 455 [M+H]$^+$;
$^1$H NMR (500 MHz, DMSO-D$_2$O, T: 25° C.) δ ppm 7.77 (s, 1H) 7.70 (s, 1H) 7.66 (s, 1H) 7.18 (d, J=7.63 Hz, 1H) 6.85 (s, 1H) 6.77 (d, J=7.63 Hz, 1H) 4.39-4.45 (m, 2H) 4.11-4.17 (m, 2H) 4.02 (q, J=7.12 Hz, 2H) 3.88 (s, 3H) 3.81 (s, 3H) 3.67-3.71 (m, 2H) 3.27 (s, 3H) 2.29 (s, 3H) 1.29 (t, J=7.02 Hz, 3H).

The compounds of the following examples 294 to 323 were prepared in analogy to the processes described in the examples above.

Example 294

2-Ethyl-N-(2-isobutoxy-4-methylbenzyl)-6,7-dimethoxy-1-oxo-1,2-dihydroisoquinoline-4-carboxamide ESI-MS: m/z 453 [M+H]$^+$;
$^1$H NMR (500 MHz, DMSO-D$_2$O, T: 25° C.) δ ppm 7.78 (s, 1H) 7.74 (s, 1H) 7.66 (s, 1H) 7.16 (d, J=7.63 Hz, 1H) 6.81 (s, 1H) 6.75 (d, J=7.63 Hz, 1H) 4.42-4.46 (m, 2H) 4.01 (q, J=7.22 Hz, 2H) 3.88 (s, 3H) 3.82 (s, 3H) 3.78 (d, J=6.41 Hz, 2H) 2.29 (s, 3H) 2.00-2.12 (m, 1H) 1.29 (t, J=7.02 Hz, 3H) 1.00 (d, J=6.71 Hz, 6H).

Example 295

2-Ethyl-N-(2-(furan-2-ylmethoxy)-4-methylbenzyl)-6,7-dimethoxy-1-oxo-1,2-dihydroisoquinoline-4-carboxamide ESI-MS: m/z 477 [M+H]$^+$
$^1$H NMR (500 MHz, DMSO-D$_2$O, T: 25° C.) δ ppm 7.77 (s, 1H) 7.71 (s, 1H) 7.65 (s, 2H) 7.19 (d, J=7.63 Hz, 1H) 7.01 (s, 1H) 6.80 (d, J=7.63 Hz, 1H) 6.60 (d, J=3.05 Hz, 1H) 6.42-6.51 (m, 1H) 5.11 (s, 2H) 4.35-4.43 (m, 2H) 4.02 (q, J=7.02 Hz, 2H) 3.88 (s, 3H) 3.81 (s, 3H) 2.31 (s, 3H) 1.29 (t, J=7.02 Hz, 3H).

Example 296

2-Ethyl-6,7-dimethoxy-N-(4-methyl-2-(pentyloxy)benzyl)-1-oxo-1,2-dihydroisoquinoline-4-carboxamide ESI-MS: m/z 467 [M+H]$^+$;
$^1$H NMR (500 MHz, DMSO-D$_2$O, T: 25° C.) δ ppm 7.78 (s, 1H) 7.74 (s, 1H) 7.66 (s, 1H) 7.16 (d, J=7.63 Hz, 1H) 6.82 (s, 1H) 6.74 (d, J=7.63 Hz, 1H) 4.40-4.44 (m, 2H) 3.96-4.06 (m, 4H) 3.88 (s, 3H) 3.82 (s, 3H) 2.29 (s, 3H) 1.68-1.77 (m, 2H) 1.36-1.46 (m, 2H) 1.26-1.34 (m, 5H) 0.83 (t, J=7.17 Hz, 3H).

Example 297

N-(2-Ethoxy-4-methylbenzyl)-2-ethyl-6,7-dimethoxy-1-oxo-1,2-dihydroisoquinoline-4-carboxamide ESI-MS: m/z 425 [M+H]$^+$;
$^1$H NMR (500 MHz, DMSO-D$_2$O, T: 25° C.) δ ppm 7.77 (s, 1H) 7.72 (s, 1H) 7.66 (s, 1H) 7.17 (d, J=7.63 Hz, 1H) 6.82 (s, 1H) 6.75 (d, J=7.32 Hz, 1H) 4.39-4.45 (m, 2H) 3.98-4.10 (m, 4H) 3.88 (s, 3H) 3.82 (s, 3H) 2.29 (s, 3H) 1.35 (t, J=6.87 Hz, 3H) 1.29 (t, J=7.17 Hz, 3H).

Example 298

N-(2-sec-Butoxy-4-methylbenzyl)-2-ethyl-6,7-dimethoxy-1-oxo-1,2-dihydroisoquinoline-4-carboxamide ESI-MS: m/z 453 [M+H]$^+$
$^1$H NMR (500 MHz, DMSO-D$_2$O, T: 25° C.) δ ppm 7.76 (s, 1H) 7.74 (s, 1H) 7.66 (s, 1H) 7.16 (d, J=7.63 Hz, 1H) 6.83 (s, 1H) 6.73 (d, J=7.63 Hz, 1H) 4.38-4.47 (m, 3H) 4.01 (q, J=7.02 Hz, 2H) 3.88 (s, 3H) 3.82 (s, 3H) 2.29 (s, 3H) 1.56-1.76 (m, 2H) 1.29 (t, J=7.17 Hz, 3H) 1.25 (d, J=6.10 Hz, 3H) 0.93 (t, J=7.32 Hz, 3H).

Example 299

2-Ethyl-N-(2-(isopentyloxy)-4-methylbenzyl)-6,7-dimethoxy-1-oxo-1,2-dihydroisoquinoline-4-carboxamide ESI-MS: m/z 467 [M+H]$^+$
$^1$H NMR (500 MHz, DMSO-D$_2$O, T: 25° C.) δ ppm 7.78 (s, 1H) 7.74 (s, 1H) 7.66 (s, 1H) 7.16 (d, J=7.63 Hz, 1H) 6.84 (s, 1H) 6.75 (d, J=7.63 Hz, 1H) 4.38-4.44 (m, 2H) 4.01 (q, J=6.82 Hz, 4H) 3.88 (s, 3H) 3.82 (s, 3H) 2.29 (s, 3H) 1.75-1.86 (m, 1H) 1.64 (q, J=6.41 Hz, 2H) 1.29 (t, J=7.17 Hz, 3H) 0.90 (d, J=6.71 Hz, 6H).

Example 300

2-Ethyl-6,7-dimethoxy-N-(4-methyl-2-propoxybenzyl)-1-oxo-1,2-dihydroisoquinoline-4-carboxamide ESI-MS: m/z 439 [M+H]$^+$;
$^1$H NMR (500 MHz, DMSO-D$_2$O, T: 25° C.) δ ppm 7.77 (s, 1H) 7.73 (s, 1H) 7.66 (s, 1H) 7.16 (d, J=7.63 Hz, 1H) 6.82 (s, 1H) 6.75 (d, J=7.63 Hz, 1H) 4.43 (s, 2H) 4.02 (q, J=7.02 Hz, 2H) 3.96 (t, J=6.26 Hz, 2H) 3.88 (s, 3H) 3.82 (s, 3H) 2.29 (s, 3H) 1.69-1.84 (m, 2H) 1.29 (t, J=7.02 Hz, 3H) 1.00 (t, J=7.32 Hz, 3H).

Example 301

2-Ethyl-6,7-dimethoxy-N-(4-methyl-2-(methylthio)benzyl)-1-oxo-1,2-dihydroisoquinoline-4-carboxamide ESI-MS: m/z 427 [M+H]$^+$
$^1$H NMR (500 MHz, DMSO-D$_2$O, T: 25° C.) δ ppm 7.80 (s, 1H) 7.73 (s, 1H) 7.66 (s, 1H) 7.23 (d, J=7.63 Hz, 1H) 7.13 (s, 1H) 7.00 (d, J=7.93 Hz, 1H) 4.45 (s, 2H) 4.02 (q, J=7.02 Hz, 2H) 3.88 (s, 3H) 3.82 (s, 3H) 2.49 (s, 3H) 2.31 (s, 3H) 1.30 (t, J=7.02 Hz, 3H).

Example 302

2-Ethyl-N-(2-isopropoxy-4-methylbenzyl)-6,7-dimethoxy-1-oxo-1,2-dihydroisoquinoline-4-carboxamide ESI-MS: m/z 439 [M+H]$^+$
$^1$H NMR (500 MHz, DMSO-D$_2$O, T: 25° C.) δ ppm 7.76 (s, 1H) 7.73 (s, 1H) 7.66 (s, 1H) 7.16 (d, J=7.63 Hz, 1H) 6.84

(s, 1H) 6.73 (d, J=7.93 Hz, 1H) 4.56-4.68 (m, 1H) 4.40 (s, 2H) 4.02 (q, J=7.02 Hz, 2H) 3.88 (s, 3H) 3.82 (s, 3H) 2.29 (s, 3H) 1.24-1.34 (m, 9H).

Example 303

2-Ethyl-6,7-dimethoxy-N-(4-methyl-2-(tetrahydrofuran-3-yloxy)benzyl)-1-oxo-1,2-dihydroisoquinoline-4-carboxamide ESI-MS: m/z 467 [M+H]$^+$;
$^1$H NMR (500 MHz, DMSO-D$_2$O, T: 25° C.) δ ppm 7.75 (s, 1H) 7.73 (s, 1H) 7.65 (s, 1H) 7.19 (d, J=7.63 Hz, 1H) 6.82 (s, 1H) 6.77 (d, J=7.63 Hz, 1H) 5.07 (dd, J=5.80, 4.58 Hz, 1H) 4.39 (s, 2H) 4.01 (q, J=7.02 Hz, 2H) 3.73-3.95 (m, 10H) 2.30 (s, 3H) 2.16-2.27 (m, 1H) 2.03 (dd, J=12.51, 6.10 Hz, 1H) 1.29 (t, J=7.17 Hz, 3H).

Example 304

2-Ethyl-6,7-dimethoxy-1-oxo-N-(2,4,5-trimethylbenzyl)-1,2-dihydroisoquinoline-4-carboxamide ESI-MS: m/z 409 [M+H]$^+$;
$^1$H NMR (500 MHz, DMSO-D$_2$O, T: 25° C.) δ ppm 7.73 (s, 1H) 7.69 (s, 1H) 7.65 (s, 1H) 7.07 (s, 1H) 6.96 (s, 1H) 4.40 (s, 2H) 4.01 (q, J=7.22 Hz, 2H) 3.88 (s, 3H) 3.80 (s, 3H) 2.27 (s, 3H) 2.17 (s, 6H) 1.28 (t, J=7.17 Hz, 3H).

Example 305

2-Ethyl-6,7-dimethoxy-N-(4-methyl-2-((tetrahydrofuran-2-yl)methoxy)benzyl)-1-oxo-1,2-dihydroisoquinoline-4-carboxamide ESI-MS: m/z 481 [M+H]$^+$;
$^1$H NMR (500 MHz, DMSO-D$_2$O, T: 25° C.) δ ppm 7.77 (s, 1H) 7.70 (s, 1H) 7.65 (s, 1H) 7.17 (d, J=7.63 Hz, 1H) 6.85 (s, 1H) 6.77 (d, J=7.32 Hz, 1H) 4.42 (s, 2H) 4.16-4.24 (m, 1H) 3.98-4.06 (m, 3H) 3.92-3.97 (m, 1H) 3.88 (s, 3H) 3.81 (s, 3H) 3.67-3.71 (m, 1H) 3.59-3.67 (m, 1H) 2.29 (s, 3H) 1.95-2.05 (m, 1H) 1.68-1.93 (m, 3H) 1.29 (t, J=7.17 Hz, 3H).

Example 306

2-Ethyl-6,7-dimethoxy-N-(4-methyl-2-(4-methylpentan-2-yloxy)benzyl)-1-oxo-1,2-dihydroisoquinoline-4-carboxamide ESI-MS: m/z 481 [M+H]$^+$;
$^1$H NMR (500 MHz, DMSO-D$_2$O, T: 25° C.) δ ppm 7.76 (s, 1H) 7.75 (s, 1H) 7.66 (s, 1H) 7.16 (d, J=7.63 Hz, 1H) 6.84 (s, 1H) 6.72 (d, J=7.32 Hz, 1H) 4.50-4.58 (m, 1H) 4.39 (s, 2H) 3.96-4.06 (m, 2H) 3.88 (s, 3H) 3.82 (s, 3H) 2.29 (s, 3H) 1.70-1.82 (m, 1H) 1.61-1.70 (m, 1H) 1.34-1.44 (m, 1H) 1.29 (t, J=7.02 Hz, 3H) 1.24 (d, J=5.80 Hz, 3H) 0.87 (dd, J=8.54, 6.71 Hz, 6H).

Example 307

2-Ethyl-6,7-dimethoxy-N-(4-methyl-2-(4-methylpentyloxy)benzyl)-1-oxo-1,2-dihydroisoquinoline-4-carboxamide ESI-MS: m/z 481 [M+H]$^+$;
$^1$H NMR (500 MHz, DMSO-D$_2$O, T: 25° C.) δ ppm 7.78 (s, 1H) 7.75 (s, 1H) 7.65 (s, 1H) 7.16 (d, J=7.63 Hz, 1H) 6.82 (s, 1H) 6.74 (d, J=7.32 Hz, 1H) 4.41 (s, 2H) 3.94-4.06 (m, 4H) 3.88 (s, 3H) 3.81 (s, 3H) 2.25-2.31 (m, 3H) 1.66-1.80 (m, 2H) 1.47-1.60 (m, 1H) 1.26-1.34 (m, 5H) 0.83 (d, J=6.71 Hz, 6H).

Example 308

2-Ethyl-6,7-dimethoxy-N-(2-methoxy-4-methylbenzyl)-1-oxo-1,2-dihydroisoquinoline-4-carboxamide ESI-MS: m/z 411 [M+H]$^+$;
$^1$H NMR (500 MHz, DMSO-D$_2$O, T: 25° C.) δ ppm 7.77 (s, 1H) 7.71 (s, 1H) 7.66 (s, 1H) 7.17 (d, J=7.63 Hz, 1H) 6.84 (s, 1H) 6.76 (d, J=7.32 Hz, 1H) 4.40 (s, 2H) 4.02 (q, J=7.22 Hz, 2H) 3.88 (s, 3H) 3.82 (s, 6H) 2.30 (s, 3H) 1.29 (t, J=7.17 Hz, 3H).

Example 309

2-Ethyl-6,7-dimethoxy-1-oxo-N-(thiazol-4-ylmethyl)isoquinoline-4-carboxamide

ESI-MS: m/z 374.1 [M+H]$^+$

Example 310

2-Ethyl-6,7-dimethoxy-1-oxo-N-[[4-(trifluoromethyl)phenyl]-methyl]isoquinoline-4-carboxamide $^1$H NMR (DMSO-d$_6$, 600 MHz): δ=8.99 (br. s., 1H), 7.89 (s, 1H), 7.78 (s, 1H), 7.73 (m, 2H), 7.63 (m, 3H), 4.57 (br. S., 2H), 4.03 (m, 2H), 3.87 (s, 3H), 3.81 (s, 3H), 1.27-1.32 (m, 3H).

Example 311

2-Ethyl-6,7-dimethoxy-1-oxo-N-[(1S)-1-(p-tolyl)ethyl]isoquinoline-4-carboxamide

ESI-MS: m/z 395.2 [M+H]$^+$

Example 312

2-Ethyl-N-[(4-isopropylphenyl)methyl]-6,7-dimethoxy-1-oxo-isoquinoline-4-carboxamide ESI-MS: m/z 409.2 [M+H]$^+$

Example 313

2-Ethyl-N-[(4-ethylphenyl)methyl]-6,7-dimethoxy-1-oxo-isoquinoline-4-carboxamide ESI-MS: m/z 395.2 [M+H]$^+$

Example 314

2-Ethyl-6,7-dimethoxy-1-oxo-N-[(1R)-1-(p-tolyl)ethyl]isoquinoline-4-carboxamide

ESI-MS: m/z 395.2 [M+H]$^+$

Example 315

N-[[4-(Difluoromethyl)phenyl]methyl]-2-ethyl-6,7-dimethoxy-1-oxo-isoquinoline-4-carboxamide ESI-MS: m/z 417.1 [M+H]$^+$

Example 316

2-Ethyl-6,7-dimethoxy-N-[(2-methylthiazol-4-yl)methyl]-1-oxo-isoquinoline-4-carboxamide ESI-MS: m/z 388.1 [M+H]$^+$

Example 317

2-Ethyl-6,7-dimethoxy-N-[(4-methyl-2-thienyl)methyl]-1-oxo-isoquinoline-4-carboxamide ESI-MS: m/z 387.1 [M+H]$^+$

Example 318

N-[(4-Cyclopropylphenyl)methyl]-2-ethyl-6,7-dimethoxy-1-oxo-isoquinoline-4-carboxamide ESI-MS: m/z 407.2 [M+H]$^+$

Example 319

N-Indan-1-yl-6,7-dimethoxy-2-[2-(5-methyl-2-pyridyl)ethyl]-1-oxo-isoquinoline-4-carboxamide ESI-MS: m/z 484.20 [M+H]$^+$

Example 320

N-Butyl-6,7-dimethoxy-2-[2-(5-methyl-2-pyridyl)ethyl]-1-oxo-isoquinoline-4-carboxamide ESI-MS: m/z 424.20 [M+H]$^+$

Example 321

2-Ethyl-6,7-dimethoxy-N-[2-(6-methoxy-2-pyridyl)ethyl]-1-oxo-isoquinoline-4-carboxamide; 2,2,2-trifluoroacetic acid ESI-MS: m/z 412.10 [M+H]$^+$

Example 322

N-Butyl-6,7-dimethoxy-1-oxo-2-[2-(2-quinolyl)ethyl]isoquinoline-4-carboxamide; 2,2,2-trifluoroacetic acid ESI-MS: m/z 460.20 [M+H]$^+$

Example 323

N-Indan-1-yl-6,7-dimethoxy-1-oxo-2-[2-(2-quinolyl)ethyl]isoquinoline-4-carboxamide; 2,2,2-trifluoroacetic acid ESI-MS: m/z 520.20 [M+H]$^+$

Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM MgCl$_2$, 0.1% bovine serum albumin) containing enzyme and substrate. The PDE enzymes concentration ranged from 10 pM 250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, IC$_{50}$ value of inhibitor can be obtained by plotting inhibitor concentration against PDE activity at that concentration. The results are shown in Table 1.

TABLE 1

| Example | IC$_{50}$[1) |
|---|---|
| 1 | ++ |
| 15 | + |
| 20 | + |
| 21 | + |
| 23 | + |
| 24 | + |
| 26 | ++ |
| 28 | + |
| 29 | + |
| 30 | + |
| 31 | + |
| 32 | + |
| 33 | + |
| 34 | + |
| 35 | + |
| 36 | ++ |
| 37 | ++ |
| 39 | ++ |
| 40 | ++ |
| 51 | + |
| 129 | +++ |
| 135 | +++ |
| 136 | +++ |
| 139 | + |
| 140 | + |
| 141 | ++ |
| 142 | ++ |
| 145 | + |
| 146 | + |
| 147 | ++ |
| 148 | + |
| 149 | + |
| 151 | + |
| 152 | + |
| 153 | ++ |

TABLE 1-continued

| Example | IC$_{50}$[1] |
|---|---|
| 154 | ++ |
| 156 | + |
| 158 | ++ |
| 161 | +++ |
| 162 | + |
| 164 | + |
| 165 | ++ |
| 167 | + |
| 168 | + |
| 169 | + |
| 171 | + |
| 172 | ++ |
| 173 | + |
| 174 | + |
| 175 | + |
| 176 | + |
| 177 | + |
| 182 | ++ |
| 186 | ++ |
| 187 | + |
| 188 | ++ |
| 189 | ++ |
| 190 | ++ |
| 191 | + |
| 192 | +++ |
| 193 | +++ |
| 194 | +++ |
| 195 | ++ |
| 197 | ++ |
| 198 | + |
| 199 | + |
| 200 | + |
| 201 | + |
| 202 | +++ |
| 205 | + |
| 216 | +++ |
| 219 | +++ |
| 228 | ++ |
| 230 | ++ |
| 233 | ++ |
| 236 | ++ |
| 237 | ++ |
| 238 | ++ |
| 239 | ++ |
| 241 | ++ |
| 242 | + |
| 244 | + |
| 246 | ++ |
| 247 | ++ |
| 248 | ++ |
| 249 | + |
| 251 | ++ |
| 252 | ++ |
| 253 | +++ |
| 254 | +++ |
| 255 | + |
| 256 | +++ |
| 257 | ++ |
| 258 | ++ |
| 259 | + |
| 260 | ++ |
| 261 | + |
| 262 | ++ |
| 263 | ++ |
| 264 | + |
| 265 | + |
| 266 | + |
| 267 | ++ |
| 268 | + |
| 269 | + |
| 273 | + |
| 276 | + |
| 277 | + |
| 278 | + |
| 288 | + |
| 290 | + |
| 293 | + |
| 298 | + |
| 302 | + |
| 303 | + |
| 305 | + |
| 308 | + |
| 309 | + |
| 311 | + |
| 313 | + |
| 316 | + |
| 317 | ++ |
| 318 | + |
| 322 | +++ |
| 323 | + |

[1] +++: IC$_{50}$ <100 nM ++: 100 nM ≤ IC$_{50}$ ≤ 200 nM +: 200 nM < IC$_{50}$ < 500 nM b) Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomoleculur Screening, 2003, 453-462; Obach, D M D, 1999 vol 27. N 11, 1350-1359). The results are shown in Table 2.

TABLE 2

| Ex. | Rat mCl[2] [µl min$^{-1}$ mg$^{-1}$] | Human mCl[2] [µl min$^{-1}$ mg$^{-1}$] |
|---|---|---|
| 40 | ++ | ++ |
| 136 | o | + |
| 141 | ++ | ++ |
| 147 | ++ | ++ |
| 158 | ++ | ++ |
| 161 | ++ | ++ |
| 165 | ++ | ++ |
| 171 | ++ | ++ |
| 172 | ++ | ++ |
| 186 | ++ | ++ |
| 190 | + | o |
| 192 | + | o |
| 195 | + | + |
| 196 | ++ | ++ |
| 197 | + | o |
| 198 | ++ | + |
| 199 | ++ | ++ |
| 200 | ++ | ++ |
| 201 | ++ | ++ |
| 202 | + | o |
| 203 | ++ | ++ |
| 204 | ++ | + |
| 205 | ++ | ++ |
| 219 | + | + |
| 228 | ++ | ++ |

TABLE 2-continued

| Ex. | Rat mCl[2]) [μl min⁻¹ mg⁻¹] | Human mCl[2]) [μl min⁻¹ mg⁻¹] |
|---|---|---|
| 236 | ++ | + |
| 238 | + | ++ |
| 239 | + | + |
| 241 | + | ++ |
| 244 | ++ | ++ |
| 246 | + | o |
| 247 | ++ | + |
| 248 | ++ | + |
| 251 | o | + |
| 256 | + | o |
| 263 | ++ | ++ |
| 267 | o | + |
| 309 | nd | ++ |
| 310 | ++ | ++ |
| 311 | nd | ++ |
| 312 | ++ | + |
| 313 | ++ | ++ |
| 314 | ++ | ++ |
| 315 | ++ | ++ |
| 316 | ++ | ++ |
| 317 | + | ++ |
| 318 | ++ | ++ |

Ex. Example
mCl mikrosomal clearance
[2])++: <100 μl min⁻¹ mg⁻¹ +: 100-220 μl min⁻¹ mg⁻¹ o: >220 μl min⁻¹ mg⁻¹ nd: not determined

We claim:

1. A compound of formula (I)

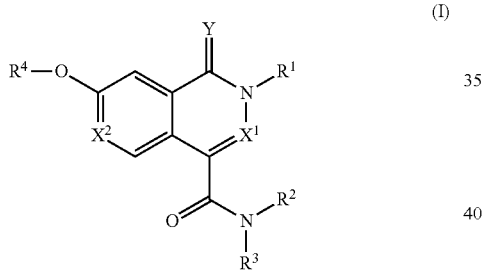

wherein
$X^1$ is CH;
$X^2$ is C—$R^5$;
Y is O or S;
$R^1$ is selected from the group consisting of $C_2$-$C_8$-alkyl, $C_2$-$C_8$-alkenyl, $C_1$-$C_4$-fluoroalkyl, $C_3$-$C_8$-cycloalkyl, $C_5$-$C_8$-cycloalkyl carrying a fused benzene ring, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$) and a moiety $Z^1$—$Ar^1$;
$R^2$ is a radical of the formula $CR^{21}R^{22}R^{23}$, where
$R^{21}$ and $R^{22}$ together with the carbon atom, to which they are bound form a saturated 5- to 7-membered carbocyclic ring or a saturated 5- to 7-membered heterocyclic ring which has 1, 2 or 3 heteroatoms or heteroatom containing groups selected from the group consisting of O, N, S, SO and $SO_2$ as ring members, where the carbocyclic ring or the heterocyclic ring are unsubstituted or substituted by 1, 2 or 3 identical or different substituents $R^g$, and where the carbocyclic ring or the heterocyclic ring carry a fused benzene ring or a fused 5- or 6-membered heteroaromatic ring, where the fused rings themselves are unsubstituted or carry 1, 2 or 3 substituents $R^h$,
$R^{23}$ is selected from the group consisting of hydrogen, fluorine, $C_1$-$C_8$-alkyl and $C_1$-$C_4$-fluoroalkyl;
$R^3$ is selected from the group consisting of hydrogen, $C_1$-$C_8$-alkyl, $C_2$-$C_8$-alkenyl, $C_1$-$C_4$-fluoroalkyl, $C_3$-$C_8$-cycloalkyl, $C_3$-$C_8$-cycloalkyl-$C_1$-$C_4$-alkyl, $C_1$-$C_4$-alkoxy-$C_1$-$C_4$-alkyl, hydroxy-$C_1$-$C_4$-alkyl, $C_1$-$C_4$-alkyl-N($R^b$)($R^c$), and trimethylsilyl;
$R^4$ is selected from the group consisting of $C_1$-$C_4$-alkyl, $C_1$-$C_4$-fluoroalkyl, $C_3$-$C_6$-cycloalkyl, $C_3$-$C_6$-cycloalkyl-$C_1$-$C_4$-alkyl and $Z^4$—$Ar^4$;
$R^5$ is selected from the group consisting of hydrogen, halogen, $C_1$-$C_4$-alkyl, $C_1$-$C_4$-fluoroalkyl, $C_1$-$C_4$-alkoxy, $C_1$-$C_4$-fluoroalkoxy, —$Z^5$—$Ar^5$, —O—$Z^5$—$Ar^5$, $C_3$-$C_6$-cycloalkyl, $C_3$-$C_6$-cycloalkyl-$C_1$-$C_4$-alkyl, $C_3$-$C_6$-cycloalkoxy and $C_3$-$C_6$-cycloalkyl-$C_1$-$C_4$-alkoxy, where the cyclic radical in the last four mentioned groups may be unsubstituted, partially or completely fluorinated or carries 1, 2, 3 or 4 methyl groups;
$Ar^1$ is selected from the group consisting of phenyl, monocyclic 5- or 6-membered hetaryl and bicyclic 9- or 10-membered hetaryl, where hetaryl has 1, 2 or 3 heteroatoms as ring members which are selected from the group consisting of O, S and N, where phenyl and hetaryl are unsubstituted or may carry 1, 2 or 3 identical or different substituents $R^h$;
$Ar^4$ and $Ar^5$ are independently of each other selected from the group consisting of phenyl and monocyclic 5- or 6-membered hetaryl having 1, 2 or 3 heteroatoms as ring members which are selected from the group consisting of O, S and N, where phenyl and monocyclic hetaryl are unsubstituted or may carry 1, 2 or 3 identical or different substituents $R^k$;
$Z^1$, $Z^4$, and $Z^5$ are independently of each other $C_1$-$C_4$-alkylene;
$R^b$, and $R^c$, independently of each other are selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl; or $R^b$ and $R^c$ form together with the N atom to which they are attached a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl;
$R^d$ is selected from the group consisting of $C_1$-$C_4$-alkyl, $C_1$-$C_4$-fluoroalkyl, $C_3$-$C_6$-cycloalkyl, $C_3$-$C_6$-cycloalkylmethyl and benzyl;
$R^e$, and $R^f$, independently of each other are selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl; or $R^e$ and $R^f$ form together with the N atom to which they are attached a 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 $C_1$-$C_4$-alkyl substituents;
$R^g$ is selected from the group consisting of halogen, CN, OH, $C_1$-$C_6$-alkyl, $C_2$-$C_6$-alkenyl, $C_1$-$C_4$-fluoroalkyl, $C_3$-$C_6$-cycloalkyl, fluorinated $C_3$-$C_6$-cycloalkyl, $C_3$-$C_6$-cycloalkyl-$C_1$-$C_4$-alkyl, fluorinated $C_3$-$C_6$-cycloalkyl-C i-$C_4$-alkyl, $C_1$-$C_4$-alkoxy-$C_1$-

$C_4$-alkyl, hydroxy-$C_1$-$C_4$-alkyl, $C_1$-$C_4$-alkyl-N($R^b$)($R^c$), $C_1$-$C_4$-alkoxy, and fluorinated $C_1$-$C_4$-alkoxy, where one $R^g$ together with a carbon atom to which $R^g$ is attached may also form a carbonyl group, where one $R^g$ may also be phenyl or benzyl, where the phenyl ring in the last 2 mentioned radicals is unsubstituted or carries 1, 2 or 3 radicals $R^h$;

$R^h$ is selected from the group consisting of halogen, CN, OH, $C_1$-$C_4$-alkyl, fluorinated $C_1$-$C_4$-alkyl, $C_1$-$C_6$-alkoxy, fluorinated $C_1$-$C_4$-alkoxy, $C_1$-$C_4$-alkylsulfanyl, $C_1$-$C_4$-alkoxy-$C_1$-$C_4$-alkoxy, $C_3$-$C_6$-cycloalkyl, fluorinated $C_3$-$C_6$-cycloalkyl, $C_3$-$C_6$-cycloalkoxy, $C_3$-$C_6$-cycloalkyl-$C_1$-$C_4$-alkoxy, phenoxy, N($R^b$)($R^c$), $C_1$-$C_4$-alkyl-N($R^b$)($R^c$), C(O)O—$R^d$, C(O)N($R^e$)($R^f$), N($R^{ee}$)S(O)$_2$($R^{ff}$), S(O)$_2$N($R^e$)($R^f$), 3- to 7-membered heterocyclyloxy, 3- to 7-membered heterocyclyl-$C_1$-$C_4$-alkoxy, where heterocyclyl in the two last mentioned radicals has 1, 2 or 3 heteroatoms as ring members which are selected from the group consisting of O, S and N, and 5- to 6-membered hetaryl-$C_1$-$C_4$-alkoxy, where hetaryl has 1, 2 or 3 heteroatoms as ring members which are selected from the group consisting of O, S and N;

$R^k$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, N($R^b$)($R^c$), C(O)O—$R^d$, C(O)N($R^e$)($R^f$), N($R^{ee}$)S(O)$_2$($R^{ff}$) and S(O)$_2$N($R^e$)($R^f$); or two radicals $R^k$ that are bound to adjacent carbon atoms together with said carbon atoms may form a fused benzene ring or a fused 5- or 6-membered heteroaromatic ring having 1 or 2 ring members selected from the group consisting of O, N and S, where the fused benzene ring and the fused heteroaromatic ring are unsubstituted or may carry 1, 2 or 3 radicals $R^h$;

$R^{ee}$ is selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkylmethyl and benzyl;

$R^{ff}$ is selected from the group consisting of $C_1$-$C_4$-alkyl, $C_1$-$C_4$-fluoroalkyl and phenyl, which is unsubstituted or carries 1, 2 or 3 radicals $R^h$; and m is 0, 1, 2, 3 or 4;

or an N-oxide, hydrate, or tautomer thereof, or a pharmaceutically acceptable salt thereof.

2. The compound of claim 1, where $R^h$ is selected from the group consisting of halogen, CN, OH, $C_1$-$C_4$-alkyl, fluorinated $C_1$-$C_4$-alkyl, $C_1$-$C_4$-alkoxy, fluorinated $C_1$-$C_4$-alkoxy, $C_3$-$C_6$-cycloalkyl, fluorinated $C_3$-$C_6$-cycloalkyl, N($R^b$)($R^c$), $C_1$-$C_4$-alkyl-N($R^b$)($R^c$), C(O)O—$R^d$, C(O)N($R^e$)($R^f$), N($R^{ee}$)S(O)$_2$($R^{ff}$) and S(O)$_2$N($R^e$)($R^f$).

3. The compound of claim 1, where Y is O.

4. The compound of claim 1, where $R^1$ is $C_2$-$C_8$-alkyl, $C_3$-$C_8$-cycloalkyl or $C_3$-$C_8$-cycloalkylmethyl.

5. The compound of claim 4, where $R^1$ is a radical of the formula CHR$^{1a}$R$^{1b}$, where $R^{1a}$ is selected from the group consisting of hydrogen and $C_1$-$C_3$-alkyl and where $R^{1b}$ is $C_1$-$C_4$-alkyl.

6. The compound of claim 1, where $R^1$ is a moiety $Z^1$—Ar$^1$.

7. The compound of claim 1, where $R^{21}$ and $R^{22}$ together with the carbon atom, to which they are bound form a saturated 5- to 7-membered carbocyclic ring or a saturated 5- to 7-membered heterocyclic ring which has 1, 2 or 3 heteroatoms or heteroatom containing groups selected from the group consisting of O, N, S, SO and SO$_2$ as ring members, where the carbocyclic ring or the heterocyclic ring are unsubstituted or substituted by 1, 2 or 3 identical or different substituents $R^g$, and where the carbocyclic ring or the heterocyclic ring carry a fused benzene ring or a fused 5- or 6-membered heteroaromatic ring, where the fused rings themselves are unsubstituted or carry 1, 2 or 3 substituents $R^h$, and where $R^{23}$ is hydrogen.

8. The compound of claim 1, where $R^{21}$ and $R^{22}$ together with the carbon atom, to which they are bound form a saturated 5- to 7-membered carbocyclic ring, a 3-tetrahydrofuryl, or a 3-tetrahydrothienyl, where the 5- to 7-membered carbocyclic ring, the 3-tetrahydrofuryl, or the 3-tetrahydrothienyl ring carry a fused benzene ring or a fused 5- or 6-membered heteroaromatic ring, where the fused rings themselves are unsubstituted or carry 1, 2 or 3 substituents $R^h$, and where $R^{23}$ is hydrogen.

9. The compound of claim 1, where $R^3$ is hydrogen or $C_1$-$C_4$-alkyl.

10. The compound of claim 1, where $R^4$ is $C_1$-$C_4$-alkyl.

11. The compound of claim 1, where $R^5$ is hydrogen, fluorine, $C_1$-$C_4$-alkoxy or a radical O—$Z^5$—Ar$^5$.

12. The compound of claim 11, where $R^4$ is methyl and $R^5$ is hydrogen, fluorine or methoxy.

13. The compound of claim 11, where $R^4$ is methyl and $R^5$ is O—Z—Ar$^5$.

14. The compound of claim 1 which is a compound of the formula (Ia)

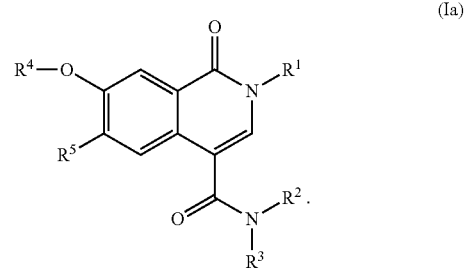

(Ia)

15. The compound of claim 14, where $R^1$ is a radical of the formula CHR$^{1a}$R$^{1b}$, where $R^{1a}$ is selected from the group consisting of hydrogen and $C_1$-$C_3$-alkyl and where $R^{1b}$ is $C_1$-$C_4$-alkyl;

$R^3$ is hydrogen or $C_1$-$C_4$-alkyl;

$R^4$ is $C_1$-$C_4$-alkyl; and $R^5$ is hydrogen, fluorine, $C_1$-$C_4$-alkoxy or a radical O—$Z^5$—Ar$^5$.

16. The compound of claim 14, where $R^1$ is a moiety $Z^1$—Ar$^1$;

$R^3$ is hydrogen or $C_1$-$C_4$-alkyl;

$R^4$ is $C_1$-$C_4$-alkyl; and $R^5$ is hydrogen, fluorine or $C_1$-$C_4$-alkoxy.

17. The compound of claim 15, where $R^{21}$ and $R^{22}$ together with the carbon atom, to which they are bound form a saturated 5- to 7-membered carbocyclic ring, which carries a fused benzene ring or a fused 5- or 6-membered heteroaromatic ring, where the fused rings themselves are unsubstituted or carry 1, 2 or 3 substituents $R^h$, and where $R^{23}$ is hydrogen.

18. The compound of claim 14, where $R^4$ is methyl and $R^5$ is hydrogen, fluorine or methoxy.

19. The compound of claim 14, where $R^4$ is methyl and $R^5$ is O—$Z^5$—$Ar^5$.

20. The compound of claim 1, which is selected from the group consisting of
- 2-Ethyl-6,7-dimethoxy-1-oxo-1,2-dihydro-isoquinoline-4-carboxylic acid indan-1-ylamide;
- 2-Ethyl-6,7-dimethoxy-1-oxo-1,2-dihydro-isoquinoline-4-carboxylic acid indan-2-ylamide;
- 4-(Azetidine-1-carbonyl)-2-ethyl-6,7-dimethoxy-2H-isoquinolin-1-one;
- 2-(1-Ethyl-propyl)-6,7-dimethoxy-1-oxo-1,2-dihydro-isoquinoline-4-carboxylic acid indan-1-ylamide;
- 2-(1-Ethyl-propyl)-7-methoxy-1-oxo-1,2-dihydro-isoquinoline-4-carboxylic acid indan-1-ylamide;
- 7-Methoxy-1-oxo-2-(2-quinolin-2-yl-ethyl)-1,2-dihydro-isoquinoline-4-carboxylic acid indan-1-ylamide;
- 2-(1-Ethyl-propyl)-6,7-dimethoxy-1-oxo-1,2-dihydro-isoquinoline-4-carboxylic acid (6,7-dihydro-5H-[1]pyrindin-5-yl)-amide;
- 2-(1-Ethyl-propyl)-6,7-dimethoxy-1-oxo-1,2-dihydro-isoquinoline-4-carboxylic acid (R)-indan-1-ylamide;
- 2-(1-Ethyl-propyl)-6,7-dimethoxy-1-oxo-1,2-dihydro-isoquinoline-4-carboxylic acid (S)-indan-1-ylamide;
- 2-Ethyl-6,7-dimethoxy-1-oxo-1,2-dihydro-isoquinoline-4-carboxylic acid (1,2,3,4-tetrahydro-naphthalen-1-yl)-amide;
- 2-Ethyl-6,7-dimethoxy-1-oxo-1,2-dihydro-isoquinoline-4-carboxylic acid (6-methyl-indan-1-yl)-amide;
- 2-Ethyl-6,7-dimethoxy-1-oxo-1,2-dihydro-isoquinoline-4-carboxylic acid (5-chloro-indan-1-yl)-amide;
- 2-Ethyl-6,7-dimethoxy-1-oxo-1,2-dihydro-isoquinoline-4-carboxylic acid (6-chloro-indan-1-yl)-amide;
- 2-Ethyl-6,7-dimethoxy-1-oxo-1,2-dihydro-isoquinoline-4-carboxylic acid (6-fluoro-indan-1-yl)-amide;
- 2-Ethyl-6,7-dimethoxy-1-oxo-1,2-dihydro-isoquinoline-4-carboxylic acid (5,6-dihydro-4H-cyclopenta[b]thiophen-4-yl)-amide;
- 2-Ethyl-6,7-dimethoxy-1-oxo-1,2-dihydro-isoquinoline-4-carboxylic acid (4-fluoro-indan-1-yl)-amide;
- 2-Ethyl-6,7-dimethoxy-1-oxo-1,2-dihydro-isoquinoline-4-carboxylic acid (4-methyl-indan-1-yl)-amide;
- 2-Ethyl-6,7-dimethoxy-1-oxo-1,2-dihydro-isoquinoline-4-carboxylic acid (5-methyl-indan-1-yl)-amide;
- 2-Ethyl-6,7-dimethoxy-1-oxo-1,2-dihydro-isoquinoline-4-carboxylic acid (6-methoxy-indan-1-yl)-amide;
- 2-Ethyl-6,7-dimethoxy-1-oxo-1,2-dihydro-isoquinoline-4-carboxylic acid (5-fluoro-indan-1-yl)-amide;
- 2-(1-Ethyl-propyl)-6,7-dimethoxy-1-oxo-1,2-dihydro-isoquinoline-4-carboxy-lic acid (5,6-dihydro-4H-cyclopenta[b]thiophen-4-yl)-amide;
- 2-(1-Ethyl-propyl)-6,7-dimethoxy-1-oxo-1,2-dihydro-isoquinoline-4-carboxylic acid (2,3-dihydro-benzofuran-3-yl)-amide;
- 2-(1-Ethyl-propyl)-6,7-dimethoxy-1-oxo-1,2-dihydro-isoquinoline-4-carboxylic acid (6-oxo-5,6-dihydro-4H-cyclopenta[b]thiophen-4-yl)-amide;
- 2-Cyclopropyl-6,7-dimethoxy-1-oxo-1,2-dihydro-isoquinoline-4-carboxylic acid indan-1-ylamide;
- 2-sec-Butyl-6,7-dimethoxy-1-oxo-1,2-dihydro-isoquinoline-4-carboxylic acid indan-1-ylamide;
- 2-Isopropyl-6,7-dimethoxy-1-oxo-1,2-dihydro-isoquinoline-4-carboxylic acid indan-1-ylamide;
- 2-Ethyl-6,7-dimethoxy-1-oxo-1,2-dihydro-isoquinoline-4-carboxylic acid (S)indan-1-ylamide;
- 2-Ethyl-6,7-dimethoxy-1-oxo-1,2-dihydro-isoquinoline-4-carboxylic acid (R)indan-1-ylamide;
- 2-Ethyl-6,7-dimethoxy-1-oxo-1,2-dihydro-isoquinoline-4-carboxylic acid (S)(5,6-dihydro-4H-cyclopenta[b]thiophen-4-yl)-amide;
- 2-Ethyl-6,7-dimethoxy-1-oxo-1,2-dihydro-isoquinoline-4-carboxylic acid (R)(5,6-dihydro-4H-cyclopenta[b]thiophen-4-yl)-amide;
- 2-(1-Ethyl-propyl)-6,7-dimethoxy-1-oxo-1,2-dihydro-isoquinoline-4-carboxylic acid 3-(4-chloro-benzenesulfonylamino)-benzylamide; and
- 2-(1-Ethyl-propyl)-6,7-dimethoxy-1-oxo-1,2-dihydro-isoquinoline-4-carboxylic acid (2,3-dihydro-benzo[b]thiophen-3-yl)-amide;

or an N-oxide, tautomer, hydrate, or a pharmaceutically acceptable salt thereof.

21. The compound of claim 1, which is selected from the group consisting of
- N-(5-Fluoro-2,3-dihydro-1H-inden-1-yl)-6,7-dimethoxy-1-oxo-2-(pentan-3-yl-)-1,2-dihydro-isoquinoline-4-carboxamide;
- 6,7-Dimethoxy-N-(5-methyl-2,3-dihydro-1H-inden-1-yl)-1-oxo-2-(pentan-3-yl)-1,2-dihydro-isoquinoline-4-carboxamide;
- 6,7-Dimethoxy-N-(4-methyl-2,3-dihydro-1H-inden-1-yl)-1-oxo-2-(pentan-3-yl)-1,2-dihydro-isoquinoline-4-carboxamide;
- 6,7-Dimethoxy-N-(6-methoxy-2,3-dihydro-1H-inden-1-yl)-1-oxo-2-(pentan-3-y-l)-1,2-dihydro-isoquinoline-4-carboxamide;
- 6,7-Dimethoxy-N-(6-methyl-2,3-dihydro-1H-inden-1-yl)-1-oxo-2-(pentan-3-yl)-1,2-dihydro-isoquinoline-4-carboxamide;
- N-(4-Chloro-2,3-dihydro-1H-inden-1-yl)-6,7-dimethoxy-1-oxo-2-(pentan-3-yl)-1,2-dihydroisoquinoline-4-carboxamide;
- N-Indan-1-yl-6,7-dimethoxy-2-[2-(5-methyl-2-pyridyl)-ethyl]-1-oxo-isoquinoline-4-carboxamide; and
- N-Indan-1-yl-6,7-dimethoxy-1-oxo-2-[2-(2-quinolyl)ethyl]isoquinoline- -4-carboxamide;

or an N-oxide, tautomer, hydrate, or a pharmaceutically acceptable salt thereof.

22. A pharmaceutical composition which comprises a carrier and a compound of claim 1, or a pharmaceutically acceptable salt thereof.

23. The compound of claim 1 where $R^1$ is propyl, 1-methylethyl, n-butyl, 1-methylpropyl, 1,1-dimethylpropyl, or 1-ethylpropyl.

24. The compound of claim 1, where $R^1$ is 1-ethylpropyl.

25. A compound that is 2-(1-ethyl-propyl)-6,7-dimethoxy-1-oxo-1,2-dihydroisoquinoline-4-carboxylic acid indan-1-ylamide, or a N-oxide thereof, or a tautomer thereof, or a hydrate thereof or a pharmaceutically acceptable salt thereof.

26. A compound that is 2-(1-ethyl-propyl)-6,7-dimethoxy-1-oxo-1,2-dihydro-isoquinoline-4-carboxylic acid (S)-indan-1-ylamide, or a N-oxide thereof, or a tautomer thereof, or a hydrate thereof or a pharmaceutically acceptable salt thereof.

* * * * *